US008916514B2

(12) United States Patent
Blais et al.

(10) Patent No.: US 8,916,514 B2
(45) Date of Patent: Dec. 23, 2014

(54) CASB7439 CONSTRUCTS

(75) Inventors: Normand Blais, Laval (CA); Martine Harvey, Laval (CA); Anthony Pilorget, Laval (CA); Clement Rioux, Laval (CA); Remi Palmantier, Rixensart (BE)

(73) Assignee: GlaxoSmithKline Biologicals, S.A., Rixensart (BE)

( * ) Notice: Subject to any disclaimer, the term of this patent is extended or adjusted under 35 U.S.C. 154(b) by 80 days.

(21) Appl. No.: 13/322,282

(22) PCT Filed: May 25, 2010

(86) PCT No.: PCT/EP2010/057141
§ 371 (c)(1),
(2), (4) Date: Nov. 23, 2011

(87) PCT Pub. No.: WO2010/136443
PCT Pub. Date: Dec. 2, 2010

(65) Prior Publication Data

US 2012/0070491 A1 Mar. 22, 2012

Related U.S. Application Data

(60) Provisional application No. 61/181,380, filed on May 27, 2009, provisional application No. 61/220,396, filed on Jun. 25, 2009.

(51) Int. Cl.
*C07K 14/00* (2006.01)
*C07H 21/02* (2006.01)
*C07K 14/47* (2006.01)
*C07K 16/30* (2006.01)
*A61K 39/00* (2006.01)

(52) U.S. Cl.
CPC ......... *A61K 39/0011* (2013.01); *C07K 14/4748* (2013.01); *C07K 14/4702* (2013.01); *A61K 2039/55572* (2013.01); *A61K 2039/55577* (2013.01); *A61K 2039/6068* (2013.01); *C07K 16/3046* (2013.01); *A61K 2039/55561* (2013.01); *A61K 2039/55555* (2013.01)
USPC ............................... 514/1; 530/350; 536/23.1

(58) Field of Classification Search
USPC ............................... 514/1; 530/350; 536/23.1
See application file for complete search history.

(56) References Cited

U.S. PATENT DOCUMENTS

| | | | | |
|---|---|---|---|---|
| 6,030,945 | A * | 2/2000 | Ashkenazi | 514/18.9 |
| 6,087,168 | A | 7/2000 | Levesque et al. | |
| 6,451,320 | B1 | 9/2002 | Stephenne et al. | |
| 6,551,795 | B1 | 4/2003 | Rubenfield et al. | |
| 7,803,379 | B2 * | 9/2010 | Cabezon-Silva et al. | 424/184.1 |
| 7,811,574 | B2 * | 10/2010 | Cassart et al. | 424/184.1 |
| 8,039,602 | B2 | 10/2011 | Ryan | |
| 8,207,123 | B2 * | 6/2012 | Cabezon-Silva et al. | 514/19.3 |
| 2005/0260634 | A1 | 11/2005 | Baldwin et al. | |

FOREIGN PATENT DOCUMENTS

| | | | |
|---|---|---|---|
| WO | WO9315763 | | 8/1993 |
| WO | 9517210 | | 6/1995 |
| WO | WO9514772 | | 6/1995 |
| WO | 9602555 | | 2/1996 |
| WO | WO9728820 | | 8/1997 |
| WO | WO9940188 | | 8/1999 |
| WO | WO0053748 | | 9/2000 |
| WO | WO0157275 | | 1/2001 |
| WO | WO0157276 | | 1/2001 |
| WO | WO 01/62778 | A2 | 8/2001 |
| WO | WO0102828 | | 11/2001 |
| WO | WO 02/066506 | A2 | 8/2002 |
| WO | WO 02/092627 | A2 | 11/2002 |
| WO | WO 2004/019857 | A2 | 3/2004 |
| WO | WO 2008/030559 | A2 | 3/2008 |

OTHER PUBLICATIONS

Jubb, et al. Oncogene, vol. 25(4): 3445-3457 (2006).
Esposito, et al. Current Opinion in Biotechnology, vol. 17(4): 353-358 (2006).
Dyson, et al. BMC Biotechnology, vol. 4(1): 32 (2004).
Kyewski et al., Intrathymic Presentation of Circulating Non-MHC Antigens by medullary Dendritic Cells, An antigen-dependent Microenvironment for T Cell Differentiation, J. Exp. Med., 163:231-245 (1986).
Lazar et al., Molecular and Cell Biology 8:1247-1252 (1988).
Marchand et al., Tumor Regressions Observed in Patients with Metastitic melanoma Treated with an Antigenic Peptide Encoded by Gene MAGE-3 and Presented by HLA-A1, Int. J. Cancer 80:219-230 (1999).
Oka et al., Induction of WT1 (Wilms' tumor gene)-specific cytotoxic T lymphocytes by WTI peptide vaccine and the resultant cancer regression, PNAS 101(38):13885-13890 (Sep. 2004).
Rosenberg et al., Cancer Immunotherapy: moving beyond current vaccines, Nat Med 10(9):909-915 (Sep. 2004).
Tao et al., The J. of Immunology 143(8):2595-2601 (1989).
Tsuruma et al., Peptide-based vaccination for colorectal cancer, Expert Opin. Biol. Ther. 5(6):799-807 (2005).
Zhang et al., Induction of Specific T Cell Tolerance by Fas Ligand-Expressing Antigen-Presenting Cells, J. of Immunology 162:1423-1430 (1999).
Homology Search for HASH2; Gencor version 5.1.6 (Compugen 1993-2004) (Jun. 16, 2004).
Hill, Issue and Procedures in Women's Health—Molar Pregnancy http://www.obgyn.net/women/articles/molarpreg.dah.htm (Jun. 24, 2005).
Bendayan, Possibilities of False Immunocytochemical Results Generated by the Use of Monoclonal Antibodies: the Example of the Anti-proinsulin Antibody, Journal of Histochemistry and Cytochemistry 3(9):881-886, (1995).
Bost et al., Antibodies Against a Peptide Sequence within the HIV Envelope Protein Crossreacts with Human Interleukin-2, Immunological Investigations 17(6&7):577-586 (1988).

(Continued)

*Primary Examiner* — Karen Cochrane Carlson
(74) *Attorney, Agent, or Firm* — Eric J. Kron

(57) ABSTRACT

The present disclosure relates to compounds and methods for increasing the recombinant production of CASB7439 polypeptides, and for methods of utilizing the same.

16 Claims, 35 Drawing Sheets

(56) References Cited

OTHER PUBLICATIONS

Holmes, PSMA specific antibodies and their diagnostic and therapeutic use, Expert Opinion on Investigations Drugs 10(3):511-519 (2001).
Arteaga (2002) "Trastuzumab, an appropriate first-line single-agent therapy for HER2-overexpressing metastitic breast cancer," Breast Cancer Res. 5:96-100.
Mitchell (2002) "Cancer vaccines, a critical review—Part II," Curr Opin Investig Drugs. 3:150-8.
Reiter (1998) "Prostate stem cell antigen: A cell surface marker overexpressed in prostate cancer," PNAS 95:1735-1740.
Ross (2002) "Prostate Stem Cell Antigen as Therapy Target: Tissue Expression and in Vivo Efficacy of an Immunoconjugate," Cancer Research 62:2546-2553.
Garcia-Hernandez (2008) "Prostate Stem Cell Antigen Vaccination Induces a Long-term Protective Immune Response against Prostate Cancer in the Absence of Autoimmunity," Cancer Research 68:861-869.
GlaxoSmithKline Biologicals, No. 001, "Antigen Specific Cancer Immunotherapeutics: Educating the patient's immune defense to fight cancer" (2007).
Roitt et al., 1998 Immunology, 4th ed. Mosby, London p. 5,6.
Bodey et al., 2000, Anticancer Res. 20:2665-2676.
Mellman I, 2006, The Scientist, 20(1):47-56.
Kaiser (Science, 2006, 313, 1370.
Smith RT, 1994 (Clin. Immunol, 41(4):841-849.
White et al., 2001, Ann Rev Med, 52:125-146.
Boon, 1992 (Adv Can Res, 56:177-210).
Kirkin et al, 1998 (APMIS, 106 (665-679).
Gaiger, A et al. 2000 (Blood, 96(4): 1480-1489).
Ezzell (J. NIH Res, 1995, 7:46-49).
Spitler, 1995 (Cancer Biotherapy, 10:1-3).
Roitt et al. 1998 (Immunology, 4th ed., Mosby, London p. 7.7-7.9).
Schmid S et al, 2001 (J Comparative Neurology, 430(2): 160-71).
Conner et al, 1996 (Mol Brain Res. 42: 1-17).
Johnson et al GenBank Accession No. S11562 in MPSRCH 2006 search report, us-10-650-608-25 rpr,pp. 1-3.
Harlow and Lane, Antibodies, a Laboratory Manual, Cold Spring Harbour Laboratory Press, 1988, p. 53-137 and 141-142.
Disis, J. Immunology, (1996), 156: 3151-3158.
Spisek, et al., "Requent and Specific Immunity to the Embroyonal Stem cell associated antigen soX2 in patients with monoclonal gammopathy", The Journal of Experimental Medicine, 204:4, pp. 831-840, Apr. 16, 2007.
Marchand, et al., "Tumor Regression Observed in Patients with Metastic Melanoma Treated with an Antigenic Peptide Excoded by Gene MAGE-3 and Presented by HLA-A1," International Journal of Cancer, 80: 219-230 (1999).
Luo, et al., "Transcription factor Fos-related antigen 1 is an effective target for a breast cancer vaccine," PNAS, pp. 8850-8855, 100"5 Jul. 22, 2003.
Kotelkin A.T., et al., Vestn Ross Akad Med Mauk, 4:29:33 (1998).
Hunt et al., "Normal trophoblasts Resist induction of class 1 HLA" The Journal of Immunology, 138:8, pp. 2481-2487 (1987).
Hamada et al., J. Biosci Bioeng, 87:(1) 97-102 (1999).
Dong et al,, Zinc-Finger protein ZNF165 us a novel cancer-testis antigen capable of eliciting antibody response in heptacellular carcinoma patients, Britsh Journal of Cancer, 91: pp. 156-1570, 2004.
Depuydt C.E. et al., Int. J. Androl, 20(5): 304-314 1997.
Declaration of Anthony Pilogret signed Jun. 24, 2009.
Database—Swiss-Prot Accession No. Q99929 (Nov. 1, 1997).
Database—EMBL Accession No. U77629 (Nov. 27, 1997).
Alders, et al., The Human Achaete-Scute Homologue 2 (ASCL2, HASH2) Maps to Chromosome 11p15.5, Close to IGF2 and is Expressed in Extravillus Trophoblasts, Human Molecular Genetics vol. 6, No. 6 pp. 859-867 (1997).
Database—Swiss-Prot Accession No. Q9WUJ7 (Nov. 1, 1999).
Database—Swiss-Prot Accession No. 035885 (Jan. 1, 1998).
Database—EMBL Accession No. U77628 (Nov. 27, 1997).
Database—EMBL Accession No. X53724 (Sep. 22, 1990).
Miyamoto, et al., "The Human ASCL2 Gene Escaping Genomc Imprinting and its Expression Pattern," J. Assist. Reprod. Gene. (19)(5):240 (2002).
Westerman, et al., The Human Achaete Scute Homolog 2 gene contains two promotors, generating overlapping transcripts and encoding two proteins with different nuclear localization. Placenta Jul. 2001;22(6):511-8.
Jiang, et al., Hypoxia prevents induction of aromatase expression in human trophoblast cells in culture: potential inhibitory role of the hypoxia-inducible transcription factor Mash-2 (mammalian achaete-scute homologous protein-2). Mol Endocrinol Oct. 2000;14(10):1661-73.
Scott IC, et al., The HAND1 basic helix-loop-helix transcription factor regulates trophoblast differentiation via multiple mechanisms. Mol Cell Biol Jan. 2000;20(2):530-41.
Tanaka, et al., Parental origin-specific expression of Mash2 is established at the time of implantation with its imprinting mechanism highly resistant to genome-wide demethylation. Mech Dev Sep. 1999;87(1-2):129-42.
Janatpour, et al., A repertoire of differentially expressed transcription factors that offers insight into mechanisms of human cytotrophoblast differentiation. 1999: 25 (2): 146-57.
Kraut, et al., Requirement of the mouse I-mfa gene for placental development and skeletal patterning. EMBO J Nov. 2, 1998;17(21):6276-88.
Rossant, et al., Mash2 is expressed in oogenesis and preimplantation development but is not required for blastocyst formation. Mech Dev May 1998;73(2):183-91.
Miyamoto, et al., A SacII polymorphism in the human ASCL2 (HASH2) gene region. J Hum Genet 1998;43(1):69-70.
Hu, et al., A 2.5-Mb transcript map of a tumor-suppressing subchromosomal transferable fragment from 11p15.5, and isolation and sequence analysis of three novel genes. Genomics Nov. 15, 1997;46(1):9-17.
Tanaka, et al., Mash2 acts cell autonomously in mouse spongiotrophoblast development. Dev Biol Oct. 1, 1997;190 (1):55-65.
Nakayama, et al., Developmental restriction of Mash-2 expression in trophoblast correlates with potential activation of the notch-2 pathway. Dev Genet 1997;21(1):21-30.
Miyamoto, et al., Genomic cloning and localization to chromosome 11p15.5 of the human achaete-scute homolog 2 (ASCL2). Cytogenet Cell Genet 1996;73(4):312-4.
Leighton, et al., An enhancer deletion affects both H19 and Igf2 expression. Genes Dev Sep. 1, 1995;9(17):2079-89.
Guillemot, et al., Genomic imprinting of Mash2, a mouse gene required for trophoblast development. Nat Genet Mar. 1995;9(3):235-42.
Guillemot, et al., Essential role of Mash-2 in extraembryonic development. AL. Nature Sep. 22, 1994;371(6495):333-6.
Johnson, et al., Induction and repression of mammalian achaete-scute homologue (MASH) gene expression during neuronal differentiation of P19 embryonal carcinoma cells. Development Jan. 1992;114(1):75-87.
Johnson, et al., DNA binding and transcriptional regulatory activity of mammalian achaete-scute homologous (MASH) proteins revealed by interaction with a muscle-specific enhancer. Proc Natl Acad Sci U S A Apr. 15, 1992;89 (8):3596-600.
Johnson, et al., Two rat homologues of *Drosophila* achaete-scute specifically expressed in neuronal precursors. Nature Aug. 30, 1990;346(6287):858-61.
Protein GenPep Accession No. NP_005161 (Journal: Hum. Mol. Genet. 6(6), 859-867 (1997)).
Protein GenPep Accession No. AAB39362.1, (Journal: Hum. Mol. Genet. 6(6), 859-867 (1997)).
Banerjea et al., Colorectal cancers with microsatellite instability display mRNA expression signatures characteristic of increased immunogenicity, Molecular Cancer 3:31 (2004).
Cui et al., Loss of imprinting in normal tissue of colorectal cancer patients with microsatellite instability, Nature Medicine 4(11):1276 (1998).

(56) References Cited

OTHER PUBLICATIONS

Jiang and Mendelson, USF1 and USF2 Mediate Inhibition of Human Trophoblast Differentiation and CYP19 Gene Expression by Mash-2 and Hypoxia, Moleculare and Cellular Biology, 23(17):6117 (2003).
Jiang and Mendelson, O2 Enhancement of Human Trophoblast Differentiation and hCYP19 (Aromatase) Gene Expression are Mediated by Proteasomal Degradation of USF1 and USF2, Molecular and Cellular Biology, 25(20): 8824 (2005).
Koide et al., The Expression of Proprotein convertaase PACE4 is Highly Regulated by Hash-2 in Placenta: Possible Role of Placenta-Specific Basic Helix-Loop-Helix Transcription Factor, Human Achaete-Scute Homologue-2, J. Biochem 134:433 (2003).
Massari and Murre, Helix-Loop-Helix Proteins: Regulators of Transcription in Eucaryotic Organisms, Molecular and Cellular Biology 20(2):429 (2000).
Spink et al., Structural basis of the Axin-adenomatous polyposis coli interaction, The EMBO Journal 19(10):2270 (2000).
Zhang et al., JMJD2A is a Novel N-CoR-Interacting Protein and is Involved in Repression of the Human Transcription Factor Achaete Scute-Like Homologue 2 (ASCL2/Hash2), Molecular and Cellular Biology 25(15):6404 (2005).
Bowie et al., Science 257:1306-1310 (1990).
Burgess et al., J. of Cell Bilogy 11:2129-2138 (1990).
Fowlkes et al., T-Cell Tolerance, Current Opinino in Immunology 5:873-879 (1993).
Gillies et al.m, Human Antibodies and Hybrodomas, 1(1):47-54 (1990).
Hoos et al., A Clinical Development Paradigm for Cancer Vaccines and Related Biologics, J. Immunotherapy 30 (1):1-15 (Jan. 2007).
mRNA-DNA Gen Bank Accession Number: AF442769.1, published 2001.
mRNA-DNA Gen Bank Accession Number: NM-005170.1, published 1996.
mRNA-DNA Gen Bank Accession Number: S82817.1, published 1996.
mRNA-DNA Gen Bank Accession Number: XM-113673.1, database date 2002.
mRNA-DNA Gen Bank Accession Number: XM-113699.1, database date 2002.
Protein GenPep Accession Number: AAB86993.1, published 1994 (journal: Hum. Mol. Genet. 6(6), 859-867 (1997)).
Protein GenPep Accession Number: AAL35362.1, published 2001.
Protein GenPep Accession Number: XP-113673.1, database date 2002.
Protein GenPep Accession Number: XP-113699.1, database 2002.
Edelman, "An overview of adjuvant use", from Methods in Molecular Medicin, vol. 42, Vaccine Adjuvants: Preparation Methods and Research Protools, 42:1-27, O'Hagan, ed., Humana Pres, Totowa, NJ, 2000.
Deutscher, Guide to Protein Purification, vol. 182, Academic Press (1990) pp. 663-670.
Lipford, Grayson B., (2000); CpG-DNA-Mediated Transient Lymphadenopathy Is Associated with a State of Th1 Predisposition to Antigen-Drived Responses, The Journal of Immunology, No. 165; pp. 1228-1235.
Krieg et al., (2002); CpG Motifs in Bacterial DNA and Their Immune Effects, Annual Rev. Immunology, No. 20; pp. 709-760.
Stills, et al., (2005); Adjuvants and Antibody Production: Dispelling the Myths Associated with Freund's Complete and Other Adjuvants, ILAR Journal; vol. 46; No. 3; pp. 280-293.
Jiang, et al., (2012); USF1 and USF2 Mediate Inhibition of Human Trophoblast Differentiation and CYP19 Gene Expression by Mash-2 and Hypoxia; Molecular and Cellular Biology; No. 23(17); pp. 6117-6128.
Campbell, Monoclonal Antibody Technology eds. Elseiver, pp. 1-32, (1984).
Roitt et ai, 1998, Immunology, 4th ed, Mosby, London, p. 113-114.
Khong et al. (J. Immunol. Jan. 15, 2002; 168 (2): 951-956).
Lu et al. (Cancer Research 62: 5807-5812,2002).
Jubb et al. "ASC12 and 11p15.5 amplification in Colorectal Cancer" Gut, (2011) vol. 60, pp. 1606-1607.

* cited by examiner

```
CASB7439   (1) -----------------------MDGGTLPRSAPPAPPVPVGCAARRRPASPELLRCSRR
  LVL088   (1) -----------------------MDGGTLPRSAPPAPPVPVGCAARRRPASPELLRCSRR
  LVL111   (1) MGHHHHHHHHHHSSGHIDDDDKHMDGGTLPRSAPPAPPVPVGCAARRRPASPELLRCSRR
  LVL137   (1) MGHHHHHHHHHHSSGHIDDDDKHMDGGTLPRSAPPAPPVPVGCAARRRPASPELLRCSRR
  LVL138   (1) -----MHHHHHH------------DGGTLPRSAPPAPPVPVGCAARRRPASPELLRCSRR
  LVL168   (1) -MHHHHHHHHHH------------DGGTLPRSAPPAPPVPVGCAARRRPASPELLRCSRR

               61                                                       120
CASB7439  (38) RRPATAETGGGAAAVARRNERERNRVKLVNLGFQALRQHVPHGGASKKLSKVETLRSAVE
  LVL088  (38) RRPATAETGGGAAAVARRNERERNRVKLVNLGFQALRQHVPHGGASKKLSKVETLRSAVE
  LVL111  (61) RRPATAETGGGAAAVARRNERERNRVKLVNLGFQALRQHVPHGGASKKLSKVETLRSAVE
  LVL137  (61) RRPATAETGGGAAAVARRNERERNRVKLVNLGFQALRQHVPHGGASKKLSKVETLFSAVE
  LVL138  (44) RRPATAETGGGAAAVARRNERERNRVKLVNLGFQALRQHVPHGGASKKLSKVETLRSAVE
  LVL168  (48) RRPATAETGGGAAAVARRNERERNRVKLVNLGFQALRQHVPHGGASKKLSKVETLRSAVE

               121                                                      180
CASB7439  (98) YIRALQRLLAEHDAVRNALAGGLRPQAVRPSAPRGPPGTTPVAASPSRASSSPGRGGSSE
  LVL088  (98) YIRALQRLLAEHDAVRNALAGGLRPQAVRPSAPRG---------------------GSSE
  LVL111 (121) YIRALQRLLAEHDAVRNALAGGLRPQAVRPSAPRG---------------------GSSE
  LVL137 (121) YIRALQRLLAEHDAVRNALAGGLRPQAVRPSAPRG---------------------GSSE
  LVL138 (104) YIRALQRLLAEHDAVRNALAGGLRPQAVRPSAPRG---------------------GSSE
  LVL168 (108) YIRALQRLLAEHDAVRNALAGGLRPQAVRPSAPRG---------------------GSSE

               181                                   222
CASB7439 (158) PGSPRSAYSSDDSGCEGALSPAERELLDFSSWLGGY------
  LVL088 (137) PGSPRSAYSSDDSGCEGALSPAERELLDFSSWLGGYHHHHHH
  LVL111 (160) PGSPRSAYSSDDSGCEGALSPAERELLDFSSWLGGYHHHHHH
  LVL137 (160) PGSPRSAYSSDDSGCEGALSPAERELLDFSSWLGGY------
  LVL138 (143) PGSPRSAYSSDDSGCEGALSPAERELLDFSSWLGGY------
  LVL168 (147) PGSPRSAYSSDDSGCEGALSPAERELLDFSSWLGGY------
```

FIG. 5

```
                1                                                         60
HASH2     (1)   ------------------------------------------------------------
LVL168    (1)   ------------------------------------------------------------
PD1/3     (1)   MDPSSHSSNMANTQMKSDKIIIAHRGASGYLPEHTLESKALAFAQQADYLEQDLAMTKDG
LVL144    (1)   MDPSSHSSNMANTQMKSDKIIIAHRGASGYLPEHTLESKALAFAQQADYLEQDLAMTKDG

                61                                                       120
HASH2     (1)   --------------------------------------------------MDGGTLPRSA
LVL168    (1)   ----------------------------------------MHHHHHHHHHHDGGTLPRSA
PD1/3    (61)   RLVVIHDHFLDGLTDVAKKFPHRHRKDGRYYVIDFTLKEIQSLEMTENFEI---------
LVL144   (61)   RLVVIHDHFLDGLTDVAKKFPHRHRKDGRYYVIDFTLKEIQSLEMTENFEIDGGTLPRSA

                121                                                      180
HASH2    (11)   PPAPPVPVGCAARRRPASPELLRCSRRRRPATAETGGGAAAVARRNERERNRVKLVNLGF
LVL168   (21)   PPAPPVPVGCAARRRPASPELLRCSRRRRPATAETGGGAAAVARRNERERNRVKLVNLGF
PD1/3   (112)   ------------------------------------------------------------
LVL144  (121)   PPAPPVPVGCAARRRPASPELLRCSRRRRPATAETGGGAAAVARRNERERNRVKLVNLGF

                181                                                      240
HASH2    (71)   QALRQHVPHGGASKKLSKVETLRSAVEYIRALQRLLAEHDAVRNALAGGLRPQAVRPSAP
LVL168   (81)   QALRQHVPHGGASKKLSKVETLRSAVEYIRALQRLLAEHDAVRNALAGGLRPQAVRPSAP
PD1/3   (112)   ------------------------------------------------------------
LVL144  (181)   QALRQHVPHGGASKKLSKVETLRSAVEYIRALQRLLAEHDAVRNALAGGLRPQAVRPSAP

                241                                                      300
HASH2   (131)   RGPPGTTPVAASPSRASSSPGRGGSSEPGSPRSAYSSDDSGCEGALSPAERELLDFSSWL
LVL168  (141)   RG---------------------GSSEPGSPRSAYSSDDSGCEGALSPAERELLDFSSWL
PD1/3   (112)   ------------------------------------------------------------
LVL144  (241)   RG---------------------GSSEPGSPRSAYSSDDSGCEGALSPAERELLDFSSWL

                301
HASH2   (191)   GGY------
LVL168  (180)   GGY------
PD1/3   (112)   ---------
LVL144  (280)   GGYHHHHHH
```

FIG. 6

| HASH2 expression in CRC samples (X-fold median of HASH2 expression in normal colon tissues) | % of samples | Number of samples |
|---|---|---|
| More than 5X | 76 | 63/83 |
| More than 10X | 63 | 52/83 |
| More than 20X | 40 | 33/83 |
| More than 40X | 17 | 14/83 |

| | | | |
|---|---|---|---|
| Peptide 1 | H-MDGGTLPRSAPPAPP-OH | Peptide 24 | H-RSAVEYIRALQRLLA-OH |
| Peptide 2 | H-TLPRSAPPAPPVPVG-OH | Peptide 25 | H-EYIRALQRLLAEHDA-OH |
| Peptide 3 | H-SAPPAPPVPVGCAAR-OH | Peptide 26 | H-ALQRLLAEHDAVRNA-OH |
| Peptide 4 | H-APPVPVGCAARRRPA-OH | Peptide 27 | H-LLAEHDAVRNALAGG-OH |
| Peptide 5 | H-PVGCAARRRPASPEL-OH | Peptide 28 | H-HDAVRNALAGGLRPQ-OH |
| Peptide 6 | H-AARRRPASPELLRCS-OH | Peptide 29 | H-RNALAGGLRPQAVRP-OH |
| Peptide 7 | H-RPASPELLRCSRRRR-OH | Peptide 30 | H-AGGLRPQAVRPSAPR-OH |
| Peptide 8 | H-PELLRCSRRRRPATA-OH | Peptide 31 | H-RPQAVRPSAPRGPPG-OH |
| Peptide 9 | H-RCSRRRRPATAETGG-OH | Peptide 32 | H-VRPSAPRGPPGTTPV-OH |
| Peptide 10 | H-RRRPATAETGGGAAA-OH | Peptide 33 | H-APRGPPGTTPPVAASP-OH |
| Peptide 11 | H-ATAETGGGAAAVARR-OH | Peptide 34 | H-PPGTTPVAASPSRAS-OH |
| Peptide 12 | H-TGGGAAAVARRNERE-OH | Peptide 35 | T-TPVAASPSRASSSPG-OH |
| Peptide 13 | H-AAAVARRNERERNRV-OH | Peptide 36 | H-ASPSRASSSPGRGGS-OH |
| Peptide 14 | H-ARRNERERNRVKLVN-OH | Peptide 37 | H-RASSSPGRGGSSEPG-OH |
| Peptide 15 | H-ERERNRVKLVNLGFQ-OH | Peptide 38 | H-SPGRGGSSEPGSPRS-OH |
| Peptide 16 | H-NRVKLVNLGFQALRQ-OH | Peptide 39 | H-GGSSEPGSPRSAYSS-OH |
| Peptide 17 | H-LVNLGFQALRQHVPH-OH | Peptide 40 | H-EPGSPRSAYSSDDSG-OH |
| Peptide 18 | H-GFQALRQHVPHGGAS-OH | Peptide 41 | H-PRSAYSSDDSGCEGA-OH |
| Peptide 19 | H-LRQHVPHGGASKKLS-OH | Peptide 42 | H-YSSDDSGCEGALSPA-OH |
| Peptide 20 | H-VPHGGASKKLSKVET-OH | Peptide 43 | H-DSGCEGALSPAEREL-OH |
| Peptide 21 | H-GASKKLSKVETLRSA-OH | Peptide 44 | H-EGALSPAERELLDFS-OH |
| Peptide 22 | H-KLSKVETLRSAVEYI-OH | Peptide 45 | H-SPAERELLDFSSWLG-OH |
| Peptide 23 | H-VETLRSAVEYIRALQ-OH | Peptide 46 | H-AERELLDFSSWLGGY-OH |

FIG. 9

| | Pool 7 | Pool 8 | Pool 9 | Pool 10 | Pool 11 | Pool 12 | Pool 13 | Pool 14 |
|---|---|---|---|---|---|---|---|---|
| Pool 1 | 1 | 2 | 3 | 4 | 5 | 6 | 7 | 8 |
| Pool 2 | 9 | 10 | 11 | 12 | 13 | 14 | 15 | 16 |
| Pool 3 | 17 | 18 | 19 | 20 | 21 | 22 | 23 | 24 |
| Pool 4 | 25 | 26 | 27 | 28 | 29 | 30 | 31 | 32 |
| Pool 5 | 33 | 34 | 35 | 36 | 37 | 38 | 39 | 40 |
| Pool 6 | 41 | 42 | 43 | 44 | 45 | 46 | | |

FIG. 10

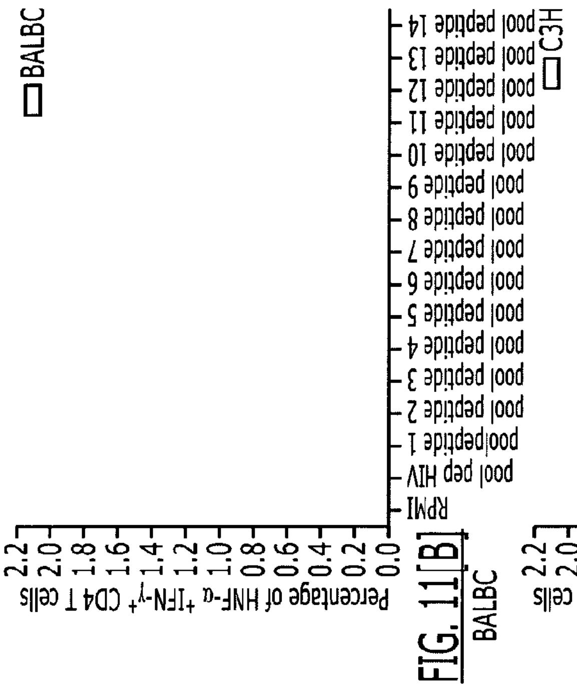
FIG. 11[B]
BALBC
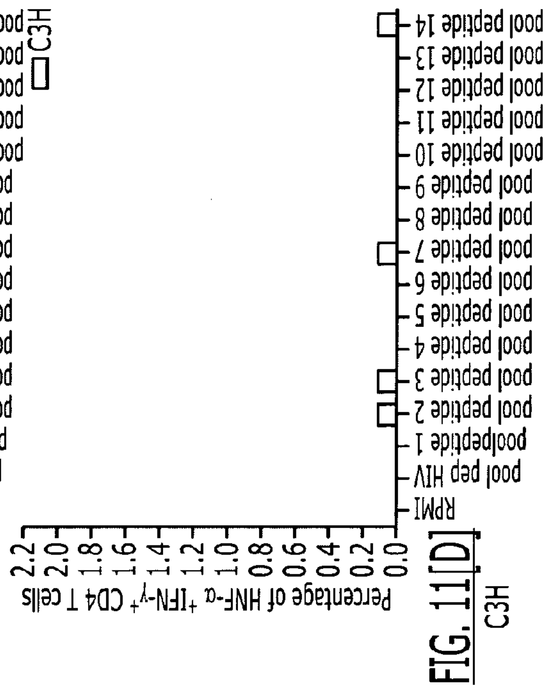
FIG. 11[D]
C3H
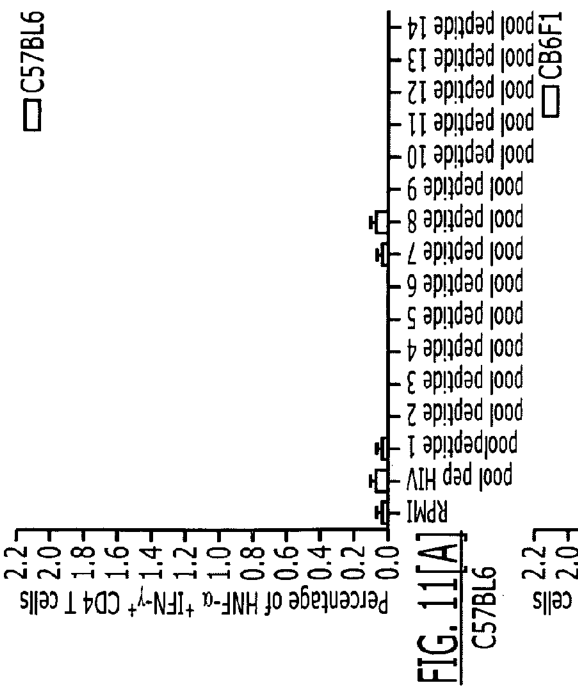
FIG. 11[A]
C57BL6
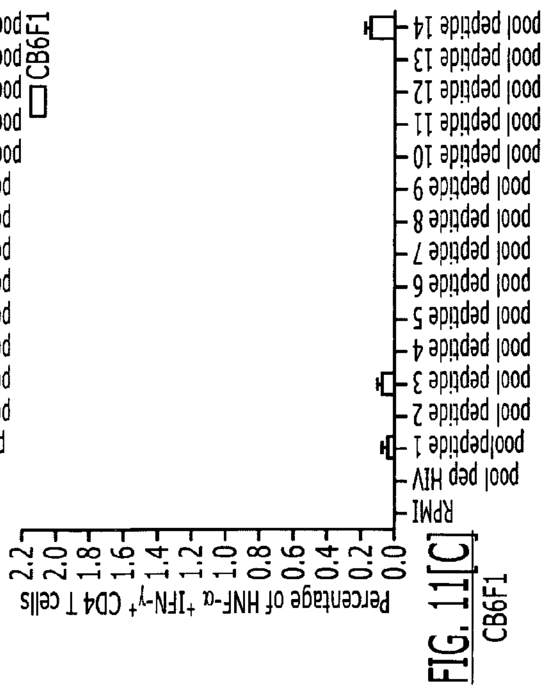
FIG. 11[C]
CB6F1

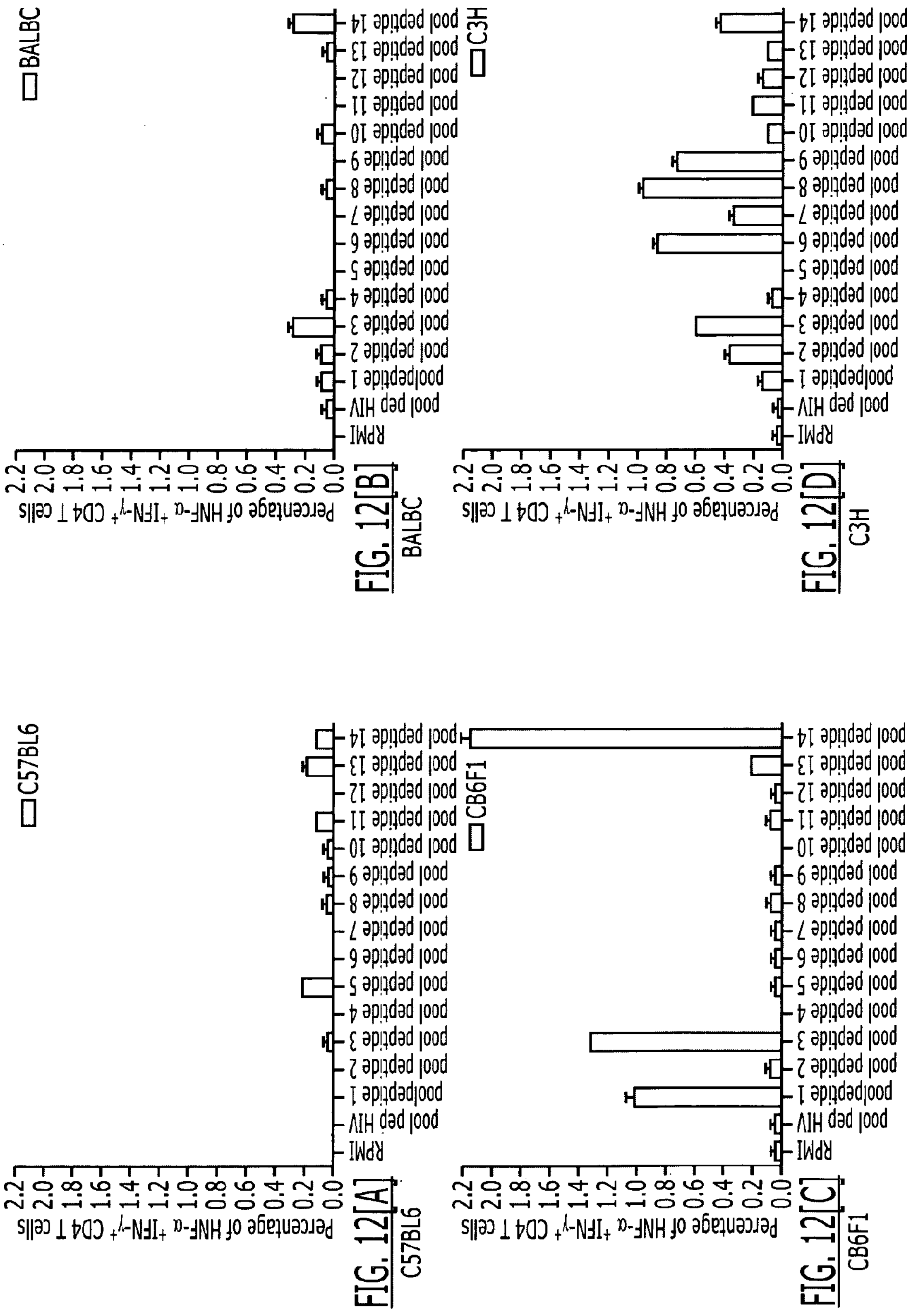
FIG. 12[A] C57BL6
FIG. 12[B] BALBC
FIG. 12[C] CB6F1
FIG. 12[D] C3H

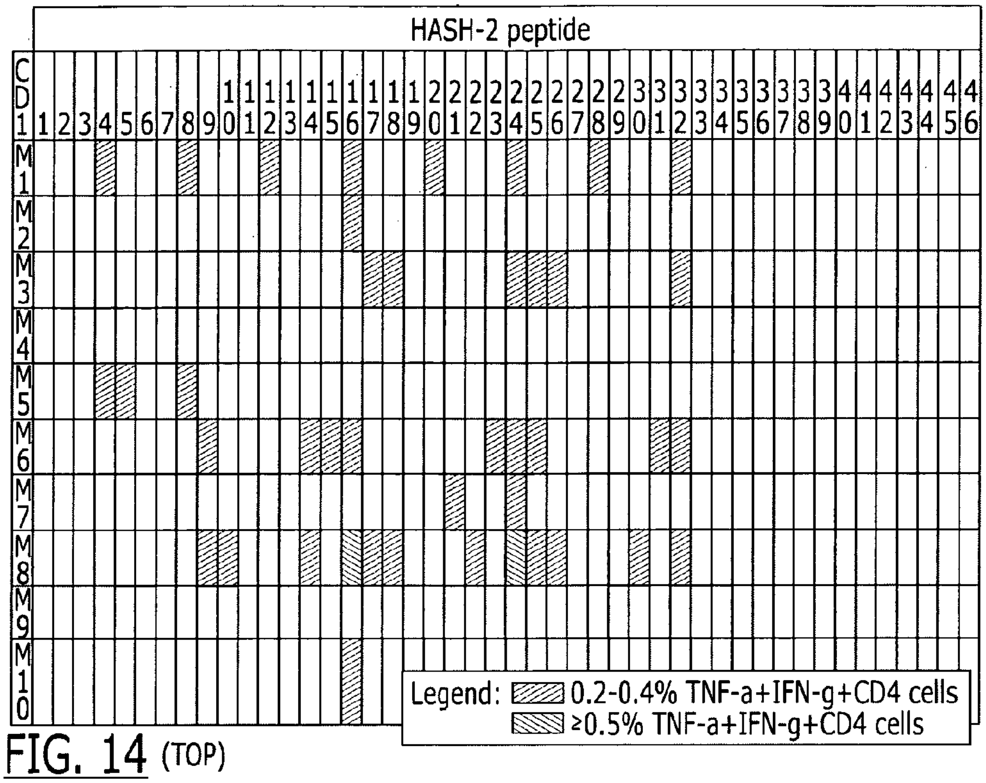
FIG. 14 (TOP)
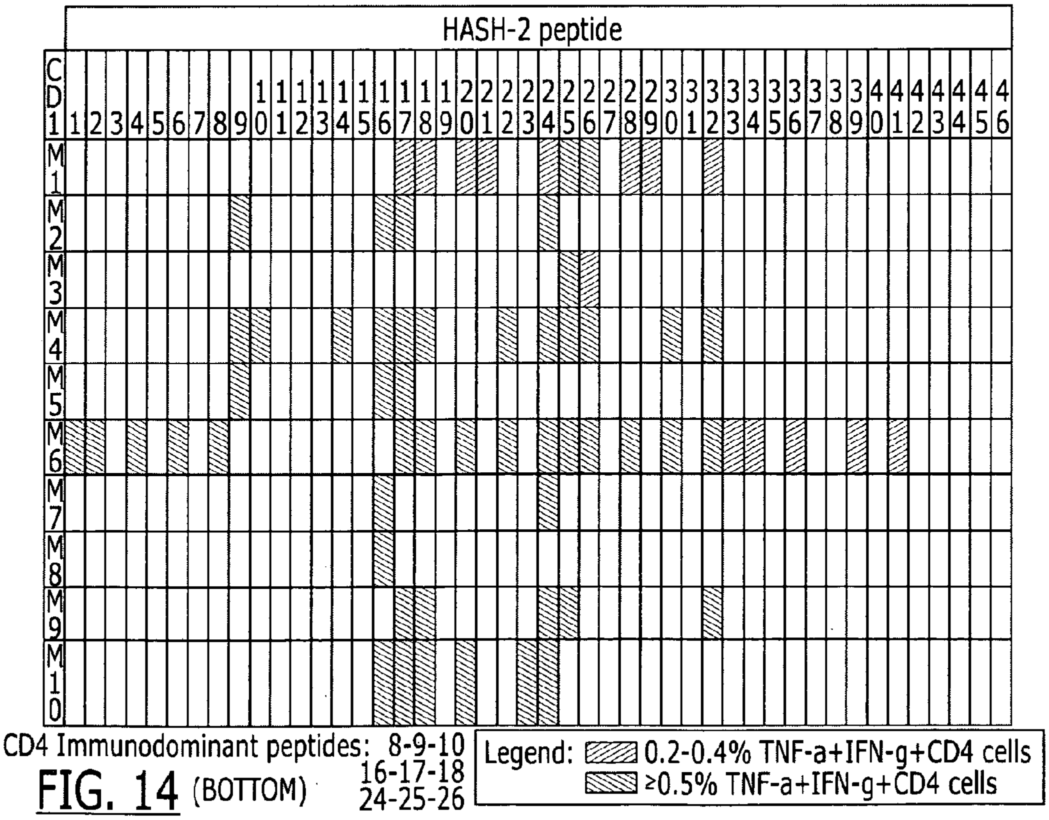
CD4 Immunodominant peptides: 8-9-10
16-17-18
24-25-26
FIG. 14 (BOTTOM)

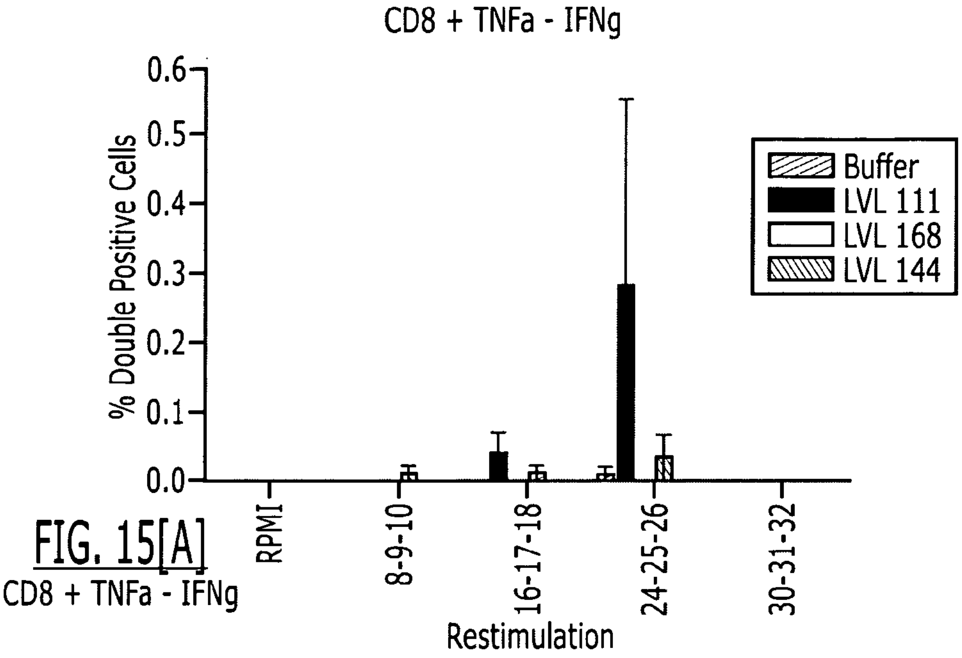
FIG. 15[A]
CD8 + TNFa - IFNg
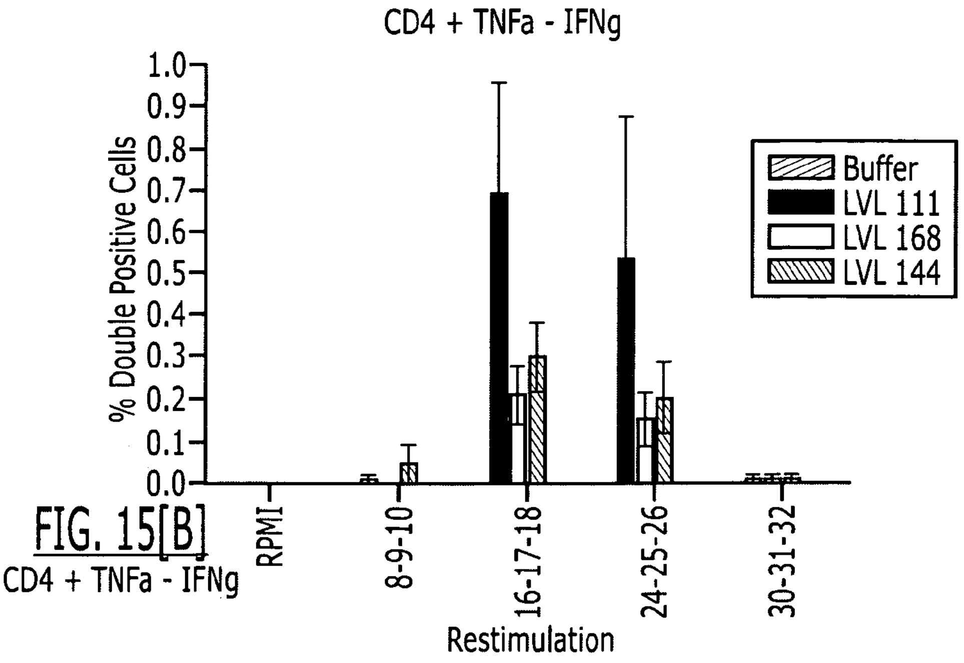
FIG. 15[B]
CD4 + TNFa - IFNg

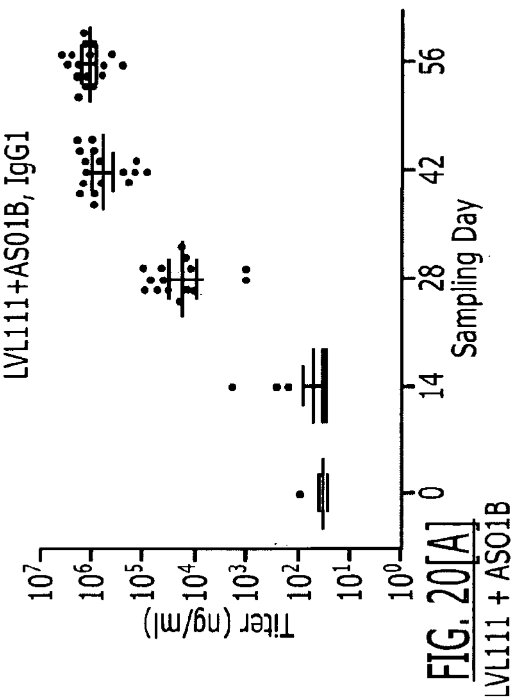
FIG. 20[A]
LVL111 + AS01B
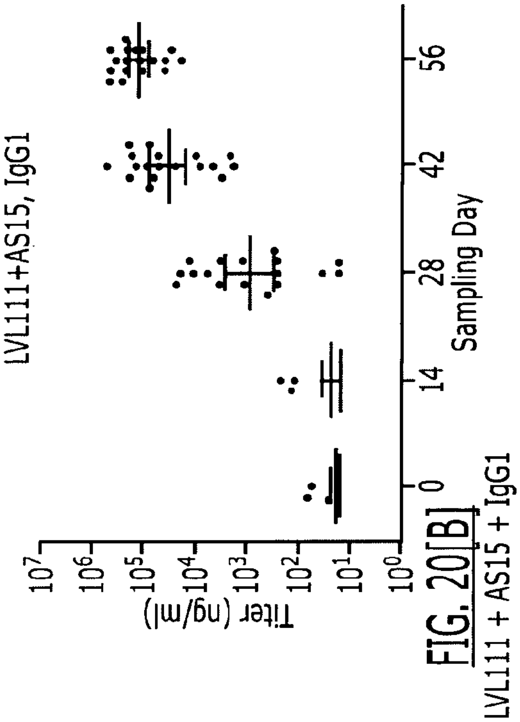
FIG. 20[B]
LVL111 + AS15 + IgG1
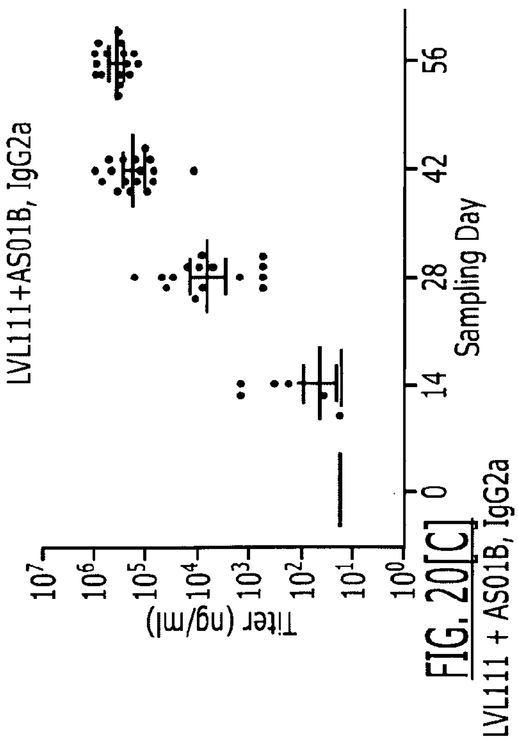
FIG. 20[C]
LVL111 + AS01B, IgG2a
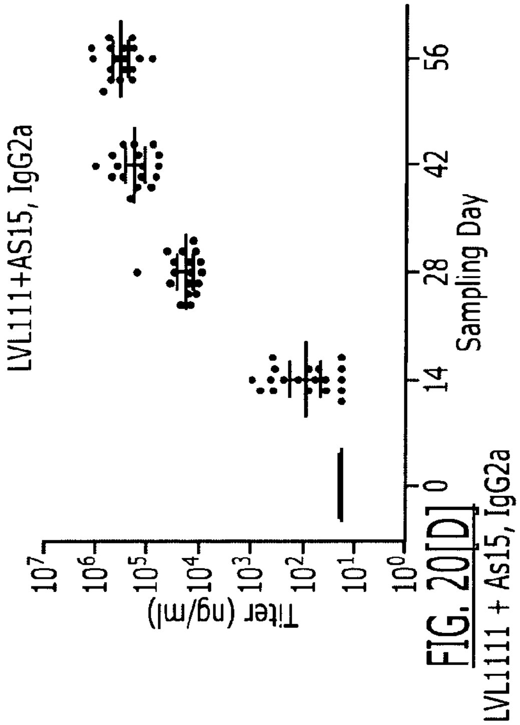
FIG. 20[D]
LVL1111 + As15, IgG2a

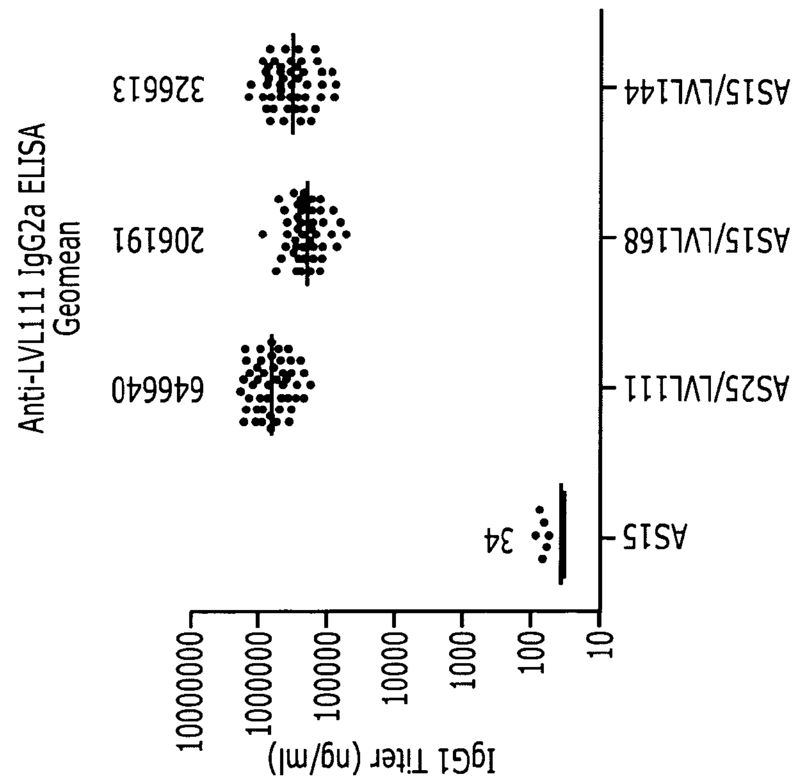
FIG. 21[B]
Anti-LVL111 IgG2a ELISA
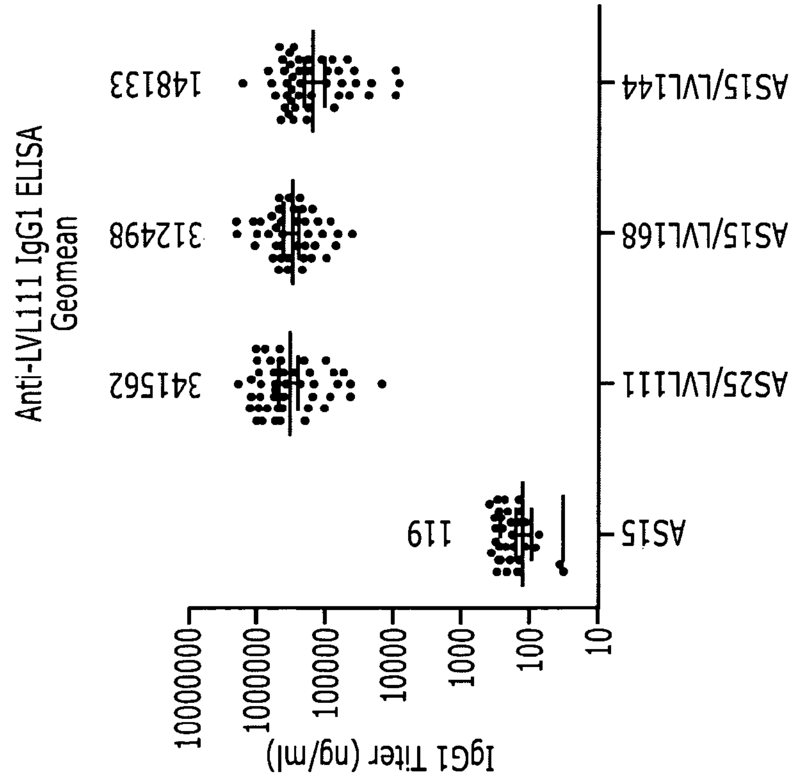
FIG. 21[A]
Anti_LVL111/G1 ELISA

TOP

BOTTOM

TOP

MIDDLE

BOTTOM

TOP

BOTTOM

TOP

MIDDLE

BOTTOM

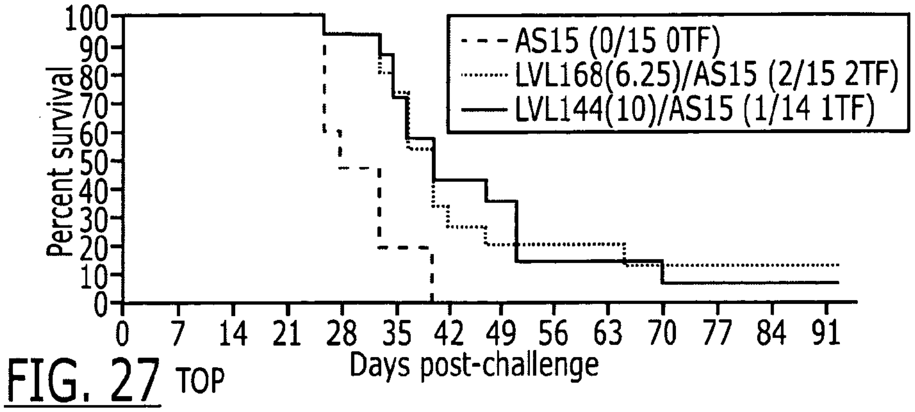
FIG. 27 TOP
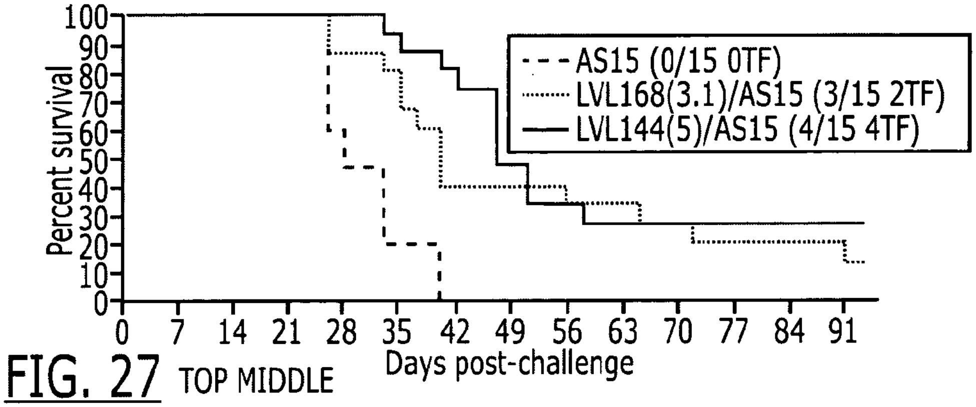
FIG. 27 TOP MIDDLE
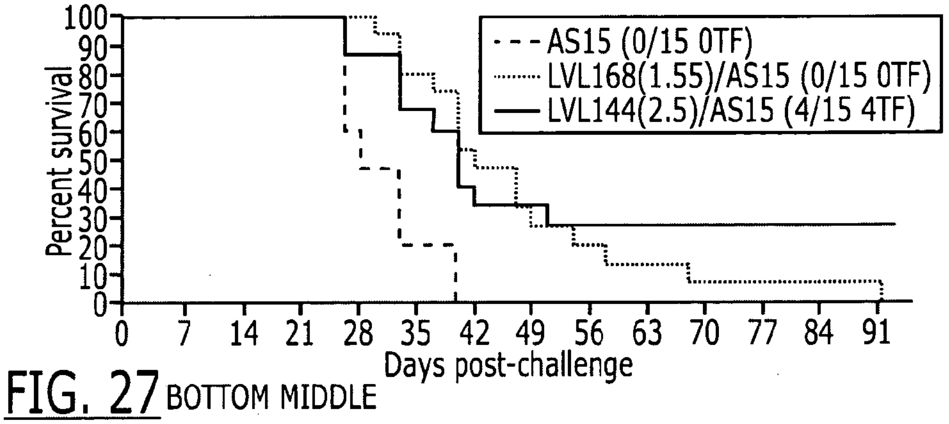
FIG. 27 BOTTOM MIDDLE
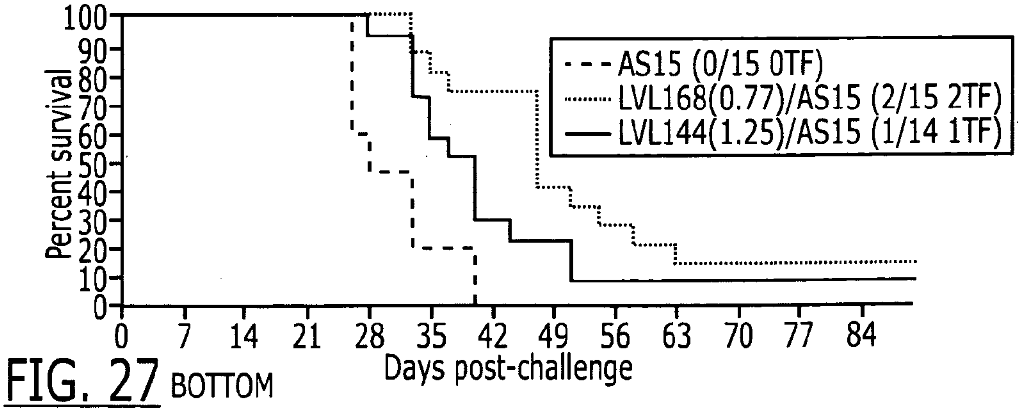
FIG. 27 BOTTOM

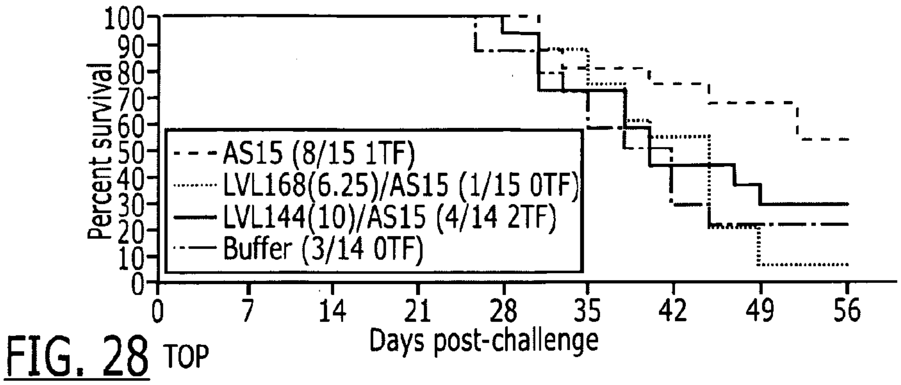
FIG. 28 TOP
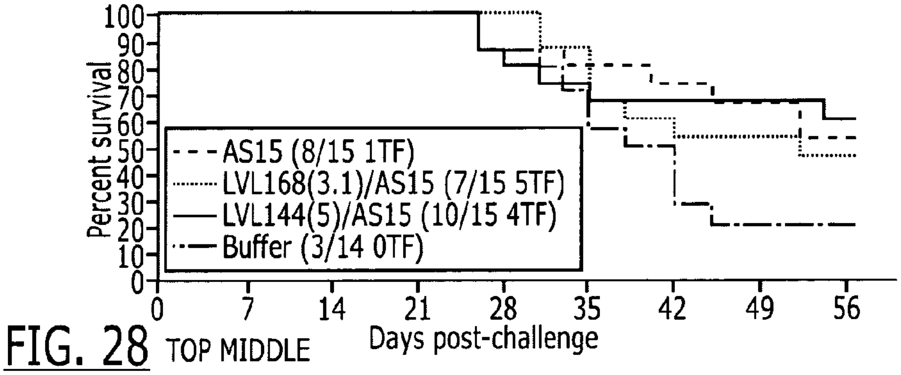
FIG. 28 TOP MIDDLE
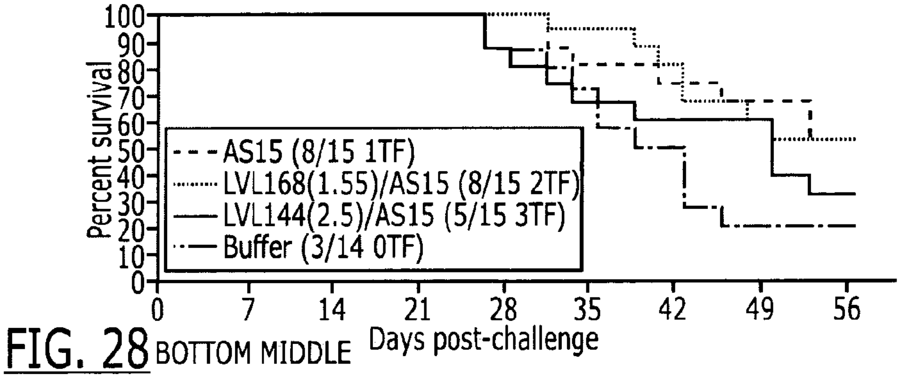
FIG. 28 BOTTOM MIDDLE
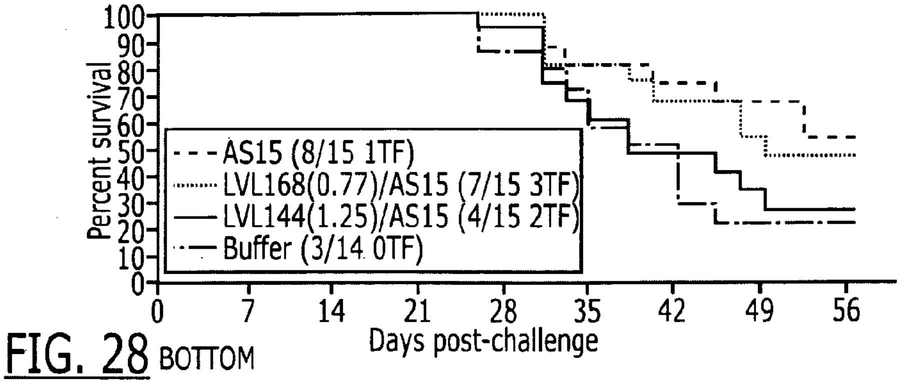
FIG. 28 BOTTOM

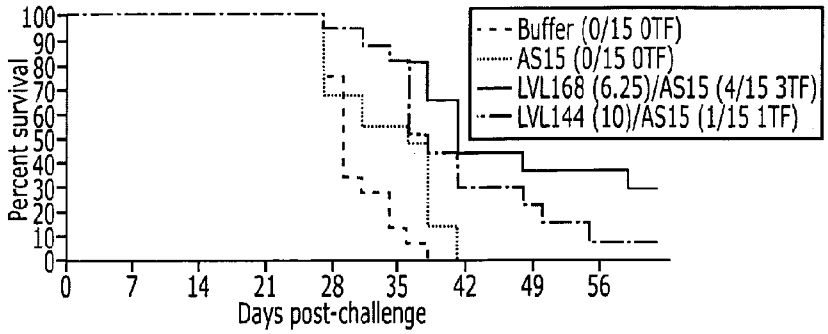
FIG. 29 Top
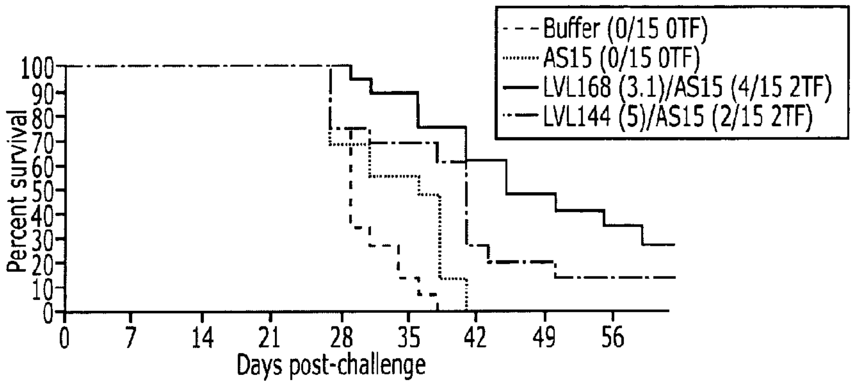
FIG. 29 Middle
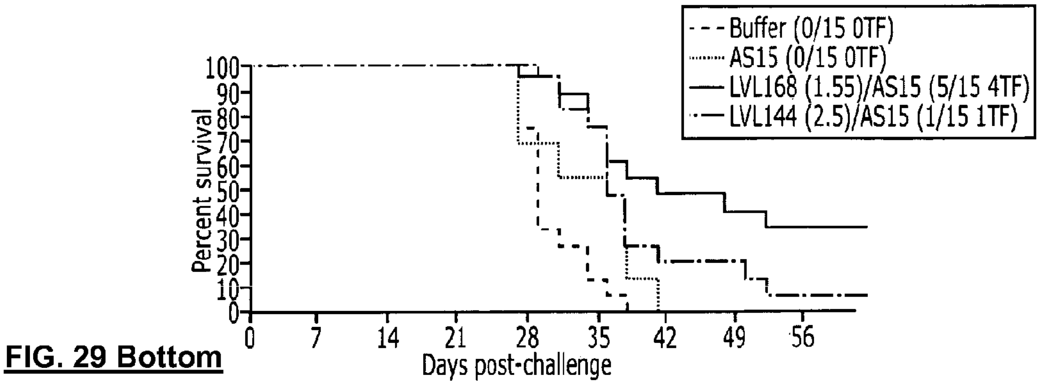
FIG. 29 Bottom

TOP

MIDDLE

BOTTOM

TOP

BOTTOM

HASH-2 (LVL168) anti-tumor efficacy
and gender comparison in CB6F1 & C57BL/6 mice (120 mice)

Survival curve of CB6F1 mice

TOP

HASH-2 (LVL168) anti-tumor efficacy
and gender comparison in CB6F1 & C57BL/6 mice (120 mice)

Survival curve of C57Bl/6 mice

BOTTOM

TOP

BOTTOM

TOP

BOTTOM

CASB7439 CONSTRUCTS

This application is a 371 of International Application No. PCT/EP2010/057141, filed 25 May 2010, which claims the benefit of U.S. Provisional Application Nos. 61/220,396, filed 25 Jun. 2009 and 61/181,380, filed 27 May 2009, which are incorporated herein in their entireties.

BACKGROUND

The mammalian Achaete-Scute homologs are conserved mammalian cognates of the *Drosophila* Achaete-Scute complex. They are members of the basic helix-loop-helix (bHLH or HLH) gene family that function as lineage-specific transcription factors essential for development. One murine member of the family, MASH2, is essential for development of a placenta, but not important for the development of the embryo proper. HASH2, the human ortholog of the MASH2 gene, was cloned in 1997 by Alders et al. (designated "ASCL2" by the authors). Alders et al. (1997) *Hum. Molec. Genet.* 6: 859-867.

As described in WO01/62778, expression studies revealed that the HASH2 transcript (termed CASB7439 therein) is over-expressed in colorectal tumors compared to adjacent normal colon and to other tested normal tissues. This gene is over expressed in patients with stage I to IV adenocarcinoma. Thus, the protein can be considered as a cancer antigen useful in an immunotherapeutic approach for ameliorating a subject's cancer, for instance by using recombinant CASB7439 as an antigen specific cancer immunotherapeutic (ASCI).

SUMMARY OF THE INVENTION

Compounds and methods for increasing the recombinant production of CASB7439 polypeptides are provided herein. In some embodiments are provided modified CASB7439 polypeptides, as well as protein constructs comprising such modified CASB7439 polypeptides. Said modified CASB7439 polypeptides comprise at least one modification for enhanced production of CASB7439. Applicants also disclose nucleic acid molecules comprising a polynucleotide sequence encoding modified CASB7439 polypeptides and protein constructs comprising such modified CASB7439 polypeptides as described herein. In certain aspects, Applicants disclose protein constructs having the amino acid (aa) sequences and the nucleotide sequence (DNA) encoding them, as follows:

LVL055 [SEQ ID NO:1 (aa); SEQ ID NO:2 (DNA)];
LVL111 [SEQ ID NO:3 (aa); SEQ ID NO:4 (DNA)];
LVL137 [SEQ ID NO:5 (aa); SEQ ID NO:6 (DNA)];
LVL141 [SEQ ID NO:7 (aa); SEQ ID NO:8 (DNA)];
LVL144 [SEQ ID NO:9 (aa); SEQ ID NO:10 (DNA)]; and
LVL168 [SEQ ID NO:11 (aa); SEQ ID NO:12 (DNA)].

Methods and processes utilizing the nucleic acid molecules described herein for the production of protein constructs are also disclosed.

Applicants also disclose immunogenic compositions, these compositions comprising one or more of the modified CASB7439 polypeptides or constructs described herein, and a pharmaceutically acceptable carrier or excipient, wherein the carrier or excipient may optionally comprise a buffer.

In some embodiments are disclosed the use of the modified CASB7439 polypeptides or protein constructs described herein—or the nucleic acid molecules encoding them—in the preparation of a medicament for treating colorectal cancer. In some embodiments are disclosed protein constructs as disclosed herein for use in therapy, particularly colorectal cancer therapy. In some embodiments are disclosed methods for eliciting an immune response against CASB7439 in a subject with colorectal cancer, the method comprising: (a) selecting a subject with colorectal cancer; and (b) administering to the subject an effective amount of an immunogenic composition comprising the modified CASB7439 polypeptides or construct as described herein and a pharmaceutically acceptable carrier or excipient, wherein the carrier or excipient may optionally comprise a buffer.

BRIEF DESCRIPTION OF THE FIGURES

FIG. 5/35. This figure presents an amino acid sequence alignment between the protein constructs of Example 6. CASB7439=the HASH2 amino acid sequence (SEQ ID NO:13); LVL088 (SEQ ID NO:27); LVL111 (SEQ ID NO:3); LVL137 (SEQ ID NO:5); LVL138 (SEQ ID NO:33); LVL168 (SEQ ID NO:11).

FIG. 6/35. This figure presents an alignment between the HASH2 (CASB7439) amino acid sequence (SEQ ID NO:13) and the following protein constructs: LVL168 (SEQ ID NO:11); pD1/3 (SEQ ID NO:39); and LVL144 (SEQ ID NO:9).

FIG. 9/35: The bank of peptides covering the entire CASB7439 protein sequence used for splenocytes restimulation after immunization with various CASB7439 constructs is set forth in this table. See Example 10.

FIG. 10/35. The CASB7439 peptide matrix used for T-cell immunogenicity investigations is shown. See Example 10.

FIG. 11/35. CD4 response expressed as percent double positive (IFNγ/TNFα) CD4 T-cells in four strains of inbred mice (C57BL6, BALBC, CB6F1, and C3H) immunized with LVL111+AS01B following re-stimulation with CASB7439 overlapping peptides (pools, matrix approach). See Example 10, Inbred Mouse Multistrain Comparison Experiment.

FIG. 12/35. CD4 response expressed as percent double positive (IFNγ/TNFα) CD4 T-cells in the four strains of inbred mice immunized with LVL111+AS15 following re-stimulation with CASB7439 overlapping peptides (pools, matrix approach). See Example 10, Inbred Mouse Multistrain Comparison Experiment.

FIG. 14/35. Identification of CD4 Immunogenic CASB7439 peptides in outbred CD1 mice (AS01B Top panel; AS15 Bottom panel). Light gray=0.2-0.4% double positive (IFNγ/TNFα) CD4 T-cells; dark gray ≥0.5% double positive (IFNγ/TNFα) T-CD4 cells. See Example 10, Immunogenicity of CASB7439 in Mice: CASB7439 T-cell Immunogenicity in Outbred Mice.

FIG. 15/35. CD4 and CD8 T-cell responses expressed as percent double positive (IFNγ/TNFα) in individual CD1 outbred mice immunized with LVL111, LVL168, or LVL144 formulated with AS15, following re-stimulation with CASB7439 overlapping peptides (pools of immunodominant peptides). See Example 10, Studies of LVL111, LVL168, and LVL144 in out-bred Mice.

FIG. 20/35. Time-course analysis of the CASB7439-specific antibody response (IgG1 and IgG2a) triggered upon LVL111+AS01B or LVL111+AS15 immunizations in CB6f1 inbred mice. See Example 10, Immunogenicity of CASB7439 in Mice: CASB7439-mediated Humoral Response.

FIG. 21/35. CASB7439-specific humoral response in inbred CB6f1 mice (IgG1 and IgG2a) upon immunizations with LVL111, LVL168, or LVL144 formulated with AS15 adjuvant or with AS15 adjuvant alone. See Example 10, Immunogenicity of CASB7439 in Mice: CASB7439-mediated Humoral Response.

FIG. 27/35. Survival curves from Example 11, Study #2.1 are presented. TF: tumor-free. (Top) Survival curve of CB6f1 mice immunized with 6.25 μg of LVL168 and 10 μg of LVL144 formulated with AS15, or AS15 alone, and challenged with TC1/CASB7439 #14-2 cells. The group of mice inoculated with LVL168 had a slightly higher percent survival. (Top middle) Survival curve of CB6f1 mice immunized with 3.1 μg of LVL168 and 5 μg of LVL144 formulated with AS15, or AS15 alone, and challenged with TC1/CASB7439 #14-2 cells. The group of mice inoculated with LVL144 had a slightly higher percent survival. (Bottom middle) Survival curve of CB6f1 mice immunized with 1.55 μg of LVL168 and 2.5 μg of LVL144 formulated with AS15, or with AS15 alone, and challenged with TC1/CASB7439 #14-2 cells. The group of mice inoculated with LVL144 had the highest survival percentage. (Bottom) Survival curve of CB6f1 mice immunized with 0.77 μg of LVL168 and 1.25 μg of LVL144 formulated with AS15, or with AS15 alone, and challenged with TC1/CASB7439 #14-2 cells. The group of mice inoculated with LVL168 had a slightly higher percent survival.

FIG. 28/35. Survival curves from Example 11, Study #2.2 are presented. TF: tumor-free. (Top) Survival curve of C57Bl/6 mice immunized with 6.25 μg of LVL168 or 10 μg of LVL144 formulated with AS15, or AS15 alone, and challenged with TC1/CASB7439 #14-2 cells. (Top middle) Survival curve of C57Bl/6 mice immunized with 3.1 μg of LVL168 or 5 μg of LVL144 formulated with AS15, or AS15 alone, and challenged with TC1/CASB7439 #14-2 cells. (Bottom middle) Survival curve of C57Bl/6 mice immunized with 1.55 μg of LVL168 or 2.5 μg of LVL144 formulated with AS15, or AS15 alone, and challenged with TC1/CASB7439 #14-2 cells. (Bottom) Survival curve of C57Bl/6 mice immunized with 0.77 μg of LVL168 or 1.25 μg of LVL144 formulated with AS15, or AS15 alone, and challenged with TC1/CASB7439 #14-2 cells.

FIG. 29/35. Survival curves from Example 11, Study #2.3 are presented. TF: tumor-free. (FIG. 29/35 Top) Survival curve of CB6f1 mice immunized with 6.25 μg of LVL168 or 10 μg of LVL144 formulated with AS15 and challenged with TC1/CASB7439 #14-2 cells. The group of mice receiving LVL168 had the highest percent survival, followed by the group receiving LVL144. There were no survivors in the group receiving only AS15. (FIG. 29/35 Middle) Survival curve of CB6f1 mice immunized with 3.1 μg of LVL168 and 5 μg of LVL144 formulated with AS15 and challenged with TC1/CASB7439 #14-2 cells. The group of mice receiving LVL168 had the highest percent survival, followed by the group receiving LVL144. There were no survivors in the group receiving only AS15. (FIG. 29/35 Bottom) Survival curve of CB6f1 mice immunized with 1.55 μg of LVL168 and 2.5 μg of LVL144 formulated with AS15 and challenged with TC1/CASB7439 #14-2 cells. The group of mice receiving LVL168 had the highest percent survival, followed by the group receiving LVL144. There were no survivors in the group receiving only AS15. Saline buffer or AS15 alone were used as controls.

DETAILED DESCRIPTION

Figure 1:
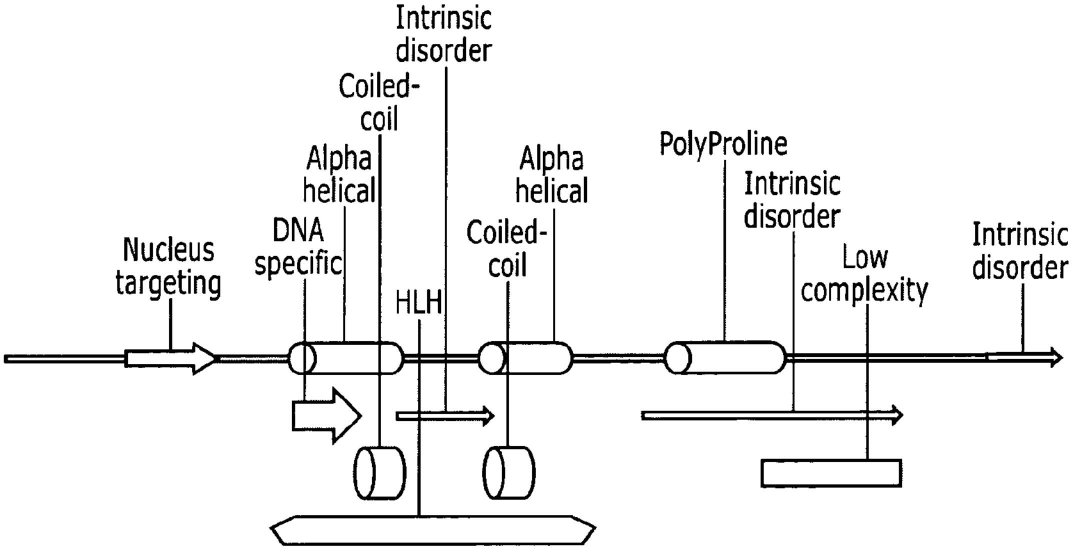
FIG. 1/35. This figure presents a schematic diagram depicting various regions of the CASB7439 polypeptide, specifically: the DNA specific (DNA binding) domain, the bHLH domain, and the proline-rich region. See Example 2 for details. Schematic representations are also shown of the following regions: Nucleus targeting (gray arrow); alpha helical (gray cylinders); coiled-coil (black cylinders); intrinsic disorder (black arrows); and low complexity (gray box).

One hurdle to a commercially acceptable immunotherapeutic is the production of commercially acceptable amounts of the recombinant cancer antigen. In general and without limitation, a commercially acceptable production level for a recombinant polypeptide is roughly 5% of total protein produced by the host cell, as estimated on a Coomasie blue stained SDS-PAGE gel.

There are numerous reasons why a native polypeptide sequence may yield only small quantities when produced by recombinant means. Approaches to increasing polypeptide production include varying host expression systems or codon optimization. However, these standard approaches do not always result in acceptable polypeptide production and the production for some polypeptides remains commercially prohibitive. As described in greater detail below, Applicants' investigated whether a modified CASB7439 polypeptide would produce acceptable protein levels by recombinant means.

In some embodiments are provided modified CASB7439 polypeptides, wherein the modification consists of or comprises C-terminal truncation of the CASB7439 polypeptide such that all or a portion of the proline-rich region is removed. In some embodiments the CASB7439 polypeptide modification consists of or comprises deletion of all or a portion of the proline-rich region. In some embodiments are provided modified CASB7439 polypeptides that retain at least amino acid residue 193 of SEQ ID NO:13, but wherein all or a portion of the proline-rich region is deleted.

In other embodiments are provided protein constructs comprising a modified CASB7439 polypeptide as described herein. In some embodiments, such protein constructs further comprise one or more heterologous polypeptides. In some embodiments, the heterologous polypeptide is a fusion partner, as described in greater detail elsewhere. In particularly suitable embodiments, such protein constructs comprise a heterologous polypeptide located N-terminal of the modified CASB7439 polypeptide. In further particularly suitable embodiments are provided protein constructs wherein the heterologous polypeptide is a fragment of the *H. influenzae* Protein D (as described in greater detail below) located N-terminal of the modified CASB7439 polypeptide.

In some embodiments are provided protein constructs wherein the heterologous polypeptide comprises a polyhistidine region. In further embodiments the polyhistidine sequence is located in the C-terminal portion of the protein construct. In other embodiments the polyhistidine sequence is located at the C-terminus of the protein construct. In further embodiments the polyhistidine sequence is located in the N-terminal portion of the protein construct. In other embodiments the polyhistidine sequence is located at the N-terminus of the protein construct. In suitable embodiments the polyhistidine region comprises ten or more consecutive histidine residues. In particularly suitable embodiments the polyhistidine region comprises ten or more consecutive histidine residues located N-terminal of the modified CASB7439 polypeptide. In some embodiments, more than one polyhistidine region may be included at one or more of the locations described herein.

In some embodiments are provided protein constructs wherein the heterologous polypeptide is a carrier protein chemically conjugated to the modified CASB7439 polypeptide.

In some embodiments are provided protein constructs comprising a heterologous polypeptide that is a polyhistidine region and a heterologous polypeptide that is a carrier protein. In some embodiments are provided protein constructs comprising a heterologous polypeptide that is a polyhistidine region and a heterologous polypeptide that is a fusion partner. In some embodiments are provided protein constructs comprising a heterologous polypeptide that is a polyhistidine region, a heterologous polypeptide that is a fusion partner, and a heterologous polypeptide that is a carrier protein.

Applicants also disclose embodiments of each of the constructs described in the paragraphs herein in which some or all of any heterologous polypeptide, such as a polyhistidine region, has been removed. Compositions and methods for the removal of heterologous polypeptides are known in the art, including without limitation digestion with endo- or exopeptidases, chemical modification or breakage of the bond between the heterologous polypeptide and the remainder of the molecule, and the like.

Applicants also disclose herein immunogenic compositions, these compositions comprising any modified CASB7439 polypeptide or protein construct comprising a modified CASB7439 polypeptide as described herein, and a pharmaceutically acceptable carrier or excipient, wherein the carrier or excipient may optionally comprise a buffer. In certain aspects, these compositions further comprise an adjuvant. In certain aspects, these compositions comprise an adjuvant that elicits at least a TH1 immune response. In certain aspects, the adjuvant described herein comprises at least one of: 3D-MPL, QS21, and CpG. In some embodiments the composition comprises 3D-MPL. In other embodiments the composition comprises CpG. In some embodiments the composition comprises QS21. In some embodiments the composition comprises QS21 and cholesterol. In some embodiments the composition comprises cholesterol, 3D-MPL, and QS21 in a liposomal formulation.

Applicants also disclose herein nucleic acid molecules comprising polynucleotide sequences that encode the modified CASB7439 polypeptides and constructs as described herein. In some embodiments are disclosed a vector comprising such nucleic acid molecules as described herein. In some embodiments the vector comprises a prokaryotic expression vector. In some embodiments the vector comprises a eukaryotic expression vector. In some embodiments the polynucleotide sequence that encodes the construct has been codon optimized for expression in a host cell.

Applicants also disclose host cells comprising (i) a nucleic acid molecule as described herein or (ii) a vector comprising a nucleic acid molecule as described herein. In some embodiments the host cell is selected from the group of: bacterial cells, insect cells and mammalian cells.

Some embodiments provide an immunogenic composition comprising (i) a nucleic acid molecule described herein or (ii) a vector comprising a nucleic acid molecule as described herein, and a pharmaceutically acceptable carrier or excipient.

In some embodiments the use of modified CASB7439 polypeptides or the protein constructs described herein (or the nucleic acid molecules encoding them) in the preparation of a medicament for treating colorectal cancer is provided. In some embodiments are disclosed modified CASB7439 polypeptides or the protein constructs described herein (or the nucleic acid molecules encoding them) for use in therapy, particularly colorectal cancer therapy. In some embodiments are provided methods for eliciting an immune response against CASB7439 in a subject with colorectal cancer, the method comprising: (i) selecting a subject with colorectal cancer; and (ii) administering to the subject an effective amount of an immunogenic composition comprising a modified CASB7439 polypeptide or protein construct as described herein, and a pharmaceutically acceptable carrier or excipient, wherein the carrier or excipient may optionally comprise a buffer. In some embodiments of the methods disclosed herein, the immunogenic composition further comprises an adjuvant. In some embodiments of the method described herein, the adjuvant elicits at least a TH1 immune response. In some embodiments of the method disclosed herein, the adjuvant comprises at least one of: 3D-MPL, QS21, and CpG. In some embodiments of the method described herein, the subject is a human subject.

Protein Constructs

CASB7439 Polypeptides

CASB7439, as it has been termed herein, is also known as HASH2 or ASCL2. HASH2 is a 193 amino acid residue polypeptide of human origin (SEQ ID NO:13). See, e.g., Accession No. AAB86993. Herein, reference to CASB7439 features will be made in terms of the polypeptide sequence provided in SEQ ID NO:13.

Proline-rich Region

A region of high proline-periodicity of is found in SEQ ID NO:13 in the region of amino acids 127-158. Applicants termed the region of SEQ ID NO:13 from amino acid 133 to amino acid 153, inclusive, the "proline-rich," "polyproline," "polyproline-like," or "polypro" region or domain. Accordingly, as used herein, "proline-rich," "polyproline," "polyproline-like," and "polypro" refers to this region (or domain) of the CASB7439 protein.

Modifications

This disclosure provides protein constructs comprising a CASB7439 polypeptide comprising at least one expression enhancement modification. In some embodiments a portion of the CASB7439 polypeptide is removed, said portion comprising all or a portion of the proline-rich region. In some embodiments the entire C-terminal portion of the CASB7439 polypeptide is removed, resulting in a truncated CASB7439 polypeptide comprising amino acid residues 1-117 of SEQ ID NO:13. In some embodiments a heterologous polypeptide is positioned N-terminal of the CASB7439 polypeptide.

As used herein, "expression enhancement" or "enhanced expression" in the context of a modified CASB7439 polypeptide refers to a modification intended to increase expression levels of a protein construct comprising said modified CASB7439 polypeptide compared to the expression of an otherwise-equivalent protein construct comprising an unmodified CASB7439 polypeptide of SEQ ID NO:13, i.e., same vector, host cell, etc. Any of the methods known in the art for determining protein quantity are acceptable to determine whether a given construct comprising a modified CASB7439 polypeptide has an increased expression level as compared to an otherwise-equivalent protein construct comprising an unmodified CASB7439 polypeptide. In some embodiments production may be assessed using SDS-PAGE and Coomasie Blue staining.

Removal of the Proline-rich Region

In some embodiments the modification of the CASB7439 polypeptide comprises the deletion of some of the proline-rich region. In some embodiments the modification of the CASB7439 polypeptide comprises the deletion of all of the proline-rich region. In some embodiments the modification of the CASB7439 polypeptide comprises the deletion of amino acids outside of the proline-rich region, in addition to deletion of the proline-rich region.

In some embodiments modification is accomplished by the truncation of the C-terminal portion of SEQ ID NO:13. Thus, in some embodiments a protein construct is generated in which the C-terminal amino acid residue of the modified CASB7439 polypeptide corresponds to a residue located N-terminal of the proline-rich region of SEQ ID NO:13. In some embodiments a protein construct is generated in which the C-terminal amino acid residue of the modified CASB7439 polypeptide corresponds to a residue located within the proline-rich region of SEQ ID NO:13. In some embodiments the C-terminal amino acid residue of the modified CASB7439 polypeptide corresponds to amino acid residue 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, or 152 of SEQ ID NO:13.

In some embodiments the modification comprises the deletion of part or all of the proline-rich region. In some embodiments a modified CASB7439 polypeptide sequence corresponds to SEQ ID NO:13 from which 21 or more contiguous amino acid residues have been deleted. These 21 or more contiguous residues correspond to a contiguous amino acid sequence of SEQ ID NO:13 starting at any one of residues 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, or 152, inclusive. In further embodiments, a modified CASB7439 polypeptide sequence corresponds to SEQ ID NO:13 from which 21 contiguous amino acid residues have been deleted, said 21 contiguous residues starting at any one of residues 131, 132, and 133.

In some embodiments the modified CASB7439 polypeptide sequence corresponds to SEQ ID NO:13 from which one or more of residues 133, 134, 135, 136, 137, 138, 139, 140, 141, 142, 143, 144, 145, 146, 147, 148, 149, 150, 151, 152, 153 have been deleted. In some embodiments the modified CASB7439 polypeptide sequence corresponds to SEQ ID NO:13 from which two or more contiguous amino acid residues have been deleted in the region of amino acid residues 133-153, inclusive.

In some embodiments the modified CASB7439 polypeptide sequence corresponds to SEQ ID NO:13 from which residues 133 to 153, inclusive, of SEQ ID NO: 13 have been deleted. Exemplary non-limiting embodiments include the following:

LVL055, SEQ ID NO:1 (aa);
LVL111, SEQ ID NO:3 (aa);
LVL137, SEQ ID NO:5 (aa);
LVL141, SEQ ID NO:7 (aa);
LVL144, SEQ ID NO:9 (aa); and
LVL168, SEQ ID NO:11 (aa).

Heterologous Sequences

In some embodiments the modified CASB7439 polypeptide is combined with a heterologous polypeptide. The term "heterologous" with respect to a nucleic acid molecule, a polypeptide or another cellular component, indicates that the component occurs where it is not normally found in nature and/or that it originates from a different source or species than a reference molecule. As used herein, "heterologous" molecules include without limitation fusion proteins, carrier proteins, and purification tags.

In some embodiments the heterologous polypeptide may be chemically conjugated to the modified CASB7439 polypeptide, i.e., a carrier protein. In other embodiments the heterologous polypeptide and the modified CASB7439 polypeptide may be expressed as a single recombinant fusion protein. In other embodiments, a modified CASB7439 polypeptide and heterologous polypeptide are expressed as a single recombinant fusion protein and chemically conjugated to another heterologous polypeptide.

The heterologous polypeptide may assist in providing T helper epitopes, including T helper epitopes recognized by humans. In the case of a protein construct comprising a CASB7439 polypeptide and a heterologous polypeptide that is a fusion protein, the heterologous polypeptide (fusion partner) may assist in providing such epitopes or assist in expressing the protein (expression enhancer) at higher yields than the native recombinant protein. The fusion partner may be both an immunological fusion partner and an expression enhancing partner.

Carrier Proteins

A carrier protein is chemically conjugated to another polypeptide of interest. The chemical coupling of a polypeptide to a carrier protein can be carried out in any manner known in the art. Thus, for direct covalent coupling it is possible to utilize a carbodiimide, glutaraldehyde or N-[γ-maleimidobutyryloxy]succinimide ester, utilizing common commercially available heterobifunctional linkers such as CDAP and SPDP (using manufacturer's instructions). After the coupling reaction, the polypeptide-carrier protein conjugate can easily be isolated and purified by means of a dialysis method, a gel filtration method, a fractionation method, etc.

The types of carrier proteins used in some embodiments will be readily known to the person skilled in the art. The function of some carrier proteins is to provide cytokine help in order to help induce an immune response against the coupled polypeptide. For example, a non-exhaustive list of carrier proteins which may be used in the present invention include: Keyhole limpet Haemocyanin (KLH), serum albumins such as bovine serum albumin (BSA), inactivated bacterial toxins such as tetanus or diptheria toxins (TT and DT), or recombinant fragments thereof (for example, Domain 1 of Fragment C of TT, or the translocation domain of DT), or the purified protein derivative of tuberculin (PPD).

Fusion Partners

Despite the availability of numerous gene fusion systems, recombinant protein expression in *Escherichia coli* remains difficult. Establishing the fusion partner that best enhances expression of difficult-to-express proteins remains empirical. Common fusion partners include the C termini of maltose-binding protein (MBP), glutathione S-transferase (GST), thioredoxin (TRX), NUS A, ubiquitin (Ub), and Small Ubiquitin-like Modifier (SUMO) tags, each of which is described in the literature. See, e.g., Marblestone (2006) *Prot. Sci.* 15:182-7; Hunt (2005) *Protein Exp. & Purif* 40:1-22; Hammarstom et al. (2002) *Protein Sci.* 11:313-321.

Immunogenic fusion partners include protein D from *Haemophilus influenza* B and the non-structural protein from influenzae virus, NS1 (hemagglutinin). Another immunological fusion partner is the protein known as LYTA. The C terminal portion of the molecule may be used. LYTA is derived from *Streptococcus pneumoniae* which synthesize an N-acetyl-L-alanine amidase, amidase LYTA, (coded by the lytA gene García et al. (1986) *Gene* 43:265-272). It is possible to use the repeat portion of the Lyta molecule found in the C terminal end starting at residue 178, for example residues 188-305. Another suitable fusion partner is an adenylate cyclase (CyaA) protein or of a fragment thereof, wherein said CyaA fragment retains the property of said adenylate cyclase protein to target Antigen Presenting Cells. See WO2005089792.

In one embodiment of the invention a heterologous polypeptide is Protein D from *Haemophilus influenzae* (EP 0 594 610 B1), or a fragment thereof. Protein D is an IgD-binding protein from *Haemophilus influenzae* (WO 91/18926, granted EP 0 594 610 B1). In some circumstances, for example in recombinant immunogen expression systems it may be desirable to use N-terminal fragments of protein D, for example comprising from about 100 to about 110 N-terminal amino acids of protein D (GB 9717953.5) (pD1/3, SEQ ID NO:39).

*H. influenzae* Protein D is synthesized as a precursor with an 18 amino acid signal sequence (SEQ ID NO:41, see also Accession Number AAA24998). When the signal sequence is processed during secretion, the cysteine residue at position 19 in the precursor molecule becomes the amino terminal residue.

In one embodiment, a heterologous polypeptide sequence comprises the first approximately one-third of the processed *H. influenzae* Protein D molecule, or the N-terminal 100-110 amino acids of processed Protein D. In one embodiment, the heterologous protein comprises amino acid residues Met-Asp-Pro joined to the N-terminal 109 amino acids of processed Protein D. In another embodiment, the heterologous protein comprises amino acid residues Met-Asp-Pro joined to amino acid residues 2-109 of processed Protein D (SEQ ID NO:39).

In one embodiment, a modified CASB7439 polypeptide or protein construct is chemically coupled to CyaA protein or a fragment thereof. See WO2005054851. In another embodiment, a modified CASB7439 polypeptide or protein construct is chemically coupled to the B subunit of Shiga Toxin or an immunologically functional equivalent thereof. See U.S. Pat. No. 6,613,882; WO02060937; WO2005112991.

Polyhistidine Tags, Unrelated Amino Acids.

It is often advantageous to include a heterologous polypeptide which contains secretory or leader sequences, pro-sequences, sequences which aid in purification such as a histidine tag, e.g., a polyhistidine sequence (comprised of multiple histidine residues), or an additional sequence for stability during recombinant production.

Histidine tag vectors and kits are commercially available. For instance, the vectors for adding a six histidine tag to a polypeptide are available from Roche. Kits for making and using histidine tagged polypeptides are available from Qiagen, Sigma, Thermo Scientific, GE Healthcare and others. The histidine tag may also be followed by a suitable amino acid sequence that facilitates a removal of the polyhistidine sequence using endopeptidases. An exopeptidase, for instance, the Qiagen TAGZyme, can be used to remove a terminal polyhistidine sequence without the additional sequence.

In some embodiments the polyhistidine sequence is located in the N-terminal region of the protein construct. In further embodiments the polyhistidine sequence is located at the N-terminus of the protein construct. In some embodiments the polyhistidine sequence comprises 6, 7, 8, 9, 10, 11, 12, 13, 14, 15, or more consecutive histidines. In further embodiments the polyhistidine sequence comprises ten consecutive histidines.

In some embodiments the heterologous polypeptide includes a polyhistidine sequence and one or more unrelated amino acids. By "unrelated amino acids" is intended one or more amino acids that are not a part of the polyhistidine sequence, or fusion protein, and are not naturally a part of the CASB7439 polypeptide sequence. For instance, unrelated amino acids may be those included to provide a peptidase site, they may simply be extraneous sequence such as a cloning artifact, or the like.

Nucleic Acid Molecules Encoding CASB7439 Constructs

Other embodiments of this disclosure concern recombinant nucleic acids that encode the modified CASB7439 polypeptides and protein constructs as described herein. In certain embodiments, the recombinant nucleic acids are codon optimized for expression in a selected prokaryotic or eukaryotic host cell. To facilitate replication and expression, the nucleic acids can be incorporated into a vector, such as a prokaryotic or a eukaryotic expression vector. Host cells including recombinant modified CASB7439 polypeptides or protein construct-encoding nucleic acids are also a feature of this disclosure. Favorable host cells include prokaryotic (i.e., bacterial) host cells, such as *E. coli*, as well as numerous eukaryotic host cells, including fungal (e.g., yeast) cells, insect cells, and mammalian cells (such as HEK293, CHO and VERO cells).

Expression Vectors

To facilitate replication and expression, the nucleic acids can be incorporated into a vector, such as a prokaryotic or a eukaryotic expression vector. Although the nucleic acids disclosed herein can be included in any one of a variety of vectors (including, for example, bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others), most commonly the vector will be an expression vector suitable for generating polypeptide expression products. In an expression vector, the nucleic acid encoding the protein construct is typically arranged in proximity and orientation to an appropriate transcription control sequence (promoter, and optionally, one or more enhancers) to direct mRNA synthesis. That is, the polynucleotide sequence of interest is operably linked to an appropriate transcription control sequence. Examples of such promoters include: the immediate early promoter of CMV, LTR or SV40 promoter, polyhedron promoter of baculovirus, *E. coli* lac or trp promoter, phage T7 and lambda PL promoter, and other promoters known to control expression of genes in prokaryotic or eukaryotic cells or their viruses. The expression vector typically also contains a ribosome binding site for translation initiation, and a transcription terminator. The vector optionally includes appropriate sequences for amplifying expression. In addition, the expression vectors optionally comprise one or more selectable marker genes to provide a phenotypic trait for selection of transformed host cells, such as dihydrofolate reductase or neomycin resistance for eukaryotic cell culture, or such as tetracycline or ampicillin resistance in *E. coli.*

Exemplary procedures sufficient to guide one of ordinary skill in the art through the production of recombinant CASB7439 nucleic acids can be found in Sambrook et al., *Molecular Cloning: A Laboratory Manual,* 2d ed., Cold Spring Harbor Laboratory Press, 1989; Sambrook et al., *Molecular Cloning: A Laboratory Manual,* 3d ed., Cold Spring Harbor Press, 2001; Ausubel et al., *Current Protocols in Molecular Biology*, Greene Publishing Associates, 1992 (and Supplements to 2003); and Ausubel et al., *Short Protocols in Molecular Biology: A Compendium of Methods from Current Protocols in Molecular Biology,* 4th ed., Wiley & Sons, 1999.

Exemplary nucleic acid molecules that encode protein constructs are represented by SEQ ID NO:2, SEQ ID NO:4, SEQ ID NO:6, SEQ ID NO:8, SEQ ID NO:10, and SEQ ID NO:12. Additional sequence variants that share sequence identity with the exemplary nucleic acid molecule can be produced by those of skill in the art. Typically, the nucleic acid variants will encode polypeptides that differ by no more than 1%, or 2%, or 5%, or 10%, or 15%, or 20% of the amino acid residues. That is, the encoded polypeptides share at least 80%, or 85%, more commonly, at least about 90% or more, such as 95%, 98%, 99%, or 99.5% sequence identity. It will be immediately understood by those of skill in the art, that the polynucleotide sequences encoding the protein constructs can themselves share less sequence identity due to the redundancy of the genetic code. In some instances, the modified CASB7439 polypeptide or protein construct has one or more amino acid modification relative to the amino acid sequence of the exemplary constructs set forth herein (e.g., in addition to the aforementioned modifications). Such differences can be an addition, deletion or substitution of one or more nucleotides or amino acids, respectively. A variant typically differs by no more than about 1%, or 2%, or 5%, or 10%, or 15%, or 20% or 25% or 30% of the nucleotide residues. For example, a variant CASB7439 polypeptide or protein construct encoding nucleic acid can include 1, or 2, or up to 5, or up to about 10, or up to about 15, or up to about 50, or up to about 100 nucleotide differences as compared to the exemplary CASB7439 polypeptide or protein construct encoding nucleic acids of SEQ ID NO:2, SEQ ID NO:4, SEQ ID NO:6, SEQ ID NO:8, SEQ ID NO:10, and SEQ ID NO:12. Thus, a variant in the context of a CASB7439 polypeptide or protein construct encoding nucleic acid, typically shares at least 70%, or 75%, or 80%, or 85%, or 90%, or 95%, or 98%, or 99%, or 99.5% sequence identity with a reference sequence, e.g. the reference sequences illustrated by SEQ ID NO:2, SEQ ID NO:4, SEQ ID NO:6, SEQ ID NO:8, SEQ ID NO:10, and SEQ ID NO:12, or any of the other exemplary CASB7439 polypeptide, protein construct encoding nucleic acids disclosed herein. Additional variants can arise through genetic drift, or can be produced artificially using site directed or random mutagenesis, or by recombination of two or more preexisting variants. Such additional variants are also suitable in the context of the CASB7439 polypeptide or protein constructs disclosed herein.

In addition to the variant nucleic acids previously described, nucleic acids that hybridize to one or more of the exemplary nucleic acids represented by SEQ ID NO:2, SEQ ID NO:4, SEQ ID NO:6, SEQ ID NO:8, SEQ ID NO:10, and SEQ ID NO:12 can also be used to encode CASB7439 polypeptides or protein constructs disclosed herein. One of skill in the art will appreciate that in addition to the percent (%) sequence identity measure discussed herein, another indicia of sequence similarity between two nucleic acids is the ability to hybridize. The more similar are the sequences of the two nucleic acids, the more stringent the conditions at which they will hybridize. The stringency of hybridization conditions are sequence-dependent and are different under different environmental parameters. Thus, hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found, for example, in Sambrook et al., *Molecular Cloning: A Laboratory Manual*, Cold Spring Harbor Laboratory Press, Cold Spring Harbor, N.Y., 2001; Tijssen, *Hybridization With Nucleic Acid Probes, Part I: Theory and Nucleic Acid Preparation*, Laboratory Techniques in Biochemistry and Molecular Biology, Elsevier Science Ltd., NY, N.Y., 1993 and Ausubel et al. *Short Protocols in Molecular Biology*, $4^{th}$ ed., John Wiley & Sons, Inc., 1999.

For purposes of the present disclosure, "stringent conditions" encompass conditions under which hybridization will only occur if there is less than 25% mismatch between the hybridization molecule and the target sequence. "Stringent conditions" can be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize. In contrast, nucleic acids that hybridize under "low stringency conditions" include those with much less sequence identity, or with sequence identity over only short subsequences of the nucleic acid. It will, therefore, be understood that the various variants of nucleic acids that are encompassed by this disclosure are able to hybridize under stringent conditions to at least one of SEQ ID NO:2, SEQ ID NO:4, SEQ ID NO:6, SEQ ID NO:8, SEQ ID NO:10, and SEQ ID NO:12 over substantially their entire length.

Production of Protein Constructs

The protein constructs disclosed herein may be produced using well established procedures for the expression and purification of recombinant proteins. Procedures sufficient to guide one of skill in the art can be found in the following references: Sambrook et al., *Molecular Cloning: A Laboratory Manual*, Cold Spring Harbor Laboratory Press, Cold Spring Harbor, N.Y., 200; and Ausubel et al. *Short Protocols in Molecular Biology*, $4^{th}$ ed., John Wiley & Sons, Inc., 999. Additional and specific details are provided hereinbelow.

Recombinant nucleic acids that encode the protein constructs may be introduced into host cells by any of a variety of well-known procedures, such as electroporation, liposome mediated transfection (e.g., using a commercially available liposomal transfection reagent, such as LIPOFECTAMINE™2000 or TRANSFECTIN™), Calcium phosphate precipitation, infection, transfection and the like, depending on the selection of vectors and host cells.

The host cells can be cultured in conventional nutrient media modified as appropriate for activating promoters, selecting transformants, or amplifying the inserted polynucleotide sequences. The culture conditions, such as temperature, pH and the like, are typically those previously used with the host cell selected for expression, and will be apparent to those skilled in the art and in the references cited herein, including, e.g., Freshney (1994) *Culture of Animal Cells, a Manual of Basic Technique*, third edition, Wiley-Liss, New York and the references cited therein. In some embodiments, a suitable culture temperature is 16° C.; in others 37° C. Expression products corresponding to the nucleic acids of the invention can also be produced in non-animal cells such as plants, yeast, fungi, bacteria and the like. In addition to Sambrook, Berger and Ausubel, details regarding cell culture can be found in Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Host Cells

Host cells that include recombinant protein construct-encoding nucleic acids are, thus, also a feature of this disclosure. Favorable host cells include prokaryotic (i.e., bacterial) host cells, such as *E. coli*, as well as numerous eukaryotic host cells, including fungal (e.g., yeast, such as *Saccharomyces cerevisiae* and *Pichia pastoris*) cells, insect cells, plant cells, and mammalian cells (such as CHO cells). Recombinant protein construct nucleic acids are introduced (e.g., transduced, transformed or transfected) into host cells, for example, via a vector, such as an expression vector. As described herein, the vector is most typically a plasmid, but such vectors can also be, for example, a viral particle, a phage, etc. Examples of appropriate expression hosts include: bacterial cells, such as *E. coli, Streptomyces*, and *Salmonella typhimurium*; fungal cells, such as *Saccharomyces cerevisiae, Pichia pastoris*, and *Neurospora crassa*; insect cells such as *Drosophila* and *Spodoptera frugiperda*; mammalian cells such as 3T3, COS, CHO, BHK, HEK293 or Bowes melanoma; plant cells, including algae cells, etc.

A host cell is optionally chosen for its ability to modulate the expression of the inserted sequences or to process the expressed protein in the desired fashion. Such modifications of the protein include, but are not limited to, glycosylation, (as well as, e.g., acetylation, carboxylation, phosphorylation, lipidation and acylation). Post-translational processing for example, which cleaves a precursor form into a mature form of the protein (for example, by a furin protease) is optionally performed in the context of the host cell. Different host cells such as 3T3, COS, CHO, HeLa, BHK, MDCK, HEK293, WI38, etc. have specific cellular machinery and characteristic mechanisms for such post-translational activities and can be chosen to ensure the correct modification and processing of the introduced, foreign protein.

For long-term, high-yield production of recombinant protein constructs disclosed herein, stable expression systems are typically used. For example, nucleic acid molecules that stably express a protein construct are introduced into the host cell using expression vectors which contain viral origins of replication or endogenous expression elements and a selectable marker gene. Following the introduction of the vector, cells are allowed to grow for 1-2 days in an enriched media before they are switched to selective media. The purpose of the selectable marker is to confer resistance to selection, and its presence allows growth and recovery of cells which successfully express the introduced sequences. For example, resistant groups or colonies of stably transformed cells can be proliferated using tissue culture techniques appropriate to the cell type. Host cells transformed with a nucleic acid encoding a protein construct are optionally cultured under conditions suitable for the expression and recovery of the encoded protein from cell culture.

Expressed protein constructs can be recovered and purified from recombinant cell cultures by any of a number of methods well known in the art, including ammonium sulfate or ethanol precipitation, acid extraction, filtration, ultrafiltration, centrifugation, anion or cation exchange chromatography, phosphocellulose chromatography, hydrophobic interaction chromatography, affinity chromatography (e.g., using any of the tagging systems noted herein), hydroxylapatite chromatography, and lectin chromatography. Protein refolding steps can be used, as desired, in completing configuration of the mature protein. Finally, high performance liquid chromatography (HPLC) can be employed in the final purification steps. In addition to the references noted herein, a variety of purification methods are well known in the art, including, e.g., those set forth in Sandana (1997) *Bioseparation of Proteins*, Academic Press, Inc.; and Bollag et al. (1996) *Protein Methods, 2$^{nd}$ Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, U.K.; Scopes (1993) *Protein Purification: Principles and Practice 3$^{rd}$ Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ.

In certain examples, the nucleic acids are introduced into cells via vectors suitable for introduction and expression in prokaryotic cells, e.g., *E. coli* cells. For example, a nucleic acid including a polynucleotide sequence that encodes a protein construct can be introduced into any of a variety of commercially available or proprietary vectors, such as the pET series of expression vectors (e.g., pET9b and pET2d). Expression of the coding sequence is inducible by isopropyl β-D-1-thiogalactopyranoside (IPTG), resulting in high levels of protein expression. The polynucleotide sequence encoding the CASB7439 protein construct is transcribed under the phage T7 promoter. Alternate vectors, such as pURV22 that include a heat-inducible lambda pL promoter are also suitable.

The expression vector is introduced (e.g., by electroporation) into a suitable bacterial host. Numerous suitable strains of *E. coli* are available and can be selected by one of skill in the art (for example, BLR DE3, BL21 DE3 and Rosetta DE3 strains have proven favorable for expression of recombinant vectors containing polynucleotide sequences that encode protein constructs).

Optionally, the polynucleotides that encode the protein constructs are incorporated into expression vectors that are suitable for introduction and expression in eukaryotic (e.g., insect or mammalian cells). Favorably, such nucleic acids are codon optimized for expression in the selected vector/host cell. Selected cells can be clonally expanded and characterized for expression of the desired protein construct. Techniques for codon optimization are known in the art. In addition, commercial molecular biology service providers offer codon optimization, among other routine technical services.

Prokaryotic

In bacterial systems, a number of expression vectors can be selected depending upon the use intended for the expressed product. For example, when large quantities of a polypeptide or fragments thereof are needed for the production of antibodies, vectors which direct high level expression of fusion proteins that are readily purified are favorably employed. Such vectors include, but are not limited to, multifunctional *E. coli* cloning and expression vectors such as BLUESCRIPT (Stratagene), in which the coding sequence of interest, e.g., a polynucleotide of the invention as described herein, can be ligated into the vector in-frame with sequences for the amino-terminal translation initiating Methionine and the subsequent 7 residues of beta-galactosidase producing a catalytically active beta galactosidase fusion protein; pIN vectors (Van Heeke & Schuster (1989) *J Biol Chem* 264:5503-5509); pET vectors (Novagen, Madison Wis.), in which the amino-terminal methionine is ligated in frame with a histidine tag; and the like. In some embodiments, a suitable vector is pET19; in others, pET24; in others, pET26.

Eukaryotic

Similarly, in yeast, such as *Saccharomyces cerevisiae*, a number of vectors containing constitutive or inducible promoters such as alpha factor, alcohol oxidase and PGH can be used for production of the desired expression products. For reviews, see Berger, Ausubel, and, e.g., Grant et al. (1987; *Methods in Enzymology* 153:516-544). In mammalian host cells, a number of expression systems, including both plasmids and viral-based systems, can be utilized.

Immunogenic Compositions

Pharmaceutically Acceptable Carriers or Excipients

Pharmaceutically acceptable carriers and excipients are well known and can be selected by those of skill in the art. For example, the carrier or excipient can favorably include a buffer. Optionally, the carrier or excipient also contains at least one component that stabilizes solubility and/or stability. Examples of solubilizing/stabilizing agents include detergents, for example, lauryl sarcosine and/or tween. Alternative solubilizing/stabilizing agents include arginine, and glass forming polyols (such as sucrose, trehalose and the like). Numerous pharmaceutically acceptable carriers and/or pharmaceutically acceptable excipients are known in the art and are described, e.g., in *Remington's Pharmaceutical Sciences*, by E. W. Martin, Mack Publishing Co., Easton, Pa., 5th Edition (975).

Accordingly, suitable excipients and carriers can be selected by those of skill in the art to produce a formulation suitable for delivery to a subject by a selected route of administration.

Suitable excipients include, without limitation: glycerol, Polyethylene glycol (PEG), Sorbitol, Trehalose, N-lauroylsarcosine sodium salt, L-proline, Non detergent sulfobetaine, Guanidine hydrochloride, Urea, Trimethylamine oxide, KCl, $Ca^{2+}$, $Mg^{2+}$, $Mn^{2+}$, $Zn^{2+}$ and other divalent cation related salts, Dithiothreitol, Dithioerytrol, and β-mercaptoethanol. Other excipients can be detergents (including: Tween80, Tween20, Triton X-00, NP-40, Empigen BB, Octylglucoside, Lauroyl maltoside, Zwittergent 3-08, Zwittergent 3-0, Zwittergent 3-2, Zwittergent 3-4, Zwittergent 3-6, CHAPS, Sodium deoxycholate, Sodium dodecyl sulphate, Cetyltrimethylammonium bromide).

Adjuvants

Optionally, the immunogenic compositions also include an adjuvant. In the context of an immunogenic composition suitable for administration to a subject, such as a human subject, for the purpose of eliciting an immune response against CASB7439, the adjuvant is selected to elicit a Th1 biased immune response. The adjuvant is typically selected to enhance a Th1 biased immune response in the subject, or population of subjects, to whom the composition is administered.

Th1 Immune Response

A "Th1" type immune response is characterized by the induction of CD4+ T helper cells that produce IL-2 and IFN-γ. In contrast, a "Th2" type immune response is characterized by the induction of CD4+ helper cells that produce IL-4, IL-5, and IL-13.

TLR Affectors, Including without Limitation 3D-MPL

One suitable adjuvant for use in combination with modified CASB7439 polypeptides is a TLR-4-modulator. One example is a non-toxic derivative of lipid A, such as monophosphoryl lipid A or more particularly 3-Deacylated monophoshoryl lipid A (3D-MPL). 3D-MPL is sold under the name MPL by GlaxoSmithKline Biologicals S.A., and is referred throughout the document as MPL or 3D-MPL. See, for example, U.S. Pat. Nos. 4,436,727; 4,877,611; 4,866,034 and 4,912,094. 3D-MPL primarily promotes CD4+ T cell responses with an IFN-γ (Th1) phenotype. 3D-MPL can be produced according to the methods disclosed in GB2220211 A. Chemically it is a mixture of 3-deacylated monophosphoryl lipid A with 3, 4, 5 or 6 acylated chains. In the compositions of the present invention small particle 3D-MPL can be used. Small particle 3D-MPL has a particle size such that it can be sterile-filtered through a 0.22 μm filter. Such preparations are described in WO94/21292.

In other embodiments the lipopolysaccharide can be a β(1-6) glucosamine disaccharide, as described in U.S. Pat. No. 6,005,099 and EP Patent No. 0 729 473 B1. One of skill in the art would be readily able to produce various lipopolysaccharides, such as 3D-MPL, based on the teachings of these references. In addition to the aforementioned immunostimulants (that are similar in structure to that of LPS or MPL or 3D-MPL), acylated monosaccharide and disaccharide derivatives that are a sub-portion to the herein structure of MPL are also suitable adjuvants. In other embodiments the adjuvant is a synthetic derivative of lipid A, some of which are described as TLR-4 agonists, and include, but are not limited to: OM174 (2-deoxy-6-o-[2-deoxy-2-[(R)-3-dodecanoyloxytetra-decanoylamino]-4-o-phosphono-β-D-glucopyranosyl]-2-[(R)-3-hydroxytetradecanoylamino]-α-D-glucopyranosyldihydrogenphosphate), (WO 95/14026); OM 294 DP (3S,9R)-3-[(R)-dodecanoyloxytetradecanoylamino]-4-oxo-5-aza-9(R)-[(R)-3-hydroxytetradecanoylamino]decan-1,10-diol,1,10-bis(dihydrogenophosphate) (WO 99/64301 and WO 00/0462); and OM 197 MP-Ac DP (3S-,9R)-3-[(R)-dodecanoyloxytetradecanoylamino]-4-oxo-5-aza-9-[(R)-3-hydroxytetradecanoylamino]decan-1,10-diol,1-dihydrogenophosphate 10-(6-aminohexanoate) (WO 01/46127).

Other TLR-4 ligands which can be used are alkyl Glucosaminide phosphates (AGPs) such as those disclosed in WO 98/50399 or U.S. Pat. No. 6,303,347 (processes for preparation of AGPs are also disclosed), suitably RC527 or RC529 or pharmaceutically acceptable salts of AGPs as disclosed in U.S. Pat. No. 6,764,840. Some AGPs are TLR-4 agonists, and some are TLR-4 antagonists. Both are thought to be useful as adjuvants.

Other suitable TLR-4 ligands, capable of causing a signaling response through TLR-4 (Sabroe et al, JI 2003 p1630-5) are, for example, lipopolysaccharide from gram-negative bacteria and its derivatives, or fragments thereof, in particular a non-toxic derivative of LPS (such as 3D-MPL). Other suitable TLR agonists are: heat shock protein (HSP) 10, 60, 65, 70, 75 or 90; surfactant Protein A, hyaluronan oligosaccharides, heparan sulphate fragments, fibronectin fragments, fibrinogen peptides, b-defensin-2, and muramyl dipeptide (MDP). In one embodiment the TLR agonist is HSP 60, 70 or 90. Other suitable TLR-4 ligands are as described in WO 2003/011223 and in WO 2003/099195, such as compound I, compound II and compound III disclosed on pages 4-5 of WO2003/011223 or on pages 3-4 of WO2003/099195 and in particular those compounds disclosed in WO2003/011223 as ER803022, ER803058, ER803732, ER804053, ER804057, ER804058, ER804059, ER804442, ER804680, and ER804764. For example, one suitable TLR-4 ligand is ER804057.

Saponin Adjuvants

Other adjuvants that can be used in immunogenic compositions with CASB7439, e.g., on their own or in combination with 3D-MPL, or another adjuvant described herein, are saponins, such as QS21.

Saponins are taught in: Lacaille-Dubois, M and Wagner H. (1996. A review of the biological and pharmacological activities of saponins. Phytomedicine vol 2 pp 363-386). Saponins are steroid or triterpene glycosides widely distributed in the plant and marine animal kingdoms. Saponins are noted for forming colloidal solutions in water which foam on shaking, and for precipitating cholesterol. When saponins are near cell membranes they create pore-like structures in the membrane which cause the membrane to burst. Haemolysis of erythrocytes is an example of this phenomenon, which is a property of certain, but not all, saponins.

Saponins, particularly immunologically active saponin fractions, are known as adjuvants in vaccines for systemic administration. The adjuvant and haemolytic activity of individual saponins has been extensively studied in the art (Lacaille-Dubois and Wagner, supra). For example, Quil A (derived from the bark of the South American tree Quillaja i Saponaria Molina), and fractions thereof, are described in U.S. Pat. No. 5,057,540 and "Saponins as vaccine adjuvants", Kensil, C. R., Crit. Rev Ther Drug Carrier Syst, 1996, 12 (1-2):1-55; and EP 0 362 279 B1. Particulate structures, termed Immune Stimulating Complexes (ISCOMS), comprising fractions of Quil A are haemolytic and have been used in the manufacture of vaccines (Morein, B., EP 0 109 942 B1; WO 96/11711; WO 96/33739). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1. Other saponins which have been used in systemic vaccination studies include those derived from other plant species such as *Gypsophila* and *Saponaria* (Bomford et al., Vaccine, 10(9):572-577, 1992).

Such formulations comprising QS21 and cholesterol have been shown to be successful Th1 stimulating adjuvants when formulated together with an antigen. Thus, for example, CASB7439 can favorably be employed in immunogenic compositions with an adjuvant comprising a combination of QS21 and cholesterol.

Immunostimmulatory Oligonucleic Acids

One suitable adjuvant for use in combination with CASB7439 is a bacterial DNA TLR agonist capable of causing a signaling response through TLR-9, i.e., a TLR-9 agonist, more specifically DNA containing unmethylated CpG nucleotides, in particular sequence contexts known as CpG motifs. CpG-containing oligonucleotides induce a predominantly Th1 response. Such oligonucleotides are well known and are described, for example, in WO 96/02555, WO 99/33488 and U.S. Pat. Nos. 6,008,200 and 5,856,462. Suitably, CpG nucleotides are CpG oligonucleotides. Suitable oligonucleotides for use in the immunogenic compositions of the present invention are CpG containing oligonucleotides, optionally containing two or more dinucleotide CpG motifs separated by at least three, suitably at least six or more nucleotides. A CpG motif is a Cytosine nucleotide followed by a Guanine nucleotide. The CpG oligonucleotides of the present invention are typically deoxynucleotides. In a specific embodiment the internucleotide in the oligonucleotide is phosphorodithioate, or suitably a phosphorothioate bond, although phosphodiester and other internucleotide bonds are within the scope of the invention. In some embodiments are oligonucleotides with mixed internucleotide linkages. Methods for producing phosphorothioate oligonucleotides or phosphorodithioate are described in U.S. Pat. Nos. 5,666,153, 5,278,302 and WO 95/26204.

In an alternative embodiment, a TLR agonist is used that is capable of causing a signaling response through TLR-9. In one embodiment, the TLR agonist capable of causing a signaling response through TLR-9 is HSP90. Combinations of different adjuvants, such as those mentioned herein, can also be used in compositions with CASB7439. For example, as already noted, QS21 can be formulated together with 3D-MPL. The ratio of QS21:3D-MPL will typically be in the order of 1:10 to 10:1; such as 1:5 to 5:1, and often substantially 1:1. Typically, the ratio is in the range of 2.5:1 to 1:1 3D-MPL: QS21. Another combination adjuvant is 3DMPL plus QS21 in a liposomal formulation, also in combination with CpG.

Subjects with Colorectal Cancer

Selection of a subject with colorectal cancer for participation in the methods described herein can be by clinical diagnosis, molecular diagnosis, or a combination thereof. In some embodiments a subject is tested to determine if their cancerous cells express CASB7439 (HASH2). Clinical methods for diagnosing colorectal cancer are known in the art. Molecular techniques and methods for determining whether a cancerous cell or tissue expresses CASB7439 (HASH2) are disclosed in WO01/62778.

EXPERIMENTAL EXAMPLES

Example 1

Two nucleic acid molecules encoding protein constructs comprising a CASB7439 polypeptide were generated in the pET19b vector. A His-tag was juxtaposed to the N-terminal end of the CASB7439 sequence. These clones were termed LVL007 [SEQ ID NO:15(aa); SEQ ID NO:16 (DNA)] and LVL010 [SEQ ID NO:17 (aa); SEQ ID NO:18 (DNA)], respectively). It was observed that an unintended mutation had occurred in the LVL007 clone, resulting in a one amino substitution of proline to leucine (at amino acid residue 17 with reference to SEQ ID NO:13). The nucleic acid molecules were utilized with three different host cell types, namely the *E. coli* strains BLR DE3, BL21 DE3, and Rosetta DE3. Inductions were carried out at two temperatures per induction (16° C. or 37° C.) and with 1 mM of IPTG. See Materials and Methods section, below, for protocol details.

Proteins were harvested for each induction and analyzed by Western blot and by SDS-PAGE with Coomassie-blue staining. In these experiments, the detection of the protein was visible only in western blot.

Example 2

Bioinformatic analyses of the CASB7439 gene were carried out, revealing the following structural features:

- a hairpin RNA structural element located between nucleotide 2 and 27 of SEQ ID NO:14
- 62% GC content of the nucleotide sequence
- nucleotide sequence rich in Arginine codons (26/193 amino acids encoded)
- amino acid sequence with a high level of basic amino acids residues
- amino acid sequence with a high isoelectric point (11.18)
- a low complexity region within the amino acid sequence (residues 7-27 of SEQ ID NO:13
- helix-loop-helix domain (HLH) (IPRO00014) within the amino acid sequence (residues 56-108 of SEQ ID NO:13)
- a first region of intrinsic disorder within the amino acid sequence (residues 118-164 of SEQ ID NO:13)
- a second region of intrinsic disorder within the amino acid sequence (residues 118-164 of SEQ ID NO:13)

Applicants also identified a region with a high proline periodicity from amino acid 127 to 158. Applicants designated the region from amino acid 133-153, inclusive, of SEQ ID NO:13 (aa) the proline-rich region. The proline-rich region, along with some of the other features mentioned in this example are depicted in schematic fashion in FIG. 1/35, along with regions mentioned elsewhere herein.

Example 3

The unmodified CASB7439 DNA nucleotide sequence (SEQ ID NO:14) was codon-optimized by the commercial DNA synthesis services provider, Geneart (unique identifier 0606597), and cloned. Geneart AG, BioPark, Josef-Engert-Str. 11 D-93053 Regensburg, Germany. The CASB7439 nucleotide sequence was obtained from the clone by PCR amplification and used to generate two constructs. In the first construct, LVL016 [SEQ ID NO:29 (aa), SEQ ID NO:30 (DNA)] the CASB7439 sequence was inserted in the pET21b (+) vector in fusion with the pD1/3 protein (from *Haemophilus influenzae*) at the N-terminal end of the CASB7439 sequence. In the second construct, LVL018 [SEQ ID NO:31 (aa); SEQ ID NO:32 (DNA)], the CASB7439 was inserted in the pET21b (+) vector (without any Protein D component). These constructs were evaluated for production in the BLR DE3 *E. coli* at 16° C. and 37° C. with 1 mM of IPTG. Production was detectable by Western blot as an insoluble protein, mainly produced at 16° C.

Four of the CASB7439 domains were chosen for further investigation to improve protein production: the nucleus targeting domain, the proline-rich region, the DNA binding domain, and the HLH domain.

Example 4

The nucleus targeting domain, the DNA binding domain, the bHLH domain and the proline-rich region of the CASB7439 were chosen to investigate protein production from constructs comprising nucleotide sequences encoding CASB7439 polypeptides. Different sections of the CASB7439 nucleotide sequence were PCR amplified from the codon-optimized Geneart clone described herein and inserted in the pET19b (+) vector, resulting in five constructs having a different CASB7439 sequence (truncated in some fashion or complete); each construct with a polyhistidine tail at the N-terminal of the CASB7439 sequence. See FIG. 2/35.

Figure 2:
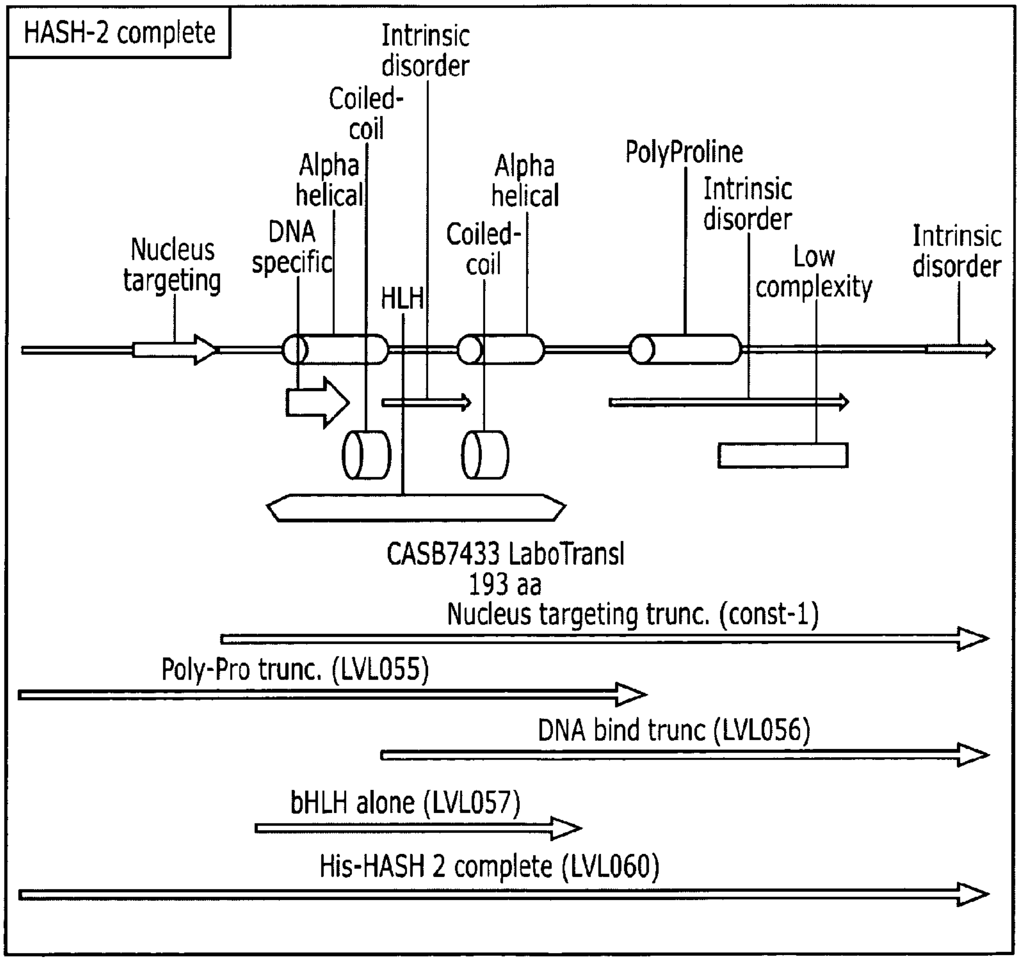
FIG. 2/35. This figure presents a schematic diagram depicting various truncates of the CASB7439 polypeptide (black arrows) aligned with the complete CASB7439 polypeptide. See Example 4 for details.

Those constructs shown on FIG. 2/35 were evaluated for protein expression in BLR DE3 *E. coli* strain at 37° C. and 16° C. with 1 mM of IPTG. As depicted in FIG. 2/35, these constructs comprised full-length CASB7439 [LVL060, SEQ ID NO:19 (aa), SEQ ID NO:20 (DNA)]; CASB7439 truncated to remove the nucleus targeting domain [Const-1, SEQ ID NO:21 (aa), SEQ ID NO:22 (DNA)]; CASB7439 truncated to remove the proline-rich region [LVL055, SEQ ID NO:1 (aa), SEQ ID NO:2 (DNA)]; CASB7439 truncated to remove the DNA binding domain [LVL056, SEQ ID NO:23 (aa), SEQ ID NO:24 (DNA)]; CASB7439 truncated to leave the basic helix-loop-helix (bHLH) domain [LVL057, SEQ ID NO:25 (aa), SEQ ID NO:26 (DNA)]. Due to experimental error, Const-1 lacked a stop codon, resulting in the translation of a portion of the vector nucleotide sequence (resulting with an additional 21 amino acids in the C-terminal region, starting with LED . . . ). The production of LVL055 following incubation at 16° C. (C-terminal truncated) was clearly detectable on a Coomassie-blue stained SDS-PAGE gel.

Example 5

Figure 3:
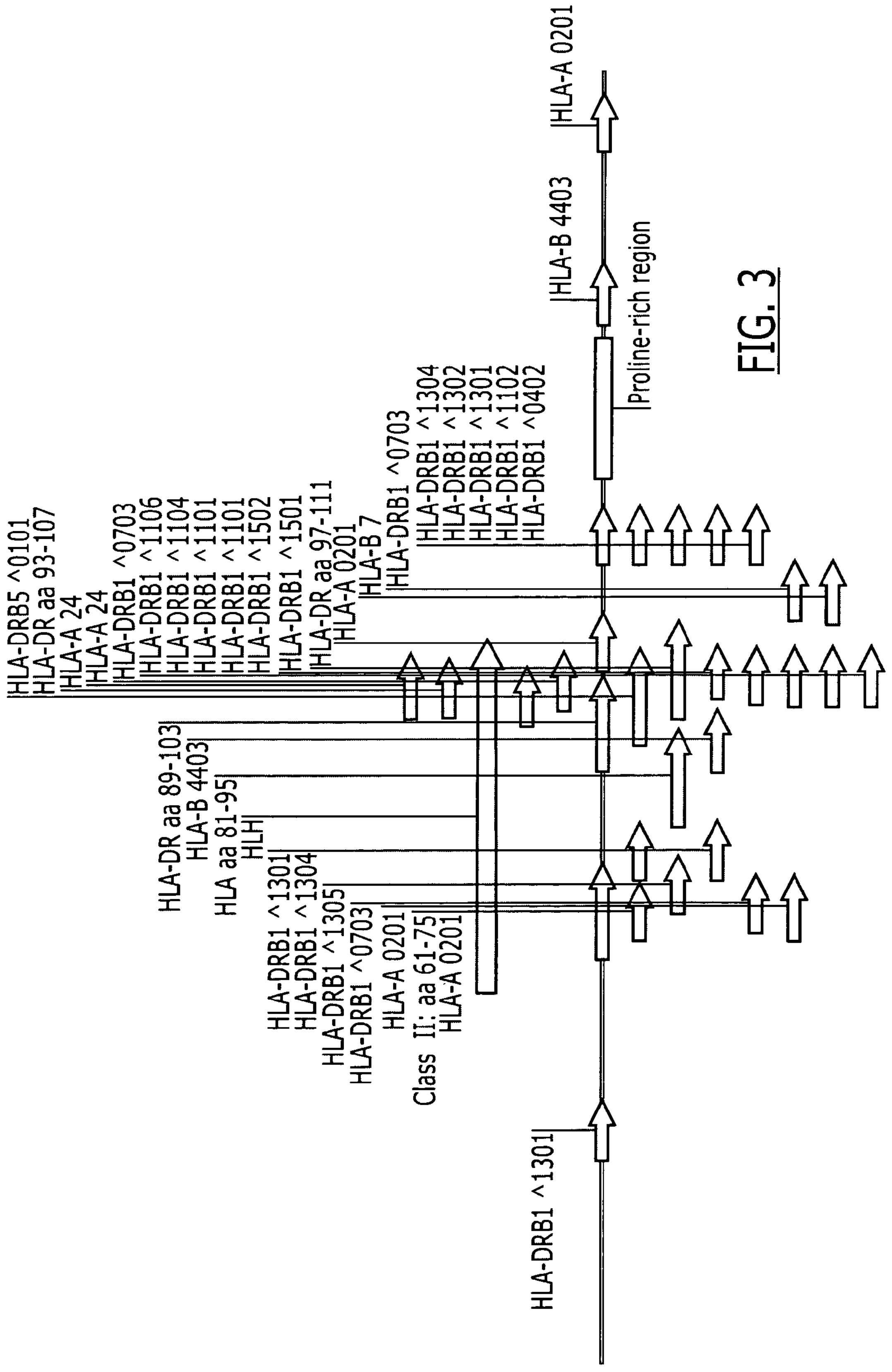
FIG. 3/35. This figure presents a schematic diagram of CASB7439 showing the approximate location of the proline rich region, and identified and predictive epitopes. Various embodiments comprise a CASB7439 polypeptide modified by removal of some or all of the amino acids within the proline-rich region. Such modified CASB7439 polypeptides retain a high portion of epitopes within the CASB7439 polypeptide.
Figure 4:
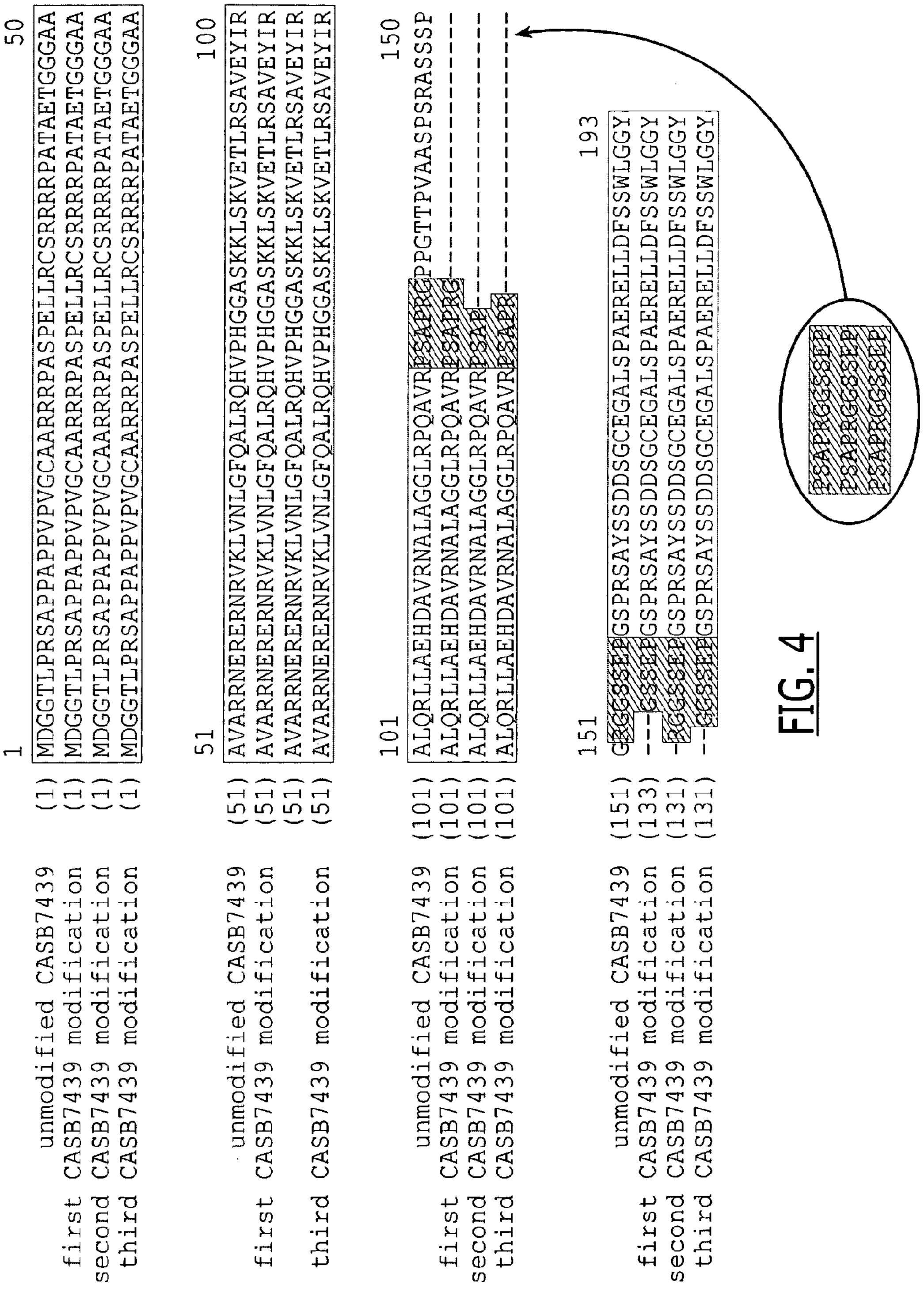
FIG. 4/35. An alignment is shown between the sequence of the unmodified CASB7439 polypeptide (SEQ ID NO:13) and the polypeptide sequence resulting from two possible modifications to the CASB7439 polypeptide: the first in which 21 contiguous amino acid residues (133-153, inclusive) are deleted; the second in which 21 contiguous amino acid residues (131-151, inclusive) are deleted. Further, a third modification to the CASB7439 polypeptide can be envisioned in which 21 contiguous amino acid residues (132-152, inclusive) are deleted. As shown in the Figure the resulting modified CASB7439 polypeptide sequence (inset, circled) in the region of the deletion is the same for all three modifications. This is because of the repeated RG amino acid residues at positions 131-132 and 152-153 of SEQ ID NO:13.

Based on the results described in Example 4, new constructs were designed to (i) remove the proline-rich region while (ii) retaining other regions of the C-terminal portion of the polypeptide. See the description of FIGS. 3/35 and 4/35, which discuss (i) various identified or predicted epitopes within the polypeptide and (ii) various alternate approaches for removal of the proline-rich region.

A codon optimized synthetic nucleic acid gene sequence coding for a modified CASB7439 polypeptide was then ordered from Geneart (unique identifier 0706840), digested and inserted in parallel in two different vectors to generate the following constructs:

(i) LVL088, comprising the CASB7439 gene with the 21 amino acid proline-rich region deleted, fused with a polyhistidine-tail at the C-terminal in the pET26b (+) vector (SEQ ID NO:27 (aa), SEQ ID NO:28 (DNA)) and (ii) LVL111, comprising the CASB7439 gene with the 21 amino acid proline-rich region deleted and both an N-terminal- and C-terminal-polyhistidine-tail in the pET19b (+) vector (SEQ ID NO:3 (aa), SEQ ID NO:4 (DNA)).

The LVL111 construct (see SEQ ID NO:3) was cloned following the same strategy used for the LVL055, i.e., using the pET19 (+) vector which includes a polyhistidine-tail composed of 10 histidines followed by the enterokinase site. This resulted in a 23 amino acid fusion partner (SEQ ID NO:42) at the N-terminus.

Other constructs were generated with the codon optimized synthetic gene discussed in Example 3 (unique identifier 0606597), including the following:

LVL090 (a protein construct comprising (from the N-terminus) Protein D, full-length optimized CASB7439, and a 6-His in pET21 vector) (SEQ ID NO:43 (aa); SEQ ID NO:44 (DNA))

LVL112 (a protein construct comprising (from the N-terminus) SUMO Protein, full-length optimized CASB7439 in a pSUMO vector) (SEQ ID NO:45 (aa); SEQ ID NO:46 (DNA))

LVL113 (a protein construct comprising (from the N-terminus) SUMO Protein, pD1/3 protein, full-length optimized CASB7439 in a pSUMO vector) (SEQ ID NO:47 (aa); SEQ ID NO:48 (DNA))

LVL114 (a protein construct comprising (from the N-terminus) SUMO Protein, CASB7439 truncated at amino acid 117 in a pSUMO vector) (SEQ ID NO:49 (aa); SEQ ID NO:50 (DNA))

LVL115 (a protein construct comprising (from the N-terminus) SUMO Protein, modified CASB7439 with the proline-rich region removed in a pSUMO vector) (SEQ ID NO:51 (aa); SEQ ID NO:52 (DNA))

No production improvement was observed, although only one repetition was carried out (Data not shown).

Production of LVL088 was analyzed after an overnight induction with 1 mM IPTG at 37° C. and at 16° C. When analyzed electrophoretically, LVL088 production was visualized only by Western blot. One purification lot from four 800 mL culture flasks resulted in 0.4 mg of protein. On the other hand, LVL111 was easily detectable following Coomassie-blue staining. The recombinant protein LVL111 was produced and purified over 8 lots. Several lots of LVL111 (each from four 800 mL culture flasks) were estimated to produce in the range from 3.3 mg/lot to 10 mg/lot of purified protein. Thus, production of LVL088 was lower than that seen for LVL111. The purified protein was also tested for its reactivity with several anti-CASB7439 monoclonal antibodies and a positive reactivity was obtained in all cases.

Example 6

Removal of the C-terminal polyhistidine-tail from the LVL111 construct was investigated. The nucleic acid molecule encoding the polypro (−) CASB7439 polypeptide without the portion encoding the C-terminal polyhistidine was amplified by PCR from the LVL111 construct and cloned into the pET19b vector. This construct was designated LVL137. The LVL137 construct was essentially LVL111 without the nucleotide sequence encoding a C-terminal polyhistidine tail. SEQ ID NO:5 (aa); SEQ ID NO:6 (DNA). The removal of the C-terminal polyhistidine-tail had no apparent impact on the production level. As analyzed by coomasie-stained SDS-PAGE gel, LVL137 produced the same level of protein as LVL111.

The nucleic acid molecule encoding the polypro (−) CASB7439 polypeptide was then amplified by PCR from the Geneart (0706840) synthetic CASB7439 sequence and cloned into a pET26 vector with a six polyhistidine tag at the N-terminal (LVL138). SEQ ID NO:33 (aa); SEQ ID NO:34 (DNA). This construct exhibited a significantly reduced level of protein production and was difficult to detect by Western blot.

A nucleic acid molecule encoding a six polyhistidine tag at the N-terminal of the polypro (−) CASB7439 polypeptide was generated in a pET24 kanamycin resistant vector. A new linker design was utilized to remove a hairpin structure created between the polyhistidine-tag sequence and the 5' end of the CASB7439 gene. Specifically, the codons for the first eight amino acid residues of the protein construct were altered to the following nucleotide sequence: 5' ATG CAT CAT CAT CAT CAT CAT GAC . . . 3' (SEQ ID NO:35). (The original codons were 5' ATG CAC CAT CAC CAT CAC CAT GAT . . . 3' (SEQ ID NO:36).) This construct was designated LVL160. SEQ ID NO:37 (aa); SEQ ID NO:38 (DNA). By gel and Western blot analysis, protein production appeared as weak as that obtained with LVL138.

A nucleic acid molecule encoding a protein construct with a ten polyhistidine tag at the N-terminal of the polypro (−) CASB7439 polypeptide was generated in a pET24 kanamycin resistant vector. This construct was identified as LVL168. SEQ ID NO:11 (aa); SEQ ID NO:12 (DNA). The production level was comparable to the level observed for LVL111. An alignment of several of the constructs discussed in this Example is found in FIG. 5/35.

The results for the constructs discussed in this Example and Example 1 are summarized in Table 1, below.

TABLE 1

Expression levels for constructs discussed in Examples 1, 3, and 6.

| # LVL | Description | Vector | Production |
|---|---|---|---|
| LVL007 | Long His-CASB7439 | pET19b(+) | gel−/blot+ |
| LVL010 | Long His-CASB7439 | pET19b(+) | gel−/blot+ |
| LVL016 | pD1/3-CASB7439-OPT-6His | pET21b(+) | gel−/blot+ |
| LVL111 | Long His-Del-poly-Pro-domain-His-OPT | pET19b(+) | gel+++/blot+++ |
| LVL137 | Long His-Del-poly-Pro-domain-OPT | pET19b(+) | gel+++/blot+++ |
| LVL138 | 6His-Del-poly-Pro-domain-OPT | pET26b(+) | gel−/blot+ |
| LVL160 | Hismodif--Del-poly-pro-domain-OPT | pET24b(+) | gel−/blot+ |
| LVL168 | 10His-del-poly-pro-domain-OPT | pET24b(+) | gel+++/blot+++ |

A construct that results in "gel−/blot+" production generally is visible only by western blot when whole-cell lysate is subjected to SDS-PAGE. A construct that results in "gel+++/blot+++" production is clearly visible by Coomase blue staining when whole-cell lysate is subjected to SDS-PAGE.

6His: Histidine tag = 6 histidine residues

Long His = 23aa (MGHHHHHHHHHHSSGHIDDDDKH) (SEQ ID NO: 42)

Del-poly-Pro-domain: CASB7439 modified by deletion of the proline-rich region,

OPT: codon optimized

Hismodif: Histidine tag modified for codon selection (see herein, Example 6),

1/3pD: protein D construct described herein

10His: Histidine tag with 10 histidine residues

Example 7

Another CASB7439 construct was generated in fusion with a fragment of protein D from *Haemophilus influenzae*. As shown in SEQ ID NO:39 (aa) (SEQ ID NO:40 (DNA)), amino acids Met-Asp-Pro were fused to 108 N-terminal amino acids of processed Protein D (amino acid residues 2-109 of processed Protein D). SEQ ID NO:39 is referred to herein as 1/3pD or 1/3Protein D. The synthetic CASB7439 nucleotide sequence obtained from Geneart (0706840) (proline-rich region deleted) was subcloned in pET26-1/3pD, a kanamycin resistant plasmid which contains the 1/3pD, to obtain LVL141. The sequence of LVL141 is set forth in SEQ ID NO:7 (aa) and SEQ ID NO:8 (DNA). Production was comparable to LVL111.

This clone was then mutated by PCR to remove the four amino acid linker (Ala-Ala-Ala-His) between the 1/3pD and CASB7439 components. The sequence of the resulting construct, designated LVL144, is set forth in SEQ ID NO:9 (aa) and SEQ ID NO:10 (DNA). Production was comparable to LVL111. FIG. 6/35 shows an alignment of CASB7439 (SEQ ID NO:13); LVL168 (SEQ ID NO:12), PD1/3 (SEQ ID NO:39), and LVL144 (SEQ ID NO:9).

Example 8

Solubilization Tests of LVL168

Generally, purified protein constructs comprising CASB7439 were solubilzed in 6M guanidine buffer, transferred to 8M urea buffer, and stored in 4M Urea, 20 mM HEPES, 1 mM TCEP, 150 mM NaCl, pH7.0. Preliminary results performed in small volumes suggested that LVL168 could also be solubilized in a phosphate buffer without urea nor any reducing agents, such as EDTA or TCEP, and with or without NaCl. No precipitation was observed after dialysis in those buffers. Solubilization assays were performed to characterize LVL168 protein in the sixteen buffers listed in Table 2. One hundred microliters of purified LVL168 protein samples in 8M Urea buffer, 20 mM HEPES, 150 mM NaCl, 1 mM TCEP, pH7.0 were put into mini dialysis unit 10000 MWCO (Biolynx), previously conditioned with the buffer by two rinses. Dialysis was performed overnight in 100 mL of each of the sixteen buffers listed in Table 2 under agitation at 4° C. Samples were then harvested from units, put into eppendorfs and centrifuged for 5 minutes at 20,000 g. Soluble proteins stayed in suspension but non-soluble proteins precipitated and lead to pellets after centrifugation. Buffers in which the LVL168 protein was soluble are listed in Table 2.

Supernatants were tested by gel SDS-PAGE and the concentrations of the remaining soluble proteins were measured by the RC DC method using the manufacturer's instructions. A kit for carrying out the RC DC method of the Modified Lowry method is available from BioRad Laboratories, 1000 Alfred Nobel Drive, Hercules, Calif. 94547). Samples were kept at 4° C. for a stability test.

Stability Tests of LVL168

LVL168 proteins from the solubility assay were kept for 7 days at 4° C. Twenty microliters of each of the samples 2, 3, 5, 6, 9 to 16 were transferred to other tubes and tested for their stability at 4° C., 37° C. or room temperature for 2 additional days. Samples were centrifuged for 5 minutes at 20,000 g. Supernatants were resolved by SDS-PAGE and profiles were analyzed for degradation, aggregation or loss of protein by comparison to the original purified protein. The protein was stable in the majority of the buffers tested.

TABLE 2

Solubility and stability tests of LVL168.

| Sample # | Buffer | Solubility |
|---|---|---|
| 1 | PBS 1X pH7.3 | Insoluble |
| 2 | 2M Urea, 20 mM Tris, 150 mM NaCl + 1 mM TCEP, pH 8.0 | Soluble |
| 3 | 4M Urea, 20 mM Tris, 150 mM NaCl + 1 mM TCEP, pH 7.0 | Soluble |
| 4 | PBS 1X, 1 mM TCEP, 1 mM EDTA, pH7.3 | Insoluble |
| 5 | 10 mM NaAc 1 mM EDTA. 1 mM, TCEP, 5 mM NaCl, pH 5.01 | Soluble |
| 6 | 20 mM Imidazol, 150 mM, NaCl, 1 mM EDTA, 1 mM TCEP, pH 6.0 | Soluble |
| 7 | 20 mM Bicine, 138 mM NaCl, 1 mM EDTA, 1 mM TCEP, pH 8.7 | Insoluble |
| 8 | 50 mM Tris, 250 mM NaCl, 27 mM Sucrose, 0.1% Tween80, 1 mM TCEP, pH 8.5 | Insoluble |
| 9 | 50 mM Tris, 250 mM NaCl, 270 mM Sucrose, 0.3ML-Arginine, 1 mM TCEP, pH 8.5 | Soluble |
| 10 | 20 mM $Na_2HPO_4$, 150 mM NaCl, 1 mM EDTA + 1 mM TCEP, pH 6.0 | Soluble |
| 11 | 20 mM $N3_2HPO_4$, 5 Mm NaCl, 1 mM EDTA + 1 Mm TCEP, pH 6.0 | Soluble |
| 12 | 20 mM $Na_2HPO_4$, 5 mM NaCl, 1 mM EDTA pH 6.0 | Soluble |
| 13. | 20 mM $Na_2HPO_4$, 5 mM NaCl + 1 mM TCEP + pH 6.0 | Soluble |
| 14 | 20 mM $Na_2HPO_4$, 5 mM NaCl pH 6.0 | Soluble |
| 15 | 20 mM $Na_2HPO_4$, 5 mM NaCl pH 6.5 | Soluble |
| 16 | 20 mM $Na_2HPO_4$, 150 mM NaCl pH 6.0 | Soluble |

For the reader's convenience, a summary of the constructs mentioned herein and their relative production is provided in Table 3.

TABLE 3

| # LVL | Description | Vector | Production |
|---|---|---|---|
| LVL007 | Long His-CASB7439 | pET19b(+) | gel−/blot+ |
| LVL010 | Long His-CASB7439 | pET19b(+) | gel−:blot+ |
| LVL016 | pD1/3-CASB7439-OPT-6His | pET21b(+) | gel−/blot+ |
| LVL018 | CASB7439-OPT-6His | pET21b(+) | gel−/blot+ |
| Const-1 | Long His-CASB7439-OPT-Const-1 (nucleus targeting trunc.) | pET19b(+) | gel−/blot+ |
| LVL055 | Long His-poly-Pro-domain-trunc-OPT | pET19b(+) | gel+++/blot+++ |
| LVL056 | Long His-DNA bind trunc-OPT | pET19b(+) | gel−/blot− |
| LVL057 | Long His-bHLH alone-OPT | pET19b(+) | gel−/blot− |
| LVL060 | Long His-C7439-OPT | pET19b(+) | gel−/blot+ |

TABLE 3-continued

| # LVL | Description | Vector | Production |
|---|---|---|---|
| LVL088 | Del-poly-Pro-domain-OPT-6His | pET26b(+) | gel−/blot+ |
| LVL111 | Long His-Del-poly-Pro-domain-His-OPT | pET19b(+) | gel+++/blot+++ |
| LVL137 | Long His-Del-poly-Pro-domain-OPT | pET19b(+) | gel+++/blot+++ |
| LVL138 | 6His-Del-poly-Pro-domain-OPT | pET26b(+) | gel−/blot+ |
| LVL141 | 1/3pD-Del-poly-Pro-domain-OPT-6His | pET26b(+) | gel+++/blot+++ |
| LVL144 | 1/3pD-Del-poly-Pro-domain-OPTHis mut linker | pET26b(+) | gel+++/blot+++ |
| LVL160 | Hismodif--Del-poly-pro-domain-OPT | pET24b(+) | gel−/blot+ |
| LVL168 | 10His-del-poly-pro-domain-OPT | pET24b(+) | gel+++/blot+++ |

See Table 1 abbreviations.
The following additional abbreviations are utilized in Table 3:
trunc: truncated
const: construction
mut: sequence mutated to remove unrelated amino acids between the pD1/3 and modified CASB7439 polypeptide
linker: unrelated amino acids between two part of the molecule
DNA bind: DNA binding domain
bHLH alone: Basic helix-loop-helix domain Materials and Methods Expression—Small Scale Inductions:

*E. coli* BLR (DE3) strains were transformed with constructions mentioned herein, put on Luria Broth (LB) agar plates containing the appropriate antibiotic (40 μg/ml of Kanamycin or 100 μg/ml carbenicilin) and incubated overnight at 37° C. The resulting bacterial lawn was used to inoculate 20 mL of LB Alternative Protein Source (APS) medium with the appropriate antibiotic (40 μg/ml of Kanamycin or 100 μg per ml of carbenicilin) and put at 37° C. to reach an OD600 of 0.5 to 1.0.

Inductions were done by the addition of 1 mM IPTG, at either 16° C. or 37° C. In order to induce at 16° C., the growing culture was cooled down on ice 1 hr before inducing the expression of the recombinant protein. The culture was then put back to grow at 16° C. and maintained under those conditions for 16 hrs. To induce at 37° C., expression of the recombinant proteins was immediately induced by the addition of IPTG to the growing culture. Induction was maintained at 37° C. for 3 hours. Small aliquots of 1 mL were taken before and after induction.

Aliquots were then centrifuged (10 min, 4° C., 20000×g) and bacterial pellets were kept at −20° C. until analysis. The analysis was performed following a BugBuster protein extraction according to the manufacturer's recommendations. BugBuster, manufactured by Novagen, is commercially available from VWR. Expression level was determined by Coomassie-blue staining of SDS-PAGE gels and by Western blots. The solubility was evaluated after detection of the protein in the pellets or in the supernatants from the BugBuster's extraction.

Expression—Lame Scale Inductions:

*E. coli* BLR (DE3) strains were transformed with constructions as described herein, put on LB agar plates containing the appropriate antibiotic and incubated overnight at 37° C. The resulting bacterial lawn was used to inoculate the desired number of 800 mL flasks of LB APS medium with the appropriate antibiotic (40 μg/ml of Kanamycin or 100 μg per ml of carbenicilin) and put at 37° C. to reach an $OD_{600}$ of 0.5 to 1.0. The 2.5 L flasks containing 800 ml of growing culture were then cooled down on ice 1 hr before inducing the expression of the recombinant protein by the addition of 1 mM IPTG. To induce at 16° C., the growing culture was cooled down on ice one hour before induction. The cultures were then put back to grow at 16° C. and maintained under those conditions for 16 hours.

Cultures were centrifuged (15 min, 4° C., 6000×g) and bacterial pellets were kept at −80° C. until purification process. Small aliquots of 1 mL were also taken before and after induction for BugBuster and analysed by SDS-PAGE and Western blots before purification.

Purification

Bacterial pellets were resuspended in Lysis buffer (20 mM Tris buffer (pH 8.0) containing 500 mM NaCl, 10 mM TCEP) and a mixture of protease inhibitors (Complete EDTA-free). Bacteria were lysed either by sonication using a 13 mm probe on a Vibra cell ultrasonic processor, by Emulsiflex C3 (Avestin) or with the Constant Cell disruption system (Constant System). Soluble (supernatant) and insoluble (pellet) components were separated by centrifugation at 20 000 g for 20 minutes at 4° C. Because CASB7439 recombinant proteins are expected in the pellets, supernatants were discarded.

Usually, the insoluble components (pellets) were resolubilized in 50 mM bicine buffer pH 8.0 containing 6M guanidine HCl, 500 mM NaCl, 10 mM TCEP, and then centrifuged (20 000×g for 20 min). The supernatant was loaded on a 5 ml H is Trap column (GE Healthcare) already preequilibrated in the previous buffer but with TCEP concentration lowered to 1 mM. After loading, the column was washed once with the same buffer. The 6M GnHCl chaotrope agent was replaced by 8M Urea (8M Urea, 20 mM HEPES, 500 mM NaCl, 1 mM TCEP, pH 8.0). Elution was performed using a 20 mM HEPES buffer (pH 8.0) containing 8M Urea, 500 mM NaCl, 1 mM TCEP and 250 mM imidazole. Samples from elution fractions were analyzed by SDS-PAGE, and fractions containing the protein of interest were pooled, concentrated on a centrifugal device if needed, and used for the second step of purification.

One or two steps of SEC (size exclusion chromatography) (Superdex 200, GE Healthcare) were done, depending of the purity needed, in 8M Urea, 20 mM HEPES, 500 mM NaCl, 1 mM TCEP, pH 8.0, before the last desalting step. The desalting was done on a G25 desalting column preequilibrated with the final 20 mM HEPES buffer (pH 7.0) containing 4M Urea, 150 mM NaCl and 1 mM TCEP.

Protein samples were 1 ml-aliquoted in tubes and stored at −80° C.

Protein Analysis—Concentration Determination

Protein concentration was determined using an RC DC protein assay (Modified Lowry method by BioRad). This assay was used due to the incompatibility of some components of the final buffer with classic Lowry or BCA assays (high contents of urea and reducer agents). Known quantities of final protein preparation were also analyzed by SDS-PAGE, Western blot and for LAL-content to assess aggregation or degradation, *E. coli* protein and LPS contamination level.

Example 9

CASB7439 Expression Validation in Normal and Colorectal Cancer (CRC) Tissues

Figure 7:
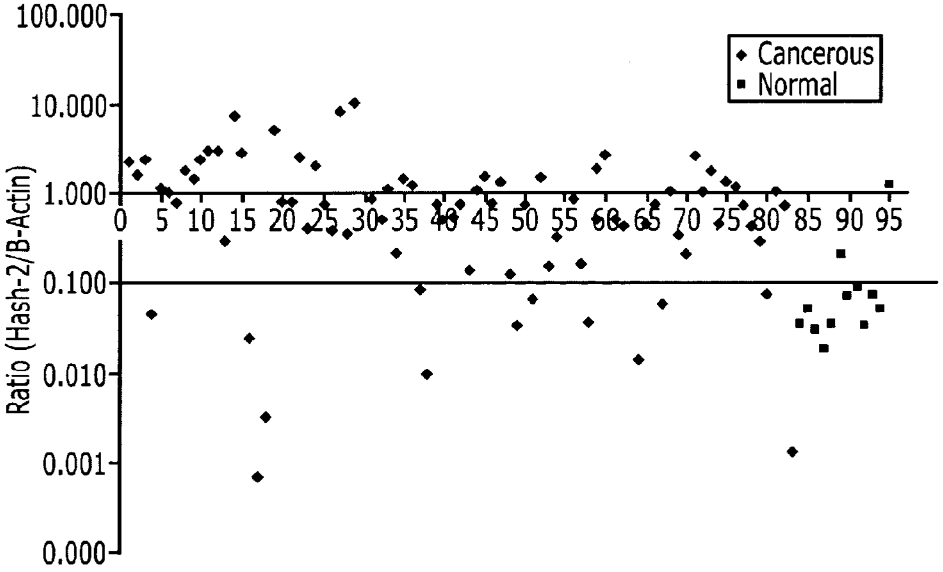
FIG. 7/35. Real-time qPCR analysis of CASB7439 mRNA expression in normal (12) and colorectal cancer (83) tissues. See Example 9.

Applicants performed real-time qPCR analysis of CASB7439 mRNA expression in 83 CRC samples and 12 normal colon samples obtained from Corixa Corporation. CASB7439 mRNA was at least 10-fold overexpressed in CRC compared to normal colon in 63% of CRC samples tested compared to normal tissues (data reported as average CASB7439β-actin expression ratio) (FIG. 7/35). In addition, Applicants detected CASB7439 protein by immunofluorescence (IF) in human CRC tissues using a rabbit anti-CASB7439 monoclonal antibody (40-12) (antibody discussed elsewhere herein); no CASB7439 protein was detected in normal adjacent tissue sections.

Additional expression data for CASB7439 were generated by GeneLogic (Gene Microarray) analysis using standard techniques. CASB7439 mRNA was found to be highly expressed in CRC samples from all stages of the disease (data not shown). Applicants performed real-time qPCR analysis of CASB7439 mRNA expression in 83 CRC samples and 12 normal colon samples obtained from Corixa Corporation. CASB7439 mRNA was at least 10-fold overexpressed in CRC compared to normal colon in 63% of CRC samples tested compared to normal tissues (data reported as average CASB7439β-actin expression ratio) (FIG. 7/35).

Independent literature reports detection of CASB7439, i.e., HASH-2, mRNA by in situ hybridization (ISH) at a very low level at the bottom of colonic crypts but not in any other normal tissues except placenta. Jubb et al. (2006) Oncogene 25: 3445-3457. In colorectal cancer (CRC) tissues, CASB7439 mRNA has been shown to be 15-fold overexpressed in 70% of human tissues tested.

CASB7439 Protein Expression in CRC and Normal Adjacent Colon Tissues

In order to analyze CASB7439 protein expression by immunofluorescence in normal and CRC tissues, a specific rabbit anti-CASB7439 monoclonal antibody (40-12) was developed. Rabbit hybridomas raised against CASB7439 were obtained from the commercial provider Epitomics Inc. and screened by Applicants. The mAbs produced by the hybridomas were first screened by ELISA using the recombinant protein LVL111 (SEQ ID NO:3). The specificity of the mAbs were verified by Western blot using LVL111 and cell lysate obtained from a recombinant cell line engineered to express CASB7439 (see below, TC1/CASB7439). CASB7439 protein expression in TC1/CASB7439 tumors (grown in mice), SW-620 and SW-480 cells (CASB7439 positive human colorectal cancer cell line), and in HCT-116 cells (CASB7439 negative human colorectal cancer cell line) was assessed by immunofluorescence with the mAbs. The mAb 40-12 was selected for CASB7439 protein expression validation.

Applicants obtained from NDRI (National Disease Research Interchange, 8 Penn Center, 8$^{th}$ Floor, 1628 JFK Boulevard, Philadelphia, Pa. 19103) OCT-embedded frozen tissue samples of both CRC and normal adjacent tissue from 17 different individuals; for 5 of these individuals, metastatic tissues were also obtained. Applicants screened 17 primary tumors, 17 normal adjacent tissues and 5 metastasis. Out of 17 primary CRC tumors analyzed, 13 were positive for CASB7439 protein expression (76.5%). All these CASB7439-positive samples were adenocarcinomas. None of the normal adjacent tissues expressed detectable levels of CASB7439 protein. Of the metastatic tissues, 3 of 5 were positive (60%) for CASB7439 protein expression.

Figure 8:
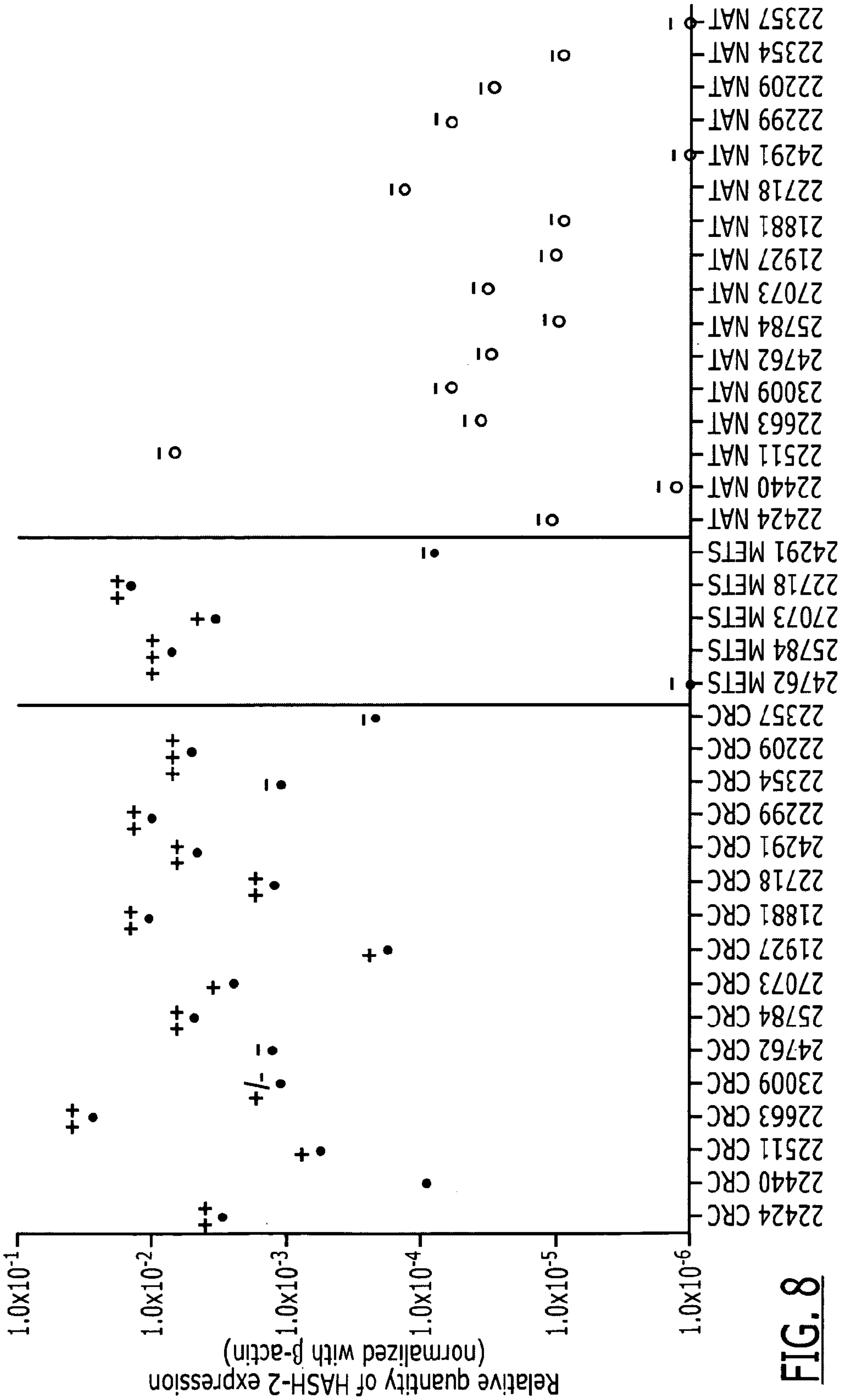
FIG. 8/35. Correspondence between CASB7439 mRNA and protein expression in various human colorectal (CRC) samples. ● (black circles) represent the CASB7439 mRNA expression in colon cancer samples, whereas ○ (open circles) represent the CASB7439 mRNA expression in normal adjacent tissues. The corresponding level of CASB7439 protein detected by immunofluorescence is indicated above each sample (– no expression, +/– very low expression, + low expression, ++ strong expression and +++ very strong expression). CRC: primary tumors, METS: metastasis, NAT: normal adjacent tissues. All samples are colon adenocarcinomas except the samples 22440 and 24762 which are mucinous carcinomas. See Example 9.

The correlation between the CASB7439 protein and mRNA expression was studied in 16 CRC tissues by real-time qPCR analysis performed using routine techniques on both cancer and normal adjacent colon tissues. Ki67 staining was used as a proliferation marker. The correlation between CASB7439 protein and mRNA expression is presented in FIG. 8/35. Tissue samples which exhibited CASB7439 protein by immunofluorescence also displayed the highest CASB7439 mRNA levels.

Example 10

Immunogenicity of CASB7439 in Mice: CASB7439 T-Cell Immunogenicity in Inbred Mice To study the T-cell immunogenicity of CASB7439 in mice, a bank of peptides was generated by routine synthesis methods to cover the entire sequence of the CASB7439 protein (FIG. 9/35). Each peptide was a 15-mer, overlapping the next peptide by 11 amino acids. To investigate the immunodominant regions, 14 pools of peptides were arranged according to a matrix such that any two pools of peptides had only one common peptide (FIG. 10/35).

For T-cell immunogenicity studies in mice, up to 15 inbred mice and up to 10 outbred mice per group have received four intramuscular immunizations every two weeks, with various doses (from 0 to 30 μg) of various recombinant CASB7439 proteins formulated with AS01B or AS15, both of which are GSK proprietary adjuvants. Once formulated with antigen, AS01B is composed of MPL (100 μg/ml) and QS21 (100 μg/ml) in liposomes). Once formulated with antigen, AS15 is composed of MPL (100 μg/ml), QS21 (100 μg/ml) and CpG7909 (840 μg/ml) in liposomes. Each immunization contained 25 μl of recombinant CASB7439 protein mixed with 25 μl of a 2× concentration adjuvant. Therefore, each mouse in the AS01B group received 5 μg MPL and 5 μg QS21. Each mouse in the AS15 group received 5 μg MPL, 5 μg QS21, and 5 μg CpG7909. After the last immunization, spleens or PBLs were obtained from the mice. For CASB7439 immunogenicity analysis in inbred mice, spleens or PBLs were analyzed individually or pooled. For CASB7439 immunogenicity analysis in CD1 outbred mice, each spleen was processed individually.

The PBLs or isolated splenocytes were resuspended at a final concentration of $10\times10^6$ cells per ml in RPMI 1640 culture medium with the following additives: Penicillin-Streptomycin (1×), non-essential amino acids (1×), 2-Mercaptoethanol (55 mM), sodium pyruvate (100 mM), L-Glutamine (200 mM). Cells have been stimulated with the peptides from the CASB7439 sequence (used at a final concentration of 1 μg/ml/peptide in RPMI 1640+additives+5% heat-inactivated FBS). An intracellular staining (ICS) for CD4, CD8, IL-2, IL-5, IFNγ and TNFα has been performed, according to classical procedures. After stimulation, cells were treated with brefeldin A and fixed. Surface staining of CD4 and CD8 was done with CD4 and CD8 specific monoclonal antibodies. Then, cells were permeabilized and stained with specific monoclonal antibodies raised against IL-2, IL-5, IFNγ and TNFα proteins. Cells have been analyzed by flow cytometry using a BD FACSCanto II. Data are expressed in percentages of double-positive IFNγ+ and TNFα+ CD4 or CD8 T-cells.

Inbred Mouse Multistrain T-Cell Immunogenicity Comparison Experiment

Applicants compared the immunogenicity of the CASB7439 protein, formulated with either AS01B or AS15, in C57Bl/6, Balb/C, CB6f1 (first generation progeny of C57Bl/6 crossed with Balb/C mice) and C3H inbred mice purchased from Charles River, Senneville, QC, Canada. Five mice per group were immunized with 10 μg of recombinant CASB7439 protein (LVL111) formulated with either AS01B or AS15. The spleens were collected and pooled (one pool of five spleens per group). The CD4 T-cell response (double-positive IFNγ+ and TNFα+) to LVL111 for each strain is presented in FIG. 11/35 for the AS01B formulation and in FIG. 12/35 for the AS15 formulation. No CD8 T-cell (double-positive IFNγ+ and TNFα+) response was observed in any of the four inbred mouse strains.

Figure 13:
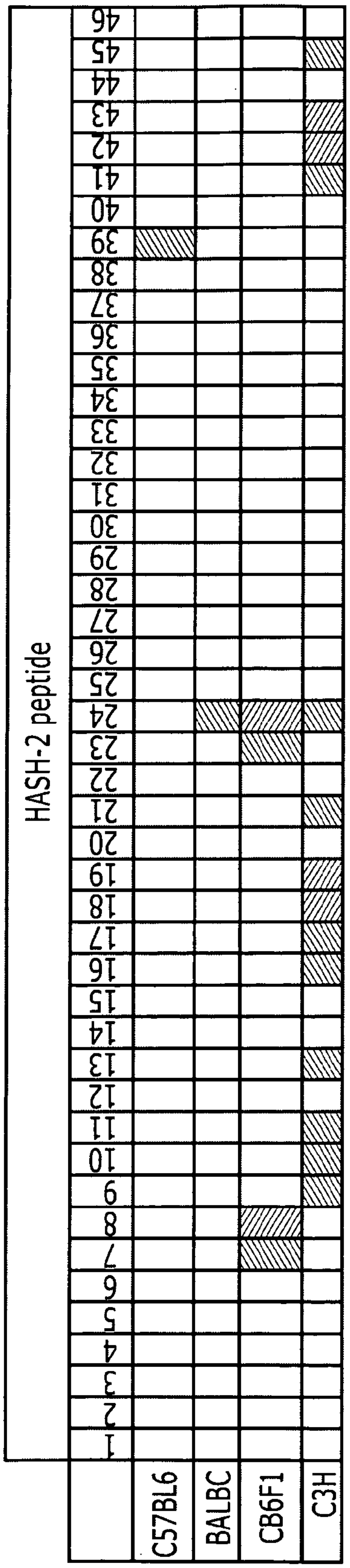
FIG. 13/35. Identification of CD4 Immunogenic CASB7439 peptides in the four inbred mouse strains discussed in the preceding paragraph. Light gray=0.2-0.4% double positive (IFNγ/TNFα) CD4 T-cells; dark gray 0.5% double positive (IFNγ/TNFα) CD4 T-cells. See Example 10, Inbred Mouse Multistrain Comparison Experiment.
Figure 16:
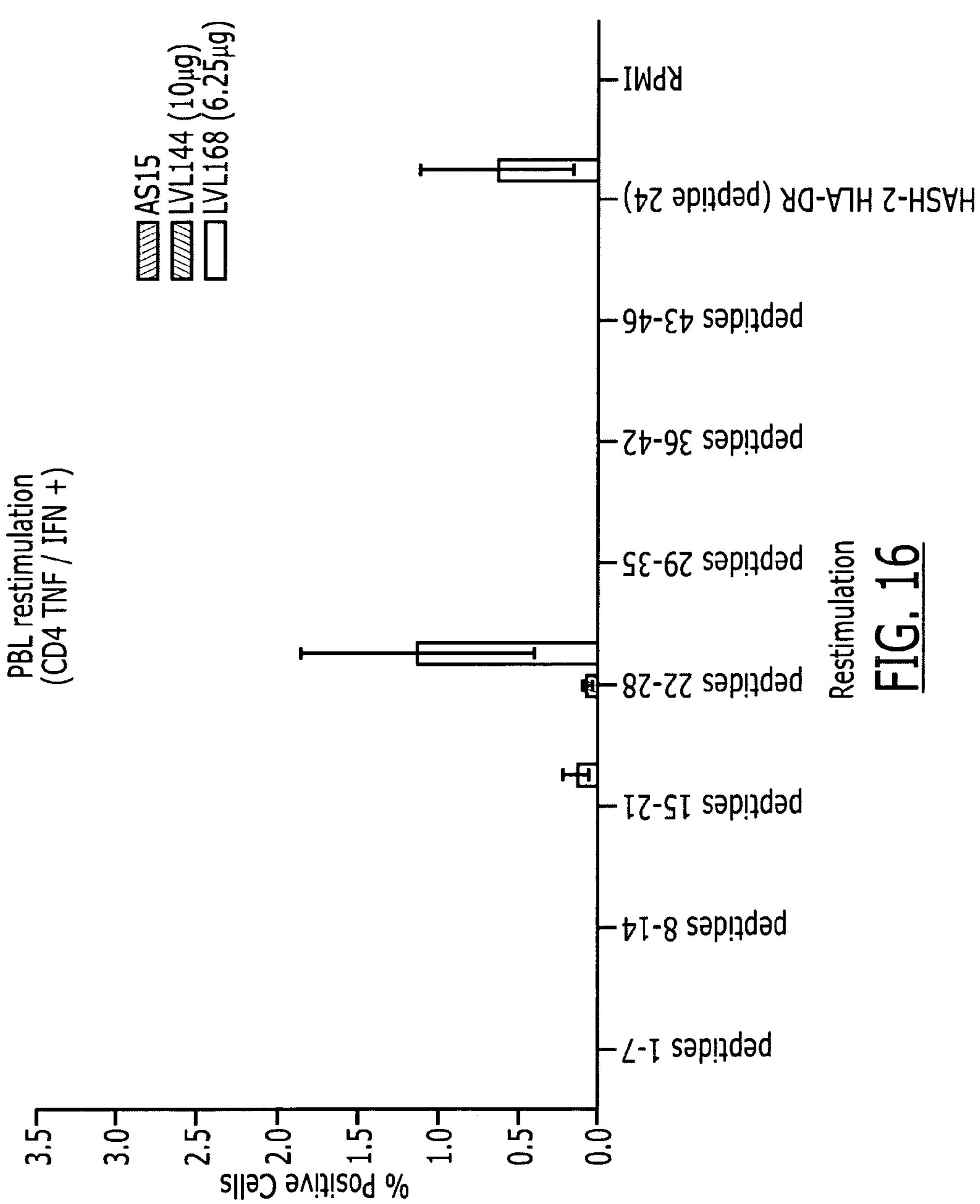
FIG. 16/35. CD4 T-cell responses (expressed as percent double positive (IFNγ/TNFα)) in pooled peripheral blood leukocytes (PBL) isolated from HLA A2.1/DR-1 transgenic mice immunized with either LVL168 (SEQ ID NO:11) or LVL144 (SEQ ID NO:9), formulated with AS15, following re-stimulation with CASB7439 overlapping peptides (7 pools of 7 peptides/pool+peptide 24 (SEQ ID NO:76)).
Figure 17:
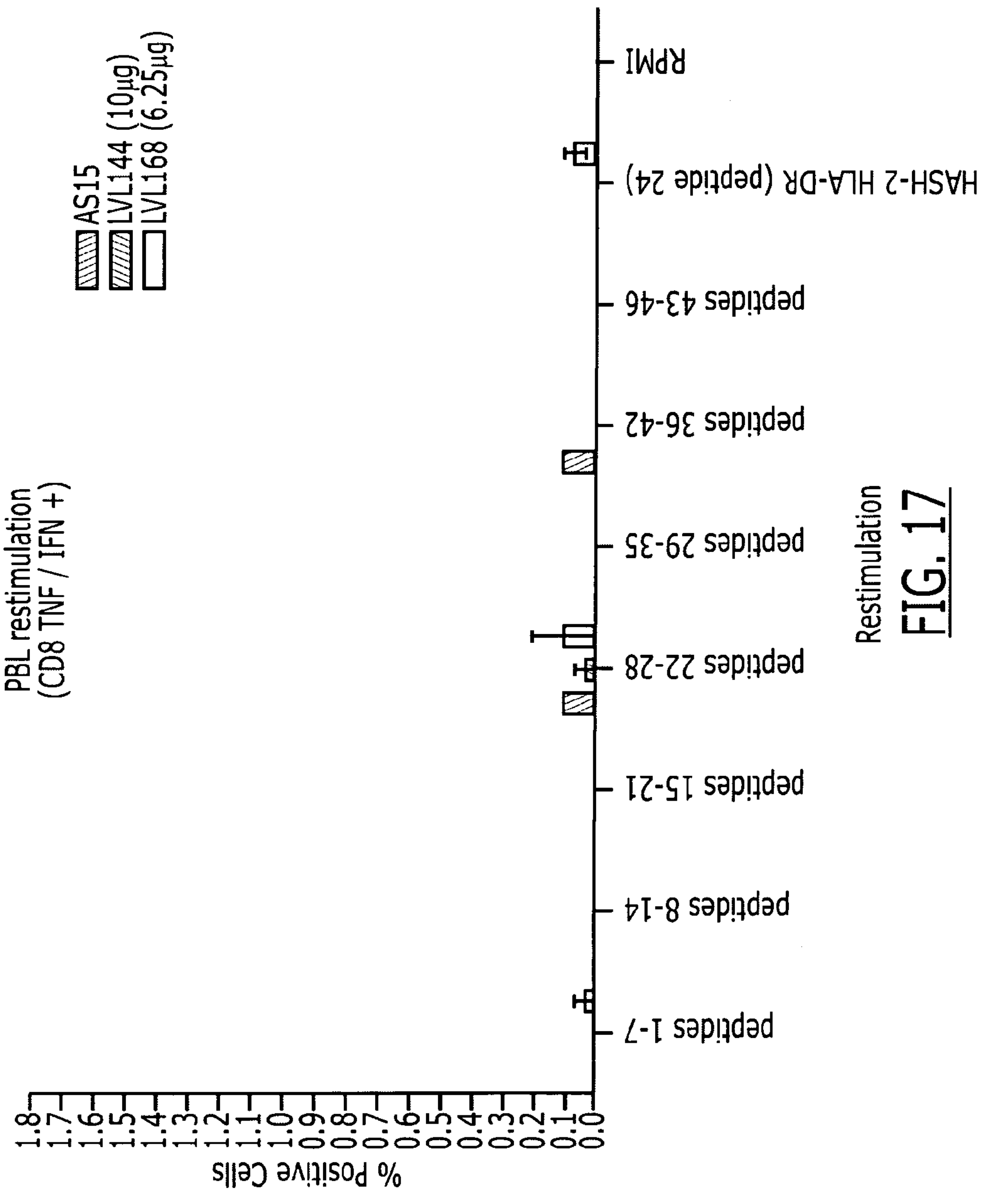
FIG. 17/35. CD8 T-cell responses (expressed as percent double positive (IFNγ/TNFα)) in pooled PBL isolated from HLA A2.1/DR-1 transgenic mice immunized with either LVL168 (SEQ ID NO:11) or LVL144 (SEQ ID NO:9), formulated with AS15, following re-stimulation with CASB7439 overlapping peptides (7 pools of 7 peptides+ peptide 24 (SEQ ID NO:76)).
Figure 18:
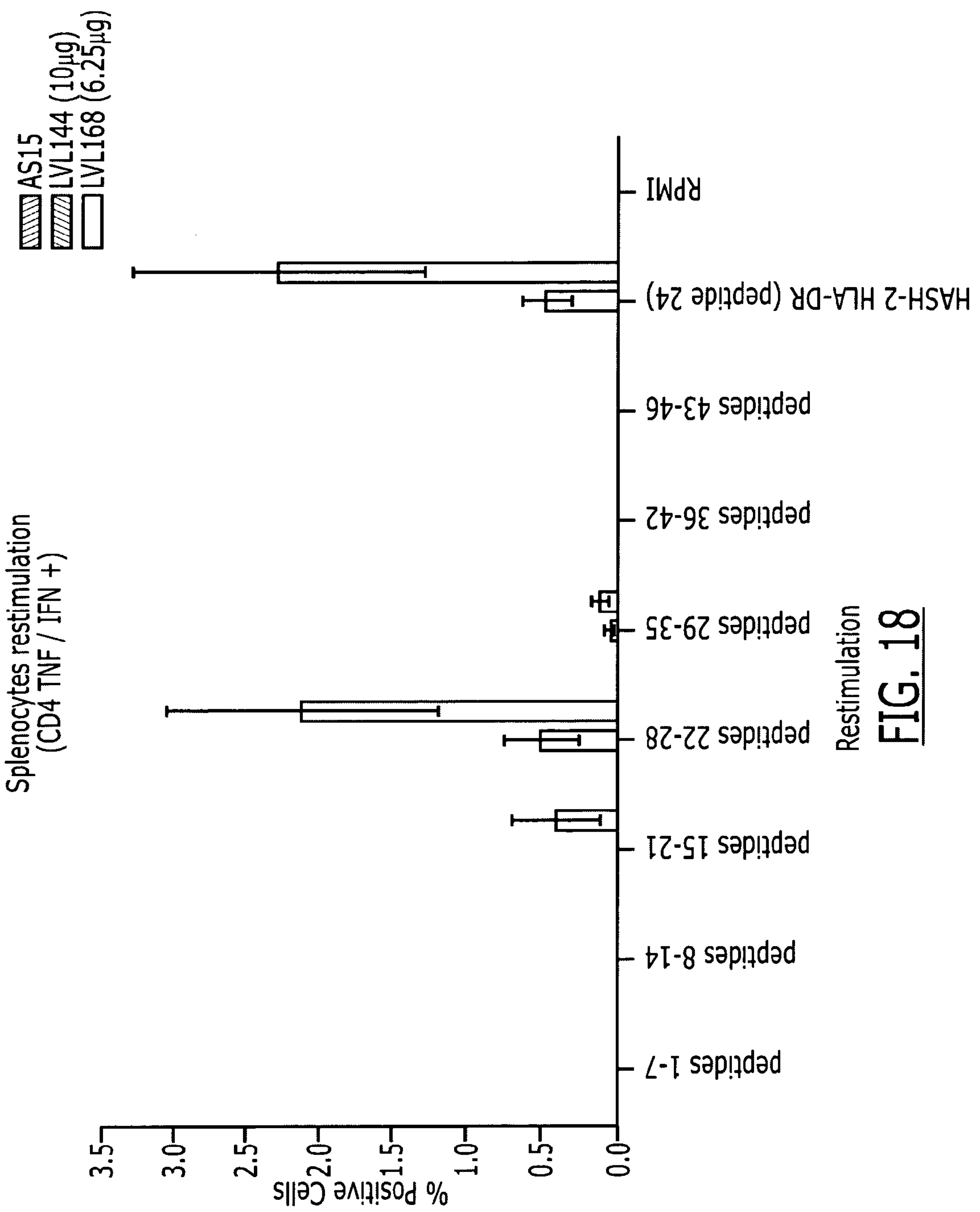
FIG. 18/35. CD4 T-cell responses (expressed as percent double positive (IFNγ/TNFα)) in splenocytes isolated from HLA A2.1/DR-1 transgenic mice immunized with either LVL168 (SEQ ID NO:11) or LVL144 (SEQ ID NO:9), formulated with AS15, following re-stimulation with CASB7439 overlapping peptides (7 pools of 7 peptides+ peptide 24 (SEQ ID NO:76)).
Figure 19:
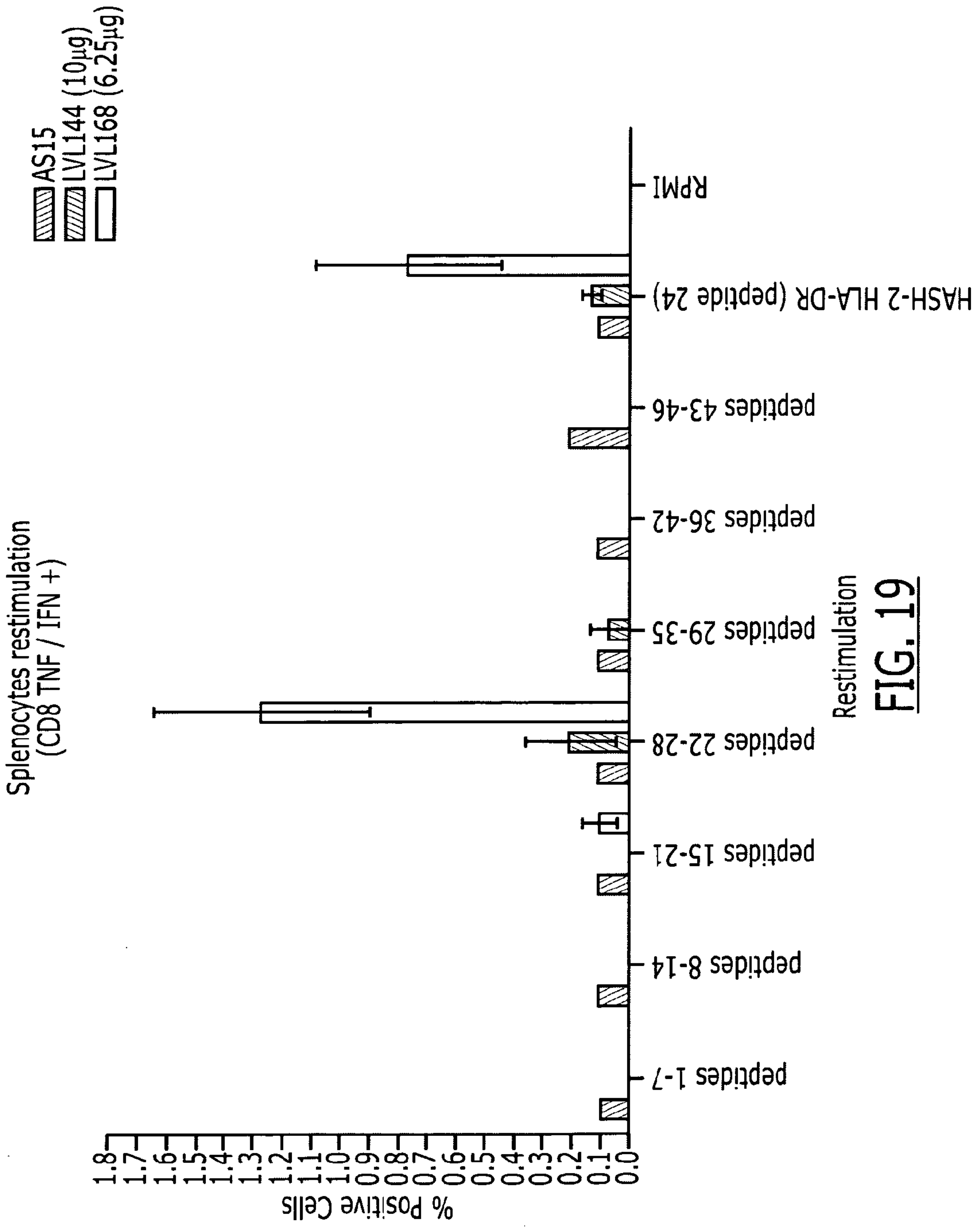
FIG. 19/35. CD8 T-cell responses (expressed as percent double positive (IFNγ/TNFα)) in splenocytes isolated from HLA A2.1/DR-1 transgenic mice immunized with either LVL168 (SEQ ID NO:11) or LVL144 (SEQ ID NO:9), formulated with AS15, following re-stimulation with CASB7439 overlapping peptides (7 pools of 7 peptides+ peptide 24 (SEQ ID NO:76)).

The CASB7439 immunodominant peptides identified in inbred mice immunized with CASB7439+AS15 are presented in FIG. 13/35. The immunodominant peptides and the with the corresponding regions of SEQ ID NO:13 are:

C57Bl/6: peptide 39 (SEQ ID NO:91) (aa 153 to 167 of SEQ ID NO:13)

Balb/c: peptide 24 (aa 93 to 107 of SEQ ID NO:13)

CB6f1: peptides 7-8 (aa 25 to 43 of SEQ ID NO:13) and 23-24 (aa 89 to 107 of SEQ ID NO:13)

C3H: peptides 9-11 (aa 33 to 55 of SEQ ID NO:13), 16-19 (aa 61 to 87 of SEQ ID NO:13) and 41-43 (aa 161-183 of SEQ ID NO:13).

Inbred Mouse T-Cell Immunogenicity Studies of LVL111, LVL168 and LVL144

Immunogenicity of LVL111, LVL168, and LVL144 were studied in inbred CB6f1 mice. In this experiment, five mice per group (Charles River, Senneville, QC, Canada) have been immunized four times every two weeks with the recombinant CASB7439 proteins (LVL111, LVL168 and LVL144) formulated with AS15. Each immunization contained 25 μl of recombinant CASB7439 protein mixed with 25 μl of a 2× concentration adjuvant as described elsewhere herein. The CD4 and CD8 T-cell responses (double positive IFNγ and TNFα) were measured by intracellular staining and flow cytometry analysis in individual inbred CB6f1 mice, after restimulation of splenocytes with the CASB7439 peptides matrix. (Data not shown) The immunizations with the all three constructs triggered a CD4 T-cell immune response against the same immunogenic regions (aa 25 to 43 of SEQ ID NO:13 and aa 89 to 107 of SEQ ID NO:13) in CB6f1 inbred mice.

Immunogenicity of CASB7439 in Mice: CASB7439 T-Cell Immunogenicity in Outbred Mice CD1 outbred mice (Charles River, Senneville, QC, Canada) were immunized four times every two weeks with the recombinant CASB7439 protein (LVL111) formulated with either AS01B or AS15. Each immunization contained 25 μl of recombinant CASB7439 protein mixed with 25 μl of a 2× concentration adjuvant as described elsewhere herein. The CD4 and CD8 T-cell responses (double positive IFNγ and TNFα) were measured by intracellular staining and flow cytometry analysis in individual CD1 mice, after restimulation of splenocytes with the CASB7439 peptides matrix.

Tables of the CASB7439 CD4-immunogenic peptides identified in outbred mice immunized with either CASB7439+AS01B or CASB7439+AS15 are presented in FIG. 14/35 top and bottom, respectively. The CD4 T-cell immunogenic regions identified in CD1 outbred mice covers the following regions of CASB7439 (expressed in terms of the amino acid positions of SEQ ID NO:13): peptides 8-10 (aa 29 to 51 of SEQ ID NO:13), peptides 16-18 (aa 61 to 83 of SEQ ID NO:13) and peptides 24-26 (aa 93 to 115 of SEQ ID NO:13). The CD8 T-cell immunodominant regions identified in CD1 outbred mice cover the following portions of CASB7439 (SEQ ID NO:13): peptides 16-18 (aa 61 to 83 of SEQ ID NO:13), peptides 24-26 (aa 93 to 115 of SEQ ID NO:13) and peptide 32 (aa 125 to 139 of SEQ ID NO:13). (Data not shown.)

Outbred Mouse T-Cell Immunogenicity Studies of LVL111, LVL168 and LVL144

The CASB7439+AS15-mediated CD4 and CD8-T-cell responses induced by LVL111, LVL168 and LVL144 were tested in individual outbred CD1 mice purchased from Charles River, Senneville, QC, Canada. Five mice per group received four intramuscular immunizations every two weeks composed of 10 μg of CASB7439 recombinant protein (LVL111, LVL168 or LVL144) formulated with AS15. (Each immunization contained 25 μl of recombinant CASB7439 protein mixed with 25 μl of a 2× concentration adjuvant as described elsewhere herein. Five mice in the control group were immunized with a saline buffer.

Two weeks after the fourth immunization, the mice were sacrificed. The CD4 and CD8 T-cell responses (double positive IFNγ and TNFα) were measured by intracellular staining and flow cytometry analysis after splenocytes restimulation with four pools of peptides (pool 1: peptides 8-9-10, pool 2: peptides 16-17-18, pool 3: peptides 24-25-26 and pool 4: peptides 30-31-32). The data are presented in FIG. 15/35. The same CD4 T-cell immunogenic regions of SEQ ID NO:13, specifically peptides 16-18 (aa 61 to 83 of SEQ ID NO:13) and peptides 24-26 (aa 93 to 115 of SEQ ID NO:13) were activated after immunizations with each of the three CASB7439 constructs formulated with AS15.

HLA A2.1/DR1-Transgenic Mouse T-Cell Immunogenicity Studies of LVL144 and LVL168

The CASB7439+AS15-mediated CD4 and CD8-T-cell responses induced by two constructs (LVL168 or LVL144) were tested in pooled HLA A2.1/DR1-transgenic mice (3 pools of 3 mice) purchased from the Pasteur Institute, Paris, France. 9 mice per group received four intramuscular immunizations every two weeks composed of 6.25 μg of LVL168 or 10 μg LVL144, formulated with AS15. Each immunization contained 25 μl of recombinant CASB7439 protein mixed with 25 μl of a 2× concentration adjuvant as described elsewhere herein. Two mice in the control group were immunized with the adjuvant alone.

Two weeks after the fourth immunization, the mice were sacrificed. The CD4 and CD8 T-cell responses (double positive IFNγ and TNFα) were measured by intracellular staining and flow cytometry analysis after PBLs and splenocytes restimulation with 7 pools of peptides covering the entire CASB7439 sequence [pool 1: peptides 1-7 (SEQ ID NOS: 53-59), pool 2: peptides 8-14 (SEQ ID NOS:60-66), pool 3: peptides 15-21 (SEQ ID NOS:67-73), pool 4: peptides 22-28 (SEQ ID NOS:74-80), pool 5: peptides 29-35 (SEQ ID NOS81-87), pool 6: peptides 36-42 (SEQ ID NOS:88-94) and pool 7: peptides 43-46 (SEQ ID NOS:95-98)]. Moreover, the human HLA DR immunodominant peptide 24 (SEQ ID NO:76) was tested individually. The results presented in FIGS. 16-19 show that the same CD4 and CD8 T-cell immunodominant region (peptides 22-28+peptide 24) is activated after immunizations with each of the two CASB7439 constructs formulated with AS15. Thus, peptide 24 is also a human HLA A2.1 immunodominant peptide. These results were confirmed in a second experiment in which the same CASB7439 peptides were used to restimulate splenocytes obtained from 5 individual mice per group immunized with either LVL168 or LVL144 formulated with AS15. (Data not shown.)

Immunogenicity of CASB7439 in Mice: CASB7439-Mediated Humoral Response CB6f1 Mouse Studies CASB7439-mediated humoral response to 10 μg of CASB7439 (LVL111) formulated with either AS01B or AS15, used at 1/10 of the human dose, was assessed in inbred CB6f1 mice (Charles River, Senneville, QC, Canada). Nineteen mice per group received four intramuscular immunizations every two weeks. Each immunization contained 25 μl of recombinant CASB7439 protein mixed with 25 μl of adjuvant (2× concentration). The mice were bled just prior to each immunization and two weeks after the fourth immunization. In another experiment, CASB7439-mediated humoral response to LVL111, LVL168 or LVL144 was assessed in inbred CB6f1 mice (Charles River, Senneville, QC, Canada). Fifty mice per group received four intramuscular immunizations every two weeks with 10 μg of CASB7439 recombinant protein (LVL111, LVL168 or LVL144) formulated with AS15 or with AS15 alone as a control group. Each immunization contained 25 μl of recombinant CASB7439 protein mixed with 25 μl of a 2×concentration adjuvant as described elsewhere herein. The mice were bled two weeks after the fourth immunization.

The anti-CASB7439 IgG1 and IgG2a serum antibody titers have been determined by ELISA, according to standard procedures. Briefly, the CASB7439 recombinant protein was coated in a 96-well plate in phosphate buffer saline (PBS). After blocking with bovine serum albumin 1% in PBS-Tween (0.1%), sera from immunized mice was incubated in the plates for one hour at 37° C. After plate washing, a specific goat anti-IgG1 or IgG2a-HRP labeled mouse antibody (Southern Biotech Associates, Birmingham, Ala., USA) was added for one hour at 37° C. After plate washing, a TMB substrate Reagent (BD Pharmingen, Mississauga, ON, Canada) was added for 15 minutes. The colorimetric reaction was stopped by adding 1M sulfuric acid. The OD have been measured at 450 nm using a Spectramax spectrophotometer (Molecular Device, Sunnyvale, Calif., USA). The antibody titer has been determined with a standard curve, using specific total IgG, IgG1 or IgG2a capture antibodies and an internal CASB7439 positive mouse serum.

FIG. 20/35 depicts the time-course analysis of the IgG1 and IgG2a antibody titers in sera of mice immunized with CASB7439 (LVL111) formulated with either AS01B or AS15. The data demonstrate that AS15 triggers a higher Th1 (approximately 10-fold higher IgG2a/IgG1 ratio after 4 immunizations compared to AS01B (IgG2a is a surrogate marker of type 1 immune response). As shown in FIG. 21/35, CASB7439 protein formulated with AS15 triggers a very strong IgG1 and IgG2a antibody response in inbred CB6f1 mice, whatever the construct used (LVL111, LVL168 or LVL144).

Immunogenicity of CASB7439 in Mice: CASB7439-mediated Humoral Response CD1 Mouse Studies CASB7439-mediated humoral response upon CASB7439 immunizations (LVL111, LVL168 or LVL144) was assessed in outbred CD1 mice (Charles River, Senneville, QC, Canada). Ten mice per group received four intramuscular immunizations every two weeks with 10 μg of CASB7439 recombinant protein (LVL111, LVL168 or LVL144) formulated with AS15 (or with AS15 alone as a control group). Each immunization contained 25 μl of recombinant CASB7439 protein mixed with 25 μl of a 2× concentration adjuvant as described elsewhere herein.

Figure 22:
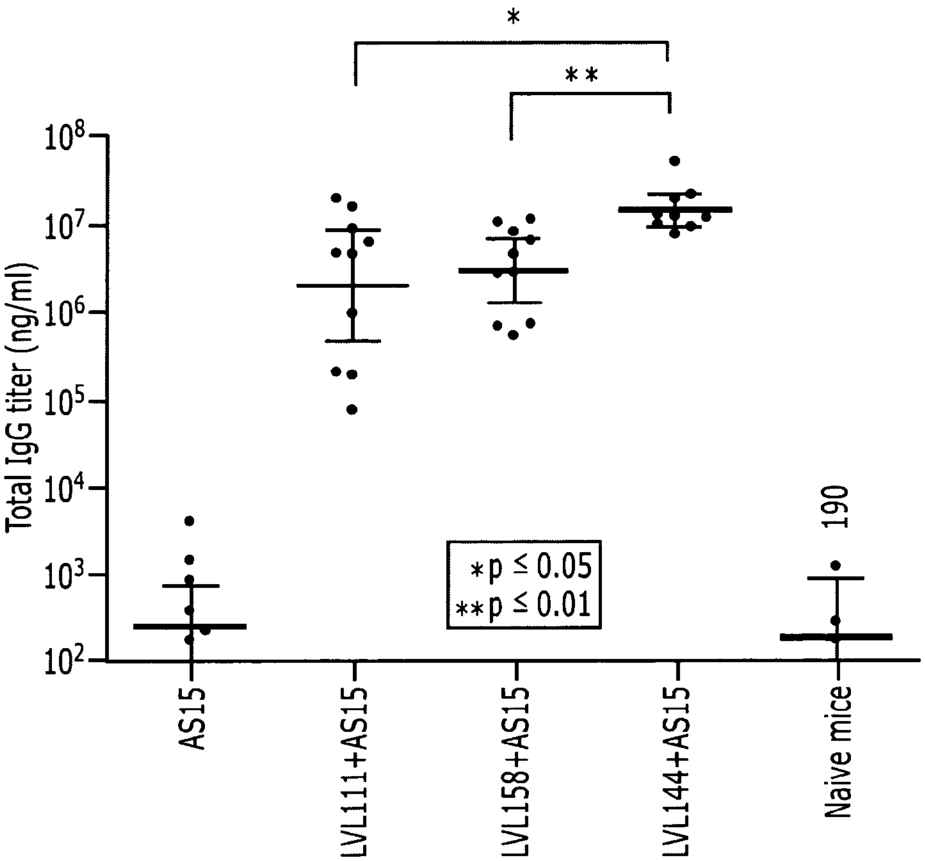
FIG. 22/35. CASB7439-specific humoral immune response (IgG titer) in CD1 outbred mice immunized with LVL111, LVL168, or LVL144 formulated with AS15 adjuvant, or with AS15 adjuvant alone; naive mice were used as control. See Example 10, CD1 Mouse Studies.

Two weeks after the fourth immunization, the mice were bled and the anti-CASB7439 total IgG serum antibody titers were determined by ELISA, as already described. CD1 mice immunized with various CASB7439 constructs (LVL111, LVL168 or LVL144) develop a very strong CASB7439-specific humoral immune response (FIG. 22/35). The data indicates that a 8 to 10-fold higher anti-CASB7439 total IgG titer was induced by LVL144 as compared to LVL168 and LVL111 respectively in CD1 outbred mice.

Example 11

Anti-tumor Efficacy of CASB7439 ASCI in Mice: Murine Tumor Model Development A murine tumor model expressing the CASB7439 protein using TC-1 murine tumor cells or MC38 murine colorectal cancer cells were developed to study CASB7439-mediated in vivo tumor protection in mice. TC-1 tumor cells were kindly provided by T. C. Wu (Johns Hopkins University, Baltimore, Md.). They were generated from primary lung cells of C57Bl/6 mice by the successive transfer of HPV16 E6 and E7 genes and an activated ras oncogene as described previously (Lin et al. (1996) *Cancer Res*. Jan 1; 56(1):21-6. MC38 cells, a murine colorectal adenocarcinoma cell line, were purchased from ATCC (Manassas, Va.).

These cells were stably transfected with a construct encoding CASB7439 using the non-liposomal transfectant reagent Fugene-6 (Roche, Mississauga, ON, Canada), according to the manufacturer's recommendations. Briefly, a plasmid (pcDNA3.1/Zeocine) coding for the entire sequence of the CASB7439 protein and containing a zeocine-resistance gene, has been mixed with Fugene-6 and added on top of TC-1 or MC38 tumor cells in serum-free medium overnight. After transfection, cells were allowed to recover for 24 hours in culture medium+10% heat-inactivated FBS. Cells were then harvested and distributed in 96-well plates (50 μl of cell suspension per well) for limiting dilutions. After cell seeding, the medium was replaced with culture medium+10% heat-inactivated FBS containing 100 μg/ml of zeocine (Invitrogen, Burlington, ON, Canada). After selection, each clone was harvested and allowed to grow in 24-well plates and frozen. The expression of CASB7439 mRNA in TC1/CASB7439 and MC38/CASB7439 cells was verified by real-time qPCR, using CASB7439-specific TaqMan primers and probe. The real-time qPCR reactions have been performed with a TaqMan reaction kit using a TaqMan 7900 machine (Applied Biosystem, Foster City, Calif., USA). The CASB7439 protein expression has been assessed by Western blot and immunofluorescence, using a specific anti-CASB7439 monoclonal antibody (40-12).

The TC-1/CASB7439#14 cell population is not fully clonal but, rather, composed of at least two different subclones. Therefore, another limiting dilution step was done in order to generate a fully clonal TC-1/CASB7439 cell population: the TC-1/CASB7439#14-2 cells.

To determine the optimal dose of TC-1 or MC38 cells for tumor challenge in mice, various doses of cells (from $1\times10^5$ to $2\times10^6$ cells per mouse) were injected in CB6f1 inbred mice. The optimal dose was determined to be $2.5\times10^5$ cells per mouse for the TC-1/CASB7439#14 and TC1/CASB7439#14-2 challenges; $1\times10^5$ cells per mouse was found optimal for challenge with the MC38/CASB7439#35 cells.

Anti-tumor Efficacy in Mice: Immunizations and Challenge Experiments

A series of four studies (1.1-1.4) were designed to assess the CASB7439-mediated in vivo tumor protection. Generally, in each of these four studies, groups of CB6f1 mice were given four intramuscular immunizations at two week intervals, with various doses (0, 1, 10 or 30 μg) of the specific recombinant CASB7439 protein chosen for the study, formulated with either AS01B or AS15 at a final concentration as described elsewhere herein, with a saline buffer, with the CASB7439 protein alone or with the adjuvants alone. Two weeks after the fourth immunization, CB6f1 mice were challenged by subcutaneous injection with 250,000 TC-1/CASB7439 #14, 100,000 MC38/CASB7439#35 cells or 250,000 TC-1/CASB7439 #14-2 tumor cells. After challenge, the size of the tumors was measured three times a week for each mouse. According to protocol, mice with tumors bigger than 200 $mm^2$ were sacrificed. Survival curves were then plotted.

An additional three studies were carried out (2.1-2.4) to investigate doses other than 0, 1, 10 or 30 μg of the recombinant CASB7439 protein. Study 2.4 assessed the correlation between immunogenicity and tumor protection of CASB7439 in male and female C57Bl/6 mice; CB6f1 mice were evaluated in parallel.

Studies 1.1-2.4 are described in greater detail below.

Study #1.1

Applicants investigated the tumor protection conferred by immunization with LVL111 (1 or 10 μg) formulated with either AS01B or AS15 against a TC1/CASB7439 #14 challenge in CB6f1 mice. Ten mice per group were intramuscularly immunized four times at two-week intervals with the recombinant CASB7439 protein (LVL111) formulated with either AS01B or AS15 at a final concentration as described elsewhere herein. Two control groups immunized with either a saline buffer or the CASB7439 protein alone were also tested. Two weeks after the fourth immunization, each mouse has been subcutaneously challenged with 250,000 TC-1/CASB7439#14 cells.

Figure 23:
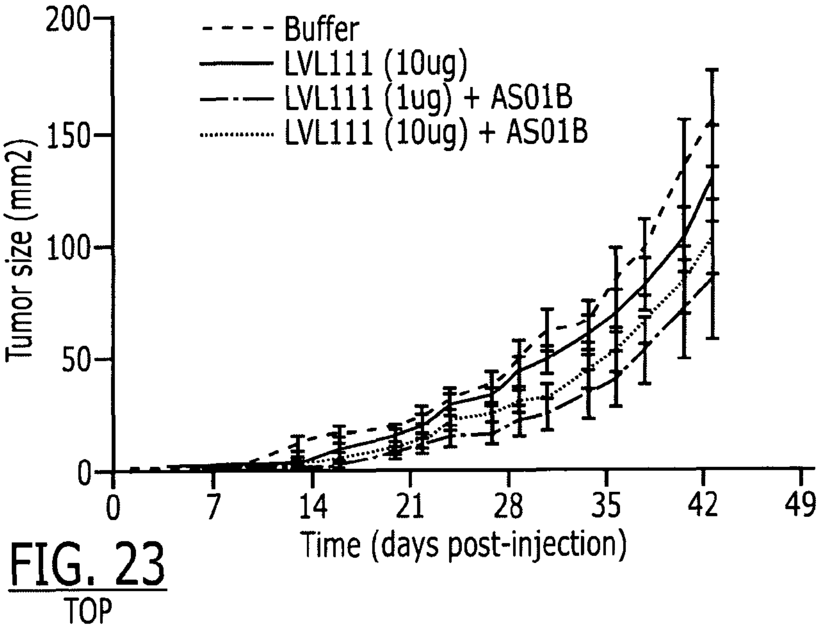
FIG. 23/35. TC1/CASB7439 #14 tumor graft in CB6f1 mice immunized with LVL111 formulated with AS01B (top) or AS15 (bottom). See Example 11, Study #1.1. In the top panel, the order of curves on the graph from top to bottom is 'buffer', LVL111 (10 μg), LVL111 (10 μg)+AS01B, and LVL111 (1 μg)+AS01B. In the bottom panel, the curve at the bottom is LVL111 (10 μg)+AS15.
Figure 23:
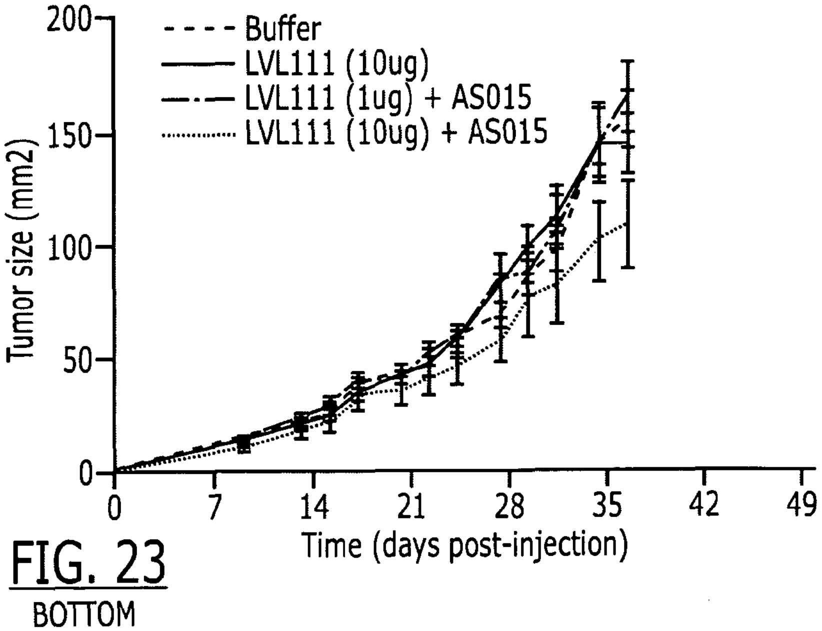

Tumor growth was followed for 42 days, but no survival curves were plotted because too few mice were sacrificed at day 42. However, tumor growth curves were plotted for each group. FIG. 23/35, top and bottom panels, present the tumor growth curves obtained with the AS01B and the AS15 formulations, respectively. (Note: AS15 is mis-identified in this figure as "AS015".) The curves show that in CB6f1 mice receiving CASB7439 protein formulated with either AS01B or AS15, the TC1/CASB7439#14 tumor growth is slowed.

Study #1.2

Groups of fourteen mice received a different dosage of LVL111 (1, 10 and 30 μg) or control. Mice were intramuscularly immunized four times at two week intervals with the different doses of LVL111 formulated with either AS01B or AS15 at a final concentration as described elsewhere herein. Four control groups were also immunized with AS01B-only, AS15-only, saline buffer-only, or 30 μg LVL111-only. Two weeks after the fourth immunization, each mouse was subcutaneously challenged with 250,000 TC-1/CASB7439#14 cells. After challenge, the size of the tumors was measured three times a week for each mouse. According to protocol, mice with tumors bigger than 200 $mm^2$ were sacrificed. A survival curve was drawn.

Figure 24:
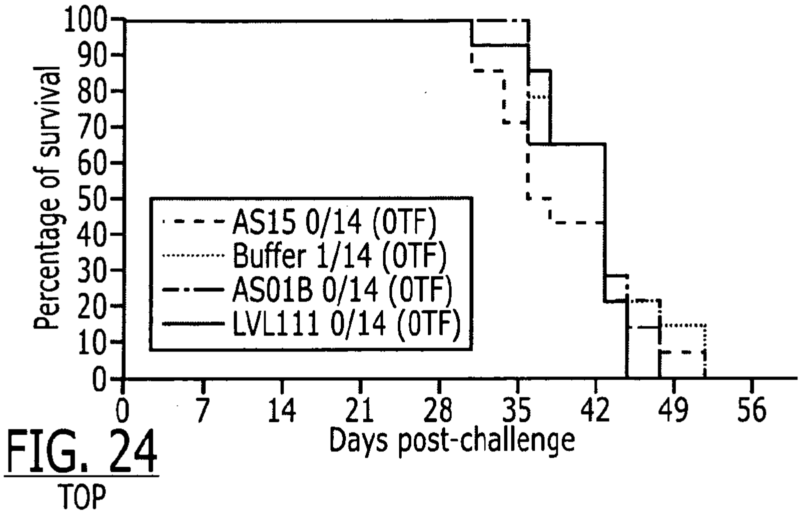
FIG. 24/35. Survival curves from Example 11, Study #1.2 are presented in top, middle, and bottom panels. TF: tumor-free. (Top) The survival curve of CB6f1 mice immunized with saline buffer, LVL111 without adjuvant, or adjuvant alone (AS01 or AS15) and challenged with TC1/CASB7439 #14 cells. The last surviving mouse from the group immunized with LVL111 died first, followed by the last surviving mouse from the AS01B group, followed by the last surviving mouse from the AS15 group and the last surviving mouse from the buffer group. (Middle) The survival curve of CB6f1 mice immunized with AS15 alone or with the indicated dosages of LVL111 formulated with AS15 and challenged with TC1/CASB7439 #14 cells. The last surviving mouse from the AS15 group expired first. Of the other groups, the 30 μg group had the fewest survivors, followed by the 1 μg group, then the 10 μg group, which had the most survivors. (Bottom) The survival curve of CB6f1 mice immunized with AS01B alone or with the indicated dosages of LVL111 formulated with AS01B and challenged with TC1/CASB7439 #14 cells. In this panel, the last surviving mice from the 10 μg and AS01B groups expired on the same day. The 1 μg and 30 μg groups had the same percentage of survival at the final day.
Figure 24:
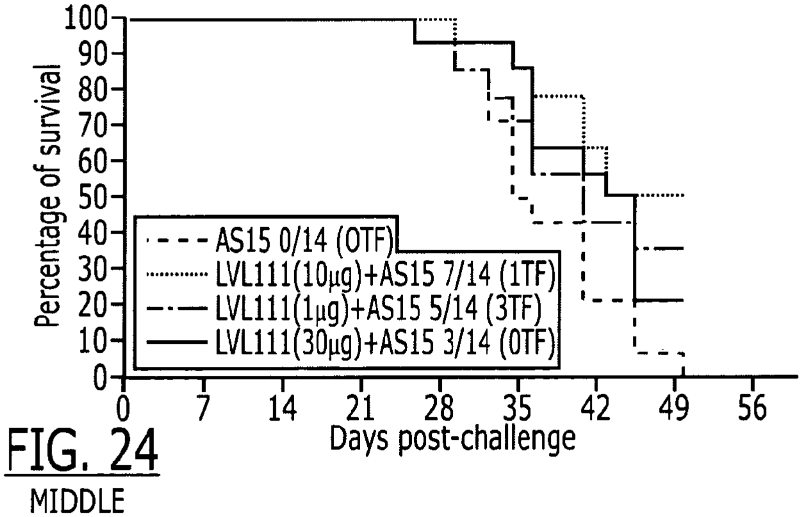
Figure 24:
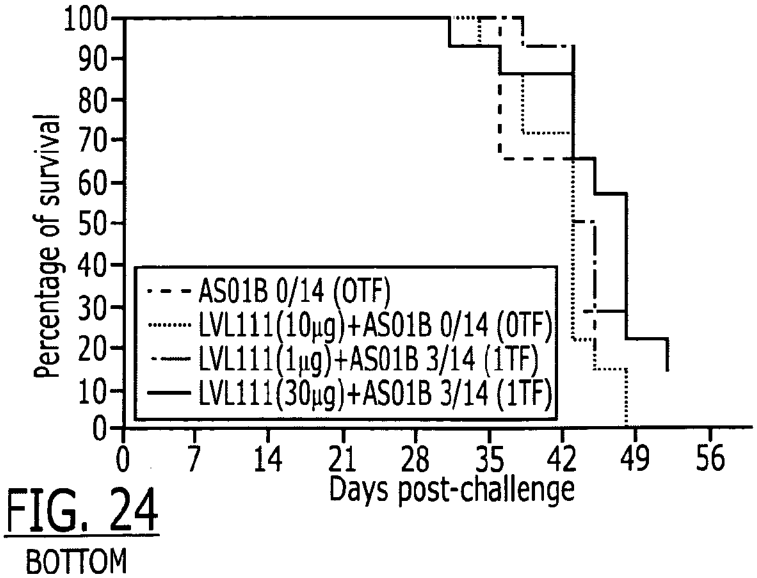

The results indicate that mice immunized with LVL111 formulated with AS15 were better protected against a TC1/CASB7439#14 tumor challenge than mice immunized with the LVL111 formulated with AS01B. The optimal results in CB6f1 mice were obtained with 10 μg of LVL111 formulated with AS15. See FIG. 24/35.

Study #1.3

Thirty eight CB6f1 mice per group were intramuscularly immunized four times at two week intervals with 10 μg of LVL111, LVL168 or LVL144 formulated with AS15 at a final concentration as described elsewhere herein. A control group immunized with AS15 alone was also tested.

Figure 25:
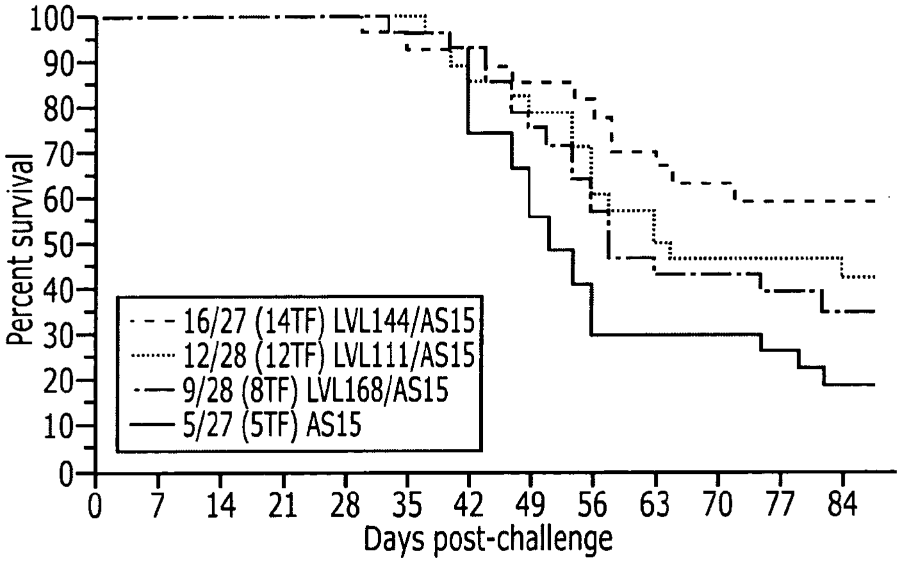
FIG. 25/35. Survival curves from Example 11, Study #1.3 are presented. TF: tumor-free. (Top) Survival curve for CB6f1 mice immunized with LVL111, LVL144, or LVL168 formulated with AS15, or AS15 alone, and challenged with TC1/CASB7439 #14 cells. (Bottom) Survival curve for CB6f1 mice immunized with LVL111, LVL144, or LVL168 formulated with AS15, or AS15 alone, and challenged with MC38/CASB7439 #35 cells.
Figure 25:
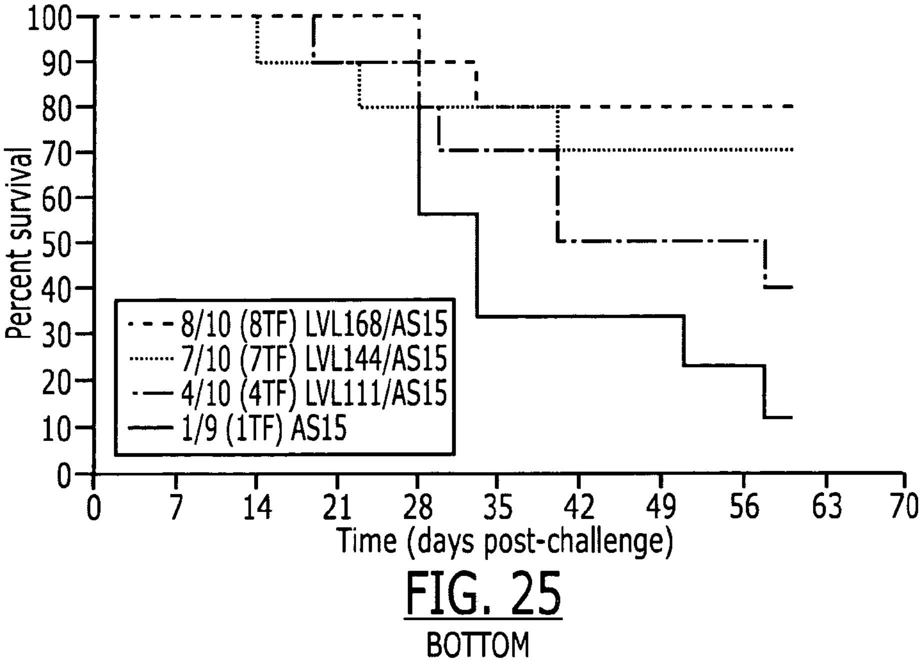

Two weeks after the fourth immunization, twenty eight mice were subcutaneously challenged with 250,000 TC-1/CASB7439#14 cells and the ten remaining mice have been subcutaneously challenged with 100.000 MC38/CASB7439#35 cells. After challenge, the size of the tumors has been measured three times a week for each mouse. According to protocol, mice with tumors bigger than 200 $mm^2$ have been sacrificed. The results indicate that LVL111, LVL168 and LVL144, formulated with AS15, are all protective against a TC1/CASB7439#14 or MC38/CASB7439#35 challenge. See FIG. 25/35.

Study #1.4

Sixty-six CB6f1 mice per group were intramuscularly immunized four times at two week intervals with 10 μg of the LVL168 or LVL144 formulated with AS15 at a final concentration as described elsewhere herein. A control group immunized with AS15 alone was also tested.

Figure 26:
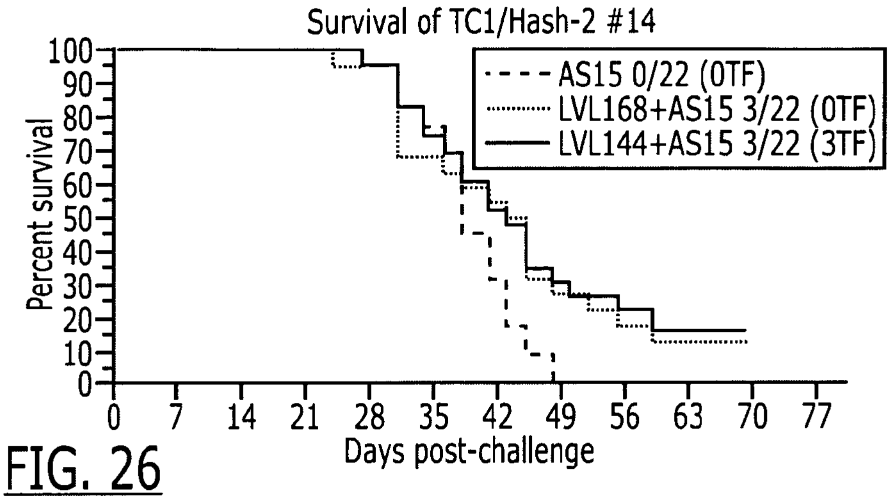
FIG. 26/35. Survival curves from Example 11, Study #1.4 are presented. TF: tumor-free. (Top) Survival curve of CB6f1 mice immunized with LVL144 or LVL168 formulated with AS15, or with AS15 alone, and challenged with TC1/CASB7439 #14 cells. The group immunized with LVL144 had a marginally greater percent survival. (Middle) Survival curve for CB6f1 mice immunized with LVL144 or LVL168 formulated with AS15, or AS15 alone, and challenged with clonal TC1/CASB7439 #14-2 cells. Mice inoculated with LVL144 had a slightly higher percentage of survival. (Bottom) Survival curve for CB6f1 mice immunized with LVL144 or LVL168 formulated with AS15, or AS15 alone, and challenged with MC38/CASB7439 #35 cells. Mice inoculated with LVL144 had no survivors.
Figure 26:
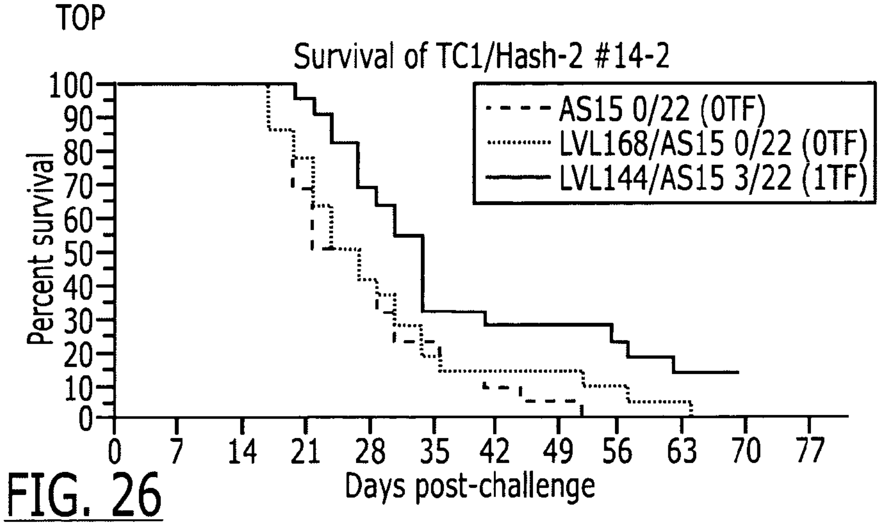
Figure 26:
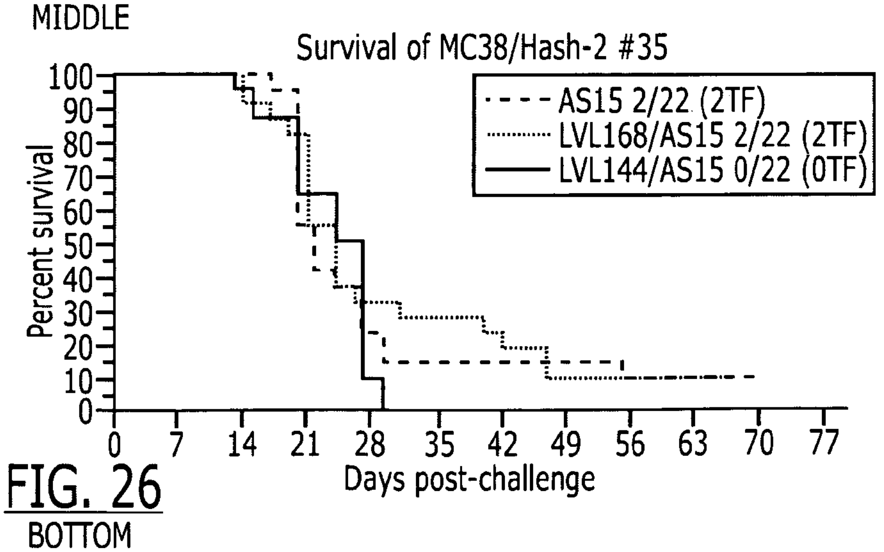
Figure 30:
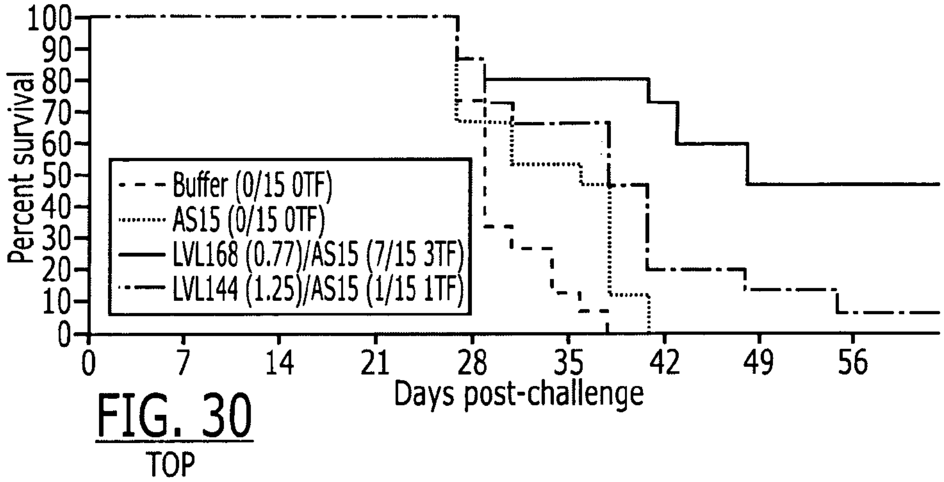
FIG. 30/35. Survival curves from Example 11, Study #2.3. TF: tumor-free. (Top) Survival curve of CB6f1 mice immunized with 0.77 μg of LVL168 or 1.25 μg of LVL144 formulated with AS15 and challenged with TC1/CASB7439 #14-2 cells. The group of mice receiving LVL168 had the highest percent survival, followed by the group receiving LVL144. There were no survivors in the group receiving only AS15. (Middle) Survival curve of CB6f1 mice immunized with 0.19 μg of LVL168 or 0.31 μg of LVL144 formulated with AS15 and challenged with TC1/CASB7439 #14-2 cells. The group of mice receiving LVL168 had the highest percent survival. The last surviving mouse from the group receiving LVL144 outlived the last survivor from both the AS15 group and the buffer group. (Bottom) Survival curve of CB6f1 mice immunized with 0.048 μg of LVL168 or 0.078 μg of LVL144 formulated with AS15 and challenged with TC1/CASB7439 #14-2 cells. The group of mice receiving LVL168 had the highest percent survival. The last surviving mouse from the group receiving LVL144 outlived the last survivor from both the AS15 group and the buffer group. Saline buffer or AS15 alone were used as controls.
Figure 30:
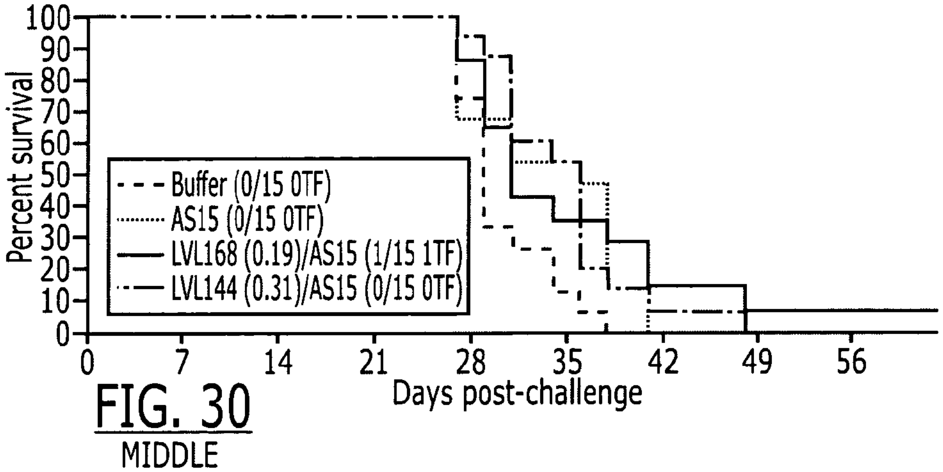
Figure 30:
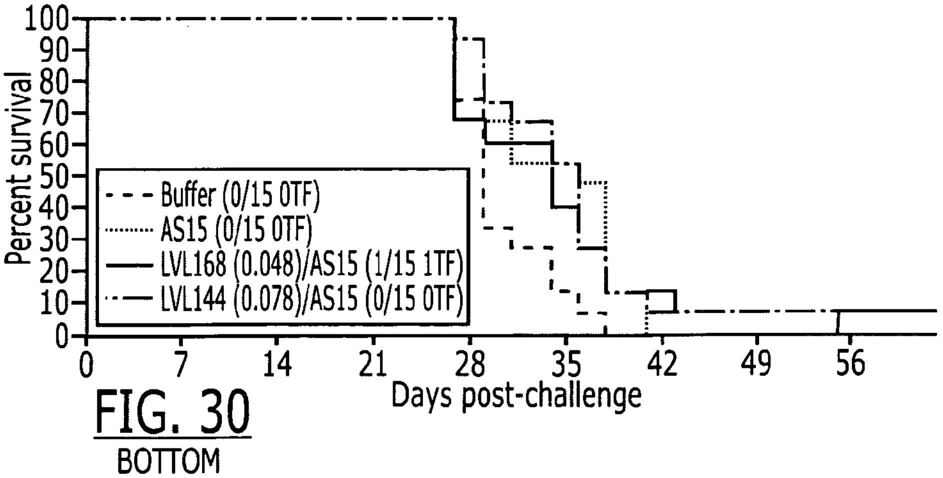

Two weeks after the fourth immunization, twenty two mice per group were subcutaneously challenged with either 250,000 TC-1/CASB7439#14 cells (non-clonal population), 250,000 TC-1/CASB7439#14-2 (clonal population) cells, or 100,000 MC38/CASB7439#35 cells. After challenge, the size of the tumors was measured three times a week for each mouse. According to protocol, mice with tumors bigger than 200 $mm^2$ were sacrificed. The TC1/CASB7439#14-2 challenge appeared more aggressive than the TC1/CASB7439#14 challenge, as evidenced by the earlier death of the control mice and the absence of a distinguishable protective effect in this particular study. See FIG. 26/35. Subsequent experiments were carried out with the more aggressive TC-1/CASB7439#14-2, as described elsewhere herein.

Study #2.1

Fifteen CB6f1 mice per group were intramuscularly immunized four times with various equimolar doses of either LVL168 or LVL144 formulated with AS15 at a final concentration as described elsewhere herein. For LVL168, the following antigen doses were used: 0.77, 1.5, 3.1 and 6.25 μg per mouse. For LVL144, the following antigen doses were used: 1.25, 2.5, 5 and 10 μg per mouse. A control group immunized with AS15 alone was also tested. Two weeks after the fourth immunization, all mice were subcutaneously challenged with 250.000 TC-1/CASB7439 #14-2 (clonal population) cells. After challenge, the size of the tumors was measured three times a week for each mouse. Mice with tumors bigger than 289 $mm^2$ (17 mm×17 mm) were sacrificed. Survival curves for each group were drawn. See FIG. 27/35, which depicts the survival curves obtained with equimolar doses of LVL168 and LVL144, formulated with AS15 after a TC1/CASB7439 #14-2 tumor challenge. TF stands for tumor-free mice. In comparison with the AS15 control group, the four sets of equimolar doses of LVL144 and LVL168 seem to inhibit tumor growth similarly in CB6f1 mice.

Study #2.2

Fifteen C57Bl/6 mice per group were intramuscularly immunized four times with various equimolar doses of LVL168 or LVL144 formulated with AS15 at a final concentration as described elsewhere herein. For LVL168, the following doses of antigen were used: 0.77, 1.5, 3.1 and 6.25 μg per mouse. For LVL144, the following doses of antigen were used: 1.25, 2.5, 5 and 10 μg per mouse. As control groups, mice were also immunized with AS15 alone or a buffer. Two weeks after the fourth immunization, all mice were subcutaneously challenged with 250.000 TC-1/CASB7439 #14-2 (clonal population) cells. After challenge, the size of the tumors was measured three times a week for each mouse. Mice with tumors bigger than 289 $mm^2$ (17 mm×17 mm) were sacrificed. Survival curves for each group were drawn. See FIG. 28/35, which depicts the survival curves obtained with the different equimolar doses of LVL168 and LVL144, formulated with AS15 after a TC1/CASB7439 #14-2 tumor challenge. TF stands for tumor-free mice. In contrast with the studies conducted with CB6f1 mice, in the present study, no statistically significant difference between the survival of C57Bl/6 mice in the immunized groups, the AS15 group, or the buffer group was observed.

Study #2.3

Fifteen CB6f1 mice per group were intramuscularly immunized four times with various equimolar doses of LVL168 or LVL144 formulated with AS15 at a final concentration as described elsewhere herein. For LVL168, the following doses were used: 0.04, 0.19, 0.77, 1.5, 3.1 and 6.25 μg per mouse.

For LVL144, the following doses were used: 0.078, 0.31, 1.25, 2.5, 5 and 10 μg per mouse. A control group immunized with AS15 alone has also been tested. Naive mice were also used as a second control group. Two weeks after the fourth immunization, all mice were subcutaneously challenged with 250,000 TC-1/CASB7439#14-2 (clonal population) cells. After challenge, the size of the tumors was measured three times a week for each mouse. Mice with tumors bigger than 289 $mm^2$ (17 mm×17 mm) were sacrificed. Survival curves for each group were drawn. See FIGS. 29/35 and 30/35, which depict the survival curves obtained with the different equimolar doses of LVL168 and LVL144, formulated with AS15 after a TC1/CASB7439 #14-2 tumor challenge. TF stands for tumor-free mice.

The two lowest equimolar doses tested did not appear to significantly inhibit the tumor growth. At the four highest doses, more tumor protection was observed in those mice immunized with LVL168 plus AS15 as compared to LVL144 plus AS15.

Study #2.4

The lack of protection observed in C57Bl/6 mice immunized with CASB7439 formulated with AS15 against a TC1/CASB7439 #14-2 tumor challenge, as observed in study #2.2, was further investigated. Fifteen CB6f1 or C57Bl/6 mice per group were intramuscularly immunized four times with 1 μg of LVL168 formulated with AS15, at a final concentration as described elsewhere herein. Male and female groups of mice immunized with 1 μg of LVL168+AS15 were studied separately. Separate control male and female groups immunized with AS15 alone were also tested.

Figure 33:
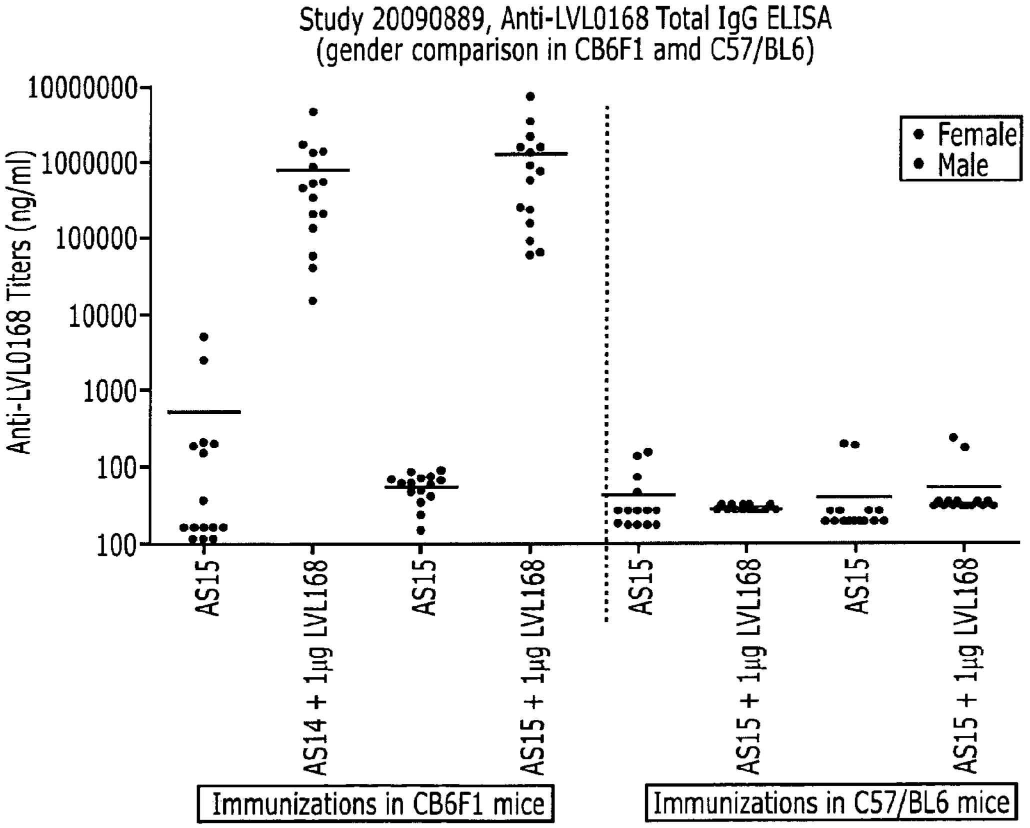
FIG. 33/35. CASB7439-specific humoral immune response (IgG titer) in male (black circles) and female (gray circles) CB6F1 mice immunized with 1 μg of LVL168 formulated with AS15, or with AS15 alone (left). CASB7439-specific humoral immune response (IgG titer) in male (black circles) and female (gray circles) C57/BL6 mice immunized with 1 μg of LVL168 formulated with AS15, or with AS15 alone (right).

Partial bleeds were obtained 7 days after the fourth immunization and the anti-CASB7439 total IgG serum antibody titers were determined by ELISA, as described in Example 10. Similar CASB7439-specific CD4 T-cell responses (approximately $1\times10^6$ ng/ml total IgG) were obtained in both male and female CB6f1 mice immunized with LVL168+AS15; no antibody response was detected in C57Bl/6 mice. See FIG. 33/35.

Figure 34:
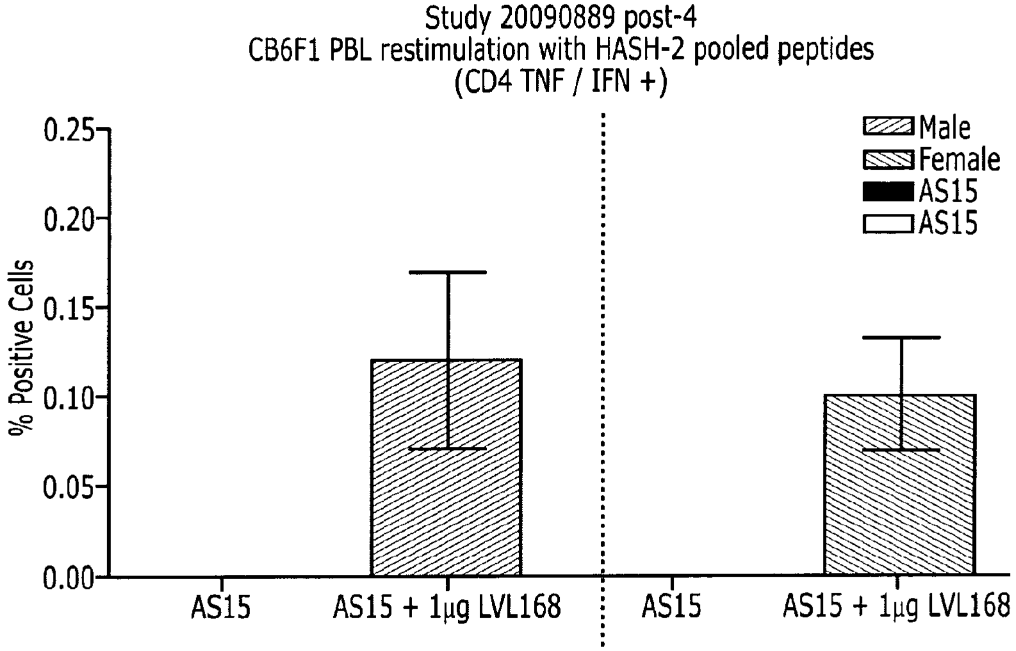
FIG. 34/35. CD4 T-cell responses (expressed as percent double positive (IFNγ/TNFα)) in pooled PBL isolated from CB6F1 mice immunized with either 1 μg of LVL168 (SEQ ID NO:11) formulated with AS15, or AS15 alone, following re-stimulation with a bank of 46 peptides (see FIG. 9) covering the entire CASB7439 protein sequence (top). CD4 T-cell responses (expressed as percent double positive (IFNγ/TNFα)) in pooled PBLs isolated from C57/BL6 mice immunized with either 1 μg of LVL168 (SEQ ID NO:11) formulated with AS15, or AS15 alone, following re-stimulation with CASB7439 pooled peptides a bank of 46 peptides (see FIG. 9) covering the entire CASB7439 protein sequence (bottom left); CASB7439 peptide 39 (SEQ ID NO:91) (bottom middle); or RPMI (bottom right).
Figure 34:
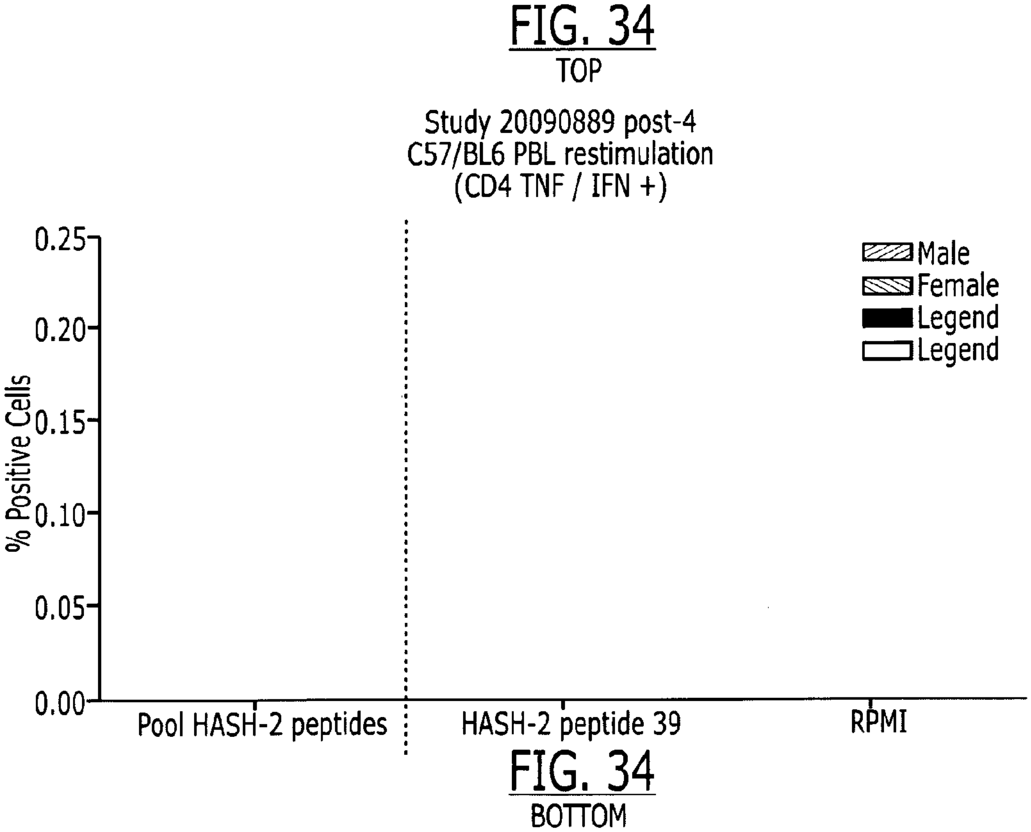
Figure 35:
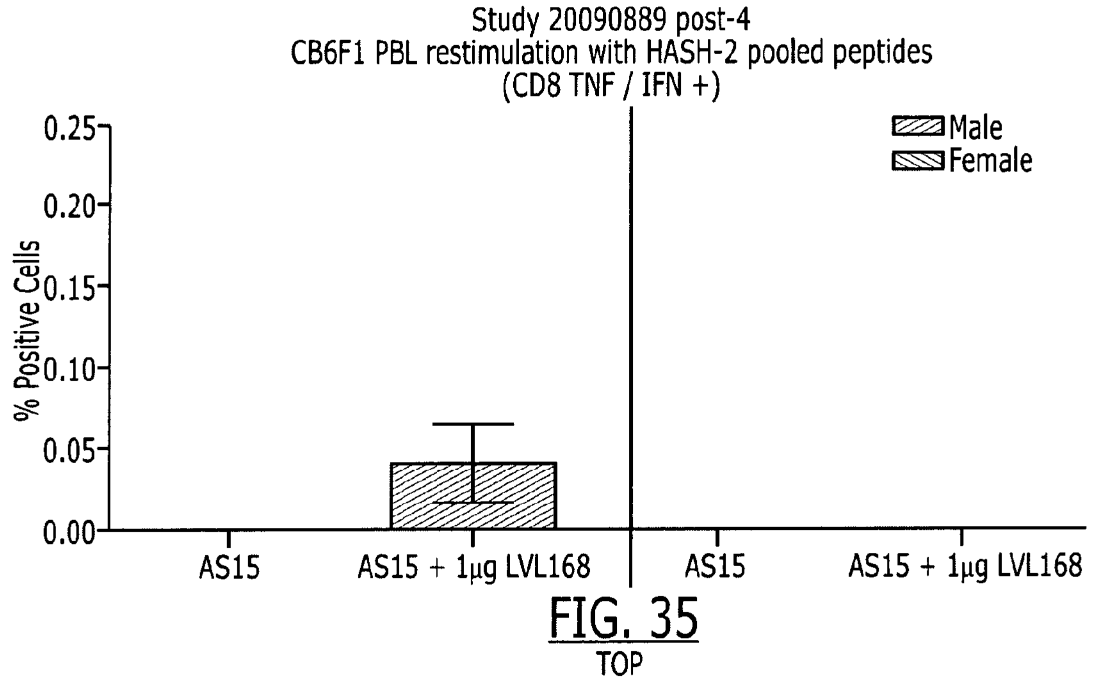
FIG. 35/35. CD8 T-cell responses (expressed as percent double positive (IFNγ/TNFα)) in pooled PBL isolated from CB6F1 mice immunized with either 1 μg of LVL168 (SEQ ID NO:11) formulated with AS15, or AS15 alone, following re-stimulation with a bank of 46 peptides (see FIG. 9) covering the entire CASB7439 protein sequence (top). CD8 T-cell responses (expressed as percent double positive (IFNγ/TNFα)) in pooled PBLs isolated from C57/BL6 mice immunized with either 1 μg of LVL168 (SEQ ID NO:11) formulated with AS15, or AS15 alone, following re-stimulation with a bank of 46 peptides (see FIG. 9) covering the entire CASB7439 protein sequence (bottom left); CASB7439 peptide 39 (SEQ ID NO:91) (bottom middle); or RPMI (bottom right).
Figure 35:
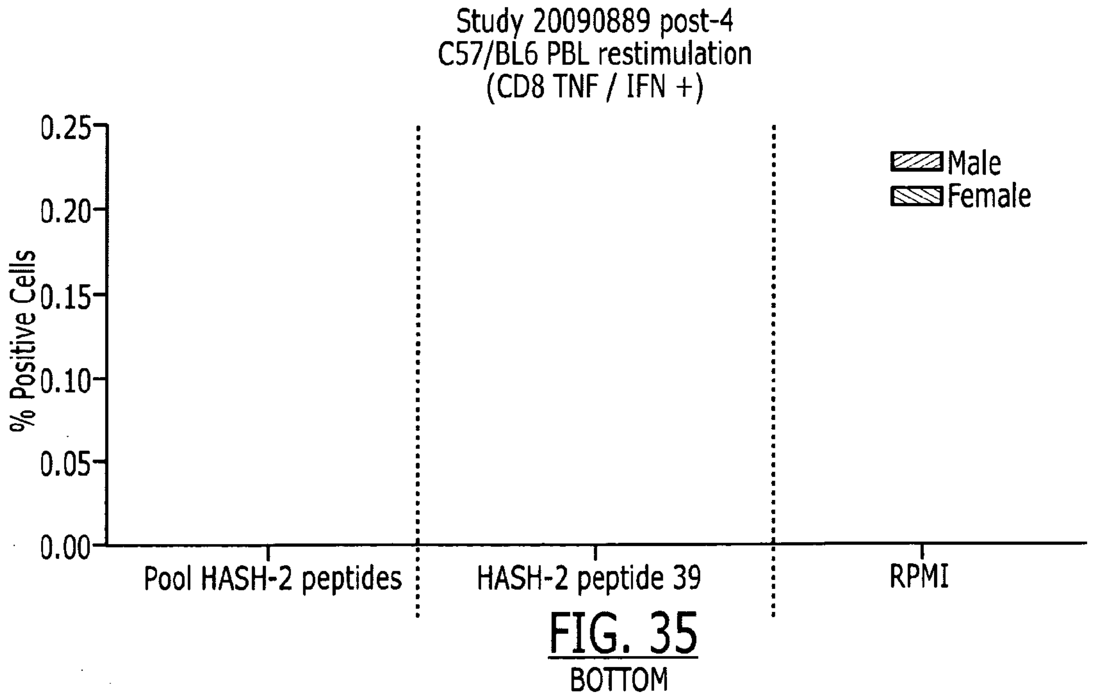

Partial bleeds were obtained 14 days after the fourth immunization. The CD4 and CD8 T-cell responses (double positive IFNγ and TNFα) were measured by intracellular staining and flow cytometry analysis, as described in Example 10, after PBLs from either CB6f1 or C57Bl/6 mice (5 pools of 3 mice per group) were restimulated with a pool of peptides covering the entire CASB7439 sequence. In addition, peptide 39 (SEQ ID NO:91) was tested with PBLs from C57Bl/6. Similar CASB7439-specific CD4 T-cell responses (approximately 0.1% frequency) were obtained in both male and female CB6f1 mice immunized with LVL168+AS15; a CASB7439-specific CD8 T-cell response (0.05% frequency) was obtained only in the male mice. See FIGS. 34/35 and 35/35, top panels. No CASB7439-specific CD4 or CD8 T-cell response was detected in C57Bl/6 mice immunized with 1 μg LVL168+AS15 after PBL restimulation with a pool of peptides covering the entire CASB7439 sequence or CASB7439 peptide 39 (SEQ ID NO:91) (aa 153 to 167 of SEQ ID NO:13). See FIGS. 34/35 and 35/35 (bottom panels). Note that the CASB7439 peptide 39 (SEQ ID NO:91) was utilized independently here because it had previously been identified as a low CD4 T cell immunogenic peptide in the splenocytes of C57Bl/6 mice immunized four times with 10 μg LVL168+AS15. See FIG. 13 in Example 10.

Figure 31:
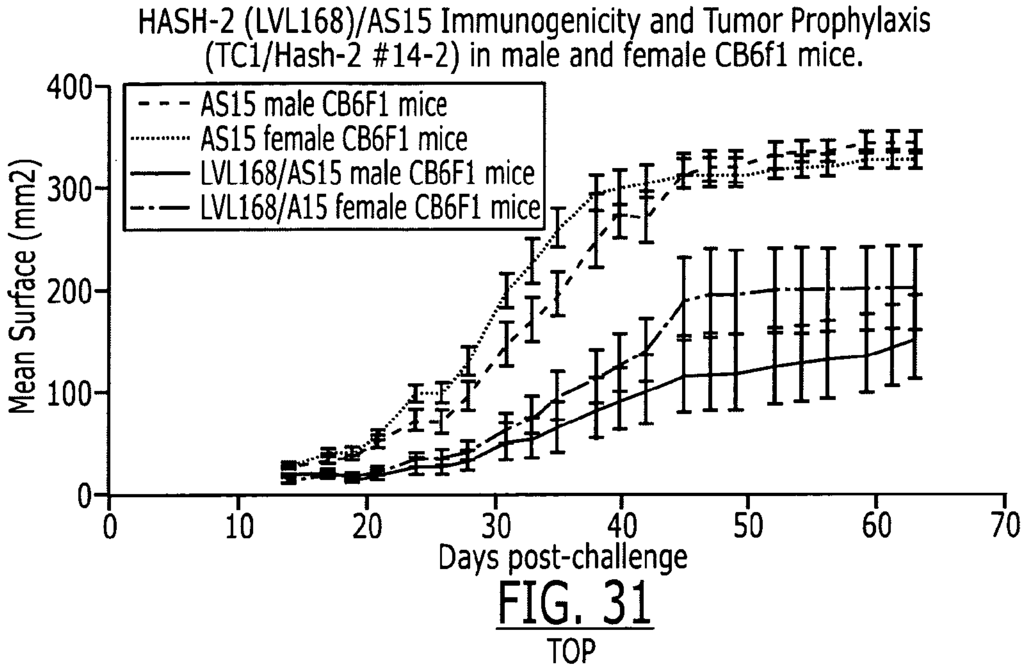
FIG. 31/35. TC1/CASB7439 #14-2 tumor graft in male and female CB6f1 mice immunized with 1 μg of LVL168 formulated with AS15; AS15 alone was used as control (top). TC1/CASB7439 #14-2 tumor graft in C57Bl/6 mice immunized with 1 μg of LVL168 formulated with AS15; AS15 alone was used as control (bottom).
Figure 31:
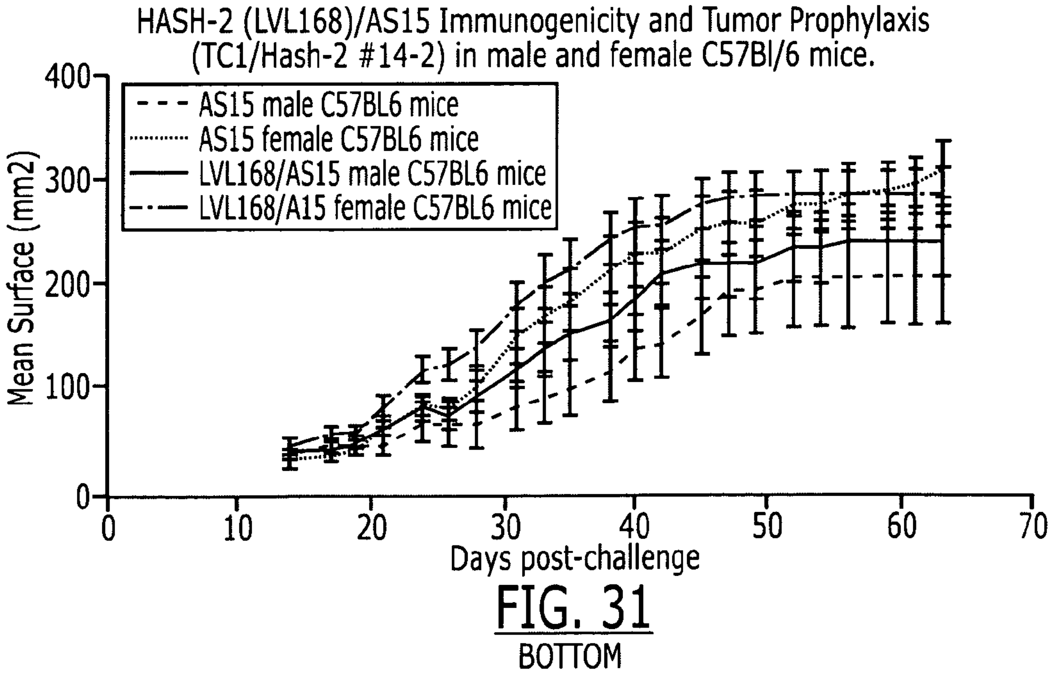
Figure 32:
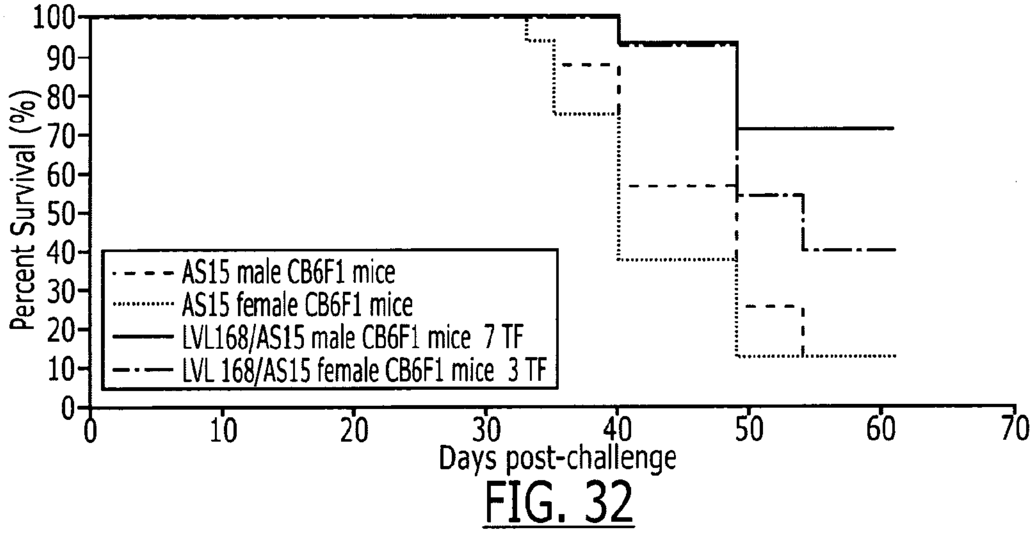
FIG. 32/35. Top panel: Survival curve of male or female CB6f1 mice immunized with 1 μg of LVL168 formulated with AS15 and challenged with TC1/CASB7439 #14-2 cells. AS15 alone was used as control in both male and female CB6f1 mice. Among the CB6f1 mice immunized with LVL168 plus AS15, there were 7 tumor-free (TF) males and 3 TF females. There were no TF among the mice receiving AS15 alone. Bottom panel: Survival curve of C57Bl/6 mice immunized with 1 μg of LVL168 formulated with AS15 and challenged with TC1/CASB7439 #14-2 cells. AS15 alone was used as control in both male and female C57Bl/6 mice. Among the C57Bl/6 mice immunized with LVL168 plus AS15, there were 2 TF males and 1 TF females. Among the mice receiving AS15 alone, there were 5 TF males and 1 TF female.
Figure 32:
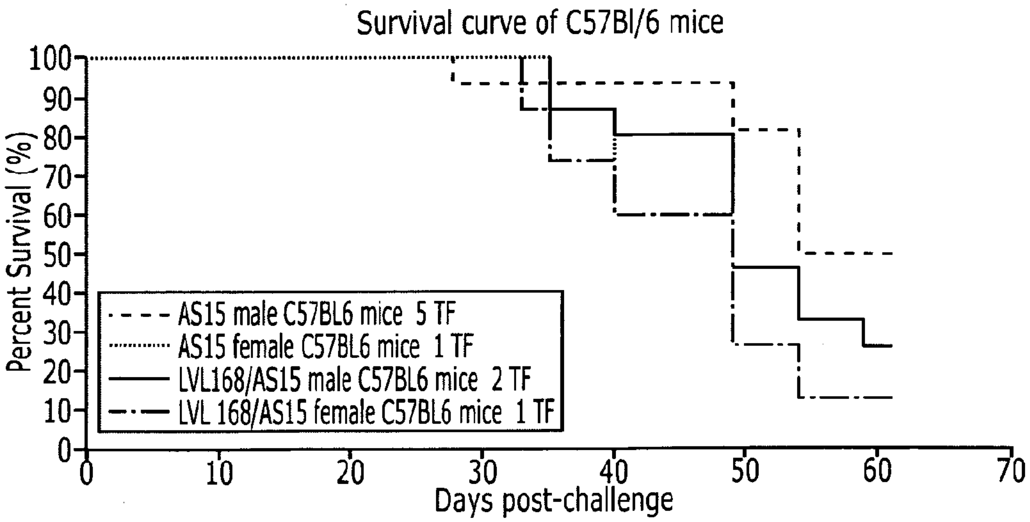

Two weeks after the fourth immunization, all mice were subcutaneously challenged with 250,000 TC-1/CASB7439#14-2 cells. After challenge, the size of the tumors was measured three times a week for each mouse. Mice with tumors bigger than 289 $mm^2$ (17 mm×17 mm) were sacrificed. Tumor growth and survival curves for each group were drawn. FIGS. 31/35 and 32/35 depict, respectively, the tumor growth and survival curves obtained with male or female CB6f1 or C57Bl/6 mice immunized with 1 μg of LVL168 or LVL144, formulated with AS15, after a TC1/CASB7439 #14-2 tumor challenge. The results indicate that CASB7439+AS15 tends to yield slower tumor growth and better survival in male CB6f1 mice compared to female CB6f1, but has no effect on tumor protection in C57Bl/6 mice. The lack of CASB7439 tumor protection in C57Bl/6 mice corresponds to the absence of detectable CASB7439-specific CD4 and CD8 T-cells, as well as the absence of a detectable CASB7439-specific antibody response in C57Bl/6 mice. This indicates that, under the experimental conditions used, C57Bl/6 mice are not an ideal mouse model to study immunogenicity and tumor protection by CASB7439. On the other hand, in CB6f1 mice, the observed CASB7439 tumor protection corresponds to the presence of significant CASB7439-specific CD4 T-cells [see immunogenic peptides 7-8 (aa 25 to 43 of SEQ ID NO:13) and 23-24 (aa 89 to 107 of SEQ ID NO:13) FIG. 13/35, Example 10] and CASB7439-specific CD8 T-cells, as well as a CASB7439-specific antibody response.

SEQUENCES:

SEQ ID NO: 1

LVL055 protein

MGHHHHHHHHHHSSGHIDDDDKHMDGGTLPRSAPPAPPVPVGCAARRRPASPELLRCSRRRRPA

TAETGGGAAAVARRNERERNRVKLVNLGFQALRQHVPHGGASKKLSKVETLRSAVEYIRALQRL

LAEHDAVRNALA

SEQ ID NO: 2

LVL055 DNA atgggccatcatcatcatcatcatcatcatcatcacagcagcggccatatcgacgacgacgaca agcatatggatggtggcaccctgccgcgtagcgctccgccggcaccgccggttccggttggttg tgcggcgcgtcgtcgtccggcgagcccggaactgctgcgttgcagccgtcgtcgccgtccggcc accgcggaaaccggtggtggtgcggcagcggttgcgcgtcgtaacgaacgtgaacgtaaccgtg tgaaactggtgaacctgggctttcaggcgctgcgtcagcatgtgccgcatggcggtgcgagcaa aaaactgagcaaagtggaaaccctgcgtagcgcggtggaatatattcgtgcgctgcaacgtctg ctggccgaacatgatgcggtgcgtaacgcgctggcctaa -continued

SEQ ID NO: 3

LVL111 protein
MGHHHHHHHHHHSSGHIDDDDKHMDGGTLPRSAPPAPPVPVGCAARRRPASPELLRCSRRRRPA

TAETGGGAAAVARRNERERNRVKLVNLGFQALRQHVPHGGASKKLSKVETLRSAVEYIRALQRL

LAEHDAVRNALAGGLRPQAVRPSAPRGGSSEPGSPRSAYSSDDSGCEGALSPAERELLDFSSWL

GGYHHHHHH

SEQ ID NO: 4

LVL111 DNA
atgggccatcatcatcatcatcatcatcatcatcatcacagcagcggccatatcgacgacgacgaca agcatatggatggtggcaccctgccgcgtagcgcaccgccggctccgccggttccggttggttg tgcggcgcgtcgtcgtccggcgagcccggaactgctgcgttgcagccgtcgtcgccgtccggcc accgcggaaaccggtggtggtgcggcagcggttgcgcgtcgtaacgaacgtgaacgtaaccgtg tgaaactggtgaacctgggctttcaggcgctgcgtcagcatgtgccgcatggcggtgcgagcaa aaaactgagcaaagtggaaaccctgcgtagcgcggtggaatatattcgtgcgctgcaacgtctg ctggccgaacatgatgcggtgcgtaacgcgctggccggtggtctgcgtccgcaggcggttcgtc cgagcgcgccgcgtggtggtagcagcgaaccgggtagcccgcgtagcgcctatagcagcgatga tagcggctgcgaaggtgccctgagcccggcggaacgtgaactgctggattttagcagctggctg ggcggctatcatcatcatcaccatcattaa

SEQ ID NO: 5

LVL137 protein
MGHHHHHHHHHHSSGHIDDDDKHMDGGTLPRSAPPAPPVPVGCAARRRPASPELLRCSRRRRPA

TAETGGGAAAVARRNERERNRVKLVNLGFQALRQHVPHGGASKKLSKVETLRSAVEYIRALQRL

LAEHDAVRNALAGGLRPQAVRPSAPRGGSSEPGSPRSAYSSDDSGCEGALSPAERELLDFSSWL

GGY

SEQ ID NO: 6

LVL137 DNA
atgggccatcatcatcatcatcatcatcatcatcatcacagcagcggccatatcgacgacgacgaca agcatatggatggtggcaccctgccgcgtagcgcaccgccggctccgccggttccggttggttg tgcggcgcgtcgtcgtccggcgagcccggaactgctgcgttgcagccgtcgtcgccgtccggcc accgcggaaaccggtggtggtgcggcagcggttgcgcgtcgtaacgaacgtgaacgtaaccgtg tgaaactggtgaacctgggctttcaggcgctgcgtcagcatgtgccgcatggcggtgcgagcaa aaaactgagcaaagtggaaaccctgcgtagcgcggtggaatatattcgtgcgctgcaacgtctg ctggccgaacatgatgcggtgcgtaacgcgctggccggtggtctgcgtccgcaggcggttcgtc cgagcgcgccgcgtggtggtagcagcgaaccgggtagcccgcgtagcgcctatagcagcgatga tagcggctgcgaaggtgccctgagcccggcggaacgtgaactgctggattttagcagctggctg ggcggctattaa

SEQ ID NO: 7

LVL141 protein
MDPSSHSSNMANTQMKSDKIIIAHRGASGYLPEHTLESKALAFAQQADYLEQDLAMTKDGRLVV

IHDHFLDGLTDVAKKFPHRHRKDGRYYVIDFTLKEIQSLEMTENFETAAAHMDGGTLPRSAPPA

PPVPVGCAARRRPASPELLRCSRRRRPATAETGGGAAAVARRNERERNRVKLVNLGFQALRQHV

PHGGASKKLSKVETLRSAVEYIRALQRLLAEHDAVRNALAGGLRPQAVRPSAPRGGSSEPGSPR

SAYSSDDSGCEGALSPAERELLDFSSWLGGYHHHHHH

-continued

SEQ ID NO: 8

LVL141 DNA
atggatccaagcagccattcatcaaatatggcgaatacccaaatgaaatcagacaaaatcatta ttgctcaccgtggtgctagcggttatttaccagagcatacgttagaatctaaagcacttgcgtt tgcacaacaggctgattatttagagcaagatttagcaatgactaaggatggtcgtttagtggtt attcacgatcactttttagatggcttgactgatgttgcgaaaaaattcccacatcgtcatcgta aagatggccgttactatgtcatcgactttaccttaaaagaaattcaaagtttagaaatgacaga aaactttgaaaccgcggccgcacatatggatggtggcaccctgccgcgtagcgcaccgccggct ccgccggttccggttggttgtgcggcgcgtcgtcgtccggcgagcccggaactgctgcgttgca gccgtcgtcgccgtccggccaccgcggaaaccggtggtggtgcggcagcggttgcgcgtcgtaa cgaacgtgaacgtaaccgtgtgaaactggtgaacctgggctttcaggcgctgcgtcagcatgtg ccgcatggcggtgcgagcaaaaaactgagcaaagtggaaaccctgcgtagcgcggtggaatata ttcgtgcgctgcaacgtctgctggccgaacatgatgcggtgcgtaacgcgctggccggtggtct gcgtccgcaggcggttcgtccgagcgcgccgcgtggtggtagcagcgaaccgggtagcccgcgt agcgcctatagcagcgatgatagcggctgcgaaggtgccctgagcccggcggaacgtgaactgc tggattttagcagctggctgggcggctatcatcatcatcaccatcattaa

SEQ ID NO: 9

LVL144 protein
MDPSSHSSNMANTQMKSDKIIIAHRGASGYLPEHTLESKALAFAQQADYLEQDLAMTKDGRLVV

IHDHFLDGLTDVAKKFPHRHRKDGRYYVIDFTLKEIQSLEMTENFETDGGTLPRSAPPAPPVPV

GCAARRRPASPELLRCSRRRRPATAETGGGAAAVARRNERERNRVKLVNLGFQALRQHVPHGGA

SKKLSKVETLRSAVEYIRALQRLLAEHDAVRNALAGGLRPQAVRPSAPRGGSSEPGSPRSAYSS

DDSGCEGALSPAERELLDFSSWLGGYHHHHHH

SEQ ID NO: 10

LVL144 DNA
atggatccaagcagccattcatcaaatatggcgaatacccaaatgaaatcagacaaaatcatta ttgctcaccgtggtgctagcggttatttaccagagcatacgttagaatctaaagcacttgcgtt tgcacaacaggctgattatttagagcaagatttagcaatgactaaggatggtcgtttagtggtt attcacgatcactttttagatggcttgactgatgttgcgaaaaaattcccacatcgtcatcgta aagatggccgttactatgtcatcgactttaccttaaaagaaattcaaagtttagaaatgacaga aaactttgaaaccgatggtggcaccctgccgcgtagcgcaccgccggctccgccggttccggtt ggttgtgcggcgcgtcgtcgtccggcgagcccggaactgctgcgttgcagccgtcgtcgccgtc cggccaccgcggaaaccggtggtggtgcggcagcggttgcgcgtcgtaacgaacgtgaacgtaa ccgtgtgaaactggtgaacctgggctttcaggcgctgcgtcagcatgtgccgcatggcggtgcg agcaaaaaactgagcaaagtggaaaccctgcgtagcgcggtggaatatattcgtgcgctgcaac gtctgctggccgaacatgatgcggtgcgtaacgcgctggccggtggtctgcgtccgcaggcggt tcgtccgagcgcgccgcgtggtggtagcagcgaaccgggtagcccgcgtagcgcctatagcagc gatgatagcggctgcgaaggtgccctgagcccggcggaacgtgaactgctggattttagcagct ggctgggcggctatcatcatcatcaccatcattaa

SEQ ID NO: 11

LVL168 protein
MHHHHHHHHHHHDGGTLPRSAPPAPPVPVGCAARRRPASPELLRCSRRRRPATAETGGGAAAVAR

RNERERNRVKLVNLGFQALRQHVPHGGASKKLSKVETLRSAVEYIRALQRLLAEHDAVRNALAG

GLRPQAVRPSAPRGGSSEPGSPRSAYSSDDSGCEGALSPAERELLDFSSWLGGY

-continued

SEQ ID NO: 12

LVL168 DNA
atgcatcatcatcatcatcatcatcatcatcatgacggtggcaccctgccgcgtagcgcaccgc cggctccgccggttccggttggttgtgcggcgcgtcgtcgtccggcgagcccggaactgctgcg ttgcagccgtcgtcgccgtccggccaccgcggaaaccggtggtggtgcggcagcggttgcgcgt cgtaacgaacgtgaacgtaaccgtgtgaaactggtgaacctgggctttcaggcgctgcgtcagc atgtgccgcatggcggtgcgagcaaaaaactgagcaaagtggaaaccctgcgtagcgcggtgga atatattcgtgcgctgcaacgtctgctggccgaacatgatgcggtgcgtaacgcgctggccggt ggtctgcgtccgcaggcggttcgtccgagcgcgccgcgtggtggtagcagcgaaccgggtagcc cgcgtagcgcctatagcagcgatgatagcggctgcgaaggtgccctgagcccggcggaacgtga actgctggattttagcagctggctgggcggctattaa

SEQ ID NO: 13

Accession No. AAB86993, HASH2 protein
MDGGTLPRSAPPAPPVPVGCAARRRPASPELLRCSRRRPATAETGGGAAAVARRNERERNRVK

LVNLGFQALRQHVPHGGASKKLSKVETLRSAVEYIRALQRLLAEHDAVRNALAGGLRPQAVRPS

APRGPPGTTPVAASPSRASSSPGRGGSSEPGSPRSAYSSDDSGCEGALSPAERELLDFSSWLGG

Y

SEQ ID NO: 14

HASH2 DNA
atggacggcggcacactgcccaggtccgcgccccctgcgccccccgtccctgtcggctgcgctg cccggcggagacccgcgtccccggaactgttgcgctgcagccggcggcggcgaccggccaccgc agagaccggaggcggcgcagcggccgtagcgcggcgcaatgagcgcgagcgcaaccgcgtgaag ctggtgaacttgggcttccaggcgctgcggcagcacgtgccgcacggcggcgccagcaagaagc tgagcaaggtggagacgctgcgctcagccgtggagtacatccgcgcgctgcagcgcctgctggc cgagcacgacgccgtgcgcaacgcgctggcgggagggctgaggccgcaggccgtgcggccgtct gcgccccgcgggccgccagggaccaccccggtcgccgcctcgccctcccgcgcttcttcgtccc cgggccgcgggggcagctcggagcccggctccccgcgttccgcctactcgtcggacgacagcgg ctgcgaaggcgcgctgagtcctgcggagcgcgagctactcgacttctccagctggttagggggc tactga

SEQ ID NO: 15

LVL007 protein
MGHHHHHHHHHHSSGHIDDDDKHMDGGTLPRSAPPAPPVLVGCAARRRPASPELLRCSRRRRPA

TAETGGGAAAVARRNERERNRVKLVNLGFQALRQHVPHGGASKKLSKVETLRSAVEYIRALQRL

LAEHDAVRNALAGGLRPQAVRPSAPRGPPGTTPVAASPSRASSSPGRGGSSEPGSPRSAYSSDD

SGCEGALSPAERELLDFSSWLGGY

SEQ ID NO: 16

LVL007 DNA
atgggccatcatcatcatcatcatcatcatcatcacagcagcggccatatcgacgacgacgaca agcatatggacggcggcacactgcccaggtccgcgccccctgcgccccccgtccttgtcggctg cgctgcccggcggagacccgcgtccccggaactgttgcgctgcagccggcggcggcgaccggcc accgcagagaccggaggcggcgcagcggccgtagcgcggcgcaatgagcgcgagcgcaaccgcg tgaagctggtgaacttgggcttccaggcgctgcggcagcacgtgccgcacggcggcgccagcaa gaagctgagcaaggtggagacgctgcgctcagccgtggagtacatccgcgcgctgcagcgcctg ctggccgagcacgacgccgtgcgcaacgcgctggcgggagggctgaggccgcaggccgtgcggc cgtctgcgccccgcgggccgccagggaccaccccggtcgccgcctcgccctcccgcgcttcttc -continued gtccccgggccgcgggggcagctcggagcccggctccccgcgttccgcctactcgtcggacgac agcggctgcgaaggcgcgctgagtcctgcggagcgcgagctactcgacttctccagctggttag ggggctactga

SEQ ID NO: 17

LVL010 protein
MGHHHHHHHHHHSSGHIDDDDKHMDGGTLPRSAPPAPPVPVGCAARRRPASPELLRCSRRRRPA

TAETGGGAAAVARRNERERNRVKLVNLGFQALRQHVPHGGASKKLSKVETLRSAVEYIRALQRL

LAEHDAVRNALAGGLRPQAVRPSAPRGPPGTTPVAASPSRASSSPGRGGSSEPGSPRSAYSSDD

SGCEGALSPAERELLDFSSWLGGY

SEQ ID NO: 18

LVL010 DNA
atgggccatcatcatcatcatcatcatcatcatcacagcagcggccatatcgacgacgacgaca agcatatggacggcggcacactgcccaggtccgcgccccctgcgccccccgtccctgtcggctg cgctgcccggcggagacccgcgtccccggaactgttgcgctgcagccggcggcggcgaccggcc accgcagagaccggaggcggcgcagcggccgtagcgcggcgcaatgagcgcgagcgcaaccgcg tgaagctggtgaacttgggcttccaggcgctgcggcagcacgtgccgcacggcggcgccagcaa gaagctgagcaaggtggagacgctgcgctcagccgtggagtacatccgcgcgctgcagcgcctg ctggccgagcacgacgccgtgcgcaacgcgctggcgggagggctgaggccgcaggccgtgcggc cgtctgcgccccgcgggccgccagggaccaccccggtcgccgcctcgccctcccgcgcttcttc gtccccgggccgcgggggcagctcggagcccggctccccgcgttccgcctactcgtcggacgac agcggctgcgaaggcgcgctgagtcctgcggagcgcgagctactcgacttctccagctggttag ggggctactga

SEQ ID NO: 19

LVL060 protein
MGHHHHHHHHHHSSGHIDDDDKHMDGGTLPRSAPPAPPVPVGCAARRRPASPELLRCSRRRRPA

TAETGGGAAAVARRNERERNRVKLVNLGFQALRQHVPHGGASKKLSKVETLRSAVEYIRALQRL

LAEHDAVRNALAGGLRPQAVRPSAPRGPPGTTPVAASPSRASSSPGRGGSSEPGSPRSAYSSDD

SGCEGALSPAERELLDFSSWLGGY

SEQ ID NO: 20

LVL060 DNA
atgggccatcatcatcatcatcatcatcatcatcacagcagcggccatatcgacgacgacgaca agcatatggatggtggcaccctgccgcgtagcgctccgccggcaccgccggttccggttggttg tgcggcgcgtcgtcgtccggcgagcccggaactgctgcgttgcagccgtcgtcgccgtccggcc accgcggaaaccggtggtggtgcggcagcggttgcgcgtcgtaacgaacgtgaacgtaaccgtg tgaaactggtgaacctgggctttcaggcgctgcgtcagcatgtgccgcatggcggtgcgagcaa aaaactgagcaaagtggaaaccctgcgtagcgcggtggaatatattcgtgcgctgcaacgtctg ctggccgaacatgatgcggtgcgtaacgcgctggccggtggtctgcgtccgcaggcggttcgtc cgagcgcaccgcgtggtccgccgggtacgacgccggttgcagcgagcccgagccgtgcgagcag ctctccgggtcgtggtggtagcagcgaaccgggtagcccgcgtagcgcctatagcagcgatgat agcggctgcgaaggtgccctgtctccggcggaacgtgaactgctggattttagcagctggctgg gcggctattaa

SEQ ID NO: 21

Const-1 Protein
MGHHHHHHHHHHSSGHIDDDDKHMATAETGGGAAAVARRNERERNRVKLVNLGFQALRQHVPHG

GASKKLSKVETLRSAVEYIRALQRLLAEHDAVRNALAGGLRPQAVRPSAPRGPPGTTPVAASPS

-continued

RASSSPGRGGSSEPGSPRSAYSSDDSGCEGALSPAERELLDFSSWLGGYLEDPAANKARKEAEL

AAATAEQ

SEQ ID NO: 22

Const-1 DNA atgggccatcatcatcatcatcatcatcatcatcacagcagcggccatatcgacgacgacgaca agcatatggccaccgcggaaaccggtggtggtgcggcagcggttgcgcgtcgtaacgaacgtga acgtaaccgtgtgaaactggtgaacctgggctttcaggcgctgcgtcagcatgtgccgcatggc ggtgcgagcaaaaaactgagcaaagtggaaaccctgcgtagcgcggtggaatatattcgtgcgc tgcaacgtctgctggccgaacatgatgcggtgcgtaacgcgctggccggtggtctgcgtccgca ggcggttcgtccgagcgcaccgcgtggtccgccgggtacgacgccggttgcagcgagcccgagc cgtgcgagcagctctccgggtcgtggtggtagcagcgaaccgggtagcccgcgtagcgcctata gcagcgatgatagcggctgcgaaggtgccctgtctccggcggaacgtgaactgctggattttag cagctggctgggcggctatctcgaggatccggctgctaacaaagcccgaaaggaagctgagttg gctgctgccaccgctgagcaataa

SEQ ID NO: 23

LVL056 Protein

MGHHHHHHHHHHSSGHIDDDDKHMNRVKLVNLGFQALRQHVPHGGASKKLSKVETLRSAVEYIR

ALQRLLAEHDAVRNALAGGLRPQAVRPSAPRGPPGTTPVAASPSRASSSPGRGGSSEPGSPRSA

YSSDDSGCEGALSPAERELLDFSSWLGGY

SEQ ID NO: 24

LVL056 DNA atgggccatcatcatcatcatcatcatcatcatcacagcagcggccatatcgacgacgacgaca agcatatgaaccgtgtgaaactggtgaacctgggctttcaggcgctgcgtcagcatgtgccgca tggcggtgcgagcaaaaaactgagcaaagtggaaaccctgcgtagcgcggtggaatatattcgt gcgctgcaacgtctgctggccgaacatgatgcggtgcgtaacgcgctggccggtggtctgcgtc cgcaggcggttcgtccgagcgcaccgcgtggtccgccgggtacgacgccggttgcagcgagccc gagccgtgcgagcagctctccgggtcgtggtggtagcagcgaaccgggtagcccgcgtagcgcc tatagcagcgatgatagcggctgcgaaggtgccctgtctccggcggaacgtgaactgctggatt ttagcagctggctgggcggctattaa

SEQ ID NO: 25

LVL057 Protein

MGHHHHHHHHHHSSGHIDDDDKHMAAAVARRNERERNRVKLVNLGFQALRQHVPHGGASKKLSK

VETLRSAVEYIRALQRLLAEHDAVRNALA

SEQ ID NO: 26

LVL057 DNA atgggccatcatcatcatcatcatcatcatcatcacagcagcggccatatcgacgacgacgaca agcatatggcggcagcggttgcgcgtcgtaacgaacgtgaacgtaaccgtgtgaaactggtgaa cctgggctttcaggcgctgcgtcagcatgtgccgcatggcggtgcgagcaaaaaactgagcaaa gtggaaaccctgcgtagcgcggtggaatatattcgtgcgctgcaacgtctgctggccgaacatg atgcggtgcgtaacgcgctggcctaa

SEQ ID NO: 27

LVL088 Protein

MDGGTLPRSAPPAPPVPVGCAARRRPASPELLRCSRRRRPATAETGGGAAAVARRNERERNRVK

LVNLGFQALRQHVPHGGASKKLSKVETLRSAVEYIRALQRLLAEHDAVRNALAGGLRPQAVRPS

APRGGSSEPGSPRSAYSSDDSGCEGALSPAERELLDFSSWLGGYHHHHHH

-continued

SEQ ID NO: 28
LVL088 DNA
atggatggtggcaccctgccgcgtagcgcaccgccggctccgccggttccggttggttgtgcgg cgcgtcgtcgtccggcgagcccggaactgctgcgttgcagccgtcgtcgccgtccggccaccgc ggaaaccggtggtggtgcggcagcggttgcgcgtcgtaacgaacgtgaacgtaaccgtgtgaaa ctggtgaacctgggctttcaggcgctgcgtcagcatgtgccgcatggcggtgcgagcaaaaaac tgagcaaagtggaaaccctgcgtagcgcggtggaatatattcgtgcgctgcaacgtctgctggc cgaacatgatgcggtgcgtaacgcgctggccggtggtctgcgtccgcaggcggttcgtccgagc gcgccgcgtggtggtagcagcgaaccgggtagcccgcgtagcgcctatagcagcgatgatagcg gctgcgaaggtgccctgagcccggcggaacgtgaactgctggattttagcagctggctgggcgg ctatcatcatcatcaccatcattaa SEQ ID NO: 29
LVL016 Protein
MDPSSHSSNMANTQMKSDKIIIAHRGASGYLPEHTLESKALAFAQQADYLEQDLAMTKDGRLVV

IHDHFLDGLTDVAKKFPHRHRKDGRYYVIDFTLKEIQSLEMTENFETAAAMDGGTLPRSAPPAP

PVPVGCAARRRPASPELLRCSRRRRPATAETGGGAAAVARRNERERNRVKLVNLGFQALRQHVP

HGGASKKLSKVETLRSAVEYIRALQRLLAEHDAVRNALAGGLRPQAVRPSAPRGPPGTTPVAAS

PSRASSSPGRGGSSEPGSPRSAYSSDDSGCEGALSPAERELLDFSSWLGGYLEHHHHHH

SEQ ID NO: 30
LVL016 DNA
atggatccaagcagccattcatcaaatatggcgaatacccaaatgaaatcagacaaaatcatta ttgctcaccgtggtgctagcggttatttaccagagcatacgttagaatctaaagcacttgcgtt tgcacaacaggctgattatttagagcaagatttagcaatgactaaggatggtcgtttagtggtt attcacgatcactttttagatggcttgactgatgttgcgaaaaaattcccacatcgtcatcgta aagatggccgttactatgtcatcgactttaccttaaaagaaattcaaagtttagaaatgacaga aaactttgaaaccgcggccgcaatggatggtggcaccctgccgcgtagcgctccgccggcaccg ccggttccggttggttgtgcggcgcgtcgtcgtccggcgagcccggaactgctgcgttgcagcc gtcgtcgccgtccggccaccgcggaaaccggtggtggtgcggcagcggttgcgcgtcgtaacga acgtgaacgtaaccgtgtgaaactggtgaacctgggctttcaggcgctgcgtcagcatgtgccg catggcggtgcgagcaaaaaactgagcaaagtggaaaccctgcgtagcgcggtggaatatattc gtgcgctgcaacgtctgctggccgaacatgatgcggtgcgtaacgcgctggccggtggtctgcg tccgcaggcggttcgtccgagcgcaccgcgtggtccgccgggtacgacgccggttgcagcgagc ccgagccgtgcgagcagctctccgggtcgtggtggtagcagcgaaccgggtagcccgcgtagcg cctatagcagcgatgatagcggctgcgaaggtgccctgtctccggcggaacgtgaactgctgga ttttagcagctggctgggcggctatctcgagcaccaccaccaccaccactga SEQ ID NO: 31
LVL018 Protein
MDGGTLPRSAPPAPPVPVGCAARRRPASPELLRCSRRRRPATAETGGGAAAVARRNERERNRVK

LVNLGFQALRQHVPHGGASKKLSKVETLRSAVEYIRALQRLLAEHDAVRNALAGGLRPQAVRPS

APRGPPGTTPVAASPSRASSSPGRGGSSEPGSPRSAYSSDDSGCEGALSPAERELLDFSSWLGG

YLEHHHHHH

SEQ ID NO: 32
LVL018 DNA
atggatggtggcaccctgccgcgtagcgctccgccggcaccgccggttccggttggttgtgcgg cgcgtcgtcgtccggcgagcccggaactgctgcgttgcagccgtcgtcgccgtccggccaccgc -continued ggaaaccggtggtggtgcggcagcggttgcgcgtcgtaacgaacgtgaacgtaaccgtgtgaaa ctggtgaacctgggctttcaggcgctgcgtcagcatgtgccgcatggcggtgcgagcaaaaaac tgagcaaagtggaaaccctgcgtagcgcggtggaatatattcgtgcgctgcaacgtctgctggc cgaacatgatgcggtgcgtaacgcgctggccggtggtctgcgtccgcaggcggttcgtccgagc gcaccgcgtggtccgccgggtacgacgccggttgcagcgagcccgagccgtgcgagcagctctc cgggtcgtggtggtagcagcgaaccgggtagcccgcgtagcgcctatagcagcgatgatagcgg ctgcgaaggtgccctgtctccggcggaacgtgaactgctggattttagcagctggctgggcggc tatctcgagcaccaccaccaccaccactga

SEQ ID NO: 33

LVL138 Protein

MHHHHHHDGGTLPRSAPPAPPVPVGCAARRRPASPELLRCSRRRRPATAETGGGAAAVARRNER

ERNRVKLVNLGFQALRQHVPHGGASKKLSKVETLRSAVEYIRALQRLLAEHDAVRNALAGGLRP

QAVRPSAPRGGSSEPGSPRSAYSSDDSGCEGALSPAERELLDFSSWLGGY

SEQ ID NO: 34

LVL138 DNA atgcaccatcaccatcaccatgatggtggcaccctgccgcgtagcgcaccgccggctccgccgg ttccggttggttgtgcggcgcgtcgtcgtccggcgagcccggaactgctgcgttgcagccgtcg tcgccgtccggccaccgcggaaaccggtggtggtgcggcagcggttgcgcgtcgtaacgaacgt gaacgtaaccgtgtgaaactggtgaacctgggctttcaggcgctgcgtcagcatgtgccgcatg gcggtgcgagcaaaaaactgagcaaagtggaaaccctgcgtagcgcggtggaatatattcgtgc gctgcaacgtctgctggccgaacatgatgcggtgcgtaacgcgctggccggtggtctgcgtccg caggcggttcgtccgagcgcgccgcgtggtggtagcagcgaaccgggtagcccgcgtagcgcct atagcagcgatgatagcggctgcgaaggtgccctgagcccggcggaacgtgaactgctggattt tagcagctggctgggcggctattaa

SEQ ID NO: 35

Modified linker DNA atgcatcatcatcatcatcatgac

SEQ ID NO: 36

Unmodified linker DNA atgcaccatcaccatcaccatgat

SEQ ID NO: 37

LVL160 Protein

MHHHHHHDGGTLPRSAPPAPPVPVGCAARRRPASPELLRCSRRRRPATAETGGGAAAVARRNER

ERNRVKLVNLGFQALRQHVPHGGASKKLSKVETLRSAVEYIRALQRLLAEHDAVRNALAGGLRP

QAVRPSAPRGGSSEPGSPRSAYSSDDSGCEGALSPAERELLDFSSWLGGY

SEQ ID NO: 38

LVL160 DNA atgcatcatcatcatcatcatgacggtggcaccctgccgcgtagcgcaccgccggctccgccgg ttccggttggttgtgcggcgcgtcgtcgtccggcgagcccggaactgctgcgttgcagccgtcg tcgccgtccggccaccgcggaaaccggtggtggtgcggcagcggttgcgcgtcgtaacgaacgt gaacgtaaccgtgtgaaactggtgaacctgggctttcaggcgctgcgtcagcatgtgccgcatg gcggtgcgagcaaaaaactgagcaaagtggaaaccctgcgtagcgcggtggaatatattcgtgc gctgcaacgtctgctggccgaacatgatgcggtgcgtaacgcgctggccggtggtctgcgtccg caggcggttcgtccgagcgcgccgcgtggtggtagcagcgaaccgggtagcccgcgtagcgcct atagcagcgatgatagcggctgcgaaggtgccctgagcccggcggaacgtgaactgctggattt tagcagctggctgggcggctattaa -continued

SEQ ID NO: 39

1/3 pD Protein
MDPSSHSSNMANTQMKSDKIIIAHRGASGYLPEHTLESKALAFAQQADYLEQDLAMTKDGRLVV

IHDHFLDGLTDVAKKFPHRHRKDGRYYVIDFTLKEIQSLEMTENFET

SEQ ID NO: 40

1/3 pD DNA
atggatccaagcagccattcatcaaatatggcgaatacccaaatgaaatcagacaaaatcatta ttgctcaccgtggtgctagcggttatttaccagagcatacgttagaatctaaagcacttgcgtt tgcacaacaggctgattatttagagcaagatttagcaatgactaaggatggtcgtttagtggtt attcacgatcactttttagatggcttgactgatgttgcgaaaaaattcccacatcgtcatcgta aagatggccgttactatgtcatcgactttaccttaaaagaaattcaaagtttagaaatgacaga aaactttgaaacc

SEQ ID NO: 41

H. influenzae Protein D
MKLKTLALSLLAAGVLAGCSSHSSNMANTQMKSDKIIIAHRGASGYLPEHTLESKALAFAQQAD

YLEQDLAMTKDGRLVVIHDHFLDGLTDVAKKFPHRHRKDGRYYVIDFTLKEIQSLEMTENFETK

DGKQAQVYPNRFPLWKSHFRIHTFEDEIEFIQGLEKSTGKKVGIYPEIKAPWFHHQNGKDIAAE

TLKVLKKYGYDKKTDMVYLQTFDFNELKRIKTELLPQMGMDLKLVQLIAYTDWKETQEKDPKGY

WVNYNYDWMFKPGAMAEVVKYADGVGPGWYMLVNKEESKPDNIVYTPLVKELAQYNVEVHPYTV

RKDALPEFFTDVNQMYDALLNKSGATGVFTDFPDTGVEFLKGIK

SEQ ID NO: 42

Long polyhistidine tag
MGHHHHHHHHHHSSGHIDDDDKH

SEQ ID NO: 43

LVL090 Protein
MDPSSHSSNMANTQMKSDKIIIAHRGASGYLPEHTLESKALAFAQQADYLEQDLAMTKDGRLVV

IHDHFLDGLTDVAKKFPHRHRKDGRYYVIDFTLKEIQSLEMTENFETKDGKQAQVYPNRFPLWK

SHFRIHTFEDEIEFIQGLEKSTGKKVGIYPEIKAPWFHHQNGKDIAAETLKVLKKYGYDKKTDM

VYLQTFDFNELKRIKTELLPQMGMDLKLVQLIAYTDWKETQEKDPKGYWVNYNYDWMFKPGAMA

EVVKYADGVGPGWYMLVNKEESKPDNIVYTPLVKELAQYNVEVHPYTVRKDALPAFFTDVNQMY

DVLLNKSGATGVFTDFPDTGVEFLKGIKAAAMDGGTLPRSAPPAPPVPVGCAARRRPASPELLR

CSRRRRPATAETGGGAAAVARRNERERNRVKLVNLGFQALRQHVPHGGASKKLSKVETLRSAVE

YIRALQRLLAEHDAVRNALAGGLRPQAVRPSAPRGPPGTTPVAASPSRASSSPGRGGSSEPGSP

RSAYSSDDSGCEGALSPAERELLDFSSWLGGYLEHHHHHH

SEQ ID NO: 44

LVL090 DNA
atggatccaagcagccattcatcaaatatggcgaatacccaaatgaaatcagacaaaatcatta ttgctcaccgtggtgctagcggttatttaccagagcatacgttagagtctaaagcacttgcgtt tgcacaacaggctgattatttagagcaagatttagcaatgactaaggatggtcgtttagtggtt attcacgatcactttttagatggcttgactgatgttgcgaaaaaattcccacatcgtcaccgta aagatggtcgttactatgtcatcgactttaccttaaaagaaattcaaagtttagaaatgacaga aaactttgaaaccaaagatggcaaacaagcgcaagtttatcctaatcgtttccccactttggaaa tcacattttagaattcatacctttgaagatgaaattgaatttatccaaggcttagaaaaatcca ctggcaaaaaagtagggatttatccagaaatcaaagcaccttggttccaccatcaaaatggtaa agatattgctgctgaaacgctcaaagtgttaaaaaaatatggctatgataagaaaaccgatatg gtttacttacaaactttcgattttaatgaattaaaacgtatcaaaacggaattacttccacaaa -continued tgggaatggatttgaaattagttcaattaattgcttatacagattggaaagaaacacaagaaaa agacccaaagggttattgggtaaactataattacgattggatgtttaaacctggtgcaatggca gaagtggttaaatatgccgatggtgttggcccaggttggtatatgttagttaataaagaagaat ccaaacctgataatattgtgtacactccgttggtaaaagaacttgcacaatataatgtggaagt gcatccttacaccgtgcgtaaagatgcactacccgcgtttttcacagacgtaaatcaaatgtat gatgtcttattgaataaatcaggggcaacaggtgtatttactgatttcccagatactggcgtgg aattcttaaaaggaataaaagcggccgcaatggatggtggcaccctgccgcgtagcgctccgcc ggcaccgccggttccggttggttgtgcggcgcgtcgtcgtccggcgagcccggaactgctgcgt tgcagccgtcgtcgccgtccggccaccgcggaaaccggtggtggtgcggcagcggttgcgcgtc gtaacgaacgtgaacgtaaccgtgtgaaactggtgaacctgggctttcaggcgctgcgtcagca tgtgccgcatggcggtgcgagcaaaaaactgagcaaagtggaaaccctgcgtagcgcggtggaa tatattcgtgcgctgcaacgtctgctggccgaacatgatgcggtgcgtaacgcgctggccggtg gtctgcgtccgcaggcggttcgtccgagcgcaccgcgtggtccgccgggtacgacgccggttgc agcgagcccgagccgtgcgagcagctctccgggtcgtggtggtagcagcgaaccgggtagcccg cgtagcgcctatagcagcgatgatagcggctgcgaaggtgccctgtctccggcggaacgtgaac tgctggattttagcagctggctgggcggctatctcgagcaccaccaccaccaccac

SEQ ID NO: 45

LVL112 Protein

MGHHHHHHGSDSEVNQEAKPEVKPEVKPETHINLKVSDGSSEIFFKIKKTTPLRRLMEAFAKRQ

GKEMDSLRFLYDGIRIQADQAPEDLDMEDNDIIEAHREQIGGDGGTLPRSAPPAPPVPVGCAAR

RRPASPELLRCSRRRRPATAETGGGAAAVARRNERERNRVKLVNLGFQALRQHVPHGGASKKLS

KVETLRSAVEYIRALQRLLAEHDAVRNALAGGLRPQAVRPSAPRGPPGTTPVAASPSRASSSPG

RGGSSEPGSPRSAYSSDDSGCEGALSPAERELLDFSSWLGGY

SEQ ID NO: 46

LVL112 DNA atgggtcatcaccatcatcatcacgggtcggactcagaagtcaatcaagaagctaagccagagg tcaagccagaagtcaagcctgagactcacatcaatttaaaggtgtccgatggatcttcagagat cttcttcaagatcaaaaagaccactcctttaagaaggctgatggaagcgttcgctaaaagacag ggtaaggaaatggactccttaagattcttgtacgacggtattagaattcaagctgatcaggccc ctgaagatttggacatggaggataacgatattattgaggctcaccgcgaacagattggaggtga tggtggcaccctgccgcgtagcgctccgccggcaccgccggttccggttggttgtgcggcgcgt cgtcgtccggcgagcccggaactgctgcgttgcagccgtcgtcgccgtccggccaccgcggaaa ccggtggtggtgcggcagcggttgcgcgtcgtaacgaacgtgaacgtaaccgtgtgaaactggt gaacctgggctttcaggcgctgcgtcagcatgtgccgcatggcggtgcgagcaaaaaactgagc aaagtggaaaccctgcgtagcgcggtggaatatattcgtgcgctgcaacgtctgctggccgaac atgatgcggtgcgtaacgcgctggccggtggtctgcgtccgcaggcggttcgtccgagcgcacc gcgtggtccgccgggtacgacgccggttgcagcgagcccgagccgtgcgagcagctctccgggt cgtggtggtagcagcgaaccgggtagcccgcgtagcgcctatagcagcgatgatagcggctgcg aaggtgccctgtctccggcggaacgtgaactgctggattttagcagctggctgggcggctat

SEQ ID NO: 47

LVL113 Protein

MGHHHHHHGSDSEVNQEAKPEVKPEVKPETHINLKVSDGSSEIFFKIKKTTPLRRLMEAFAKRQ

GKEMDSLRFLYDGIRIQADQAPEDLDMEDNDIIEAHREQIGGDPSSHSSNMANTQMKSDKIIIA

HRGASGYLPEHTLESKALAFAQQADYLEQDLAMTKDGRLVVIHDHFLDGLTDVAKKFPHRHRKD

-continued

GRYYVIDFTLKEIQSLEMTENFETAAAMDGGTLPRSAPPAPPVPVGCAARRRPASPELLRCSRR

RRPATAETGGGAAAVARRNERERNRVKLVNLGFQALRQHVPHGGASKKLSKVETLRSAVEYIRA

LQRLLAEHDAVRNALAGGLRPQAVRPSAPRGPPGTTPVAASPSRASSSPGRGGSSEPGSPRSAY

SSDDSGCEGALSPAERELLDFSSWLGGY

SEQ ID NO: 48

LVL113 DNA atgggtcatcaccatcatcatcacgggtcggactcagaagtcaatcaagaagctaagccagagg tcaagccagaagtcaagcctgagactcacatcaatttaaaggtgtccgatggatcttcagagat cttcttcaagatcaaaaagaccactcctttaagaaggctgatggaagcgttcgctaaaagacag ggtaaggaaatggactccttaagattcttgtacgacggtattagaattcaagctgatcaggccc ctgaagatttggacatggaggataacgatattattgaggctcaccgcgaacagattggaggtga tccaagcagccattcatcaaatatggcgaatacccaaatgaaatcagacaaaatcattattgct caccgtggtgctagcggttatttaccagagcatacgttagaatctaaagcacttgcgtttgcac aacaggctgattatttagagcaagatttagcaatgactaaggatggtcgtttagtggttattca cgatcactttttagatggcttgactgatgttgcgaaaaaattcccacatcgtcatcgtaaagat ggccgttactatgtcatcgactttaccttaaaagaaattcaaagtttagaaatgacagaaaact ttgaaaccgcggccgcaatggatggtggcaccctgccgcgtagcgctccgccggcaccgccggt tccggttggttgtgcggcgcgtcgtcgtccggcgagcccggaactgctgcgttgcagccgtcgt cgccgtccggccaccgcggaaaccggtggtggtgcggcagcggttgcgcgtcgtaacgaacgtg aacgtaaccgtgtgaaactggtgaacctgggctttcaggcgctgcgtcagcatgtgccgcatgg cggtgcgagcaaaaaactgagcaaagtggaaaccctgcgtagcgcggtggaatatattcgtgcg ctgcaacgtctgctggccgaacatgatgcggtgcgtaacgcgctggccggtggtctgcgtccgc aggcggttcgtccgagcgcaccgcgtggtccgccgggtacgacgccggttgcagcgagcccgag ccgtgcgagcagctctccgggtcgtggtggtagcagcgaaccgggtagcccgcgtagcgcctat agcagcgatgatagcggctgcgaaggtgccctgtctccggcggaacgtgaactgctggatttta gcagctggctgggcggctat

SEQ ID NO: 49

LVL114 Protein

MGHHHHHHGSDSEVNQEAKPEVKPEVKPETHINLKVSDGSSEIFFKIKKTTPLRRLMEAFAKRQ

GKEMDSLRFLYDGIRIQADQAPEDLDMEDNDIIEAHREQIGGDGGTLPRSAPPAPPVPVGCAAR

RRPASPELLRCSRRRRPATAETGGGAAAVARRNERERNRVKLVNLGFQALRQHVPHGGASKKLS

KVETLRSAVEYIRALQRLLAEHDAVRNALA

SEQ ID NO: 50

LVL114 DNA atgggtcatcaccatcatcatcacgggtcggactcagaagtcaatcaagaagctaagccagagg tcaagccagaagtcaagcctgagactcacatcaatttaaaggtgtccgatggatcttcagagat cttcttcaagatcaaaaagaccactcctttaagaaggctgatggaagcgttcgctaaaagacag ggtaaggaaatggactccttaagattcttgtacgacggtattagaattcaagctgatcaggccc ctgaagatttggacatggaggataacgatattattgaggctcaccgcgaacagattggaggtga tggtggcaccctgccgcgtagcgctccgccggcaccgccggttccggttggttgtgcggcgcgt cgtcgtccggcgagcccggaactgctgcgttgcagccgtcgtcgccgtccggccaccgcggaaa ccggtggtggtgcggcagcggttgcgcgtcgtaacgaacgtgaacgtaaccgtgtgaaactggt gaacctgggctttcaggcgctgcgtcagcatgtgccgcatggcggtgcgagcaaaaaactgagc -continued aaagtggaaaccctgcgtagcgcggtggaatatattcgtgcgctgcaacgtctgctggccgaac atgatgcggtgcgtaacgcgctggcc

SEQ ID NO: 51

LVL115 Protein
MGHHHHHHGSDSEVNQEAKPEVKPEVKPETHINLKVSDGSSEIFFKIKKTTPLRRLMEAFAKRQ

GKEMDSLRFLYDGIRIQADQAPEDLDMEDNDIIEAHREQIGGDGGTLPRSAPPAPPVPVGCAAR

RRPASPELLRCSRRRRPATAETGGGAAAVARRNERERNRVKLVNLGFQALRQHVPHGGASKKLS

KVETLRSAVEYIRALQRLLAEHDAVRNALAGGLRPQAVRPSAPRGGSSEPGSPRSAYSSDDSGC

EGALSPAERELLDFSSWLGGY

SEQ ID NO: 52

LVL115 DNA
atgggtcatcaccatcatcatcacgggtcggactcagaagtcaatcaagaagctaagccagagg tcaagccagaagtcaagcctgagactcacatcaatttaaaggtgtccgatggatcttcagagat cttcttcaagatcaaaaagaccactcctttaagaaggctgatggaagcgttcgctaaaagacag ggtaaggaaatggactccttaagattcttgtacgacggtattagaattcaagctgatcaggccc ctgaagatttggacatggaggataacgatattattgaggctcaccgcgaacagattggaggtga tggtggcaccctgccgcgtagcgcaccgccggctccgccggttccggttggttgtgcggcgcgt cgtcgtccggcgagcccggaactgctgcgttgcagccgtcgtcgccgtccggccaccgcggaaa ccggtggtggtgcggcagcggttgcgcgtcgtaacgaacgtgaacgtaaccgtgtgaaactggt gaacctgggctttcaggcgctgcgtcagcatgtgccgcatggcggtgcgagcaaaaaactgagc aaagtggaaaccctgcgtagcgcggtggaatatattcgtgcgctgcaacgtctgctggccgaac atgatgcggtgcgtaacgcgctggccggtggtctgcgtccgcaggcggttcgtccgagcgcgcc gcgtggtggtagcagcgaaccgggtagcccgcgtagcgcctatagcagcgatgatagcggctgc gaaggtgccctgagcccggcggaacgtgaactgctggattttagcagctggctgggcggctat

SEQ ID NO: 53

Peptide 1
MDGGTLPRSAPPAPP

SEQ ID NO: 54

Peptide 2
TLPRSAPPAPPVPVG

SEQ ID NO: 55

Peptide 3
SAPPAPPVPVGCAAR

SEQ ID NO: 56

Peptide 4
APPVPVGCAARRRPA

SEQ ID NO: 57

Peptide 5
PVGCAARRRPASPEL

SEQ ID NO: 58

Peptide 6
AARRRPASPELLRCS

SEQ ID NO: 59

Peptide 7
RPASPELLRCSRRRR

SEQ ID NO: 60

Peptide 8
PELLRCSRRRRPATA

SEQ ID NO: 61

Peptide 9
RCSRRRRPATAETGG

-continued

SEQ ID NO: 62
Peptide 10
RRRPATAETGGGAAA

SEQ ID NO: 63
Peptide 11
ATAETGGGAAAVARR

SEQ ID NO: 64
Peptide 12
TGGGAAAVARRNERE

SEQ ID NO: 65
Peptide 13
AAAVARRNERERNRV

SEQ ID NO: 66
Peptide 14
ARRNERERNRVKLVN

SEQ ID NO: 67
Peptide 15
ERERNRVKLVNLGFQ

SEQ ID NO: 68
Peptide 16
NRVKLVNLGFQALRQ

SEQ ID NO: 69
Peptide 17
LVNLGFQALRQHVPH

SEQ ID NO: 70
Peptide 18
GFQALRQHVPHGGAS

SEQ ID NO: 71
Peptide 19
LRQHVPHGGASKKLS

SEQ ID NO: 72
Peptide 20
VPHGGASKKLSKVET

SEQ ID NO: 73
Peptide 21
GASKKLSKVETLRSA

SEQ ID NO: 74
Peptide 22
KLSKVETLRSAVEYI

SEQ ID NO: 75
Peptide 23
VETLRSAVEYIRALQ

SEQ ID NO: 76
Peptide 24
RSAVEYIRALQRLLA

SEQ ID NO: 77
Peptide 25
EYIRALQRLLAEHDA

SEQ ID NO: 78
Peptide 26
ALQRLLAEHDAVRNA

SEQ ID NO: 79
Peptide 27
LLAEHDAVRNALAGG

SEQ ID NO: 80
Peptide 28
HDAVRNALAGGLRPQ

SEQ ID NO: 81
Peptide 29
RNALAGGLRPQAVRP

-continued

SEQ ID NO: 82
Peptide 30
AGGLRPQAVRPSAPR

SEQ ID NO: 83
Peptide 31
RPQAVRPSAPRGPPG

SEQ ID NO: 84
Peptide 32
VRPSAPRGPPGTTPV

SEQ ID NO: 85
Peptide 33
APRGPPGTTPVAASP

SEQ ID NO: 86
Peptide 34
PPGTTPVAASPSRAS

SEQ ID NO: 87
Peptide 35
TPVAASPSRASSSPG

SEQ ID NO: 88
Peptide 36
ASPSRASSSPGRGGS

SEQ ID NO: 89
Peptide 37
RASSSPGRGGSSEPG

SEQ ID NO: 90
Peptide 38
SPGRGGSSEPGSPRS

SEQ ID NO: 91
Peptide 39
GGSSEPGSPRSAYSS

SEQ ID NO: 92
Peptide 40
EPGSPRSAYSSDDSG

SEQ ID NO: 93
Peptide 41
PRSAYSSDDSGCEGA

SEQ ID NO: 94
Peptide 42
YSSDDSGCEGALSPA

SEQ ID NO: 95
Peptide 43
DSGCEGALSPAEREL

SEQ ID NO: 96
Peptide 44
EGALSPAERELLDFS

SEQ ID NO: 97
Peptide 45
SPAERELLDFSSWLG

SEQ ID NO: 98
Peptide 46
AERELLDFSSWLGGY

We claim:

1. A protein construct comprising a modified CASB7439 polypeptide selected from the group consisting of:

(a) LVL055 (SEQ ID NO:1);

(b) LVL111 (SEQ ID NO:3);

(c) LVL137 (SEQ ID NO:5);

(d) LVL141 (SEQ ID NO:7);

(e) LVL144 (SEQ ID NO:9); and (f) LVL168 (SEQ ID NO:11).

2. An immunogenic composition comprising the protein construct of claim 1, and a pharmaceutically acceptable carrier or excipient.

3. The immunogenic composition of claim 2, wherein the carrier or excipient comprises a buffer.

4. The immunogenic composition of claim 3, further comprising an adjuvant.

5. The immunogenic composition of claim 4, wherein the adjuvant comprises a composition selected from the group consisting of: a TLR-4 agonist, an immunologically active saponin fraction, and a TLR-9 agonist.

6. The immunogenic composition of claim 5 wherein said TLR-4 agonist is 3D-MPL.

7. The immunogenic composition of claim 5 wherein said TLR-9 agonist is a CpG oligonucleotide.

8. The immunogenic composition of claim 5 wherein said immunologically active saponin fraction is QS21.

9. The immunogenic composition of claim 5, further comprising cholesterol.

10. An immunogenic composition which comprises a protein comprising a polypeptide selected from the group consisting of:

(a) the construct set forth in SEQ ID NO:9; and (b) the construct set forth in SEQ ID NO:11;

and an adjuvant comprising 3DMPL, QS21 in a liposomal formulation, and CpG.

11. A process for producing the immunogenic composition of claim 10 comprising combining a protein comprising a polypeptide selected from the group consisting of:

(a) the construct set forth in SEQ ID NO:9; and (b) the construct set forth in SEQ ID NO:11;

with 3DMPL, QS21 in a liposomal formulation, and CpG.

12. A nucleic acid molecule comprising a polynucleotide sequence that encodes the protein construct of claim 1.

13. A method of inducing an immune response to CASB7439 in a human or non-human animal comprising administering to the human or non-human animal an effective amount of a composition comprising an adjuvant and a protein comprising a polypeptide sequence selected from the group consisting of:

(a) the polypeptide sequence set forth in SEQ ID NO:9; and (b) the polypeptide sequence set forth in SEQ ID NO:11.

14. The method of claim 13, wherein the animal is human.

15. A method of treating a human or non-human animal comprising the steps of:

(a) selecting a human or non-human animal having cancerous cells that express CASB7439; and (b) administering to the human or non-human animal an effective amount of a composition comprising an adjuvant and a protein comprising a polypeptide selected from the group consisting of:

(i) the construct set forth in SEQ ID NO:9; and (ii) the construct set forth in SEQ ID NO:11.

16. The method of claim 15, wherein the animal is human.

* * * * *

SEQUENCE LISTING

<160> NUMBER OF SEQ ID NOS: 98

<210> SEQ ID NO 1
<211> LENGTH: 140
<212> TYPE: PRT
<213> ORGANISM: Artificial Sequence
<220> FEATURE:

<223> OTHER INFORMATION: Homo Sapien

<400> SEQUENCE: 1

```
Met Gly His His His His His His His His His His Ser Ser Gly His
1               5                   10                  15

Ile Asp Asp Asp Asp Lys His Met Asp Gly Gly Thr Leu Pro Arg Ser
            20                  25                  30

Ala Pro Pro Ala Pro Pro Val Pro Val Gly Cys Ala Ala Arg Arg Arg
        35                  40                  45

Pro Ala Ser Pro Glu Leu Leu Arg Cys Ser Arg Arg Arg Arg Pro Ala
    50                  55                  60

Thr Ala Glu Thr Gly Gly Gly Ala Ala Ala Val Ala Arg Arg Asn Glu
65                  70                  75                  80

Arg Glu Arg Asn Arg Val Lys Leu Val Asn Leu Gly Phe Gln Ala Leu
                85                  90                  95

Arg Gln His Val Pro His Gly Gly Ala Ser Lys Lys Leu Ser Lys Val
            100                 105                 110

Glu Thr Leu Arg Ser Ala Val Glu Tyr Ile Arg Ala Leu Gln Arg Leu
        115                 120                 125

Leu Ala Glu His Asp Ala Val Arg Asn Ala Leu Ala
    130                 135                 140
```

<210> SEQ ID NO 2
<211> LENGTH: 423
<212> TYPE: DNA
<213> ORGANISM: Artificial Sequence
<220> FEATURE:
<223> OTHER INFORMATION: Homo Sapien

<400> SEQUENCE: 2

```
atgggccatc atcatcatca tcatcatcat catcacagca gcggccatat cgacgacgac      60

gacaagcata tggatggtgg caccctgccg cgtagcgctc cgccggcacc gccggttccg     120

gttggttgtg cggcgcgtcg tcgtccggcg agcccggaac tgctgcgttg cagccgtcgt     180

cgccgtccgg ccaccgcgga aaccggtggt ggtgcggcag cggttgcgcg tcgtaacgaa     240

cgtgaacgta accgtgtgaa actggtgaac ctgggctttc aggcgctgcg tcagcatgtg     300

ccgcatggcg gtgcgagcaa aaaactgagc aaagtggaaa ccctgcgtag cgcggtggaa     360

tatattcgtg cgctgcaacg tctgctggcc gaacatgatg cggtgcgtaa cgcgctggcc     420

taa                                                                   423
```

<210> SEQ ID NO 3
<211> LENGTH: 201
<212> TYPE: PRT
<213> ORGANISM: Artificial Sequence
<220> FEATURE:
<223> OTHER INFORMATION: Homo Sapien

<400> SEQUENCE: 3

```
Met Gly His His His His His His His His His His Ser Ser Gly His
 1               5                  10                  15

Ile Asp Asp Asp Asp Lys His Met Asp Gly Gly Thr Leu Pro Arg Ser
            20                  25                  30

Ala Pro Pro Ala Pro Pro Val Pro Val Gly Cys Ala Ala Arg Arg Arg
        35                  40                  45

Pro Ala Ser Pro Glu Leu Leu Arg Cys Ser Arg Arg Arg Arg Pro Ala
    50                  55                  60
```

-continued

```
Thr Ala Glu Thr Gly Gly Gly Ala Ala Ala Val Ala Arg Arg Asn Glu
65                  70                  75                  80

Arg Glu Arg Asn Arg Val Lys Leu Val Asn Leu Gly Phe Gln Ala Leu
                85                  90                  95

Arg Gln His Val Pro His Gly Gly Ala Ser Lys Lys Leu Ser Lys Val
            100                 105                 110

Glu Thr Leu Arg Ser Ala Val Glu Tyr Ile Arg Ala Leu Gln Arg Leu
        115                 120                 125

Leu Ala Glu His Asp Ala Val Arg Asn Ala Leu Ala Gly Gly Leu Arg
    130                 135                 140

Pro Gln Ala Val Arg Pro Ser Ala Pro Arg Gly Gly Ser Ser Glu Pro
145                 150                 155                 160

Gly Ser Pro Arg Ser Ala Tyr Ser Ser Asp Asp Ser Gly Cys Glu Gly
                165                 170                 175

Ala Leu Ser Pro Ala Glu Arg Glu Leu Leu Asp Phe Ser Ser Trp Leu
            180                 185                 190

Gly Gly Tyr His His His His His His
        195                 200


<210> SEQ ID NO 4
<211> LENGTH: 606
<212> TYPE: DNA
<213> ORGANISM: Artificial Sequence
<220> FEATURE:
<223> OTHER INFORMATION: Homo Sapien

<400> SEQUENCE: 4

atgggccatc atcatcatca tcatcatcat catcacagca gcggccatat cgacgacgac      60

gacaagcata tggatggtgg caccctgccg cgtagcgcac cgccggctcc gccggttccg     120

gttggttgtg cggcgcgtcg tcgtccggcg agcccggaac tgctgcgttg cagccgtcgt     180

cgccgtccgg ccaccgcgga aaccggtggt ggtgcggcag cggttgcgcg tcgtaacgaa     240

cgtgaacgta accgtgtgaa actggtgaac ctgggctttc aggcgctgcg tcagcatgtg     300

ccgcatggcg gtgcgagcaa aaaactgagc aaagtggaaa ccctgcgtag cgcggtggaa     360

tatattcgtg cgctgcaacg tctgctggcc gaacatgatg cggtgcgtaa cgcgctggcc     420

ggtggtctgc gtccgcaggc ggttcgtccg agcgcgccgc gtggtggtag cagcgaaccg     480

ggtagcccgc gtagcgccta tagcagcgat gatagcggct gcgaaggtgc cctgagcccg     540

gcggaacgtg aactgctgga ttttagcagc tggctgggcg gctatcatca tcatcaccat     600

cattaa                                                                606


<210> SEQ ID NO 5
<211> LENGTH: 195
<212> TYPE: PRT
<213> ORGANISM: Artificial Sequence
<220> FEATURE:
<223> OTHER INFORMATION: Homo Sapien

<400> SEQUENCE: 5

Met Gly His His His His His His His His His His Ser Ser Gly His
 1               5                  10                  15

Ile Asp Asp Asp Asp Lys His Met Asp Gly Gly Thr Leu Pro Arg Ser
            20                  25                  30

Ala Pro Pro Ala Pro Pro Val Pro Val Gly Cys Ala Ala Arg Arg Arg
        35                  40                  45

Pro Ala Ser Pro Glu Leu Leu Arg Cys Ser Arg Arg Arg Arg Pro Ala
```

-continued

```
    50                  55                  60

Thr Ala Glu Thr Gly Gly Gly Ala Ala Ala Val Ala Arg Arg Asn Glu
65                  70                  75                  80

Arg Glu Arg Asn Arg Val Lys Leu Val Asn Leu Gly Phe Gln Ala Leu
                85                  90                  95

Arg Gln His Val Pro His Gly Gly Ala Ser Lys Lys Leu Ser Lys Val
            100                 105                 110

Glu Thr Leu Arg Ser Ala Val Glu Tyr Ile Arg Ala Leu Gln Arg Leu
        115                 120                 125

Leu Ala Glu His Asp Ala Val Arg Asn Ala Leu Ala Gly Gly Leu Arg
    130                 135                 140

Pro Gln Ala Val Arg Pro Ser Ala Pro Arg Gly Gly Ser Ser Glu Pro
145                 150                 155                 160

Gly Ser Pro Arg Ser Ala Tyr Ser Ser Asp Asp Ser Gly Cys Glu Gly
                165                 170                 175

Ala Leu Ser Pro Ala Glu Arg Glu Leu Leu Asp Phe Ser Ser Trp Leu
            180                 185                 190

Gly Gly Tyr
        195


<210> SEQ ID NO 6
<211> LENGTH: 588
<212> TYPE: DNA
<213> ORGANISM: Artificial Sequence
<220> FEATURE:
<223> OTHER INFORMATION: Homo Sapien

<400> SEQUENCE: 6

atgggccatc atcatcatca tcatcatcat catcacagca gcggccatat cgacgacgac     60

gacaagcata tggatggtgg caccctgccg cgtagcgcac cgccggctcc gccggttccg    120

gttggttgtg cggcgcgtcg tcgtccggcg agcccggaac tgctgcgttg cagccgtcgt    180

cgccgtccgg ccaccgcgga aaccggtggt ggtgcggcag cggttgcgcg tcgtaacgaa    240

cgtgaacgta accgtgtgaa actggtgaac ctgggctttc aggcgctgcg tcagcatgtg    300

ccgcatggcg gtgcgagcaa aaaactgagc aaagtggaaa ccctgcgtag cgcggtggaa    360

tatattcgtg cgctgcaacg tctgctggcc gaacatgatg cggtgcgtaa cgcgctggcc    420

ggtggtctgc gtccgcaggc ggttcgtccg agcgcgccgc gtggtggtag cagcgaaccg    480

ggtagcccgc gtagcgccta tagcagcgat gatagcggct gcgaaggtgc cctgagcccg    540

gcggaacgtg aactgctgga ttttagcagc tggctgggcg gctattaa                 588


<210> SEQ ID NO 7
<211> LENGTH: 293
<212> TYPE: PRT
<213> ORGANISM: Artificial Sequence
<220> FEATURE:
<223> OTHER INFORMATION: Homo Sapien

<400> SEQUENCE: 7

Met Asp Pro Ser Ser His Ser Ser Asn Met Ala Asn Thr Gln Met Lys
 1               5                  10                  15

Ser Asp Lys Ile Ile Ile Ala His Arg Gly Ala Ser Gly Tyr Leu Pro
            20                  25                  30

Glu His Thr Leu Glu Ser Lys Ala Leu Ala Phe Ala Gln Gln Ala Asp
        35                  40                  45

Tyr Leu Glu Gln Asp Leu Ala Met Thr Lys Asp Gly Arg Leu Val Val
```

-continued

```
    50                  55                  60

Ile His Asp His Phe Leu Asp Gly Leu Thr Asp Val Ala Lys Lys Phe
65                  70                  75                  80

Pro His Arg His Arg Lys Asp Gly Arg Tyr Tyr Val Ile Asp Phe Thr
                85                  90                  95

Leu Lys Glu Ile Gln Ser Leu Glu Met Thr Glu Asn Phe Glu Thr Ala
            100                 105                 110

Ala Ala His Met Asp Gly Gly Thr Leu Pro Arg Ser Ala Pro Pro Ala
        115                 120                 125

Pro Pro Val Pro Val Gly Cys Ala Ala Arg Arg Arg Pro Ala Ser Pro
    130                 135                 140

Glu Leu Leu Arg Cys Ser Arg Arg Arg Arg Pro Ala Thr Ala Glu Thr
145                 150                 155                 160

Gly Gly Gly Ala Ala Ala Val Ala Arg Arg Asn Glu Arg Glu Arg Asn
                165                 170                 175

Arg Val Lys Leu Val Asn Leu Gly Phe Gln Ala Leu Arg Gln His Val
            180                 185                 190

Pro His Gly Gly Ala Ser Lys Lys Leu Ser Lys Val Glu Thr Leu Arg
        195                 200                 205

Ser Ala Val Glu Tyr Ile Arg Ala Leu Gln Arg Leu Leu Ala Glu His
    210                 215                 220

Asp Ala Val Arg Asn Ala Leu Ala Gly Gly Leu Arg Pro Gln Ala Val
225                 230                 235                 240

Arg Pro Ser Ala Pro Arg Gly Gly Ser Ser Glu Pro Gly Ser Pro Arg
                245                 250                 255

Ser Ala Tyr Ser Ser Asp Asp Ser Gly Cys Glu Gly Ala Leu Ser Pro
            260                 265                 270

Ala Glu Arg Glu Leu Leu Asp Phe Ser Ser Trp Leu Gly Gly Tyr His
        275                 280                 285

His His His His His
    290
```

```
<210> SEQ ID NO 8
<211> LENGTH: 882
<212> TYPE: DNA
<213> ORGANISM: Artificial Sequence
<220> FEATURE:
<223> OTHER INFORMATION: Homo Sapien

<400> SEQUENCE: 8

atggatccaa gcagccattc atcaaatatg gcgaataccc aaatgaaatc agacaaaatc     60

attattgctc accgtggtgc tagcggttat ttaccagagc atacgttaga atctaaagca    120

cttgcgtttg cacaacaggc tgattattta gagcaagatt tagcaatgac taaggatggt    180

cgtttagtgg ttattcacga tcacttttta gatggcttga ctgatgttgc gaaaaaattc    240

ccacatcgtc atcgtaaaga tggccgttac tatgtcatcg actttacctt aaaagaaatt    300

caaagtttag aaatgacaga aaactttgaa accgcggccg cacatatgga tggtggcacc    360

ctgccgcgta gcgcaccgcc ggctccgccg gttccggttg gttgtgcggc gcgtcgtcgt    420

ccggcgagcc cggaactgct gcgttgcagc cgtcgtcgcc gtccggccac cgcggaaacc    480

ggtggtggtg cggcagcggt tgcgcgtcgt aacgaacgtg aacgtaaccg tgtgaaactg    540

gtgaacctgg gctttcaggc gctgcgtcag catgtgccgc atggcggtgc gagcaaaaaa    600

ctgagcaaag tggaaaccct gcgtagcgcg gtggaatata ttcgtgcgct gcaacgtctg    660
```

```
ctggccgaac atgatgcggt gcgtaacgcg ctggccggtg gtctgcgtcc gcaggcggtt    720

cgtccgagcg cgccgcgtgg tggtagcagc gaaccgggta gcccgcgtag cgcctatagc    780

agcgatgata gcggctgcga aggtgccctg agcccggcgg aacgtgaact gctggatttt    840

agcagctggc tgggcggcta tcatcatcat caccatcatt aa                       882
```

<210> SEQ ID NO 9
<211> LENGTH: 288
<212> TYPE: PRT
<213> ORGANISM: Artificial Sequence
<220> FEATURE:
<223> OTHER INFORMATION: Homo Sapien

<400> SEQUENCE: 9

```
Met Asp Pro Ser Ser His Ser Ser Asn Met Ala Asn Thr Gln Met Lys
 1               5                  10                  15

Ser Asp Lys Ile Ile Ile Ala His Arg Gly Ala Ser Gly Tyr Leu Pro
            20                  25                  30

Glu His Thr Leu Glu Ser Lys Ala Leu Ala Phe Ala Gln Gln Ala Asp
        35                  40                  45

Tyr Leu Glu Gln Asp Leu Ala Met Thr Lys Asp Gly Arg Leu Val Val
    50                  55                  60

Ile His Asp His Phe Leu Asp Gly Leu Thr Asp Val Ala Lys Lys Phe
65                  70                  75                  80

Pro His Arg His Arg Lys Asp Gly Arg Tyr Tyr Val Ile Asp Phe Thr
                85                  90                  95

Leu Lys Glu Ile Gln Ser Leu Glu Met Thr Glu Asn Phe Glu Thr Asp
            100                 105                 110

Gly Gly Thr Leu Pro Arg Ser Ala Pro Pro Ala Pro Pro Val Pro Val
        115                 120                 125

Gly Cys Ala Ala Arg Arg Arg Pro Ala Ser Pro Glu Leu Leu Arg Cys
    130                 135                 140

Ser Arg Arg Arg Arg Pro Ala Thr Ala Glu Thr Gly Gly Gly Ala Ala
145                 150                 155                 160

Ala Val Ala Arg Arg Asn Glu Arg Glu Arg Asn Arg Val Lys Leu Val
                165                 170                 175

Asn Leu Gly Phe Gln Ala Leu Arg Gln His Val Pro His Gly Gly Ala
            180                 185                 190

Ser Lys Lys Leu Ser Lys Val Glu Thr Leu Arg Ser Ala Val Glu Tyr
        195                 200                 205

Ile Arg Ala Leu Gln Arg Leu Leu Ala Glu His Asp Ala Val Arg Asn
    210                 215                 220

Ala Leu Ala Gly Gly Leu Arg Pro Gln Ala Val Arg Pro Ser Ala Pro
225                 230                 235                 240

Arg Gly Gly Ser Ser Glu Pro Gly Ser Pro Arg Ser Ala Tyr Ser Ser
                245                 250                 255

Asp Asp Ser Gly Cys Glu Gly Ala Leu Ser Pro Ala Glu Arg Glu Leu
            260                 265                 270

Leu Asp Phe Ser Ser Trp Leu Gly Gly Tyr His His His His His His
        275                 280                 285
```

<210> SEQ ID NO 10
<211> LENGTH: 867
<212> TYPE: DNA
<213> ORGANISM: Artificial Sequence
<220> FEATURE:
<223> OTHER INFORMATION: Homo Sapien -continued

<400> SEQUENCE: 10

```
atggatccaa gcagccattc atcaaatatg gcgaataccc aaatgaaatc agacaaaatc      60
attattgctc accgtggtgc tagcggttat ttaccagagc atacgttaga atctaaagca     120
cttgcgtttg cacaacaggc tgattattta gagcaagatt tagcaatgac taaggatggt     180
cgtttagtgg ttattcacga tcacttttta gatggcttga ctgatgttgc gaaaaaattc     240
ccacatcgtc atcgtaaaga tggccgttac tatgtcatcg actttacctt aaaagaaatt     300
caaagtttag aaatgacaga aaactttgaa accgatggtg gcaccctgcc gcgtagcgca     360
ccgccggctc cgccggttcc ggttggttgt gcggcgcgtc gtcgtccggc gagcccggaa     420
ctgctgcgtt gcagccgtcg tcgccgtccg gccaccgcgg aaaccggtgg tggtgcggca     480
gcggttgcgc gtcgtaacga acgtgaacgt aaccgtgtga aactggtgaa cctgggcttt     540
caggcgctgc gtcagcatgt gccgcatggc ggtgcgagca aaaaactgag caaagtggaa     600
accctgcgta gcgcggtgga atatattcgt gcgctgcaac gtctgctggc cgaacatgat     660
gcggtgcgta acgcgctggc cggtggtctg cgtccgcagg cggttcgtcc gagcgcgccg     720
cgtggtggta gcagcgaacc gggtagcccg cgtagcgcct atagcagcga tgatagcggc     780
tgcgaaggtg ccctgagccc ggcggaacgt gaactgctgg attttagcag ctggctgggc     840
ggctatcatc atcatcacca tcattaa                                         867
```

<210> SEQ ID NO 11
<211> LENGTH: 182
<212> TYPE: PRT
<213> ORGANISM: Artificial Sequence
<220> FEATURE:
<223> OTHER INFORMATION: Homo Sapien

<400> SEQUENCE: 11

```
Met His His His His His His His His His His Asp Gly Gly Thr Leu
 1               5                  10                  15

Pro Arg Ser Ala Pro Pro Ala Pro Pro Val Pro Val Gly Cys Ala Ala
            20                  25                  30

Arg Arg Arg Pro Ala Ser Pro Glu Leu Leu Arg Cys Ser Arg Arg Arg
        35                  40                  45

Arg Pro Ala Thr Ala Glu Thr Gly Gly Gly Ala Ala Ala Val Ala Arg
    50                  55                  60

Arg Asn Glu Arg Glu Arg Asn Arg Val Lys Leu Val Asn Leu Gly Phe
65                  70                  75                  80

Gln Ala Leu Arg Gln His Val Pro His Gly Gly Ala Ser Lys Lys Leu
                85                  90                  95

Ser Lys Val Glu Thr Leu Arg Ser Ala Val Glu Tyr Ile Arg Ala Leu
            100                 105                 110

Gln Arg Leu Leu Ala Glu His Asp Ala Val Arg Asn Ala Leu Ala Gly
        115                 120                 125

Gly Leu Arg Pro Gln Ala Val Arg Pro Ser Ala Pro Arg Gly Gly Ser
    130                 135                 140

Ser Glu Pro Gly Ser Pro Arg Ser Ala Tyr Ser Ser Asp Asp Ser Gly
145                 150                 155                 160

Cys Glu Gly Ala Leu Ser Pro Ala Glu Arg Glu Leu Leu Asp Phe Ser
                165                 170                 175

Ser Trp Leu Gly Gly Tyr
            180
```

<210> SEQ ID NO 12
<211> LENGTH: 549
<212> TYPE: DNA
<213> ORGANISM: Artificial Sequence
<220> FEATURE:
<223> OTHER INFORMATION: Homo Sapien

<400> SEQUENCE: 12

```
atgcatcatc atcatcatca tcatcatcat catgacggtg gcaccctgcc gcgtagcgca     60

ccgccggctc cgccggttcc ggttggttgt gcggcgcgtc gtcgtccggc gagcccggaa    120

ctgctgcgtt gcagccgtcg tcgccgtccg gccaccgcgg aaaccggtgg tggtgcggca    180

gcggttgcgc gtcgtaacga acgtgaacgt aaccgtgtga aactggtgaa cctgggcttt    240

caggcgctgc gtcagcatgt gccgcatggc ggtgcgagca aaaaactgag caaagtggaa    300

accctgcgta gcgcggtgga atatattcgt gcgctgcaac gtctgctggc cgaacatgat    360

gcggtgcgta acgcgctggc cggtggtctg cgtccgcagg cggttcgtcc gagcgcgccg    420

cgtggtggta gcagcgaacc gggtagcccg cgtagcgcct atagcagcga tgatagcggc    480

tgcgaaggtg ccctgagccc ggcggaacgt gaactgctgg attttagcag ctggctgggc    540

ggctattaa                                                            549
```

<210> SEQ ID NO 13
<211> LENGTH: 193
<212> TYPE: PRT
<213> ORGANISM: Artificial Sequence
<220> FEATURE:
<223> OTHER INFORMATION: Homo Sapien

<400> SEQUENCE: 13

```
Met Asp Gly Gly Thr Leu Pro Arg Ser Ala Pro Pro Ala Pro Pro Val
1               5                   10                  15

Pro Val Gly Cys Ala Ala Arg Arg Arg Pro Ala Ser Pro Glu Leu Leu
            20                  25                  30

Arg Cys Ser Arg Arg Arg Arg Pro Ala Thr Ala Glu Thr Gly Gly Gly
        35                  40                  45

Ala Ala Ala Val Ala Arg Arg Asn Glu Arg Glu Arg Asn Arg Val Lys
    50                  55                  60

Leu Val Asn Leu Gly Phe Gln Ala Leu Arg Gln His Val Pro His Gly
65                  70                  75                  80

Gly Ala Ser Lys Lys Leu Ser Lys Val Glu Thr Leu Arg Ser Ala Val
                85                  90                  95

Glu Tyr Ile Arg Ala Leu Gln Arg Leu Leu Ala Glu His Asp Ala Val
            100                 105                 110

Arg Asn Ala Leu Ala Gly Gly Leu Arg Pro Gln Ala Val Arg Pro Ser
        115                 120                 125

Ala Pro Arg Gly Pro Pro Gly Thr Thr Pro Val Ala Ala Ser Pro Ser
    130                 135                 140

Arg Ala Ser Ser Ser Pro Gly Arg Gly Gly Ser Ser Glu Pro Gly Ser
145                 150                 155                 160

Pro Arg Ser Ala Tyr Ser Ser Asp Asp Ser Gly Cys Glu Gly Ala Leu
                165                 170                 175

Ser Pro Ala Glu Arg Glu Leu Leu Asp Phe Ser Ser Trp Leu Gly Gly
            180                 185                 190

Tyr
```

-continued

<210> SEQ ID NO 14
<211> LENGTH: 582
<212> TYPE: DNA
<213> ORGANISM: Artificial Sequence
<220> FEATURE:
<223> OTHER INFORMATION: Homo Sapien

<400> SEQUENCE: 14

```
atggacggcg gcacactgcc caggtccgcg ccccctgcgc cccccgtccc tgtcggctgc      60

gctgcccggc ggagacccgc gtccccggaa ctgttgcgct gcagccggcg gcggcgaccg     120

gccaccgcag agaccggagg cggcgcagcg gccgtagcgc ggcgcaatga gcgcgagcgc     180

aaccgcgtga agctggtgaa cttgggcttc caggcgctgc ggcagcacgt gccgcacggc     240

ggcgccagca agaagctgag caaggtggag acgctgcgct cagccgtgga gtacatccgc     300

gcgctgcagc gcctgctggc cgagcacgac gccgtgcgca acgcgctggc gggagggctg     360

aggccgcagg ccgtgcggcc gtctgcgccc cgcgggccgc cagggaccac cccggtcgcc     420

gcctcgccct cccgcgcttc ttcgtccccg ggccgcgggg gcagctcgga gcccggctcc     480

ccgcgttccg cctactcgtc ggacgacagc ggctgcgaag gcgcgctgag tcctgcggag     540

cgcgagctac tcgacttctc cagctggtta gggggctact ga                        582
```

<210> SEQ ID NO 15
<211> LENGTH: 216
<212> TYPE: PRT
<213> ORGANISM: Artificial Sequence
<220> FEATURE:
<223> OTHER INFORMATION: Homo Sapien

<400> SEQUENCE: 15

```
Met Gly His His His His His His His His His His Ser Ser Gly His
1               5                   10                  15

Ile Asp Asp Asp Asp Lys His Met Asp Gly Gly Thr Leu Pro Arg Ser
            20                  25                  30

Ala Pro Pro Ala Pro Pro Val Leu Val Gly Cys Ala Ala Arg Arg Arg
        35                  40                  45

Pro Ala Ser Pro Glu Leu Leu Arg Cys Ser Arg Arg Arg Arg Pro Ala
    50                  55                  60

Thr Ala Glu Thr Gly Gly Gly Ala Ala Ala Val Ala Arg Arg Asn Glu
65                  70                  75                  80

Arg Glu Arg Asn Arg Val Lys Leu Val Asn Leu Gly Phe Gln Ala Leu
                85                  90                  95

Arg Gln His Val Pro His Gly Gly Ala Ser Lys Lys Leu Ser Lys Val
            100                 105                 110

Glu Thr Leu Arg Ser Ala Val Glu Tyr Ile Arg Ala Leu Gln Arg Leu
        115                 120                 125

Leu Ala Glu His Asp Ala Val Arg Asn Ala Leu Ala Gly Gly Leu Arg
    130                 135                 140

Pro Gln Ala Val Arg Pro Ser Ala Pro Arg Gly Pro Pro Gly Thr Thr
145                 150                 155                 160

Pro Val Ala Ala Ser Pro Ser Arg Ala Ser Ser Ser Pro Gly Arg Gly
                165                 170                 175

Gly Ser Ser Glu Pro Gly Ser Pro Arg Ser Ala Tyr Ser Ser Asp Asp
            180                 185                 190

Ser Gly Cys Glu Gly Ala Leu Ser Pro Ala Glu Arg Glu Leu Leu Asp
        195                 200                 205

Phe Ser Ser Trp Leu Gly Gly Tyr
```

210 215

<210> SEQ ID NO 16
<211> LENGTH: 651
<212> TYPE: DNA
<213> ORGANISM: Artificial Sequence
<220> FEATURE:
<223> OTHER INFORMATION: Homo Sapien

<400> SEQUENCE: 16
atgggccatc atcatcatca tcatcatcat catcacagca gcggccatat cgacgacgac 60
gacaagcata tggacggcgg cacactgccc aggtccgcgc cccctgcgcc ccccgtcctt 120
gtcggctgcg ctgcccggcg gagacccgcg tccccggaac tgttgcgctg cagccggcgg 180
cggcgaccgg ccaccgcaga gaccggaggc ggcgcagcgg ccgtagcgcg gcgcaatgag 240
cgcgagcgca accgcgtgaa gctggtgaac ttgggcttcc aggcgctgcg gcagcacgtg 300
ccgcacggcg gcgccagcaa gaagctgagc aaggtggaga cgctgcgctc agccgtggag 360
tacatccgcg cgctgcagcg cctgctggcc gagcacgacg ccgtgcgcaa cgcgctggcg 420
ggagggctga ggccgcaggc cgtgcggccg tctgcgcccc gcgggccgcc agggaccacc 480
ccggtcgccg cctcgccctc ccgcgcttct tcgtccccgg gccgcggggg cagctcggag 540
cccggctccc cgcgttccgc ctactcgtcg gacgacagcg gctgcgaagg cgcgctgagt 600
cctgcggagc gcgagctact cgacttctcc agctggttag ggggctactg a 651

<210> SEQ ID NO 17
<211> LENGTH: 216
<212> TYPE: PRT
<213> ORGANISM: Artificial Sequence
<220> FEATURE:
<223> OTHER INFORMATION: Homo Sapien

<400> SEQUENCE: 17

Met Gly His His His His His His His His His His Ser Ser Gly His
1 5 10 15

Ile Asp Asp Asp Asp Lys His Met Asp Gly Gly Thr Leu Pro Arg Ser
20 25 30

Ala Pro Pro Ala Pro Pro Val Pro Val Gly Cys Ala Ala Arg Arg Arg
35 40 45

Pro Ala Ser Pro Glu Leu Leu Arg Cys Ser Arg Arg Arg Arg Pro Ala
50 55 60

Thr Ala Glu Thr Gly Gly Gly Ala Ala Ala Val Ala Arg Arg Asn Glu
65 70 75 80

Arg Glu Arg Asn Arg Val Lys Leu Val Asn Leu Gly Phe Gln Ala Leu
85 90 95

Arg Gln His Val Pro His Gly Gly Ala Ser Lys Lys Leu Ser Lys Val
100 105 110

Glu Thr Leu Arg Ser Ala Val Glu Tyr Ile Arg Ala Leu Gln Arg Leu
115 120 125

Leu Ala Glu His Asp Ala Val Arg Asn Ala Leu Ala Gly Gly Leu Arg
130 135 140

Pro Gln Ala Val Arg Pro Ser Ala Pro Arg Gly Pro Pro Gly Thr Thr
145 150 155 160

Pro Val Ala Ala Ser Pro Ser Arg Ala Ser Ser Ser Pro Gly Arg Gly
165 170 175

Gly Ser Ser Glu Pro Gly Ser Pro Arg Ser Ala Tyr Ser Ser Asp Asp
180 185 190

```
Ser Gly Cys Glu Gly Ala Leu Ser Pro Ala Glu Arg Glu Leu Leu Asp
        195                 200                 205

Phe Ser Ser Trp Leu Gly Gly Tyr
    210                 215


<210> SEQ ID NO 18
<211> LENGTH: 651
<212> TYPE: DNA
<213> ORGANISM: Artificial Sequence
<220> FEATURE:
<223> OTHER INFORMATION: Homo Sapien

<400> SEQUENCE: 18

atgggccatc atcatcatca tcatcatcat catcacagca gcggccatat cgacgacgac      60

gacaagcata tggacggcgg cacactgccc aggtccgcgc cccctgcgcc ccccgtccct     120

gtcggctgcg ctgcccggcg gagacccgcg tccccggaac tgttgcgctg cagccggcgg     180

cggcgaccgg ccaccgcaga gaccggaggc ggcgcagcgg ccgtagcgcg gcgcaatgag     240

cgcgagcgca accgcgtgaa gctggtgaac ttgggcttcc aggcgctgcg gcagcacgtg     300

ccgcacggcg gcgccagcaa gaagctgagc aaggtggaga cgctgcgctc agccgtggag     360

tacatccgcg cgctgcagcg cctgctggcc gagcacgacg ccgtgcgcaa cgcgctggcg     420

ggagggctga ggccgcaggc cgtgcggccg tctgcgcccc gcgggccgcc agggaccacc     480

ccggtcgccg cctcgccctc ccgcgcttct tcgtccccgg gccgcggggg cagctcggag     540

cccggctccc cgcgttccgc ctactcgtcg gacgacagcg gctgcgaagg cgcgctgagt     600

cctgcggagc gcgagctact cgacttctcc agctggttag ggggctactg a              651


<210> SEQ ID NO 19
<211> LENGTH: 216
<212> TYPE: PRT
<213> ORGANISM: Artificial Sequence
<220> FEATURE:
<223> OTHER INFORMATION: Homo Sapien

<400> SEQUENCE: 19

Met Gly His His His His His His His His His His Ser Ser Gly His
 1               5                  10                  15

Ile Asp Asp Asp Asp Lys His Met Asp Gly Gly Thr Leu Pro Arg Ser
            20                  25                  30

Ala Pro Pro Ala Pro Pro Val Pro Val Gly Cys Ala Ala Arg Arg Arg
        35                  40                  45

Pro Ala Ser Pro Glu Leu Leu Arg Cys Ser Arg Arg Arg Arg Pro Ala
    50                  55                  60

Thr Ala Glu Thr Gly Gly Gly Ala Ala Ala Val Ala Arg Arg Asn Glu
65                  70                  75                  80

Arg Glu Arg Asn Arg Val Lys Leu Val Asn Leu Gly Phe Gln Ala Leu
                85                  90                  95

Arg Gln His Val Pro His Gly Gly Ala Ser Lys Lys Leu Ser Lys Val
            100                 105                 110

Glu Thr Leu Arg Ser Ala Val Glu Tyr Ile Arg Ala Leu Gln Arg Leu
        115                 120                 125

Leu Ala Glu His Asp Ala Val Arg Asn Ala Leu Ala Gly Gly Leu Arg
    130                 135                 140

Pro Gln Ala Val Arg Pro Ser Ala Pro Arg Gly Pro Pro Gly Thr Thr
145                 150                 155                 160
```

```
Pro Val Ala Ala Ser Pro Ser Arg Ala Ser Ser Ser Pro Gly Arg Gly
                165                 170                 175

Gly Ser Ser Glu Pro Gly Ser Pro Arg Ser Ala Tyr Ser Ser Asp Asp
            180                 185                 190

Ser Gly Cys Glu Gly Ala Leu Ser Pro Ala Glu Arg Glu Leu Leu Asp
        195                 200                 205

Phe Ser Ser Trp Leu Gly Gly Tyr
    210                 215
```

<210> SEQ ID NO 20
<211> LENGTH: 651
<212> TYPE: DNA
<213> ORGANISM: Artificial Sequence
<220> FEATURE:
<223> OTHER INFORMATION: Homo Sapien

<400> SEQUENCE: 20

```
atgggccatc atcatcatca tcatcatcat catcacagca gcggccatat cgacgacgac      60

gacaagcata tggatggtgg caccctgccg cgtagcgctc cgccggcacc gccggttccg     120

gttggttgtg cggcgcgtcg tcgtccggcg agcccggaac tgctgcgttg cagccgtcgt     180

cgccgtccgg ccaccgcgga aaccggtggt ggtgcggcag cggttgcgcg tcgtaacgaa     240

cgtgaacgta accgtgtgaa actggtgaac ctgggctttc aggcgctgcg tcagcatgtg     300

ccgcatggcg gtgcgagcaa aaaactgagc aaagtggaaa ccctgcgtag cgcggtggaa     360

tatattcgtg cgctgcaacg tctgctggcc gaacatgatg cggtgcgtaa cgcgctggcc     420

ggtggtctgc gtccgcaggc ggttcgtccg agcgcaccgc gtggtccgcc gggtacgacg     480

ccggttgcag cgagcccgag ccgtgcgagc agctctccgg gtcgtggtgg tagcagcgaa     540

ccgggtagcc cgcgtagcgc ctatagcagc gatgatagcg gctgcgaagg tgccctgtct     600

ccggcggaac gtgaactgct ggattttagc agctggctgg gcggctatta a              651
```

<210> SEQ ID NO 21
<211> LENGTH: 199
<212> TYPE: PRT
<213> ORGANISM: Artificial Sequence
<220> FEATURE:
<223> OTHER INFORMATION: Homo Sapien

<400> SEQUENCE: 21

```
Met Gly His His His His His His His His His His Ser Ser Gly His
 1               5                  10                  15

Ile Asp Asp Asp Asp Lys His Met Ala Thr Ala Glu Thr Gly Gly Gly
            20                  25                  30

Ala Ala Ala Val Ala Arg Arg Asn Glu Arg Glu Arg Asn Arg Val Lys
        35                  40                  45

Leu Val Asn Leu Gly Phe Gln Ala Leu Arg Gln His Val Pro His Gly
    50                  55                  60

Gly Ala Ser Lys Lys Leu Ser Lys Val Glu Thr Leu Arg Ser Ala Val
65                  70                  75                  80

Glu Tyr Ile Arg Ala Leu Gln Arg Leu Leu Ala Glu His Asp Ala Val
                85                  90                  95

Arg Asn Ala Leu Ala Gly Gly Leu Arg Pro Gln Ala Val Arg Pro Ser
            100                 105                 110

Ala Pro Arg Gly Pro Pro Gly Thr Thr Pro Val Ala Ala Ser Pro Ser
        115                 120                 125

Arg Ala Ser Ser Ser Pro Gly Arg Gly Gly Ser Ser Glu Pro Gly Ser
```

```
    130                 135                 140

Pro Arg Ser Ala Tyr Ser Ser Asp Asp Ser Gly Cys Glu Gly Ala Leu
145                 150                 155                 160

Ser Pro Ala Glu Arg Glu Leu Leu Asp Phe Ser Ser Trp Leu Gly Gly
                165                 170                 175

Tyr Leu Glu Asp Pro Ala Ala Asn Lys Ala Arg Lys Glu Ala Glu Leu
            180                 185                 190

Ala Ala Ala Thr Ala Glu Gln
        195


<210> SEQ ID NO 22
<211> LENGTH: 600
<212> TYPE: DNA
<213> ORGANISM: Artificial Sequence
<220> FEATURE:
<223> OTHER INFORMATION: Homo Sapien

<400> SEQUENCE: 22

atgggccatc atcatcatca tcatcatcat catcacagca gcggccatat cgacgacgac     60

gacaagcata tggccaccgc ggaaaccggt ggtggtgcgg cagcggttgc gcgtcgtaac    120

gaacgtgaac gtaaccgtgt gaaactggtg aacctgggct ttcaggcgct gcgtcagcat    180

gtgccgcatg gcggtgcgag caaaaaactg agcaaagtgg aaaccctgcg tagcgcggtg    240

gaatatattc gtgcgctgca acgtctgctg gccgaacatg atgcggtgcg taacgcgctg    300

gccggtggtc tgcgtccgca ggcggttcgt ccgagcgcac cgcgtggtcc gccgggtacg    360

acgccggttg cagcgagccc gagccgtgcg agcagctctc cgggtcgtgg tggtagcagc    420

gaaccgggta gcccgcgtag cgcctatagc agcgatgata gcggctgcga aggtgccctg    480

tctccggcgg aacgtgaact gctggatttt agcagctggc tgggcggcta tctcgaggat    540

ccggctgcta acaaagcccg aaaggaagct gagttggctg ctgccaccgc tgagcaataa    600


<210> SEQ ID NO 23
<211> LENGTH: 157
<212> TYPE: PRT
<213> ORGANISM: Artificial Sequence
<220> FEATURE:
<223> OTHER INFORMATION: Homo Sapien

<400> SEQUENCE: 23

Met Gly His His His His His His His His His His Ser Ser Gly His
 1               5                  10                  15

Ile Asp Asp Asp Asp Lys His Met Asn Arg Val Lys Leu Val Asn Leu
            20                  25                  30

Gly Phe Gln Ala Leu Arg Gln His Val Pro His Gly Gly Ala Ser Lys
        35                  40                  45

Lys Leu Ser Lys Val Glu Thr Leu Arg Ser Ala Val Glu Tyr Ile Arg
    50                  55                  60

Ala Leu Gln Arg Leu Leu Ala Glu His Asp Ala Val Arg Asn Ala Leu
65                  70                  75                  80

Ala Gly Gly Leu Arg Pro Gln Ala Val Arg Pro Ser Ala Pro Arg Gly
                85                  90                  95

Pro Pro Gly Thr Thr Pro Val Ala Ala Ser Pro Ser Arg Ala Ser Ser
            100                 105                 110

Ser Pro Gly Arg Gly Gly Ser Ser Glu Pro Gly Ser Pro Arg Ser Ala
        115                 120                 125

Tyr Ser Ser Asp Asp Ser Gly Cys Glu Gly Ala Leu Ser Pro Ala Glu
```

130 135 140

Arg Glu Leu Leu Asp Phe Ser Ser Trp Leu Gly Gly Tyr
145 150 155

<210> SEQ ID NO 24
<211> LENGTH: 474
<212> TYPE: DNA
<213> ORGANISM: Artificial Sequence
<220> FEATURE:
<223> OTHER INFORMATION: Homo Sapien

<400> SEQUENCE: 24
atgggccatc atcatcatca tcatcatcat catcacagca gcggccatat cgacgacgac 60
gacaagcata tgaaccgtgt gaaactggtg aacctgggct ttcaggcgct gcgtcagcat 120
gtgccgcatg gcggtgcgag caaaaaactg agcaaagtgg aaaccctgcg tagcgcggtg 180
gaatatattc gtgcgctgca acgtctgctg gccgaacatg atgcggtgcg taacgcgctg 240
gccggtggtc tgcgtccgca ggcggttcgt ccgagcgcac cgcgtggtcc gccgggtacg 300
acgccggttg cagcgagccc gagccgtgcg agcagctctc cgggtcgtgg tggtagcagc 360
gaaccgggta gcccgcgtag cgcctatagc agcgatgata gcggctgcga aggtgccctg 420
tctccggcgg aacgtgaact gctggatttt agcagctggc tgggcggcta ttaa 474

<210> SEQ ID NO 25
<211> LENGTH: 93
<212> TYPE: PRT
<213> ORGANISM: Artificial Sequence
<220> FEATURE:
<223> OTHER INFORMATION: Homo Sapien

<400> SEQUENCE: 25

Met Gly His His His His His His His His His His Ser Ser Gly His
1 5 10 15

Ile Asp Asp Asp Asp Lys His Met Ala Ala Ala Val Ala Arg Arg Asn
20 25 30

Glu Arg Glu Arg Asn Arg Val Lys Leu Val Asn Leu Gly Phe Gln Ala
35 40 45

Leu Arg Gln His Val Pro His Gly Gly Ala Ser Lys Lys Leu Ser Lys
50 55 60

Val Glu Thr Leu Arg Ser Ala Val Glu Tyr Ile Arg Ala Leu Gln Arg
65 70 75 80

Leu Leu Ala Glu His Asp Ala Val Arg Asn Ala Leu Ala
85 90

<210> SEQ ID NO 26
<211> LENGTH: 282
<212> TYPE: DNA
<213> ORGANISM: Artificial Sequence
<220> FEATURE:
<223> OTHER INFORMATION: Homo Sapien

<400> SEQUENCE: 26
atgggccatc atcatcatca tcatcatcat catcacagca gcggccatat cgacgacgac 60
gacaagcata tggcggcagc ggttgcgcgt cgtaacgaac gtgaacgtaa ccgtgtgaaa 120
ctggtgaacc tgggctttca ggcgctgcgt cagcatgtgc cgcatggcgg tgcgagcaaa 180
aaactgagca aagtggaaac cctgcgtagc gcggtggaat atattcgtgc gctgcaacgt 240
ctgctggccg aacatgatgc ggtgcgtaac gcgctggcct aa 282

<210> SEQ ID NO 27
<211> LENGTH: 178
<212> TYPE: PRT
<213> ORGANISM: Artificial Sequence
<220> FEATURE:
<223> OTHER INFORMATION: Homo Sapien

<400> SEQUENCE: 27

```
Met Asp Gly Gly Thr Leu Pro Arg Ser Ala Pro Pro Ala Pro Pro Val
 1               5                  10                  15

Pro Val Gly Cys Ala Ala Arg Arg Arg Pro Ala Ser Pro Glu Leu Leu
            20                  25                  30

Arg Cys Ser Arg Arg Arg Arg Pro Ala Thr Ala Glu Thr Gly Gly Gly
        35                  40                  45

Ala Ala Ala Val Ala Arg Arg Asn Glu Arg Glu Arg Asn Arg Val Lys
    50                  55                  60

Leu Val Asn Leu Gly Phe Gln Ala Leu Arg Gln His Val Pro His Gly
65                  70                  75                  80

Gly Ala Ser Lys Lys Leu Ser Lys Val Glu Thr Leu Arg Ser Ala Val
                85                  90                  95

Glu Tyr Ile Arg Ala Leu Gln Arg Leu Leu Ala Glu His Asp Ala Val
            100                 105                 110

Arg Asn Ala Leu Ala Gly Gly Leu Arg Pro Gln Ala Val Arg Pro Ser
        115                 120                 125

Ala Pro Arg Gly Gly Ser Ser Glu Pro Gly Ser Pro Arg Ser Ala Tyr
    130                 135                 140

Ser Ser Asp Asp Ser Gly Cys Glu Gly Ala Leu Ser Pro Ala Glu Arg
145                 150                 155                 160

Glu Leu Leu Asp Phe Ser Ser Trp Leu Gly Gly Tyr His His His His
                165                 170                 175

His His
```

<210> SEQ ID NO 28
<211> LENGTH: 537
<212> TYPE: DNA
<213> ORGANISM: Artificial Sequence
<220> FEATURE:
<223> OTHER INFORMATION: Homo Sapien

<400> SEQUENCE: 28

```
atggatggtg gcaccctgcc gcgtagcgca ccgccggctc cgccggttcc ggttggttgt      60

gcggcgcgtc gtcgtccggc gagcccggaa ctgctgcgtt gcagccgtcg tcgccgtccg     120

gccaccgcgg aaaccggtgg tggtgcggca gcggttgcgc gtcgtaacga acgtgaacgt     180

aaccgtgtga aactggtgaa cctgggcttt caggcgctgc gtcagcatgt gccgcatggc     240

ggtgcgagca aaaaactgag caaagtggaa accctgcgta gcgcggtgga atatattcgt     300

gcgctgcaac gtctgctggc cgaacatgat gcggtgcgta acgcgctggc cggtggtctg     360

cgtccgcagg cggttcgtcc gagcgcgccg cgtggtggta gcagcgaacc gggtagcccg     420

cgtagcgcct atagcagcga tgatagcggc tgcgaaggtg ccctgagccc ggcggaacgt     480

gaactgctgg attttagcag ctggctgggc ggctatcatc atcatcacca tcattaa        537
```

<210> SEQ ID NO 29
<211> LENGTH: 315
<212> TYPE: PRT
<213> ORGANISM: Artificial Sequence
<220> FEATURE:

<223> OTHER INFORMATION: Homo Sapien

<400> SEQUENCE: 29

Met Asp Pro Ser Ser His Ser Ser Asn Met Ala Asn Thr Gln Met Lys
1 5 10 15

Ser Asp Lys Ile Ile Ile Ala His Arg Gly Ala Ser Gly Tyr Leu Pro
20 25 30

Glu His Thr Leu Glu Ser Lys Ala Leu Ala Phe Ala Gln Gln Ala Asp
35 40 45

Tyr Leu Glu Gln Asp Leu Ala Met Thr Lys Asp Gly Arg Leu Val Val
50 55 60

Ile His Asp His Phe Leu Asp Gly Leu Thr Asp Val Ala Lys Lys Phe
65 70 75 80

Pro His Arg His Arg Lys Asp Gly Arg Tyr Tyr Val Ile Asp Phe Thr
85 90 95

Leu Lys Glu Ile Gln Ser Leu Glu Met Thr Glu Asn Phe Glu Thr Ala
100 105 110

Ala Ala Met Asp Gly Gly Thr Leu Pro Arg Ser Ala Pro Pro Ala Pro
115 120 125

Pro Val Pro Val Gly Cys Ala Ala Arg Arg Arg Pro Ala Ser Pro Glu
130 135 140

Leu Leu Arg Cys Ser Arg Arg Arg Arg Pro Ala Thr Ala Glu Thr Gly
145 150 155 160

Gly Gly Ala Ala Ala Val Ala Arg Arg Asn Glu Arg Glu Arg Asn Arg
165 170 175

Val Lys Leu Val Asn Leu Gly Phe Gln Ala Leu Arg Gln His Val Pro
180 185 190

His Gly Gly Ala Ser Lys Lys Leu Ser Lys Val Glu Thr Leu Arg Ser
195 200 205

Ala Val Glu Tyr Ile Arg Ala Leu Gln Arg Leu Leu Ala Glu His Asp
210 215 220

Ala Val Arg Asn Ala Leu Ala Gly Gly Leu Arg Pro Gln Ala Val Arg
225 230 235 240

Pro Ser Ala Pro Arg Gly Pro Pro Gly Thr Thr Pro Val Ala Ala Ser
245 250 255

Pro Ser Arg Ala Ser Ser Ser Pro Gly Arg Gly Gly Ser Ser Glu Pro
260 265 270

Gly Ser Pro Arg Ser Ala Tyr Ser Ser Asp Asp Ser Gly Cys Glu Gly
275 280 285

Ala Leu Ser Pro Ala Glu Arg Glu Leu Leu Asp Phe Ser Ser Trp Leu
290 295 300

Gly Gly Tyr Leu Glu His His His His His His
305 310 315

<210> SEQ ID NO 30
<211> LENGTH: 948
<212> TYPE: DNA
<213> ORGANISM: Artificial Sequence
<220> FEATURE:
<223> OTHER INFORMATION: Homo Sapien

<400> SEQUENCE: 30
atggatccaa gcagccattc atcaaatatg gcgaataccc aaatgaaatc agacaaaatc 60
attattgctc accgtggtgc tagcggttat ttaccagagc atacgttaga atctaaagca 120
cttgcgtttg cacaacaggc tgattattta gagcaagatt tagcaatgac taaggatggt 180

```
cgtttagtgg ttattcacga tcacttttta gatggcttga ctgatgttgc gaaaaaattc    240

ccacatcgtc atcgtaaaga tggccgttac tatgtcatcg actttacctt aaaagaaatt    300

caaagtttag aaatgacaga aaactttgaa accgcggccg caatggatgg tggcaccctg    360

ccgcgtagcg ctccgccggc accgccggtt ccggttggtt gtgcggcgcg tcgtcgtccg    420

gcgagcccgg aactgctgcg ttgcagccgt cgtcgccgtc cggccaccgc ggaaaccggt    480

ggtggtgcgg cagcggttgc gcgtcgtaac gaacgtgaac gtaaccgtgt gaaactggtg    540

aacctgggct ttcaggcgct gcgtcagcat gtgccgcatg gcggtgcgag caaaaaactg    600

agcaaagtgg aaaccctgcg tagcgcggtg gaatatattc gtgcgctgca acgtctgctg    660

gccgaacatg atgcggtgcg taacgcgctg gccggtggtc tgcgtccgca ggcggttcgt    720

ccgagcgcac cgcgtggtcc gccgggtacg acgccggttg cagcgagccc gagccgtgcg    780

agcagctctc cgggtcgtgg tggtagcagc gaaccgggta gcccgcgtag cgcctatagc    840

agcgatgata gcggctgcga aggtgccctg tctccggcgg aacgtgaact gctggatttt    900

agcagctggc tgggcggcta tctcgagcac caccaccacc accactga                948
```

<210> SEQ ID NO 31
<211> LENGTH: 201
<212> TYPE: PRT
<213> ORGANISM: Artificial Sequence
<220> FEATURE:
<223> OTHER INFORMATION: Homo Sapien

<400> SEQUENCE: 31

```
Met Asp Gly Gly Thr Leu Pro Arg Ser Ala Pro Pro Ala Pro Pro Val
 1               5                  10                  15

Pro Val Gly Cys Ala Ala Arg Arg Arg Pro Ala Ser Pro Glu Leu Leu
            20                  25                  30

Arg Cys Ser Arg Arg Arg Arg Pro Ala Thr Ala Glu Thr Gly Gly Gly
        35                  40                  45

Ala Ala Ala Val Ala Arg Arg Asn Glu Arg Glu Arg Asn Arg Val Lys
    50                  55                  60

Leu Val Asn Leu Gly Phe Gln Ala Leu Arg Gln His Val Pro His Gly
65                  70                  75                  80

Gly Ala Ser Lys Lys Leu Ser Lys Val Glu Thr Leu Arg Ser Ala Val
                85                  90                  95

Glu Tyr Ile Arg Ala Leu Gln Arg Leu Leu Ala Glu His Asp Ala Val
            100                 105                 110

Arg Asn Ala Leu Ala Gly Gly Leu Arg Pro Gln Ala Val Arg Pro Ser
        115                 120                 125

Ala Pro Arg Gly Pro Pro Gly Thr Thr Pro Val Ala Ala Ser Pro Ser
    130                 135                 140

Arg Ala Ser Ser Ser Pro Gly Arg Gly Gly Ser Ser Glu Pro Gly Ser
145                 150                 155                 160

Pro Arg Ser Ala Tyr Ser Ser Asp Asp Ser Gly Cys Glu Gly Ala Leu
                165                 170                 175

Ser Pro Ala Glu Arg Glu Leu Leu Asp Phe Ser Ser Trp Leu Gly Gly
            180                 185                 190

Tyr Leu Glu His His His His His His
        195                 200
```

<210> SEQ ID NO 32
<211> LENGTH: 606

<212> TYPE: DNA
<213> ORGANISM: Artificial Sequence
<220> FEATURE:
<223> OTHER INFORMATION: Homo Sapien

<400> SEQUENCE: 32
atggatggtg gcaccctgcc gcgtagcgct ccgccggcac cgccggttcc ggttggttgt 60
gcggcgcgtc gtcgtccggc gagcccggaa ctgctgcgtt gcagccgtcg tcgccgtccg 120
gccaccgcgg aaaccggtgg tggtgcggca gcggttgcgc gtcgtaacga acgtgaacgt 180
aaccgtgtga aactggtgaa cctgggcttt caggcgctgc gtcagcatgt gccgcatggc 240
ggtgcgagca aaaaactgag caaagtggaa accctgcgta gcgcggtgga atatattcgt 300
gcgctgcaac gtctgctggc cgaacatgat gcggtgcgta acgcgctggc cggtggtctg 360
cgtccgcagg cggttcgtcc gagcgcaccg cgtggtccgc cgggtacgac gccggttgca 420
gcgagcccga gccgtgcgag cagctctccg ggtcgtggtg gtagcagcga accgggtagc 480
ccgcgtagcg cctatagcag cgatgatagc ggctgcgaag gtgccctgtc tccggcggaa 540
cgtgaactgc tggattttag cagctggctg ggcggctatc tcgagcacca ccaccaccac 600
cactga 606

<210> SEQ ID NO 33
<211> LENGTH: 178
<212> TYPE: PRT
<213> ORGANISM: Artificial Sequence
<220> FEATURE:
<223> OTHER INFORMATION: Homo Sapien

<400> SEQUENCE: 33

Met His His His His His His Asp Gly Gly Thr Leu Pro Arg Ser Ala
1 5 10 15

Pro Pro Ala Pro Pro Val Pro Val Gly Cys Ala Ala Arg Arg Arg Pro
20 25 30

Ala Ser Pro Glu Leu Leu Arg Cys Ser Arg Arg Arg Arg Pro Ala Thr
35 40 45

Ala Glu Thr Gly Gly Gly Ala Ala Ala Val Ala Arg Arg Asn Glu Arg
50 55 60

Glu Arg Asn Arg Val Lys Leu Val Asn Leu Gly Phe Gln Ala Leu Arg
65 70 75 80

Gln His Val Pro His Gly Gly Ala Ser Lys Lys Leu Ser Lys Val Glu
85 90 95

Thr Leu Arg Ser Ala Val Glu Tyr Ile Arg Ala Leu Gln Arg Leu Leu
100 105 110

Ala Glu His Asp Ala Val Arg Asn Ala Leu Ala Gly Gly Leu Arg Pro
115 120 125

Gln Ala Val Arg Pro Ser Ala Pro Arg Gly Gly Ser Ser Glu Pro Gly
130 135 140

Ser Pro Arg Ser Ala Tyr Ser Ser Asp Asp Ser Gly Cys Glu Gly Ala
145 150 155 160

Leu Ser Pro Ala Glu Arg Glu Leu Leu Asp Phe Ser Ser Trp Leu Gly
165 170 175

Gly Tyr

<210> SEQ ID NO 34
<211> LENGTH: 537
<212> TYPE: DNA
<213> ORGANISM: Artificial Sequence
<220> FEATURE:
<223> OTHER INFORMATION: Homo Sapien

<400> SEQUENCE: 34

```
atgcaccatc accatcacca tgatggtggc accctgccgc gtagcgcacc gccggctccg     60

ccggttccgg ttggttgtgc ggcgcgtcgt cgtccggcga gcccggaact gctgcgttgc    120

agccgtcgtc gccgtccggc caccgcggaa accggtggtg gtgcggcagc ggttgcgcgt    180

cgtaacgaac gtgaacgtaa ccgtgtgaaa ctggtgaacc tgggctttca ggcgctgcgt    240

cagcatgtgc cgcatggcgg tgcgagcaaa aaactgagca aagtggaaac cctgcgtagc    300

gcggtggaat atattcgtgc gctgcaacgt ctgctggccg aacatgatgc ggtgcgtaac    360

gcgctggccg gtggtctgcg tccgcaggcg gttcgtccga gcgcgccgcg tggtggtagc    420

agcgaaccgg gtagcccgcg tagcgcctat agcagcgatg atagcggctg cgaaggtgcc    480

ctgagcccgg cggaacgtga actgctggat tttagcagct ggctgggcgg ctattaa       537
```

<210> SEQ ID NO 35
<211> LENGTH: 24
<212> TYPE: DNA
<213> ORGANISM: Artificial Sequence
<220> FEATURE:
<223> OTHER INFORMATION: E. coli plasmid linker

<400> SEQUENCE: 35

```
atgcatcatc atcatcatca tgac                                            24
```

<210> SEQ ID NO 36
<211> LENGTH: 24
<212> TYPE: DNA
<213> ORGANISM: Artificial Sequence
<220> FEATURE:
<223> OTHER INFORMATION: E. coli plasmid linker

<400> SEQUENCE: 36

```
atgcaccatc accatcacca tgat                                            24
```

<210> SEQ ID NO 37
<211> LENGTH: 178
<212> TYPE: PRT
<213> ORGANISM: Artificial Sequence
<220> FEATURE:
<223> OTHER INFORMATION: Homo Sapien

<400> SEQUENCE: 37

```
Met His His His His His His Asp Gly Gly Thr Leu Pro Arg Ser Ala
1               5                   10                  15

Pro Pro Ala Pro Pro Val Pro Val Gly Cys Ala Ala Arg Arg Arg Pro
            20                  25                  30

Ala Ser Pro Glu Leu Leu Arg Cys Ser Arg Arg Arg Arg Pro Ala Thr
        35                  40                  45

Ala Glu Thr Gly Gly Gly Ala Ala Ala Val Ala Arg Arg Asn Glu Arg
    50                  55                  60

Glu Arg Asn Arg Val Lys Leu Val Asn Leu Gly Phe Gln Ala Leu Arg
65                  70                  75                  80

Gln His Val Pro His Gly Gly Ala Ser Lys Lys Leu Ser Lys Val Glu
                85                  90                  95

Thr Leu Arg Ser Ala Val Glu Tyr Ile Arg Ala Leu Gln Arg Leu Leu
            100                 105                 110

Ala Glu His Asp Ala Val Arg Asn Ala Leu Ala Gly Gly Leu Arg Pro
```

```
        115                 120                 125

Gln Ala Val Arg Pro Ser Ala Pro Arg Gly Gly Ser Ser Glu Pro Gly
    130                 135                 140

Ser Pro Arg Ser Ala Tyr Ser Ser Asp Asp Ser Gly Cys Glu Gly Ala
145                 150                 155                 160

Leu Ser Pro Ala Glu Arg Glu Leu Leu Asp Phe Ser Ser Trp Leu Gly
                165                 170                 175

Gly Tyr


<210> SEQ ID NO 38
<211> LENGTH: 537
<212> TYPE: DNA
<213> ORGANISM: Artificial Sequence
<220> FEATURE:
<223> OTHER INFORMATION: Homo Sapien

<400> SEQUENCE: 38

atgcatcatc atcatcatca tgacggtggc accctgccgc gtagcgcacc gccggctccg     60

ccggttccgg ttggttgtgc ggcgcgtcgt cgtccggcga gcccggaact gctgcgttgc    120

agccgtcgtc gccgtccggc caccgcggaa accggtggtg gtgcggcagc ggttgcgcgt    180

cgtaacgaac gtgaacgtaa ccgtgtgaaa ctggtgaacc tgggctttca ggcgctgcgt    240

cagcatgtgc cgcatggcgg tgcgagcaaa aaactgagca aagtggaaac cctgcgtagc    300

gcggtggaat atattcgtgc gctgcaacgt ctgctggccg aacatgatgc ggtgcgtaac    360

gcgctggccg gtggtctgcg tccgcaggcg gttcgtccga gcgcgccgcg tggtggtagc    420

agcgaaccgg gtagcccgcg tagcgcctat agcagcgatg atagcggctg cgaaggtgcc    480

ctgagcccgg cggaacgtga actgctggat tttagcagct ggctgggcgg ctattaa       537


<210> SEQ ID NO 39
<211> LENGTH: 111
<212> TYPE: PRT
<213> ORGANISM: Artificial Sequence
<220> FEATURE:
<223> OTHER INFORMATION: H. Influenzae

<400> SEQUENCE: 39

Met Asp Pro Ser Ser His Ser Ser Asn Met Ala Asn Thr Gln Met Lys
 1               5                  10                  15

Ser Asp Lys Ile Ile Ile Ala His Arg Gly Ala Ser Gly Tyr Leu Pro
            20                  25                  30

Glu His Thr Leu Glu Ser Lys Ala Leu Ala Phe Ala Gln Gln Ala Asp
        35                  40                  45

Tyr Leu Glu Gln Asp Leu Ala Met Thr Lys Asp Gly Arg Leu Val Val
    50                  55                  60

Ile His Asp His Phe Leu Asp Gly Leu Thr Asp Val Ala Lys Lys Phe
65                  70                  75                  80

Pro His Arg His Arg Lys Asp Gly Arg Tyr Tyr Val Ile Asp Phe Thr
                85                  90                  95

Leu Lys Glu Ile Gln Ser Leu Glu Met Thr Glu Asn Phe Glu Thr
            100                 105                 110


<210> SEQ ID NO 40
<211> LENGTH: 333
<212> TYPE: DNA
<213> ORGANISM: Artificial Sequence
<220> FEATURE:
<223> OTHER INFORMATION: Homo Sapien
```

<400> SEQUENCE: 40

```
atggatccaa gcagccattc atcaaatatg gcgaataccc aaatgaaatc agacaaaatc     60

attattgctc accgtggtgc tagcggttat ttaccagagc atacgttaga atctaaagca    120

cttgcgtttg cacaacaggc tgattattta gagcaagatt tagcaatgac taaggatggt    180

cgtttagtgg ttattcacga tcacttttta gatggcttga ctgatgttgc gaaaaaattc    240

ccacatcgtc atcgtaaaga tggccgttac tatgtcatcg actttacctt aaaagaaatt    300

caaagtttag aaatgacaga aaactttgaa acc                                  333
```

<210> SEQ ID NO 41
<211> LENGTH: 364
<212> TYPE: PRT
<213> ORGANISM: H. Influenzae Protein D

<400> SEQUENCE: 41

```
Met Lys Leu Lys Thr Leu Ala Leu Ser Leu Leu Ala Ala Gly Val Leu
1               5                   10                  15

Ala Gly Cys Ser Ser His Ser Ser Asn Met Ala Asn Thr Gln Met Lys
            20                  25                  30

Ser Asp Lys Ile Ile Ile Ala His Arg Gly Ala Ser Gly Tyr Leu Pro
        35                  40                  45

Glu His Thr Leu Glu Ser Lys Ala Leu Ala Phe Ala Gln Gln Ala Asp
    50                  55                  60

Tyr Leu Glu Gln Asp Leu Ala Met Thr Lys Asp Gly Arg Leu Val Val
65                  70                  75                  80

Ile His Asp His Phe Leu Asp Gly Leu Thr Asp Val Ala Lys Lys Phe
                85                  90                  95

Pro His Arg His Arg Lys Asp Gly Arg Tyr Tyr Val Ile Asp Phe Thr
            100                 105                 110

Leu Lys Glu Ile Gln Ser Leu Glu Met Thr Glu Asn Phe Glu Thr Lys
        115                 120                 125

Asp Gly Lys Gln Ala Gln Val Tyr Pro Asn Arg Phe Pro Leu Trp Lys
    130                 135                 140

Ser His Phe Arg Ile His Thr Phe Glu Asp Glu Ile Glu Phe Ile Gln
145                 150                 155                 160

Gly Leu Glu Lys Ser Thr Gly Lys Lys Val Gly Ile Tyr Pro Glu Ile
                165                 170                 175

Lys Ala Pro Trp Phe His His Gln Asn Gly Lys Asp Ile Ala Ala Glu
            180                 185                 190

Thr Leu Lys Val Leu Lys Lys Tyr Gly Tyr Asp Lys Lys Thr Asp Met
        195                 200                 205

Val Tyr Leu Gln Thr Phe Asp Phe Asn Glu Leu Lys Arg Ile Lys Thr
    210                 215                 220

Glu Leu Leu Pro Gln Met Gly Met Asp Leu Lys Leu Val Gln Leu Ile
225                 230                 235                 240

Ala Tyr Thr Asp Trp Lys Glu Thr Gln Glu Lys Asp Pro Lys Gly Tyr
                245                 250                 255

Trp Val Asn Tyr Asn Tyr Asp Trp Met Phe Lys Pro Gly Ala Met Ala
            260                 265                 270

Glu Val Val Lys Tyr Ala Asp Gly Val Gly Pro Gly Trp Tyr Met Leu
        275                 280                 285

Val Asn Lys Glu Glu Ser Lys Pro Asp Asn Ile Val Tyr Thr Pro Leu
    290                 295                 300
```

```
Val Lys Glu Leu Ala Gln Tyr Asn Val Glu Val His Pro Tyr Thr Val
305                 310                 315                 320

Arg Lys Asp Ala Leu Pro Glu Phe Phe Thr Asp Val Asn Gln Met Tyr
                325                 330                 335

Asp Ala Leu Leu Asn Lys Ser Gly Ala Thr Gly Val Phe Thr Asp Phe
            340                 345                 350

Pro Asp Thr Gly Val Glu Phe Leu Lys Gly Ile Lys
        355                 360


<210> SEQ ID NO 42
<211> LENGTH: 23
<212> TYPE: PRT
<213> ORGANISM: Artificial Sequence
<220> FEATURE:
<223> OTHER INFORMATION: E. coli vector polyhistidine tag

<400> SEQUENCE: 42

Met Gly His His His His His His His His His His Ser Ser Gly His
 1               5                  10                  15

Ile Asp Asp Asp Asp Lys His
            20


<210> SEQ ID NO 43
<211> LENGTH: 552
<212> TYPE: PRT
<213> ORGANISM: Artificial Sequence
<220> FEATURE:
<223> OTHER INFORMATION: Homo Sapien

<400> SEQUENCE: 43

Met Asp Pro Ser Ser His Ser Ser Asn Met Ala Asn Thr Gln Met Lys
 1               5                  10                  15

Ser Asp Lys Ile Ile Ile Ala His Arg Gly Ala Ser Gly Tyr Leu Pro
            20                  25                  30

Glu His Thr Leu Glu Ser Lys Ala Leu Ala Phe Ala Gln Gln Ala Asp
        35                  40                  45

Tyr Leu Glu Gln Asp Leu Ala Met Thr Lys Asp Gly Arg Leu Val Val
    50                  55                  60

Ile His Asp His Phe Leu Asp Gly Leu Thr Asp Val Ala Lys Lys Phe
65                  70                  75                  80

Pro His Arg His Arg Lys Asp Gly Arg Tyr Tyr Val Ile Asp Phe Thr
                85                  90                  95

Leu Lys Glu Ile Gln Ser Leu Glu Met Thr Glu Asn Phe Glu Thr Lys
            100                 105                 110

Asp Gly Lys Gln Ala Gln Val Tyr Pro Asn Arg Phe Pro Leu Trp Lys
        115                 120                 125

Ser His Phe Arg Ile His Thr Phe Glu Asp Glu Ile Glu Phe Ile Gln
    130                 135                 140

Gly Leu Glu Lys Ser Thr Gly Lys Lys Val Gly Ile Tyr Pro Glu Ile
145                 150                 155                 160

Lys Ala Pro Trp Phe His His Gln Asn Gly Lys Asp Ile Ala Ala Glu
                165                 170                 175

Thr Leu Lys Val Leu Lys Lys Tyr Gly Tyr Asp Lys Lys Thr Asp Met
            180                 185                 190

Val Tyr Leu Gln Thr Phe Asp Phe Asn Glu Leu Lys Arg Ile Lys Thr
        195                 200                 205

Glu Leu Leu Pro Gln Met Gly Met Asp Leu Lys Leu Val Gln Leu Ile
```

```
    210                 215                 220

Ala Tyr Thr Asp Trp Lys Glu Thr Gln Glu Lys Asp Pro Lys Gly Tyr
225                 230                 235                 240

Trp Val Asn Tyr Asn Tyr Asp Trp Met Phe Lys Pro Gly Ala Met Ala
                245                 250                 255

Glu Val Val Lys Tyr Ala Asp Gly Val Gly Pro Gly Trp Tyr Met Leu
            260                 265                 270

Val Asn Lys Glu Glu Ser Lys Pro Asp Asn Ile Val Tyr Thr Pro Leu
        275                 280                 285

Val Lys Glu Leu Ala Gln Tyr Asn Val Glu Val His Pro Tyr Thr Val
    290                 295                 300

Arg Lys Asp Ala Leu Pro Ala Phe Phe Thr Asp Val Asn Gln Met Tyr
305                 310                 315                 320

Asp Val Leu Leu Asn Lys Ser Gly Ala Thr Gly Val Phe Thr Asp Phe
                325                 330                 335

Pro Asp Thr Gly Val Glu Phe Leu Lys Gly Ile Lys Ala Ala Ala Met
            340                 345                 350

Asp Gly Gly Thr Leu Pro Arg Ser Ala Pro Pro Ala Pro Pro Val Pro
        355                 360                 365

Val Gly Cys Ala Ala Arg Arg Arg Pro Ala Ser Pro Glu Leu Leu Arg
    370                 375                 380

Cys Ser Arg Arg Arg Arg Pro Ala Thr Ala Glu Thr Gly Gly Gly Ala
385                 390                 395                 400

Ala Ala Val Ala Arg Arg Asn Glu Arg Glu Arg Asn Arg Val Lys Leu
                405                 410                 415

Val Asn Leu Gly Phe Gln Ala Leu Arg Gln His Val Pro His Gly Gly
            420                 425                 430

Ala Ser Lys Lys Leu Ser Lys Val Glu Thr Leu Arg Ser Ala Val Glu
        435                 440                 445

Tyr Ile Arg Ala Leu Gln Arg Leu Leu Ala Glu His Asp Ala Val Arg
    450                 455                 460

Asn Ala Leu Ala Gly Gly Leu Arg Pro Gln Ala Val Arg Pro Ser Ala
465                 470                 475                 480

Pro Arg Gly Pro Pro Gly Thr Thr Pro Val Ala Ala Ser Pro Ser Arg
                485                 490                 495

Ala Ser Ser Ser Pro Gly Arg Gly Gly Ser Ser Glu Pro Gly Ser Pro
            500                 505                 510

Arg Ser Ala Tyr Ser Ser Asp Asp Ser Gly Cys Glu Gly Ala Leu Ser
        515                 520                 525

Pro Ala Glu Arg Glu Leu Leu Asp Phe Ser Ser Trp Leu Gly Gly Tyr
    530                 535                 540

Leu Glu His His His His His His
545                 550


<210> SEQ ID NO 44
<211> LENGTH: 1656
<212> TYPE: DNA
<213> ORGANISM: Artificial Sequence
<220> FEATURE:
<223> OTHER INFORMATION: Homo Sapien

<400> SEQUENCE: 44

atggatccaa gcagccattc atcaaatatg gcgaataccc aaatgaaatc agacaaaatc      60

attattgctc accgtggtgc tagcggttat ttaccagagc atacgttaga gtctaaagca     120
```

-continued

```
cttgcgtttg cacaacaggc tgattattta gagcaagatt tagcaatgac taaggatggt    180
cgtttagtgg ttattcacga tcacttttta gatggcttga ctgatgttgc gaaaaaattc    240
ccacatcgtc accgtaaaga tggtcgttac tatgtcatcg actttacctt aaaagaaatt    300
caaagtttag aaatgacaga aaactttgaa accaaagatg gcaaacaagc gcaagtttat    360
cctaatcgtt tcccactttg gaaatcacat tttagaattc ataccttgaa agatgaaatt    420
gaatttatcc aaggcttaga aaaatccact ggcaaaaaag tagggattta tccagaaatc    480
aaagcacctt ggttccacca tcaaaatggt aaagatattg ctgctgaaac gctcaaagtg    540
ttaaaaaaat atggctatga taagaaaacc gatatggttt acttacaaac tttcgatttt    600
aatgaattaa aacgtatcaa aacggaatta cttccacaaa tgggaatgga tttgaaatta    660
gttcaattaa ttgcttatac agattggaaa gaaacacaag aaaaagaccc aaagggttat    720
tgggtaaact ataattacga ttggatgttt aaacctggtg caatggcaga agtggttaaa    780
tatgccgatg gtgttggccc aggttggtat atgttagtta ataaagaaga atccaaacct    840
gataatattg tgtacactcc gttggtaaaa gaacttgcac aatataatgt ggaagtgcat    900
ccttacaccg tgcgtaaaga tgcactaccc gcgtttttca cagacgtaaa tcaaatgtat    960
gatgtcttat tgaataaatc aggggcaaca ggtgtattta ctgatttccc agatactggc   1020
gtggaattct taaaaggaat aaaagcggcc gcaatggatg gtggcaccct gccgcgtagc   1080
gctccgccgg caccgccggt tccggttggt tgtgcggcgc gtcgtcgtcc ggcgagcccg   1140
gaactgctgc gttgcagccg tcgtcgccgt ccggccaccg cggaaaccgg tggtggtgcg   1200
gcagcggttg cgcgtcgtaa cgaacgtgaa cgtaaccgtg tgaaactggt gaacctgggc   1260
tttcaggcgc tgcgtcagca tgtgccgcat ggcggtgcga gcaaaaaact gagcaaagtg   1320
gaaaccctgc gtagcgcggt ggaatatatt cgtgcgctgc aacgtctgct ggccgaacat   1380
gatgcggtgc gtaacgcgct ggccggtggt ctgcgtccgc aggcggttcg tccgagcgca   1440
ccgcgtggtc cgccgggtac gacgccggtt gcagcgagcc cgagccgtgc gagcagctct   1500
ccgggtcgtg gtggtagcag cgaaccgggt agcccgcgta gcgcctatag cagcgatgat   1560
agcggctgcg aaggtgccct gtctccggcg gaacgtgaac tgctggattt tagcagctgg   1620
ctgggcggct atctcgagca ccaccaccac caccac                             1656
```

<210> SEQ ID NO 45
<211> LENGTH: 298
<212> TYPE: PRT
<213> ORGANISM: Artificial Sequence
<220> FEATURE:
<223> OTHER INFORMATION: Homo Sapien

<400> SEQUENCE: 45

```
Met Gly His His His His His His Gly Ser Asp Ser Glu Val Asn Gln
1               5                   10                  15

Glu Ala Lys Pro Glu Val Lys Pro Glu Val Lys Pro Glu Thr His Ile
            20                  25                  30

Asn Leu Lys Val Ser Asp Gly Ser Ser Glu Ile Phe Phe Lys Ile Lys
        35                  40                  45

Lys Thr Thr Pro Leu Arg Arg Leu Met Glu Ala Phe Ala Lys Arg Gln
    50                  55                  60

Gly Lys Glu Met Asp Ser Leu Arg Phe Leu Tyr Asp Gly Ile Arg Ile
65                  70                  75                  80

Gln Ala Asp Gln Ala Pro Glu Asp Leu Asp Met Glu Asp Asn Asp Ile
                85                  90                  95
```

-continued

```
Ile Glu Ala His Arg Glu Gln Ile Gly Gly Asp Gly Gly Thr Leu Pro
            100                 105                 110

Arg Ser Ala Pro Pro Ala Pro Pro Val Pro Val Gly Cys Ala Ala Arg
        115                 120                 125

Arg Arg Pro Ala Ser Pro Glu Leu Leu Arg Cys Ser Arg Arg Arg Arg
    130                 135                 140

Pro Ala Thr Ala Glu Thr Gly Gly Gly Ala Ala Ala Val Ala Arg Arg
145                 150                 155                 160

Asn Glu Arg Glu Arg Asn Arg Val Lys Leu Val Asn Leu Gly Phe Gln
                165                 170                 175

Ala Leu Arg Gln His Val Pro His Gly Gly Ala Ser Lys Lys Leu Ser
            180                 185                 190

Lys Val Glu Thr Leu Arg Ser Ala Val Glu Tyr Ile Arg Ala Leu Gln
        195                 200                 205

Arg Leu Leu Ala Glu His Asp Ala Val Arg Asn Ala Leu Ala Gly Gly
    210                 215                 220

Leu Arg Pro Gln Ala Val Arg Pro Ser Ala Pro Arg Gly Pro Pro Gly
225                 230                 235                 240

Thr Thr Pro Val Ala Ala Ser Pro Ser Arg Ala Ser Ser Ser Pro Gly
                245                 250                 255

Arg Gly Gly Ser Ser Glu Pro Gly Ser Pro Arg Ser Ala Tyr Ser Ser
            260                 265                 270

Asp Asp Ser Gly Cys Glu Gly Ala Leu Ser Pro Ala Glu Arg Glu Leu
        275                 280                 285

Leu Asp Phe Ser Ser Trp Leu Gly Gly Tyr
    290                 295
```

<210> SEQ ID NO 46
<211> LENGTH: 894
<212> TYPE: DNA
<213> ORGANISM: Artificial Sequence
<220> FEATURE:
<223> OTHER INFORMATION: Homo Sapien

<400> SEQUENCE: 46

```
atgggtcatc accatcatca tcacgggtcg gactcagaag tcaatcaaga agctaagcca     60

gaggtcaagc cagaagtcaa gcctgagact cacatcaatt taaaggtgtc cgatggatct    120

tcagagatct tcttcaagat caaaaagacc actcctttaa gaaggctgat ggaagcgttc    180

gctaaaagac agggtaagga aatggactcc ttaagattct tgtacgacgg tattagaatt    240

caagctgatc aggcccctga agatttggac atggaggata acgatattat tgaggctcac    300

cgcgaacaga ttggaggtga tggtggcacc ctgccgcgta gcgctccgcc ggcaccgccg    360

gttccggttg gttgtgcggc gcgtcgtcgt ccggcgagcc cggaactgct gcgttgcagc    420

cgtcgtcgcc gtccggccac cgcggaaacc ggtggtggtg cggcagcggt tgcgcgtcgt    480

aacgaacgtg aacgtaaccg tgtgaaactg gtgaacctgg gctttcaggc gctgcgtcag    540

catgtgccgc atggcggtgc gagcaaaaaa ctgagcaaag tggaaaccct gcgtagcgcg    600

gtggaatata ttcgtgcgct gcaacgtctg ctggccgaac atgatgcggt gcgtaacgcg    660

ctggccggtg gtctgcgtcc gcaggcggtt cgtccgagcg caccgcgtgg tccgccgggt    720

acgacgccgg ttgcagcgag cccgagccgt gcgagcagct ctccgggtcg tggtggtagc    780

agcgaaccgg gtagcccgcg tagcgcctat agcagcgatg atagcggctg cgaaggtgcc    840

ctgtctccgg cggaacgtga actgctggat tttagcagct ggctgggcgg ctat          894
```

<210> SEQ ID NO 47
<211> LENGTH: 412
<212> TYPE: PRT
<213> ORGANISM: Artificial Sequence
<220> FEATURE:
<223> OTHER INFORMATION: Homo Sapien

<400> SEQUENCE: 47

Met Gly His His His His His His Gly Ser Asp Ser Glu Val Asn Gln
1 5 10 15

Glu Ala Lys Pro Glu Val Lys Pro Glu Val Lys Pro Glu Thr His Ile
20 25 30

Asn Leu Lys Val Ser Asp Gly Ser Ser Glu Ile Phe Phe Lys Ile Lys
35 40 45

Lys Thr Thr Pro Leu Arg Arg Leu Met Glu Ala Phe Ala Lys Arg Gln
50 55 60

Gly Lys Glu Met Asp Ser Leu Arg Phe Leu Tyr Asp Gly Ile Arg Ile
65 70 75 80

Gln Ala Asp Gln Ala Pro Glu Asp Leu Asp Met Glu Asp Asn Asp Ile
85 90 95

Ile Glu Ala His Arg Glu Gln Ile Gly Gly Asp Pro Ser Ser His Ser
100 105 110

Ser Asn Met Ala Asn Thr Gln Met Lys Ser Asp Lys Ile Ile Ile Ala
115 120 125

His Arg Gly Ala Ser Gly Tyr Leu Pro Glu His Thr Leu Glu Ser Lys
130 135 140

Ala Leu Ala Phe Ala Gln Gln Ala Asp Tyr Leu Glu Gln Asp Leu Ala
145 150 155 160

Met Thr Lys Asp Gly Arg Leu Val Val Ile His Asp His Phe Leu Asp
165 170 175

Gly Leu Thr Asp Val Ala Lys Lys Phe Pro His Arg His Arg Lys Asp
180 185 190

Gly Arg Tyr Tyr Val Ile Asp Phe Thr Leu Lys Glu Ile Gln Ser Leu
195 200 205

Glu Met Thr Glu Asn Phe Glu Thr Ala Ala Ala Met Asp Gly Gly Thr
210 215 220

Leu Pro Arg Ser Ala Pro Pro Ala Pro Pro Val Pro Val Gly Cys Ala
225 230 235 240

Ala Arg Arg Arg Pro Ala Ser Pro Glu Leu Leu Arg Cys Ser Arg Arg
245 250 255

Arg Arg Pro Ala Thr Ala Glu Thr Gly Gly Gly Ala Ala Ala Val Ala
260 265 270

Arg Arg Asn Glu Arg Glu Arg Asn Arg Val Lys Leu Val Asn Leu Gly
275 280 285

Phe Gln Ala Leu Arg Gln His Val Pro His Gly Gly Ala Ser Lys Lys
290 295 300

Leu Ser Lys Val Glu Thr Leu Arg Ser Ala Val Glu Tyr Ile Arg Ala
305 310 315 320

Leu Gln Arg Leu Leu Ala Glu His Asp Ala Val Arg Asn Ala Leu Ala
325 330 335

Gly Gly Leu Arg Pro Gln Ala Val Arg Pro Ser Ala Pro Arg Gly Pro
340 345 350

Pro Gly Thr Thr Pro Val Ala Ala Ser Pro Ser Arg Ala Ser Ser Ser
355 360 365

```
Pro Gly Arg Gly Gly Ser Ser Glu Pro Gly Ser Pro Arg Ser Ala Tyr
    370                 375                 380

Ser Ser Asp Asp Ser Gly Cys Glu Gly Ala Leu Ser Pro Ala Glu Arg
385                 390                 395                 400

Glu Leu Leu Asp Phe Ser Ser Trp Leu Gly Gly Tyr
                405                 410
```

<210> SEQ ID NO 48
<211> LENGTH: 1236
<212> TYPE: DNA
<213> ORGANISM: Artificial Sequence
<220> FEATURE:
<223> OTHER INFORMATION: Homo Sapien

<400> SEQUENCE: 48

```
atgggtcatc accatcatca tcacgggtcg gactcagaag tcaatcaaga agctaagcca     60
gaggtcaagc cagaagtcaa gcctgagact cacatcaatt taaaggtgtc cgatggatct    120
tcagagatct tcttcaagat caaaaagacc actcctttaa gaaggctgat ggaagcgttc    180
gctaaaagac agggtaagga aatggactcc ttaagattct tgtacgacgg tattagaatt    240
caagctgatc aggcccctga agatttggac atggaggata acgatattat tgaggctcac    300
cgcgaacaga ttggaggtga tccaagcagc cattcatcaa atatggcgaa tacccaaatg    360
aaatcagaca aaatcattat tgctcaccgt ggtgctagcg gttatttacc agagcatacg    420
ttagaatcta aagcacttgc gtttgcacaa caggctgatt atttagagca agatttagca    480
atgactaagg atggtcgttt agtggttatt cacgatcact ttttagatgg cttgactgat    540
gttgcgaaaa aattcccaca tcgtcatcgt aaagatggcc gttactatgt catcgacttt    600
accttaaaag aaattcaaag tttagaaatg acagaaaact ttgaaaccgc ggccgcaatg    660
gatggtggca ccctgccgcg tagcgctccg ccggcaccgc cggttccggt tggttgtgcg    720
gcgcgtcgtc gtccggcgag cccggaactg ctgcgttgca gccgtcgtcg ccgtccggcc    780
accgcggaaa ccggtggtgg tgcggcagcg gttgcgcgtc gtaacgaacg tgaacgtaac    840
cgtgtgaaac tggtgaacct gggctttcag gcgctgcgtc agcatgtgcc gcatggcggt    900
gcgagcaaaa aactgagcaa agtggaaacc ctgcgtagcg cggtggaata tattcgtgcg    960
ctgcaacgtc tgctggccga acatgatgcg gtgcgtaacg cgctggccgg tggtctgcgt   1020
ccgcaggcgg ttcgtccgag cgcaccgcgt ggtccgccgg gtacgacgcc ggttgcagcg   1080
agcccgagcc gtgcgagcag ctctccgggt cgtggtggta gcagcgaacc gggtagcccg   1140
cgtagcgcct atagcagcga tgatagcggc tgcgaaggtg ccctgtctcc ggcggaacgt   1200
gaactgctgg attttagcag ctggctgggc ggctat                             1236
```

<210> SEQ ID NO 49
<211> LENGTH: 222
<212> TYPE: PRT
<213> ORGANISM: Artificial Sequence
<220> FEATURE:
<223> OTHER INFORMATION: Homo Sapien

<400> SEQUENCE: 49

```
Met Gly His His His His His His Gly Ser Asp Ser Glu Val Asn Gln
 1               5                  10                  15

Glu Ala Lys Pro Glu Val Lys Pro Glu Val Lys Pro Glu Thr His Ile
            20                  25                  30

Asn Leu Lys Val Ser Asp Gly Ser Ser Glu Ile Phe Phe Lys Ile Lys
```

```
        35                  40                  45

Lys Thr Thr Pro Leu Arg Arg Leu Met Glu Ala Phe Ala Lys Arg Gln
    50                  55                  60

Gly Lys Glu Met Asp Ser Leu Arg Phe Leu Tyr Asp Gly Ile Arg Ile
65                  70                  75                  80

Gln Ala Asp Gln Ala Pro Glu Asp Leu Asp Met Glu Asp Asn Asp Ile
                85                  90                  95

Ile Glu Ala His Arg Glu Gln Ile Gly Gly Asp Gly Gly Thr Leu Pro
            100                 105                 110

Arg Ser Ala Pro Pro Ala Pro Pro Val Pro Val Gly Cys Ala Ala Arg
        115                 120                 125

Arg Arg Pro Ala Ser Pro Glu Leu Leu Arg Cys Ser Arg Arg Arg Arg
    130                 135                 140

Pro Ala Thr Ala Glu Thr Gly Gly Gly Ala Ala Ala Val Ala Arg Arg
145                 150                 155                 160

Asn Glu Arg Glu Arg Asn Arg Val Lys Leu Val Asn Leu Gly Phe Gln
                165                 170                 175

Ala Leu Arg Gln His Val Pro His Gly Gly Ala Ser Lys Lys Leu Ser
            180                 185                 190

Lys Val Glu Thr Leu Arg Ser Ala Val Glu Tyr Ile Arg Ala Leu Gln
        195                 200                 205

Arg Leu Leu Ala Glu His Asp Ala Val Arg Asn Ala Leu Ala
    210                 215                 220
```

<210> SEQ ID NO 50
<211> LENGTH: 666
<212> TYPE: DNA
<213> ORGANISM: Artificial Sequence
<220> FEATURE:
<223> OTHER INFORMATION: Homo Sapien

<400> SEQUENCE: 50

```
atgggtcatc accatcatca tcacgggtcg gactcagaag tcaatcaaga agctaagcca      60

gaggtcaagc cagaagtcaa gcctgagact cacatcaatt taaaggtgtc cgatggatct     120

tcagagatct tcttcaagat caaaaagacc actcctttaa gaaggctgat ggaagcgttc     180

gctaaaagac agggtaagga aatggactcc ttaagattct tgtacgacgg tattagaatt     240

caagctgatc aggcccctga agatttggac atggaggata acgatattat tgaggctcac     300

cgcgaacaga ttggaggtga tggtggcacc ctgccgcgta gcgctccgcc ggcaccgccg     360

gttccggttg gttgtgcggc gcgtcgtcgt ccggcgagcc cggaactgct gcgttgcagc     420

cgtcgtcgcc gtccggccac cgcggaaacc ggtggtggtg cggcagcggt tgcgcgtcgt     480

aacgaacgtg aacgtaaccg tgtgaaactg gtgaacctgg gctttcaggc gctgcgtcag     540

catgtgccgc atggcggtgc gagcaaaaaa ctgagcaaag tggaaaccct gcgtagcgcg     600

gtggaatata ttcgtgcgct gcaacgtctg ctggccgaac atgatgcggt gcgtaacgcg     660

ctggcc                                                                666
```

<210> SEQ ID NO 51
<211> LENGTH: 277
<212> TYPE: PRT
<213> ORGANISM: Artificial Sequence
<220> FEATURE:
<223> OTHER INFORMATION: Homo Sapien

<400> SEQUENCE: 51

-continued

```
Met Gly His His His His His His Gly Ser Asp Ser Glu Val Asn Gln
 1               5                  10                  15

Glu Ala Lys Pro Glu Val Lys Pro Glu Val Lys Pro Glu Thr His Ile
            20                  25                  30

Asn Leu Lys Val Ser Asp Gly Ser Ser Glu Ile Phe Phe Lys Ile Lys
        35                  40                  45

Lys Thr Thr Pro Leu Arg Arg Leu Met Glu Ala Phe Ala Lys Arg Gln
    50                  55                  60

Gly Lys Glu Met Asp Ser Leu Arg Phe Leu Tyr Asp Gly Ile Arg Ile
65                  70                  75                  80

Gln Ala Asp Gln Ala Pro Glu Asp Leu Asp Met Glu Asp Asn Asp Ile
                85                  90                  95

Ile Glu Ala His Arg Glu Gln Ile Gly Gly Asp Gly Gly Thr Leu Pro
            100                 105                 110

Arg Ser Ala Pro Pro Ala Pro Pro Val Pro Val Gly Cys Ala Ala Arg
        115                 120                 125

Arg Arg Pro Ala Ser Pro Glu Leu Leu Arg Cys Ser Arg Arg Arg Arg
    130                 135                 140

Pro Ala Thr Ala Glu Thr Gly Gly Gly Ala Ala Ala Val Ala Arg Arg
145                 150                 155                 160

Asn Glu Arg Glu Arg Asn Arg Val Lys Leu Val Asn Leu Gly Phe Gln
                165                 170                 175

Ala Leu Arg Gln His Val Pro His Gly Gly Ala Ser Lys Lys Leu Ser
            180                 185                 190

Lys Val Glu Thr Leu Arg Ser Ala Val Glu Tyr Ile Arg Ala Leu Gln
        195                 200                 205

Arg Leu Leu Ala Glu His Asp Ala Val Arg Asn Ala Leu Ala Gly Gly
    210                 215                 220

Leu Arg Pro Gln Ala Val Arg Pro Ser Ala Pro Arg Gly Gly Ser Ser
225                 230                 235                 240

Glu Pro Gly Ser Pro Arg Ser Ala Tyr Ser Ser Asp Asp Ser Gly Cys
                245                 250                 255

Glu Gly Ala Leu Ser Pro Ala Glu Arg Glu Leu Leu Asp Phe Ser Ser
            260                 265                 270

Trp Leu Gly Gly Tyr
        275
```

<210> SEQ ID NO 52
<211> LENGTH: 831
<212> TYPE: DNA
<213> ORGANISM: Artificial Sequence
<220> FEATURE:
<223> OTHER INFORMATION: Homo Sapien

<400> SEQUENCE: 52

```
atgggtcatc accatcatca tcacgggtcg gactcagaag tcaatcaaga agctaagcca      60

gaggtcaagc cagaagtcaa gcctgagact cacatcaatt taaaggtgtc cgatggatct     120

tcagagatct tcttcaagat caaaaagacc actcctttaa gaaggctgat ggaagcgttc     180

gctaaaagac agggtaagga aatggactcc ttaagattct tgtacgacgg tattagaatt     240

caagctgatc aggcccctga agatttggac atggaggata acgatattat tgaggctcac     300

cgcgaacaga ttggaggtga tggtggcacc ctgccgcgta gcgcaccgcc ggctccgccg     360

gttccggttg gttgtgcggc gcgtcgtcgt ccggcgagcc cggaactgct gcgttgcagc     420

cgtcgtcgcc gtccggccac cgcggaaacc ggtggtggtg cggcagcggt tgcgcgtcgt     480
```

```
aacgaacgtg aacgtaaccg tgtgaaactg gtgaacctgg gctttcaggc gctgcgtcag    540

catgtgccgc atggcggtgc gagcaaaaaa ctgagcaaag tggaaaccct gcgtagcgcg    600

gtggaatata ttcgtgcgct gcaacgtctg ctggccgaac atgatgcggt gcgtaacgcg    660

ctggccggtg gtctgcgtcc gcaggcggtt cgtccgagcg cgccgcgtgg tggtagcagc    720

gaaccgggta gcccgcgtag cgcctatagc agcgatgata gcggctgcga aggtgccctg    780

agcccggcgg aacgtgaact gctggatttt agcagctggc tgggcggcta t             831
```

```
<210> SEQ ID NO 53
<211> LENGTH: 15
<212> TYPE: PRT
<213> ORGANISM: Artificial Sequence
<220> FEATURE:
<223> OTHER INFORMATION: Homo Sapien

<400> SEQUENCE: 53

Met Asp Gly Gly Thr Leu Pro Arg Ser Ala Pro Pro Ala Pro Pro
 1               5                   10                  15
```

```
<210> SEQ ID NO 54
<211> LENGTH: 15
<212> TYPE: PRT
<213> ORGANISM: Artificial Sequence
<220> FEATURE:
<223> OTHER INFORMATION: Homo Sapien

<400> SEQUENCE: 54

Thr Leu Pro Arg Ser Ala Pro Pro Ala Pro Pro Val Pro Val Gly
 1               5                   10                  15
```

```
<210> SEQ ID NO 55
<211> LENGTH: 15
<212> TYPE: PRT
<213> ORGANISM: Artificial Sequence
<220> FEATURE:
<223> OTHER INFORMATION: Homo Sapien

<400> SEQUENCE: 55

Ser Ala Pro Pro Ala Pro Pro Val Pro Val Gly Cys Ala Ala Arg
 1               5                   10                  15
```

```
<210> SEQ ID NO 56
<211> LENGTH: 15
<212> TYPE: PRT
<213> ORGANISM: Artificial Sequence
<220> FEATURE:
<223> OTHER INFORMATION: Homo Sapien

<400> SEQUENCE: 56

Ala Pro Pro Val Pro Val Gly Cys Ala Ala Arg Arg Arg Pro Ala
 1               5                   10                  15
```

```
<210> SEQ ID NO 57
<211> LENGTH: 15
<212> TYPE: PRT
<213> ORGANISM: Artificial Sequence
<220> FEATURE:
<223> OTHER INFORMATION: Homo Sapien

<400> SEQUENCE: 57

Pro Val Gly Cys Ala Ala Arg Arg Arg Pro Ala Ser Pro Glu Leu
 1               5                   10                  15
```

<210> SEQ ID NO 58
<211> LENGTH: 15
<212> TYPE: PRT
<213> ORGANISM: Artificial Sequence
<220> FEATURE:
<223> OTHER INFORMATION: Homo Sapien

<400> SEQUENCE: 58

Ala Ala Arg Arg Arg Pro Ala Ser Pro Glu Leu Leu Arg Cys Ser
1 5 10 15

<210> SEQ ID NO 59
<211> LENGTH: 15
<212> TYPE: PRT
<213> ORGANISM: Artificial Sequence
<220> FEATURE:
<223> OTHER INFORMATION: Homo Sapien

<400> SEQUENCE: 59

Arg Pro Ala Ser Pro Glu Leu Leu Arg Cys Ser Arg Arg Arg Arg
1 5 10 15

<210> SEQ ID NO 60
<211> LENGTH: 15
<212> TYPE: PRT
<213> ORGANISM: Artificial Sequence
<220> FEATURE:
<223> OTHER INFORMATION: Homo Sapien

<400> SEQUENCE: 60

Pro Glu Leu Leu Arg Cys Ser Arg Arg Arg Arg Pro Ala Thr Ala
1 5 10 15

<210> SEQ ID NO 61
<211> LENGTH: 15
<212> TYPE: PRT
<213> ORGANISM: Artificial Sequence
<220> FEATURE:
<223> OTHER INFORMATION: Homo Sapien

<400> SEQUENCE: 61

Arg Cys Ser Arg Arg Arg Arg Pro Ala Thr Ala Glu Thr Gly Gly
1 5 10 15

<210> SEQ ID NO 62
<211> LENGTH: 15
<212> TYPE: PRT
<213> ORGANISM: Artificial Sequence
<220> FEATURE:
<223> OTHER INFORMATION: Homo Sapien

<400> SEQUENCE: 62

Arg Arg Arg Pro Ala Thr Ala Glu Thr Gly Gly Gly Ala Ala Ala
1 5 10 15

<210> SEQ ID NO 63
<211> LENGTH: 15
<212> TYPE: PRT
<213> ORGANISM: Artificial Sequence
<220> FEATURE:
<223> OTHER INFORMATION: Homo Sapien

<400> SEQUENCE: 63

Ala Thr Ala Glu Thr Gly Gly Gly Ala Ala Ala Val Ala Arg Arg
1 5 10 15

<210> SEQ ID NO 64

<211> LENGTH: 15
<212> TYPE: PRT
<213> ORGANISM: Artificial Sequence
<220> FEATURE:
<223> OTHER INFORMATION: Homo Sapien

<400> SEQUENCE: 64

Thr Gly Gly Gly Ala Ala Ala Val Ala Arg Arg Asn Glu Arg Glu
1 5 10 15

<210> SEQ ID NO 65
<211> LENGTH: 15
<212> TYPE: PRT
<213> ORGANISM: Artificial Sequence
<220> FEATURE:
<223> OTHER INFORMATION: Homo Sapien

<400> SEQUENCE: 65

Ala Ala Ala Val Ala Arg Arg Asn Glu Arg Glu Arg Asn Arg Val
1 5 10 15

<210> SEQ ID NO 66
<211> LENGTH: 15
<212> TYPE: PRT
<213> ORGANISM: Artificial Sequence
<220> FEATURE:
<223> OTHER INFORMATION: Homo Sapien

<400> SEQUENCE: 66

Ala Arg Arg Asn Glu Arg Glu Arg Asn Arg Val Lys Leu Val Asn
1 5 10 15

<210> SEQ ID NO 67
<211> LENGTH: 15
<212> TYPE: PRT
<213> ORGANISM: Artificial Sequence
<220> FEATURE:
<223> OTHER INFORMATION: Homo Sapien

<400> SEQUENCE: 67

Glu Arg Glu Arg Asn Arg Val Lys Leu Val Asn Leu Gly Phe Gln
1 5 10 15

<210> SEQ ID NO 68
<211> LENGTH: 15
<212> TYPE: PRT
<213> ORGANISM: Artificial Sequence
<220> FEATURE:
<223> OTHER INFORMATION: Homo Sapien

<400> SEQUENCE: 68

Asn Arg Val Lys Leu Val Asn Leu Gly Phe Gln Ala Leu Arg Gln
1 5 10 15

<210> SEQ ID NO 69
<211> LENGTH: 15
<212> TYPE: PRT
<213> ORGANISM: Artificial Sequence
<220> FEATURE:
<223> OTHER INFORMATION: Homo Sapien

<400> SEQUENCE: 69

Leu Val Asn Leu Gly Phe Gln Ala Leu Arg Gln His Val Pro His
1 5 10 15

<210> SEQ ID NO 70
<211> LENGTH: 15

<212> TYPE: PRT
<213> ORGANISM: Artificial Sequence
<220> FEATURE:
<223> OTHER INFORMATION: Homo Sapien

<400> SEQUENCE: 70

Leu Val Asn Leu Gly Phe Gln Ala Leu Arg Gln His Val Pro His
1 5 10 15

<210> SEQ ID NO 71
<211> LENGTH: 15
<212> TYPE: PRT
<213> ORGANISM: Artificial Sequence
<220> FEATURE:
<223> OTHER INFORMATION: Homo Sapien

<400> SEQUENCE: 71

Leu Arg Gln His Val Pro His Gly Gly Ala Ser Lys Lys Leu Ser
1 5 10 15

<210> SEQ ID NO 72
<211> LENGTH: 15
<212> TYPE: PRT
<213> ORGANISM: Artificial Sequence
<220> FEATURE:
<223> OTHER INFORMATION: Homo Sapien

<400> SEQUENCE: 72

Val Pro His Gly Gly Ala Ser Lys Lys Leu Ser Lys Val Glu Thr
1 5 10 15

<210> SEQ ID NO 73
<211> LENGTH: 15
<212> TYPE: PRT
<213> ORGANISM: Artificial Sequence
<220> FEATURE:
<223> OTHER INFORMATION: Homo Sapien

<400> SEQUENCE: 73

Gly Ala Ser Lys Lys Leu Ser Lys Val Glu Thr Leu Arg Ser Ala
1 5 10 15

<210> SEQ ID NO 74
<211> LENGTH: 15
<212> TYPE: PRT
<213> ORGANISM: Artificial Sequence
<220> FEATURE:
<223> OTHER INFORMATION: Homo Sapien

<400> SEQUENCE: 74

Lys Leu Ser Lys Val Glu Thr Leu Arg Ser Ala Val Glu Tyr Ile
1 5 10 15

<210> SEQ ID NO 75
<211> LENGTH: 15
<212> TYPE: PRT
<213> ORGANISM: Artificial Sequence
<220> FEATURE:
<223> OTHER INFORMATION: Homo Sapien

<400> SEQUENCE: 75

Val Glu Thr Leu Arg Ser Ala Val Glu Tyr Ile Arg Ala Leu Gln
1 5 10 15

<210> SEQ ID NO 76
<211> LENGTH: 15
<212> TYPE: PRT

<213> ORGANISM: Artificial Sequence
<220> FEATURE:
<223> OTHER INFORMATION: Homo Sapien

<400> SEQUENCE: 76

Arg Ser Ala Val Glu Tyr Ile Arg Ala Leu Gln Arg Leu Leu Ala
1 5 10 15

<210> SEQ ID NO 77
<211> LENGTH: 15
<212> TYPE: PRT
<213> ORGANISM: Artificial Sequence
<220> FEATURE:
<223> OTHER INFORMATION: Homo Sapien

<400> SEQUENCE: 77

Glu Tyr Ile Arg Ala Leu Gln Arg Leu Leu Ala Glu His Asp Ala
1 5 10 15

<210> SEQ ID NO 78
<211> LENGTH: 15
<212> TYPE: PRT
<213> ORGANISM: Artificial Sequence
<220> FEATURE:
<223> OTHER INFORMATION: Homo Sapien

<400> SEQUENCE: 78

Ala Leu Gln Arg Leu Leu Ala Glu His Asp Ala Val Arg Asn Ala
1 5 10 15

<210> SEQ ID NO 79
<211> LENGTH: 15
<212> TYPE: PRT
<213> ORGANISM: Artificial Sequence
<220> FEATURE:
<223> OTHER INFORMATION: Homo Sapien

<400> SEQUENCE: 79

Leu Leu Ala Glu His Asp Ala Val Arg Asn Ala Leu Ala Gly Gly
1 5 10 15

<210> SEQ ID NO 80
<211> LENGTH: 15
<212> TYPE: PRT
<213> ORGANISM: Artificial Sequence
<220> FEATURE:
<223> OTHER INFORMATION: Homo Sapien

<400> SEQUENCE: 80

His Asp Ala Val Arg Asn Ala Leu Ala Gly Gly Leu Arg Pro Gln
1 5 10 15

<210> SEQ ID NO 81
<211> LENGTH: 15
<212> TYPE: PRT
<213> ORGANISM: Artificial Sequence
<220> FEATURE:
<223> OTHER INFORMATION: Homo Sapien

<400> SEQUENCE: 81

Arg Asn Ala Leu Ala Gly Gly Leu Arg Pro Gln Ala Val Arg Pro
1 5 10 15

<210> SEQ ID NO 82
<211> LENGTH: 15
<212> TYPE: PRT
<213> ORGANISM: Artificial Sequence
<220> FEATURE:
<223> OTHER INFORMATION: Homo Sapien

<400> SEQUENCE: 82

Ala Gly Gly Leu Arg Pro Gln Ala Val Arg Pro Ser Ala Pro Arg
1 5 10 15

<210> SEQ ID NO 83
<211> LENGTH: 15
<212> TYPE: PRT
<213> ORGANISM: Artificial Sequence
<220> FEATURE:
<223> OTHER INFORMATION: Homo Sapien

<400> SEQUENCE: 83

Arg Pro Gln Ala Val Arg Pro Ser Ala Pro Arg Gly Pro Pro Gly
1 5 10 15

<210> SEQ ID NO 84
<211> LENGTH: 15
<212> TYPE: PRT
<213> ORGANISM: Artificial Sequence
<220> FEATURE:
<223> OTHER INFORMATION: Homo Sapien

<400> SEQUENCE: 84

Val Arg Pro Ser Ala Pro Arg Gly Pro Pro Gly Thr Thr Pro Val
1 5 10 15

<210> SEQ ID NO 85
<211> LENGTH: 15
<212> TYPE: PRT
<213> ORGANISM: Artificial Sequence
<220> FEATURE:
<223> OTHER INFORMATION: Homo Sapien

<400> SEQUENCE: 85

Ala Pro Arg Gly Pro Pro Gly Thr Thr Pro Val Ala Ala Ser Pro
1 5 10 15

<210> SEQ ID NO 86
<211> LENGTH: 15
<212> TYPE: PRT
<213> ORGANISM: Artificial Sequence
<220> FEATURE:
<223> OTHER INFORMATION: Homo Sapien

<400> SEQUENCE: 86

Pro Pro Gly Thr Thr Pro Val Ala Ala Ser Pro Ser Arg Ala Ser
1 5 10 15

<210> SEQ ID NO 87
<211> LENGTH: 15
<212> TYPE: PRT
<213> ORGANISM: Artificial Sequence
<220> FEATURE:
<223> OTHER INFORMATION: Homo Sapien

<400> SEQUENCE: 87

Thr Pro Val Ala Ala Ser Pro Ser Arg Ala Ser Ser Ser Pro Gly
1 5 10 15

<210> SEQ ID NO 88
<211> LENGTH: 15
<212> TYPE: PRT
<213> ORGANISM: Artificial Sequence
<220> FEATURE:

-continued

<223> OTHER INFORMATION: Homo Sapien

<400> SEQUENCE: 88

Ala Ser Pro Ser Arg Ala Ser Ser Ser Pro Gly Arg Gly Gly Ser
1 5 10 15

<210> SEQ ID NO 89
<211> LENGTH: 15
<212> TYPE: PRT
<213> ORGANISM: Artificial Sequence
<220> FEATURE:
<223> OTHER INFORMATION: Homo Sapien

<400> SEQUENCE: 89

Arg Ala Ser Ser Ser Pro Gly Arg Gly Gly Ser Ser Glu Pro Gly
1 5 10 15

<210> SEQ ID NO 90
<211> LENGTH: 15
<212> TYPE: PRT
<213> ORGANISM: Artificial Sequence
<220> FEATURE:
<223> OTHER INFORMATION: Homo Sapien

<400> SEQUENCE: 90

Ser Pro Gly Arg Gly Gly Ser Ser Glu Pro Gly Ser Pro Arg Ser
1 5 10 15

<210> SEQ ID NO 91
<211> LENGTH: 15
<212> TYPE: PRT
<213> ORGANISM: Artificial Sequence
<220> FEATURE:
<223> OTHER INFORMATION: Homo Sapien

<400> SEQUENCE: 91

Gly Gly Ser Ser Glu Pro Gly Ser Pro Arg Ser Ala Tyr Ser Ser
1 5 10 15

<210> SEQ ID NO 92
<211> LENGTH: 15
<212> TYPE: PRT
<213> ORGANISM: Artificial Sequence
<220> FEATURE:
<223> OTHER INFORMATION: Homo Sapien

<400> SEQUENCE: 92

Glu Pro Gly Ser Pro Arg Ser Ala Tyr Ser Ser Asp Asp Ser Gly
1 5 10 15

<210> SEQ ID NO 93
<211> LENGTH: 15
<212> TYPE: PRT
<213> ORGANISM: Artificial Sequence
<220> FEATURE:
<223> OTHER INFORMATION: Homo Sapien

<400> SEQUENCE: 93

Pro Arg Ser Ala Tyr Ser Ser Asp Asp Ser Gly Cys Glu Gly Ala
1 5 10 15

<210> SEQ ID NO 94
<211> LENGTH: 15
<212> TYPE: PRT
<213> ORGANISM: Artificial Sequence
<220> FEATURE:
<223> OTHER INFORMATION: Homo Sapien -continued

<400> SEQUENCE: 94

Tyr Ser Ser Asp Asp Ser Gly Cys Glu Gly Ala Leu Ser Pro Ala
1 5 10 15

<210> SEQ ID NO 95
<211> LENGTH: 15
<212> TYPE: PRT
<213> ORGANISM: Artificial Sequence
<220> FEATURE:
<223> OTHER INFORMATION: Homo Sapien

<400> SEQUENCE: 95

Asp Ser Gly Cys Glu Gly Ala Leu Ser Pro Ala Glu Arg Glu Leu
1 5 10 15

<210> SEQ ID NO 96
<211> LENGTH: 15
<212> TYPE: PRT
<213> ORGANISM: Artificial Sequence
<220> FEATURE:
<223> OTHER INFORMATION: Homo Sapien

<400> SEQUENCE: 96

Glu Gly Ala Leu Ser Pro Ala Glu Arg Glu Leu Leu Asp Phe Ser
1 5 10 15

<210> SEQ ID NO 97
<211> LENGTH: 15
<212> TYPE: PRT
<213> ORGANISM: Artificial Sequence
<220> FEATURE:
<223> OTHER INFORMATION: Homo Sapien

<400> SEQUENCE: 97

Ser Pro Ala Glu Arg Glu Leu Leu Asp Phe Ser Ser Trp Leu Gly
1 5 10 15

<210> SEQ ID NO 98
<211> LENGTH: 15
<212> TYPE: PRT
<213> ORGANISM: Artificial Sequence
<220> FEATURE:
<223> OTHER INFORMATION: Homo Sapien

<400> SEQUENCE: 98

Ala Glu Arg Glu Leu Leu Asp Phe Ser Ser Trp Leu Gly Gly Tyr
1 5 10 15